(12) United States Patent
Kamiyama et al.

(10) Patent No.: US 8,318,981 B2
(45) Date of Patent: Nov. 27, 2012

(54) IMIDATE COMPOUND AND USE THEREOF FOR PEST CONTROL

(75) Inventors: Hideo Kamiyama, Nerima-ku (JP); Shigeyuki Itoh, Oita (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 373 days.

(21) Appl. No.: 12/670,294

(22) PCT Filed: Jul. 25, 2008

(86) PCT No.: PCT/JP2008/063818
§ 371 (c)(1),
(2), (4) Date: Jan. 22, 2010

(87) PCT Pub. No.: WO2009/014267
PCT Pub. Date: Jan. 29, 2009

(65) Prior Publication Data
US 2010/0210683 A1 Aug. 19, 2010

(30) Foreign Application Priority Data
Jul. 25, 2007 (JP) ................. 2007-193187

(51) Int. Cl.
| C07C 321/00 | (2006.01) |
|---|---|
| C07C 323/00 | (2006.01) |
| C07C 381/00 | (2006.01) |
| A01N 35/10 | (2006.01) |
| A01N 47/40 | (2006.01) |
| A01N 43/42 | (2006.01) |

(52) U.S. Cl. .......... 564/440; 504/343; 514/311
(58) Field of Classification Search .......... None
See application file for complete search history.

(56) References Cited

U.S. PATENT DOCUMENTS
| 4,512,989 A | 4/1985 | Ohyama et al. |
| 5,089,623 A | 2/1992 | Fisher |

FOREIGN PATENT DOCUMENTS
| EP | 0 317 265 A2 | 5/1989 |
| EP | 0 317 266 A2 | 5/1989 |
| GB | 2 230 776 A | 10/1990 |
| JP | 3-264556 A | 11/1991 |
| WO | 2007/063702 A2 | 6/2007 |

OTHER PUBLICATIONS

I.O. Bragina et al., "Radical Phenylation of Amides of Thiocinnamic Acid", Russian Chemical Bulletin, XP002507993, 1983, pp. 610-612, vol. 32, No. 3.
M.L. El Efrit et al., Addition de thiols, d'amines secondaires et de dialkylphosphites sur les iminoesters alpha, beta-insatures, Journal De La Societe Chimique De Tunesie, XP009109984, Jun. 1998, pp. 189-195, vol. 4, No. 3.
Office Action issued Jun. 19, 2012, in Chinese Patent Application No. 200880108786.1 to Sumitomo Chemical Co., Ltd., with translation.

Primary Examiner — Susanna Moore
Assistant Examiner — Jennifer C Sawyer
(74) Attorney, Agent, or Firm — Sughrue Mion, PLLC

(57) ABSTRACT

There is provided a compound having an excellent controlling effect on arthropod pests represented by the formula (I-1):

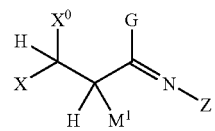

(I-1)

wherein Z represents an optionally substituted carbocyclic group or an optionally substituted heterocyclic group; G represents a $-A^1-R^1$ group, etc.; X represents a $-A^2-R^4$ group, etc.; X represents a $-A^2-R^4$ group, etc.; $X^0$ represents a $-A^3-R^6$ group, etc.; or X and $X^0$ are optionally taken together to form a $-A^2-T^0-A^3-$ group; $M^1$ represents a $-R^8$ group, etc.; $A^1$, $A^2$ and $A^3$ independently represent an oxygen atom, etc.; $R^1$ and $R^8$ independently represents an optionally substituted C1-C20 chain hydrocarbon group, etc.; $R^4$ and $R^6$ independently represent an optionally substituted C1-C6 chain hydrocarbon group, etc.; and $T^0$ represents an optionally substituted C2-C6 alkanediyl group.

24 Claims, No Drawings

IMIDATE COMPOUND AND USE THEREOF FOR PEST CONTROL

TECHNICAL FIELD

The present invention relates to an imidate compound and use thereof for pest control.

BACKGROUND ART

For controlling pests, various kinds of compounds have been developed and used practically.

Further, some imidate compounds are disclosed in Journal De La Societe Chemique De Tunisie, 1988, Vol. 4, No. 3, 189-195 pp; Bulletin De La Societe Chimique De France, 1988, No. 5, 875-872 pp; and Russian Chemical bulletin, 1983, Vol. 32, No. 3, 610-612 pp.

DISCLOSURE OF INVENTION

An object of the present invention is to provide a novel compound having an excellent controlling effect on pests.

The inventors of the present invention have intensively studied, and as a result, they have found that an imidate compound represented by the following formula (I-1) has an excellent controlling effect on pests. Thus, the present invention has been completed.

The present invention provides:
(1) An imidate compound represented by the formula (I-1):

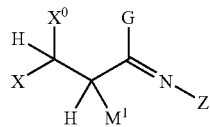

(I-1)

wherein,

Z represents a carbocyclic group having 3 to 14 ring-constituting atoms which is optionally substituted with a group selected from the group A described below, or a heterocyclic group having 3 to 14 ring-constituting atoms which is optionally substituted with a group selected from the group A described below;

G represents a $-A^1-R^1$ group, a $-S(=O)_2-R^2$ group or a $-N(R^3)-R^1$ group;

X represents a $-A^2-R^4$ group, a $-S(=O)-R^5$ group or a $-S(=O)_2-R^5$ group;

$X^0$ represents a $-A^3-R^6$ group, a $-S(=O)-R^7$ group, a $-S(=O)_2-R^7$ group or a halogen atom; or X and $X^0$ are optionally taken together to form a $-A^2-T^0-A^3-$ group;

$M^1$ represents a $-R^8$ group, a $-A^8-R^8$ group, a halogen atom or a hydrogen atom;

$A^1$, $A^2$ and $A^3$ independently represent an oxygen atom or a sulfur atom;

$R^1$ represents a C1-C20 chain hydrocarbon group which is optionally substituted with a group selected from the group D described below, a -Q group, a $-T^1$-Q group, a $-T^1$-S-Q group or a $-T^1$-O-Q group;

$R^2$ represents a C1-C20 chain hydrocarbon group which is optionally substituted with a group selected from the group E described below or a phenyl group which is optionally substituted with a group selected from the group B described below;

$R^3$ represents a C1-C20 chain hydrocarbon group which is optionally substituted with a group selected from the group D described below, a -Q group, a $-T^1$-Q group, a C1-C6 alkoxy group, a C2-C7 alkanoyl group, a mono(C1-C7 alkyl)amino group, a di(C1-C7 alkyl)amino group or a (C1-C7 alkyl)phenylamino group;

$R^4$ and $R^6$ independently represent a C1-C6 chain hydrocarbon group which is optionally substituted with a group selected from the group D described below, a -Q group, a $-T^1$-Q group, a $-C(=A^4)-R^{11}$ group, a $-C(=A^4)-A^5-R^{11}$ group or a $-S(=O)_2-R^{11}$ group;

$R^5$ and $R^7$ independently represent a C1-C6 chain hydrocarbon group which is optionally substituted with a group selected from the group E described below, a $-Q^1$ group or a $-T^2-Q^1$ group;

$R^8$ represents a C1-C20 chain hydrocarbon group which is optionally substituted with a group selected from the group E described below, a -Q group or a $-T^1$-Q group;

$A^8$ represents an oxygen atom or a sulfur atom;

$T^0$ represents a C2-C6 alkanediyl group which is optionally substituted with a halogen atom or a phenyl group and wherein a carbon-carbon single bond of the alkanediyl group may be interrupted by an oxygen atom, a sulfur atom and/or a carbonyl group, a $-Q^9$- group, a $-T^1-Q^9$- group or a $-T^1-Q^9-T^2$- group;

Q represents a carbocyclic group having 3 to 14 ring-constituting atoms which is optionally substituted with a group selected from the group A described below, or a heterocyclic group having 3 to 14 ring-constituting atoms which is optionally substituted with a group selected from the group A described below;

$Q^1$ represents a carbocyclic group having 3 to 14 ring-constituting atoms which is optionally substituted with a group selected from the group B described below, or a heterocyclic group having 3 to 14 ring-constituting atoms which is optionally substituted with a group selected from the group B described below;

$T^1$ and $T^2$ independently represent a C1-C6 alkanediyl group which is optionally substituted with a halogen atom, or a C2-C6 alkenediyl group;

$A^4$ and $A^5$ independently represent an oxygen atom or a sulfur atom;

$Q^9$ represents an o-phenylene group or a naphthalene-1,8-diyl group;

$R^{11}$ represents a C1-C6 chain hydrocarbon group which is optionally substituted with a group selected from the group E described below, or a carbocyclic group having 3 to 14 ring-constituting atoms which is optionally substituted with a group selected from the group B described below, The group A consists of: a halogen atom, a cyano group, a nitro group, a formyl group, a C1-C6 chain hydrocarbon group which is optionally substituted with a halogen atom, a $-A^6-L^1$ group, a $-N(L^3)-L^2$ group, a $-N(L^3)-N(L^2)-L^1$ group, a $-N=C(L^3)-L^2$ group, a $-S(=O)-L^1$ group, a $-S(=O)_2-L^1$ group, a $-S(=O)_2-N(L^3)-L^2$ group, a $-O-S(=O)_2-L^1$ group, a $-NL^2-S(=O)_2-L^1$ group, a $-C(=A^7)-L^1$ group, a $-C(=A^7)-O-L^1$ group, a $-O-C(=A^7)-L^1$ group, a $-NL^2-C(=A^7)-L^1$ group, a $-O-C(=O)-O-L^1$ group, a $-C(=A^7)-T^4-A^6-L^1$ group, a $-C(=A^7)-N(L^3)-L^2$ group, a $-Q^2$ group, a $-T^3-Q^2$ group, a $-A^6-Q^2$ group, a $-A^6-T^4-Q^2$ group, a $-N(L^3)-Q^2$ group, a $-N(L^3)-N(L^2)-Q^2$ group, a $-N=C(R^{12})-Q^2$ group, a $-S(=O)-Q^2$ group, a $-S(=O)_2-Q^2$ group, a $-S(=O)_2-N(L^3)-Q^2$ group, a $-O-S(=O)_2-Q^2$ group, a $-NL^2-S(=O)_2-Q^2$ group, a $-C(=A^7)-Q^2$ group, a $-C(=A^7)-A^6-Q^2$ group, a -A$^6$-C(=A$^7$)-Q$^2$ group, a —NL$^2$-C(=A$^7$)-Q$^2$ group, a —C(=A$^7$)-T$^4$-A$^6$-Q$^2$ group, and a —C(=A$^7$)-N(L$^3$)-Q$^2$ group;

The group B consists of: a halogen atom, a cyano group, a nitro group, a C1-C6 alkyl group which is optionally substituted with a halogen atom, a C2-C6 alkenyl group which is optionally substituted with a halogen atom, a C2-C6 alkynyl group which is optionally substituted with a halogen atom, a C1-C6 alkylthio group, and a C1-C6 alkoxy group;

The group D consists of: a halogen atom, a cyano group, a nitro group, a C1-C6 alkoxy group which is optionally substituted with a halogen atom, a C1-C6 alkylthio group which is optionally substituted with a halogen atom, a C1-C6 alkylsulfonyl group which is optionally substituted with a halogen atom, a (C1-C6 alkyl)carbonyl group which is optionally substituted with a halogen atom, a (C1-C6 alkoxy)carbonyl group which is optionally substituted with a halogen atom, and a (C1-C6 alkoxy)carbonyloxy group which is optionally substituted with a halogen atom; and The group E consists of: a halogen atom, a cyano group, a nitro group, a C1-C6 alkylthio group, and a C1-C6 alkoxy group;

wherein, A$^6$ and A$^7$ independently represent an oxygen atom or a sulfur atom;

L$^1$ represents a C1-C6 chain hydrocarbon group which is optionally substituted with a halogen atom;

L$^2$ and L$^3$ independently represent a hydrogen atom, a C1-C6 alkyl group which is optionally substituted with a halogen atom;

Q$^2$ represents a carbocyclic group having 3 to 14 ring-constituting atoms which is optionally substituted with a group selected from the group B described above, or a heterocyclic group having 3 to 14 ring-constituting atoms which is optionally substituted with a group selected from the group B described above;

T$^3$ and T$^4$ independently represent a C1-C6 alkanediyl group which is optionally substituted with a halogen atom; and R$^{12}$ represents a C1-C6 chain hydrocarbon group which is optionally substituted with a halogen atom or a phenyl group which is optionally substituted with a halogen atom;

(2) The imidate compound according to the above (1), wherein M$^1$ is a C1-C6 alkyl group, a C1-C6 alkoxy group, a C1-C6 alkylthio group, a phenyl group which is optionally substituted with a group selected from the E group, a phenoxy group which is optionally substituted with a group selected from the E group, a phenylthio group which is optionally substituted with a group selected from the E group, a monocyclic unsaturated heterocyclic group having 3 to 8 ring-constituting atoms which is optionally substituted with a group selected from the E group, a halogen atom or a hydrogen atom;

(3) The imidate compound according to the above (1), wherein M$^1$ is a methyl group, an ethyl group, a propyl group, a butyl group, a phenyl group, a 2-methylphenyl group, a 3-methylphenyl group, a 4-methylphenyl group, a 2-fluorophenyl group, a 3-fluorophenyl group, a 4-fluorophenyl group, a 2-chlorophenyl group, a 3-chlorophenyl group, a 4-chlorophenyl group, a methoxy group, an ethoxy group, a propoxy group, a phenoxy group, a 2-methylphenoxy group, a 3-methylphenoxy group, a 4-methylphenoxy group, a 2-fluorophenoxy group, a 3-fluorophenoxy group, a 4-fluorophenoxy group, a 2-chlorophenoxy group, a 3-chlorophenoxy group, a 4-chlorophenoxy group, a methylthio group, an ethylthio group, a propylthio group, a butylthio group, a phenylthio group, a 2-methylphenylthio group, a 3-methylphenylthio group, a 4-methylphenylthio group, a 2-fluorophenylthio group, a 3-fluorophenylthio group, a 4-fluorophenylthio group, a 2-chlorophenylthio group, a 3-chlorophenylthio group, a 4-chlorophenylthio group, a 2-thienyl group, a 3-thienyl group, a 2-furyl group, a 3-furyl group, a fluorine atom, a chlorine atom or a hydrogen atom;

(4) The imidate compound according to the above (1), wherein M$^1$ is a methyl group, an ethyl group, a propyl group, a butyl group, a methoxy group, an ethoxy group, a propoxy group, a methylthio group, an ethylthio group, a propylthio group, a fluorine atom, or a hydrogen atom;

(5) The imidate compound according to the above (1), wherein M$^1$ is a hydrogen atom;

(6) The imidate compound according to any one of the above (1) to (5), wherein Z is a carbocyclic group having 3 to 14 ring-constituting atoms which is optionally substituted with a group selected from the group A' described below, or a heterocyclic group having 3 to 14 ring-constituting atoms which is optionally substituted with a group selected from the group A' described below, and the group A' consists of: a halogen atom, a cyano group, a nitro group, a formyl group, a C1-C6 chain hydrocarbon group which is optionally substituted with a halogen atom, a -A$^6$-L$^1$ group, a —C(=A$^7$)-L$^1$ group, a —C(=A$^7$)-O-L$^1$ group, a —O—C(=A$^7$)-L$^1$ group, a —NL$^2$-C(=A$^7$)-L$^1$ group, a —C(=A$^7$)-N(L$^3$)-L$^2$ group, a -Q$^2$ group, a -T$^3$-Q$^2$ group, a -A$^6$-Q$^2$ group, a -A$^6$-T$^4$-Q$^2$ group, a —C(=A$^7$)-Q$^2$ group, a —C(=A$^7$)—O-Q$^2$ group, a —O—C(=A$^7$)-Q$^2$ group, a —NL$^3$-C(=A$^7$)-Q$^2$ group and a —C(=A$^7$)-N(L$^3$)-Q$^2$ group;

(7) The imidate compound according to any one of the above (1) to (5), wherein Z is a carbocyclic group having 3 to 14 ring-constituting atoms which is optionally substituted with a group selected from the group A$^{2'}$ described below, or a heterocyclic group having 3 to 14 ring-constituting atoms which is optionally substituted with a group selected from the group A$^{2'}$ described below, and the group A$^{2'}$ consists of: a halogen atom, a C1-C6 alkyl group which is optionally substituted with a halogen atom, a C2-C6 alkenyl group which is optionally substituted with a halogen atom, a C2-C6 alkynyl group which is optionally substituted with a halogen atom, a C1-C6 alkylthio group which is optionally substituted with a halogen atom, a C1-C6 alkoxy group which is optionally substituted with a halogen atom, and a phenyl group which is optionally substituted with a group selected from the B group as defined in the above (1);

(8) The imidate compound according to the above (7), wherein Z is a carbocyclic group having 3 to 14 ring-constituting atoms which is optionally substituted with a group selected from the group A$^{2'}$;

(9) The imidate compound according to the above (8), wherein Z is a phenyl group which is optionally substituted with a group selected from the group A$^{2'}$, a 5-indanyl group, or a naphthyl group;

(10) The imidate compound according to any one of the above (1) to (5), wherein Z is a phenyl group which is optionally substituted with a group selected from the group A$^{3'}$ described below, a 5-indanyl group, or a naphthyl group, and the group A' consists of: a halogen atom, a methyl group, an ethyl group, a propyl group, an isopropyl group, a butyl group, a trifluoromethyl group, a methoxy group, an ethoxy group, a propoxy group, an isopropoxy group, a butoxy group, a trifluoromethoxy group, a 3,4-methylenedioxy group, a methylthio group, an ethylthio group, a propylthio group, an isopropylthio group, a butylthio group, a trifluoromethylthio group, a phenyl group, a 2-methylphenyl group, a 3-methylphenyl group, a 4-methylphenyl group, a 2-ethylphenyl group, a 3-ethylphenyl group, a 4-ethylphenyl group, a 2-propylphenyl group, a 3-propylphenyl group, a 4-propylphenyl group, a 2-isopropylphenyl group, a 3-isopropylphenyl group, a 4-isopropylphenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, and a 4-bromophenyl group;

(11) The imidate compound according to any one of the above (1) to (10), wherein G is a -$A^1$-$R^1$ group or a —N($R^3$)—$R^1$ group;

(12) The imidate compound according to any one of the above (1) to (10), wherein G is a -$A^1$-$R^1$ group;

(13) The imidate compound according to any one of the above (1) to (10), wherein G is a -$A^1$-$R^1$ group, and $R^1$ is a -Q group or a -$T^1$-Q group in which Q is $Q^1$ as defined in the above (1), or a C1-C20 chain hydrocarbon group which is optionally substituted with a group selected from the group consisting of a halogen atom, a cyano group, a nitro group, a C1-C6 alkylthio group and a C1-C6 alkoxy group;

(14) The imidate compound according to any one of the above (1) to (10), wherein G is a -$A^1$-$R^1$ group; $A^1$ is S; and $R^1$ is a -Q group or a -$T^1$-Q group in which Q is a carbocyclic group having 3 to 14 ring-constituting atoms which is optionally substituted with a group selected from the group B as defined in the above (1), or a C1-C20 chain hydrocarbon group which is optionally substituted with a group selected from the group consisting of a halogen atom, a cyano group, a nitro group, a C1-C6 alkylthio group and a C1-C6 alkoxy group;

(15) The imidate compound according to any one of the above (1) to (10), wherein G is a -$A^1$-$R^1$ group; $A^1$ is S; and $R^1$ is a C1-C20 chain hydrocarbon group which is optionally substituted with a group selected from the group consisting of a halogen atom, a cyano group, a nitro group, a C1-C6 alkylthio group and a C1-C6 alkoxy group, or a -Q group or a -$T^1$-Q group in which Q is a phenyl group which is optionally substituted with a group selected from the group B as defined in claim 1 or a naphthyl group which is optionally substituted with a group selected from the group B as defined in the above (1);

(16) The imidate compound according to any one of the above (1) to (10), wherein G is a -$A^1$-$R^1$ group; $A^1$ is O; and $R^1$ is a -Q group in which Q is a phenyl group which is optionally substituted with a group selected from the group B as defined in claim 1 or a naphthyl group which is optionally substituted with a group selected from the group B as defined in the above (1);

(17) The imidate compound according to any one of the above (1) to (16), wherein X is a -$A^2$-$R^4$ group and $X^0$ is a -$A^3$-$R^6$ group, or X and $X^0$ are taken together to form a -$A^2$-$T^0$-$A^3$- group;

(18) The imidate compound according to any one of the above (1) to (16), wherein X is a -$A^2$-$R^4$ group and $X^0$ is a -$A^3$-$R^6$ group;

(19) The imidate compound according to any one of the above (1) to (16), wherein X is a -$A^2$-$R^4$ group; $X^0$ is a -$A^3$-$R^6$ group; and $R^4$ and $R^6$ are independently a -Q group or a -$T^1$-Q group in which Q is $Q^1$ as defined in the above (1), or a C1-C6 chain hydrocarbon group which is optionally substituted with a group selected from the group consisting of a halogen atom, a cyano group, a nitro group, a C1-C6 alkylthio group and a C1-C6 alkoxy group;

(20) The imidate compound according to any one of the above (1) to (16), wherein X is a -$A^2$-$R^4$ group; $X^0$ is a -$A^3$-$R^6$ group; and $R^4$ and $R^6$ are independently a -Q group or a -$T^1$-Q group in which Q is $Q^1$ as defined in the above (1);

(21) The imidate compound according to any one of the above (1) to (16), wherein X is a -$A^2$-$R^4$ group; $X^0$ is a -$A^3$-$R^6$ group; and $R^4$ and $R^6$ are independently a -Q group in which Q is a phenyl group which is optionally substituted with a group selected from the group B as defined in the above (1);

(22) The imidate compound according to any one of the above (1) to (16), wherein X is a -$A^2$-$R^4$ group; $X^0$ is a -$A^3$-$R^6$ group; $A^2$ and $A^3$ are each S; and $R^4$ and $R^6$ are independently a -Q group in which Q is a phenyl group which is optionally substituted with a group selected from the group B as defined in the above (1);

(23) A pesticidal composition comprising the compound according to any one of the above (1) to (22) as an active ingredient;

(24) Use of the compound according to any one of the above (1) to (22) for pest control;

(25) Use of the compound according to any one of the above (1) to (22) for production of a pesticidal composition; and

(26) A method of controlling a pest, which comprises applying the compound according to any one of the above (1) to (22) to the pest or a place where the pest inhabits.

The compound of the present invention had an excellent controlling effect on pests.

BEST MODE FOR CARRYING OUT THE INVENTION

Various substituents mentioned in the present specification will be described by way of examples.

Examples of the "carbocyclic group having 3 to 14 ring-constituting atoms", as used herein, include a monocyclic saturated carbocyclic group having 3 to 8 ring-constituting atoms, such as a cyclopropyl group, a cyclobutyl group, a cyclopentyl group, a cyclohexyl group, etc.; a monocyclic unsaturated carbocyclic group having 5 to 8 ring-constituting atoms, such as a cyclobutenyl group, a cyclopentenyl group, a cyclohexenyl group (e.g., a 2-cyclohexen-1-yl group, a 3-cyclohexen-1-yl group etc.), a phenyl group, etc.; a condensed polycyclic saturated carbocyclic group having 8 to 14 ring-constituting atoms, such as a bicyclo[3.1.0]hexyl group, a bicyclo[4.1.0]heptyl group, a bicyclo[3.2.0]heptyl group, a bicyclo[2.2.1]heptyl group, a bicyclo[4.2.0]octyl group, a bicyclo[3.3.0]octyl group, a bicyclo[4.3.0]nonyl group, a bicyclo[4.4.0]decyl group (also referred to as a perhydronaphthyl group), etc.; and a condensed polycyclic unsaturated carbocyclic group having 8 to 14 ring-constituting atoms, such as a naphthyl group, an anthryl group, an indanyl group, a 1,2,3,4-tetrahydronaphthyl group, a fluorenyl group, etc.

Examples of the "heterocyclic group having 3 to 14 ring-constituting atoms", as used herein, include a monocyclic saturated heterocyclic group having 3 to 8 ring-constituting atoms which is composed of carbon atoms and at least one heteroatom selected from the group consisting of an oxygen atom, a sulfur atom and a nitrogen atom; a monocyclic unsaturated heterocyclic group having 5 to 8 ring-constituting atoms which is composed of carbon atoms and at least one heteroatom selected from the group consisting of an oxygen atom, a sulfur atom and a nitrogen atom; and a condensed polycyclic heterocyclic group having 8 to 14 ring-constituting atoms which is composed of carbon atoms and at least one heteroatom selected from the group consisting of an oxygen atom, a sulfur atom and a nitrogen atom.

More specifically, examples of the "monocyclic saturated heterocyclic group having 3 to 8 ring-constituting atoms which is composed of carbon atoms and at least one heteroatom selected from the group consisting of an oxygen atom, a sulfur atom and a nitrogen atom" include a pyrrolidinyl group, an imidazolidinyl group, a piperidyl group, a piperidino group, a piperazinyl group, a morpholinyl group, a sydnonyl group, a morpholino group, a thiazolidinyl group, a thiomorpholinyl group, a thiomorpholino group, a tetrahydrothienyl group, a dithianyl group, a tetrahydrofuryl group, a tetrahydropyranyl group and a dioxanyl group.

Examples of the "monocyclic unsaturated heterocyclic group having 5 to 8 ring-constituting atoms which is composed of carbon atoms and at least one heteroatom selected from the group consisting of an oxygen atom, a sulfur atom and a nitrogen atom" include a pyrrolyl group, pyrrolinyl group, an imidazolyl group, a pyrazolyl group, pyridyl group, a dihydropyridyl group, a pyrimidinyl group, pyrazinyl group, a pyridazinyl group, a triazolyl group (e.g., a 4H-1,2,4-triazolyl group, a 1H-1,2,3-triazolyl group, a 2H-1,2,3-triazolyl group, etc.), a tetrazolyl group (e.g., a 1H-tetrazolyl group, a 2H-tetrazolyl group, etc.), an oxazolyl group, isoxazolyl group, an oxadiazolyl group (e.g., a 1,2,4-oxadiazolyl group, a 1,3,4-oxadiazolyl group, a 1,2,5-oxadiazolyl group, etc.), a thienyl group, a thiazolyl group, an isothiazolyl group, a thiadiazolyl group (e.g., a 1,2,3-thiadiazolyl group, a 1,2,4-thiadiazolyl group, a 1,3,4-thiadiazolyl group, a 1,2,5-thiadiazolyl group, etc.), a dihydrothiazinyl group, a furyl group, a dihydropyranyl group, a dioxynyl group and a dihydroxathiinyl group.

Examples of the "condensed polycyclic heterocyclic group having 8 to 14 ring-constituting atoms which is composed of carbon atoms and at least one heteroatom selected from the group consisting of an oxygen atom, a sulfur atom and a nitrogen atom" include an indolyl group, an isoindolyl group, an indolynyl group, an indolydinyl group, a benzoimidazolyl group, a quinolyl group, an isoquinolyl group, an indazolyl group, a benzotriazolyl group, an imidazopyridyl group, a pyrazolopyridyl group, a benzoxazolyl group, a benzoxadiazolyl group, a benzothiazolyl group, a benzothiadiazolyl group, an imidazothidiazolyl group, a benzofuryl group, a benzodioxolanyl group, a benzodioxanyl group, a dibenzofuranyl group, a benzothienyl group, a benzodithiinyl group, a dibenzothienyl group and a benzoxathiinyl group.

Examples of the "C1-C20 chain hydrocarbon group", as used herein, include a C1-C20 alkyl group such as a methyl group, an ethyl group, a propyl group, an isopropyl group, a butyl group, an isobutyl group, a sec-butyl group, a tert-butyl group, a pentyl group, a sec-pentyl group, an isopentyl group, a neopentyl group, a hexyl group, an isohexyl group, a heptyl group, an octyl group, a 3-methyl-1-propylbutyl group, a nonyl group, a 1-propylhexyl group, a decyl group, a 3,5-dimethyloctyl group, a 3,7-dimethyloctyl group, an undecyl group, a dodecyl group, a tridecyl group, a tetradecyl group, a hexadecyl group, a heptadecyl group, an octadecyl group, a nonadecyl group, an icosyl group, etc.; a C3-C20 alkenyl group such as a 2-propenyl group, an isopropenyl group, a 2-butenyl group, a 3-methyl-2-butenyl group, an isobutenyl group, a 1-methylallyl group, a 2-pentenyl group, a 2-hexenyl group, a heptenyl group, an octenyl group, a 3,5-dimethyloctenyl group, a 3,7-dimethyloctenyl group, etc.; and a C3-C12 alkynyl group such as a propargyl group, a 2-butynyl group, a 3-butynyl group, a 3-pentynyl group, a 3-hexynyl group, a 6-heptynyl group, a 7-octynyl group, a 3,5-dimethyl-7-octynyl group, a 3,7-dimethyl-4-octynyl group, etc.

Examples of the "C1-C6 alkoxy group", as used herein, include a methoxy group, an ethoxy group, a propoxy group and an isopropoxy group.

Examples of the "C2-C7 alkanoyl group", as used herein, include a formyl group, an acetyl group, a propanoyl group, a butanoyl group, a 2-methylpropanoyl group, a pentanoyl group, a 2,2-dimethylpropanoyl group and a hexanoyl group.

Examples of the "mono(C1-C7 alkyl)amino group", as used herein, include a methylamino group, an ethylamino group, a propylamino group and a butylamino group.

Example of the "di(C1-C7 alkyl)amino group", as used herein, include a dimethylamino group, a diethylamino group, a methylethylamino group, a methylpropylamino group and an ethylpropylamino group.

Examples of the "(C1-C7 alkyl)phenylamino group", as used herein, include an N-methyl-N-phenylamino group and an N-ethyl-N-phenylamino group.

Examples of the "C1-C6 chain hydrocarbon group", as used herein, include a C1-C6 alkyl group such as a methyl group, an ethyl group, a propyl group, an isopropyl group, a butyl group, an isobutyl group, a sec-butyl group, a tert-butyl group, a pentyl group, a sec-pentyl group, an isopentyl group, a neopentyl group, a hexyl group, an isohexyl group, etc.; a C3-C6 alkenyl group such as a 2-propenyl group, an isopropenyl group, a 2-butenyl group, a 3-methyl-2-butenyl group, an isobutenyl group, a 1-methylallyl group, a 2-pentenyl group, a 2-hexenyl group, etc.; and a C3-C6 alkynyl group such as a propargyl group, a 2-butynyl group, a 3-butynyl group, a 3-pentynyl group, a 3-hexynyl group, etc.

Examples of the C2-C6 alkanediyl group of the "C2-C6 alkanediyl group which is optionally substituted with a halogen atom or a phenyl group and wherein a carbon-carbon single bond of the alkanediyl group may be interrupted by an oxygen atom, a sulfur atom and/or a carbonyl group" include an ethane-1,2-diyl group, a propane-1,2-diyl group, a propane-1,3-diyl group, a butane-1,4-diyl group, a pentane-1,5-diyl group and a hexane-1,6-diyl group.

Examples of the "C1-C6 alkanediyl group which is optionally substituted with a halogen atom", as used herein, include a methylene group, an ethane-1,1-diyl group, a 2,2,2-trifluoroethane-1,1-diyl group, an ethane-1,2-diyl group, a propane-1,1-diyl group, a propane-1,2-diyl group, a propane-1,3-diyl group, a butane-1,4-diyl group, a pentane-1,5-diyl group and a hexane-1,6-diyl group.

Examples of the "C2-C6 alkenediyl group", as used herein, include an ethylene-1,1-diyl group and an ethylene-1,2-diyl group.

As used herein, the phrase "group which is optionally substituted" means that a hydrogen atom of said group is optionally substituted.

Herein, when two or more substituent groups are listed (for example, when a group is optionally substituted with a substituent group selected from the group A, B, D, E or the like), one or more hydrogen atoms of said group is optionally substituted with said substituent group(s). When two or more hydrogen atoms of a group are substituted, the hydrogen atoms are optionally substituted with the same substituent groups or different substituent groups.

Examples of the "halogen atom" include a fluorine atom, a chlorine atom, a bromine atom and an iodine atom.

Examples of the "C1-C6 chain hydrocarbon group which is optionally substituted with a halogen atom", as used herein, include a methyl group, a fluoromethyl group, a difluoromethyl group, a trifluoromethyl group, a chloromethyl group, a bromomethyl group, an iodomethyl group, an ethyl group, a pentafluoroethyl group, a 2,2,2-trifluoroethyl group, and a 2,2,2-trifluoro-1-(trifluoromethyl)ethyl group.

Examples of the "C1-C6 alkyl group which is optionally substituted with a halogen atom", as used herein, include a methyl group, a fluoromethyl group, a difluoromethyl group, a trifluoromethyl group, a chloromethyl group, a bromomethyl group, an iodomethyl group, an ethyl group, a pentafluoroethyl group, a 2,2,2-trifluoroethyl group, and 2,2,2-trifluoro-1-(trifluoromethyl)ethyl group.

Examples of the "C2-C6 alkenyl group which is optionally substituted with a halogen atom", as used herein, include a vinyl group, a 2-fluorovinyl group, a 2-propenyl group, and a 3,3-dichloropropenyl group.

Examples of the "C2-C6 alkynyl group which is optionally substituted with a halogen atom", as used herein, include an ethynyl group, a propargyl group, and a 4,4,4-trifluoro-2-buthynyl group.

Examples of the "C1-C6 alkoxy group which is optionally substituted with a halogen atom", as used herein, include a methoxy group, a trifluoromethoxy group, an ethoxy group, and a 2,2,2-trifluoroethyl group.

Examples of the "C1-C6 alkylthio group which is optionally substituted with a halogen atom", as used herein, include a methylthio group, a trifluoromethylthio group, and an ethylthio group.

Examples of the "C1-C6 alkylsulfonyl group which is optionally substituted with a halogen atom", as used herein, include a methylsulfonyl group, a trifluoromethylsulfonyl group, and an ethylsulfonyl group.

Examples of the "(C1-C6 alkyl)carbonyl group which is optionally substituted with a halogen atom", as used herein, include a methylcarbonyl group, and an ethylcarbonyl group.

Examples of the "(C1-C6 alkoxy)carbonyl group which is optionally substituted with a halogen atom", as used herein, include a methoxycarbonyl group, and an ethoxycarbonyl group.

Examples of the "(C1-C6 alkoxy)carbonyloxy group which is optionally substituted with a halogen atom", as used herein, include a methoxycarbonyloxy group, and an ethoxycarbonyloxy group.

As used herein, the group A includes the group B, and the group B and the group D each include the group E. As used herein, a group represented by "Q" includes a group represented by "$Q^1$".

Specific examples of the compound of the present invention include:

an imidate compound represented by the formula (I-1) wherein $M^1$ is a C1-C6 alkyl group, a C1-C6 alkoxy group, a C1-C6 alkylthio group, a phenyl group which is optionally substituted with a group selected from the group E, a phenoxy group which is optionally substituted with a group selected from the group E, a phenylthio group which is optionally substituted with a group selected from the group E, a monocyclic unsaturated heterocyclic group having 3 to 8 ring-constituting atoms which is optionally substituted with a group selected from the group E, a halogen atom, or a hydrogen atom;

an imidate compound represented by the formula (I-1) wherein $M^1$ is a methyl group, an ethyl group, a propyl group, a butyl group, a phenyl group, a 2-methylphenyl group, a 3-methylphenyl group, a 4-methylphenyl group, a 2-fluorophenyl group, a 3-fluorophenyl group, a 4-fluorophenyl group, a 2-chlorophenyl group, a 3-chlorophenyl group, a 4-chlorophenyl group, a methoxy group, an ethoxy group, a propoxy group, a phenoxy group, a 2-methylphenoxy group, a 3-methylphenoxy group, a 4-methylphenoxy group, a 2-fluorophenoxy group, a 3-fluorophenoxy group, a 4-fluorophenoxy group, a 2-chlorophenoxy group, a 3-chlorophenoxy group, a 4-chlorophenoxy group, a methylthio group, an ethylthio group, a propylthio group, a butylthio group, a phenylthio group, a 2-methylphenylthio group, a 3-methylphenylthio group, a 4-methylphenylthio group, a 2-fluorophenylthio group, a 3-fluorophenylthio group, a 4-fluorophenylthio group, a 2-chlorophenylthio group, a 3-chlorophenylthio group, a 4-chlorophenylthio group, a 2-thienyl group, a 3-thienyl group, a 2-furyl group, a 3-furyl group, a fluorine atom, a chlorine atom, or a hydrogen atom;

an imidate compound represented by the formula (I-1) wherein $M^1$ is a methyl group, an ethyl group, a propyl group, a butyl group, a methoxy group, an ethoxy group, a propoxy group, a methylthio group, an ethylthio group, a propylthio group, a fluorine atom, or a hydrogen atom;

an imidate compound represented by the formula (I-1) wherein $M^1$ is a hydrogen atom, that is, an imidate compound represented by the formula (I-2):

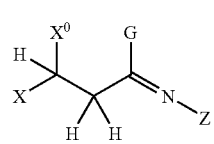

(I-2)

wherein Z, G, X and $X^0$ are as defined above;

an imidate compound represented by the formula (I-1) wherein Z is a carbocyclic group having 3 to 14 ring-constituting atoms which is optionally substituted with a group selected from the group $A^{2\prime}$, or a heterocyclic group having 3 to 14 ring-constituting atoms which is optionally substituted with a group selected from the group $A^{2\prime}$, and the group $A^{2\prime}$ consists of: a halogen atom, a C1-C6 alkyl group which is optionally substituted with a halogen atom, a C2-C6 alkenyl group which is optionally substituted with a halogen atom, a C2-C6 alkynyl group which is optionally substituted with a halogen atom, a C1-C6 alkylthio group which is optionally substituted with a halogen atom, a C1-C6 alkoxy group which is optionally substituted with a halogen atom, and a phenyl group which is optionally substituted with a group selected from the B group;

an imidate compound represented by the formula (I-1) wherein Z is a carbocyclic group having 3 to 14 ring-constituting atoms which is optionally substituted with a group selected from the group $A^{2\prime}$;

an imidate compound represented by the formula (I-1) wherein Z is a phenyl group which is optionally substituted with a group selected from the group $A^{2\prime}$, a 5-indanyl group which is optionally substituted with a group selected from the group $A^{2\prime}$ or a naphthyl group which is optionally substituted with a group selected from the group $A^{2\prime}$;

an imidate compound represented by the formula (I-1) wherein Z is a phenyl group which is optionally substituted with a group selected from the group $A^{3\prime}$, a 5-indanyl group which is optionally substituted with a group selected from the group $A^{3\prime}$ or a naphthyl group which is optionally substituted with a group selected from the group $A^{3\prime}$, and the group $A^{3\prime}$ consists of: a halogen atom, a methyl group, an ethyl group, a propyl group, an isopropyl group, a butyl group, a trifluoromethyl group, a methoxy group, an ethoxy group, a propoxy group, an isopropoxy group, butoxy group, a trifluoromethoxy group, a 3,4-methylenedioxy group, a methylthio group, an ethylthio group, a propylthio group, an isopropylthio group, a butylthio group, a trifluoromethylthio group, a phenyl group, a 2-methylphenyl group, a 3-methylphenyl group, a 4-methylphenyl group, a 2-ethylphenyl group, a 3-ethylphenyl group, a 4-ethylphenyl group, a 3-propylphenyl group, a 4-propylphenyl group, a 2-isopropylphenyl group, a 3-isopropylphenyl group, a 4-isopropylphenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, and a 4-bromophenyl group;

an imidate compound represented by the formula (I-1) wherein G is a -$A^1$-$R^1$ group or a —N($R^3$)—$R^1$ group;

an imidate compound represented by the formula (I-1) wherein G is a -$A^1$-$R^1$ group;

an imidate compound represented by the formula (I-1) wherein G is a -$A^1$-$R^1$ group, and $R^1$ is a -$Q^1$ group, a -$T^1$-$Q^1$ group, or a C1-C20 chain hydrocarbon group which is optionally substituted with a group selected from the group E;

an imidate compound represented by the formula (I-1) wherein G is a —S—$R^1$ group, $R^1$ is a -$Q^{1a}$ group, a -$T^1$-$Q^{1a}$ group, or a C1-C20 chain hydrocarbon group which is optionally substituted with a group selected from the group E, and $Q^{1a}$ is a carbocyclic group having 3 to 14 ring-constituting atoms which is optionally substituted with a group selected from the group B;

an imidate compound represented by the formula (I-1) wherein G is a —S—$R^1$ group, $R^1$ is a C1-C20 chain hydrocarbon group which is optionally substituted with a group selected from the group E, a -$Q^{1b}$ group or a -$T^1$-$Q^{1b}$ group, and $Q^{1b}$ is a phenyl group which is optionally substituted with a group selected from the group B or a naphthyl group which is optionally substituted with a group selected from the group B;

an imidate compound represented by the formula (I-1) wherein G is a —O—$R^{1a}$ group, and $R^{1a}$ is a phenyl group which is optionally substituted with a group selected from the group B or a naphthyl group which is optionally substituted with a group selected from the group B;

an imidate compound represented by the formula (I-1) wherein X is a -$A^2$-$R^4$ group and $X^0$ is a -$A^3$-$R^6$ group, or X and $X^0$ are taken together to form a -$A^2$-$T^0$-$A^3$- group;

an imidate compound represented by the formula (I-1) wherein X is a -$A^2$-$R^4$ group and $X^0$ is a -$A^3$-$R^6$ group;

an imidate compound represented by the formula (I-1) wherein X is a -$A^2$-$R^4$ group, $X^0$ is a -$A^3$-$R^6$ group, and $R^4$ and $R^6$ are independently a C1-C6 chain hydrocarbon group which is optionally substituted with a group selected from the group E, a -$Q^1$ group or a -$T^1$-$Q^1$ group;

an imidate compound represented by the formula (I-1) wherein X is a -$A^2$-$R^4$ group, $X^0$ is a -$A^3$-$R^6$ group, and $R^4$ and $R^6$ are independently a -$Q^1$ group or a -$T^1$-$Q^1$ group;

an imidate compound represented by the formula (I-1) wherein X is a -$A^2$-$R^4$ group, $X^0$ is a -$A^3$-$R^6$ group, and $R^4$ and $R^6$ are independently a phenyl group which is optionally substituted with a group selected from the group B; and an imidate compound represented by the formula (I-1) wherein X is a —S—$R^4$ group, $X^0$ is a —S—$R^6$ group, and $R^4$ and $R^6$ are independently a phenyl group which is optionally substituted with a group selected from the group B.

Specific examples of compound of the present invention further include:

an imidate compound represented by the formula (I-2), wherein Z is a carbocyclic group having 3 to 14 ring-constituting atoms which is optionally substituted with a group selected from the group A', or a heterocyclic group having 3 to 14 ring-constituting atoms which is optionally substituted with a group selected from the group A', and the group A' consists of: a halogen atom, a cyano group, a nitro group, a formyl group, a C1-C6 chain hydrocarbon group which is optionally substituted with a halogen atom, a -$A^6$-$L^1$ group, a —C(=$A^7$)-$L^1$ group, a —C(=$A^7$)-O-$L^1$ group, a —O—C(=$A^7$)-$L^1$ group, a —N$L^2$-C(=$A^7$)-$L^1$ group, a —C(=$A^7$)-N($L^3$)-$L^2$ group, a -$Q^2$ group, a -$T^3$-$Q^2$ group, a -$A^6$-$Q^2$ group, a -$A^6$-$T^4$-$Q^2$ group, a —C(=$A^7$)-$Q^2$ group, a —C(=$A^7$)—O-$Q^2$ group, a —O—C(=$A^7$)-$Q^2$ group, a —N$L^3$-C(=$A^7$)-$Q^2$ group and a —C(=$A^7$)-N($L^3$)-$Q^2$ group;

an imidate compound represented by the formula (I-2), wherein Z is a carbocyclic group having 3 to 14 ring-constituting atoms which is optionally substituted with a group selected from the group A", or a heterocyclic group having 3 to 14 ring-constituting atoms which is optionally substituted with a group selected from the group A", and the group A" consists of: a halogen atom, a formyl group, a C1-C6 alkyl group which is optionally substituted with a halogen atom, a C2-C6 alkenyl group which is optionally substituted with a halogen atom, a C2-C6 alkynyl group which is optionally substituted with a halogen atom, a C1-C6 alkoxy group which is optionally substituted with a halogen atom, a C1-C6 alkylthio group which is optionally substituted with a halogen atom, a (C1-C6 alkyl)carbonyl group which is optionally substituted with a halogen atom, a (C1-C6 alkoxy)carbonyl group which is optionally substituted with a halogen atom, a (C1-C6 alkoxy)carbonyloxy group which is optionally substituted with a halogen atom, and a phenyl group which is optionally substituted with a halogen atom or C1-C6 alkyl group;

an imidate compound represented by the formula (I-2), wherein Z is a carbocyclic group having 3 to 14 ring-constituting atoms which is optionally substituted with a group selected from the group A;

an imidate compound represented by the formula (I-2), wherein Z is a carbocyclic group having 3 to 14 ring-constituting atoms which is optionally substituted with a group selected from the group A';

an imidate compound represented by the formula (I-2), wherein Z is a carbocyclic group having 3 to 14 ring-constituting atoms which is optionally substituted with a group selected from the group A";

an imidate compound represented by the formula (I-2), wherein Z is a heterocyclic group having 3 to 14 ring-constituting atoms which is optionally substituted with a group selected from the group A;

an imidate compound represented by the formula (I-2), wherein Z is a heterocyclic group having 3 to 14 ring-constituting atoms which is optionally substituted with a group selected from the group A';

an imidate compound represented by the formula (I-2), wherein Z is a heterocyclic group having 3 to 14 ring-constituting atoms which is optionally substituted with a group selected from the group A";

an imidate compound represented by the formula (I-2), wherein Z is a phenyl group which is optionally substituted with a group selected from the group A, or a naphthyl group which is optionally substituted with the group selected from the group A;

an imidate compound represented by the formula (I-2), wherein Z is a monocyclic saturated carbocyclic group having 3 to 14 ring-constituting atoms which is optionally substituted with a group selected from the group. A;

an imidate compound represented by the formula (I-2), wherein Z is a condensed polycyclic saturated carbocyclic group having 8 to 14 ring-constituting atoms which is optionally substituted with a group selected from the group A;

an imidate compound represented by the formula (I-2), wherein Z is an indanyl group which is optionally substituted with a group selected from the group A;

an imidate compound represented by the formula (I-2), wherein Z is a phenyl group, a 4-methylphenyl group, a 4-ethylphenyl group, a 4-isopropylphenyl group, a 4-(2-pyridyl)phenyl group, a 4-phenylphenyl group, a 4-chlorophenyl group, a 4-nitrophenyl group, a 3-methylphenyl group, a 3-ethylphenyl group, a 3-isopropylphenyl group, a 3-phenylphenyl group, a 3-chlorophenyl group, a 3,4-dimethylphenyl group or a 5-indanyl group;

an imidate compound represented by the formula (I-2), wherein G is a -$A^1$-$R^1$ group or a —N($R^3$)—$R^1$ group;

an imidate compound represented by the formula (I-2), wherein G is a -$A^1$-$R^1$ group;

an imidate compound represented by the formula (I-2), wherein G is a -$A^1$-$R^1$— group and $A^1$ is a sulfur atom;

an imidate compound represented by the formula (I-2), wherein G is a -$A^1$-$R^1$ group and $A^1$ represents an oxygen atom;

an imidate compound represented by the formula (I-2), wherein G is a -$A^1$-$R^1$ and $R^1$ represents a C1-C20 chain hydrocarbon group which is optionally substituted with group selected from the group D;

an imidate compound represented by the formula (I-2), wherein G is a -$A^1$-$R^1$ group, $A^1$ is a sulfur atom, and $R^1$ is a C1-C20 chain hydrocarbon group which is optionally substituted with a group selected from the group D;

an imidate compound represented by the formula (I-2), wherein G is a -$A^1$-$R^1$ group, $A^1$ is a sulfur atom, and $R^1$ is a C1-C20 chain hydrocarbon group;

an imidate compound represented by the formula (I-2), wherein G is a -$A^1$-$R^1$ group, $A^1$ is a sulfur atom, and $R^1$ is a C1-C20 alkyl group which is optionally substituted with a group selected from the group D;

an imidate compound represented by the formula (I-2), wherein G is a -$A^1$-$R^1$ group, and $R^1$ is a -Q group, a -$T^1$-Q group, a -$T^1$-S-Q group or a -$T^1$-O-Q group;

an imidate compound represented by the formula (I-2), wherein G is a -$A^1$-$R^1$ group, $A^1$ is a sulfur atom, and $R^1$ is a -Q group, a -$T^1$-Q group, a -$T^1$-S-Q group or a -$T^1$-O-Q group;

an imidate compound represented by the formula (I-2), wherein G is a -$A^1$-$R^1$ group, $A^1$ is an oxygen atom, and $R^1$ is a -Q group, a -$T^1$-Q group, a -$T^1$-S-Q group or a -$T^1$-O-Q group;

an imidate compound represented by the formula (I-2), wherein G is a -$A^1$-$R^1$ group, and $R^1$ is a -Q group or a -$T^1$-Q group;

an imidate compound represented by the formula (I-2), wherein G is a -$A^1$-$R^1$ group, $A^1$ is a sulfur atom, and $R^1$ is a -Q group or a -$T^1$-Q group;

an imidate compound represented by the formula (I-2), wherein G is a -$A^1$-$R^1$ group, $R^1$ is a -Q group or a -$T^1$-Q group, and Q is a carbocyclic group having 3 to 14 ring-constituting atoms which is optionally substituted with a group selected from the group A;

an imidate compound represented by the formula (I-2), wherein G is a -$A^1$-$R^1$ group, $R^1$ is a -Q group or a -$T^1$-Q group, and Q is a carbocyclic group having 3 to 14 ring-constituting atoms which is optionally substituted with a group selected from the group A';

an imidate compound represented by the formula (I-2), wherein G is a -$A^1$-$R^1$ group, $R^1$ is a -Q group or a -$T^1$-Q group, and Q is a carbocyclic group having 3 to 14 ring-constituting atoms which is optionally substituted with a group selected from the group A";

an imidate compound represented by the formula (I-2), wherein G is a -$A^1$-$R^1$ group, $R^1$ is a -Q group or a -$T^1$-Q group, and Q is a phenyl group which is optionally substituted with a group selected from the group A" or a naphthyl group which is optionally substituted with a group selected from the group A";

an imidate compound represented by the formula (I-2), wherein G is a -$A^1$-$R^1$ group, $R^1$ is a -Q group or a -$T^1$-Q group, and Q is a monocyclic saturated carbocyclic group having 3 to 8 ring-constituting atoms which is optionally substituted with a group selected from the group A";

an imidate compound represented by the formula (I-2), wherein G is a -$A^1$-$R^1$ group, $A^1$ is a sulfur atom, $R^1$ is a -Q group or a -$T^1$-Q group, and Q is a carbocyclic group having 3 to 14 ring-constituting atoms which is optionally substituted with a group selected from the group A;

an imidate compound represented by the formula (I-2), wherein G is a -$A^1$-$R^1$ group, $A^1$ is an oxygen atom, $R^1$ is a -Q group or a -$T^1$-Q group, and Q is a carbocyclic group having 3 to 14 ring-constituting atoms which is optionally substituted with a group selected from the group A;

an imidate compound represented by the formula (I-2), wherein G is a -$A^1$-$R^1$ group, $A^1$ is a sulfur atom, $R^1$ is a -Q group or a -$T^1$-Q group, and Q is a carbocyclic group having 3 to 14 ring-constituting atoms which is optionally substituted with a group selected from the group A";

an imidate compound represented by the formula (I-2), wherein G is a -$A^1$-$R^1$ group, $A^1$ is an oxygen atom, $R^1$ is a -Q group or a -$T^1$-Q group, and Q is a carbocyclic group having 3 to 14 ring-constituting atoms which is optionally substituted with a group selected from the group A";

an imidate compound represented by the formula (I-2), wherein G is a -$A^1$-$R^1$ group, $A^1$ is a sulfur atom, $R^1$ is a -Q group or a -$T^1$-Q group, and Q is a phenyl group which is optionally substituted with a group selected from the group A" or a naphthyl group which is optionally substituted with a group selected from the group A";

an imidate compound represented by the formula (I-2), wherein G is a -$A^1$-$R^1$ group, $A^1$ is an oxygen atom, $R^1$ is a -Q group or a -$T^1$-Q group, and Q is a phenyl group which is optionally substituted with a group selected from the group A" or a naphthyl group which is optionally substituted with a group selected from the group A";

an imidate compound represented by the formula (I-2), wherein G is a -$A^1$-$R^1$ group, $A^1$ is a sulfur atom, $R^1$ is a -Q group or a -$T^1$-Q group, and Q is a monocyclic saturated carbocyclic group having 3 to 8 ring-constituting atoms which is optionally substituted with a group selected from the group A";

an imidate compound represented by the formula (I-2), wherein G is a -$A^1$-$R^1$ group, $A^1$ is an oxygen atom, $R^1$ is a -Q group or a -$T^1$-Q group, and Q is a monocyclic saturated carbocyclic group having 3 to 8 ring-constituting atoms which is optionally substituted with a group selected from the group A";

an imidate compound represented by the formula (I-2), wherein G is a —N($R^3$)—$R^1$ group;

an imidate compound represented by the formula (I-2), wherein G is a —N($R^3$)—$R^1$ group, and $R^1$ and $R^3$ independently represent a C1-C20 chain hydrocarbon group which is optionally substituted with a group selected from the group D, a -Q group or a -$T^1$-Q group;

an imidate compound represented by the formula (I-2), wherein G is a phenylthio group, a 4-methylphenylthio group, a 4-ethylphenylthio group, a 4-isopropylphenylthio group, a 4-methoxyphenylthio group, a 4-(2-pyridyl)phenylthio group, a 4-phenylphenylthio group, a 4-chlorophenylthio group, 4-nitrophenylthio group, a 3-methylphenylthio group, a 3-ethylpheylthio group, a 3-isopropylphenylthio group, a 3-phenylphenylthio group, a 3-chlorophenylthio group, a 3,4-dimethylphenylthio group, a 1-naphthylthio group, a 2-naphthylthio group, a 5-indanylthio group, a cyclopropylthio group, a cyclopentylthio group, a cyclohexylthio group, a 2-perhydronaphthylthio group, benzylthio group, a phenethylthio group, an α-methylbenzylthio group, a cyclopropylmethylthio group, a cyclopentylmethylthio group, a cyclohexylmethylthio group, an isopropylthio group, a sec-butylthio group, a 3-methyl-1-propylbutylthio group, an allylthio group, a propargylthio group, or an N-methyl-N-phenylamino group;

an imidate compound represented by the formula (I-2), wherein G is a phenoxy group, a 4-methylphenoxy group, a 4-ethylphenoxy group, a 4-isopropylphenoxy group, a 4-methoxyphenoxy group, a 4-phenylphenylthio group, a 4-chlorophenoxy group, a 3-methylphenoxy group, a 3-ethylphenylthio group, a 3-isopropylphenoxy group, a 3-phenylphenoxy group, a 3-chlorophenoxy group, a 3,4-dimethylphenoxy group, a 1-naphthyloxy group, a 2-naphthyloxy group or a 5-indanyloxy group;

an imidate compound represented by the formula (I-2), wherein X is a $-A^2-R^4$ group and $X^0$ is a $-A^3-R^6$ group, or X and $X^0$ are taken together to form a $-A^2-T^0-A^3-$ group;

an imidate compound represented by the formula (I-2), wherein X is a $-A^2-R^4$ group, and $X^0$ is a $-A^3-R^6$ group;

an imidate compound represented by the formula (I-2), wherein X is a $-A^2-R^4$ group, $X^0$ is a $-A^3-R^6$ group, and $A^2$ and $A^3$ are sulfur atoms;

an imidate compound represented by the formula (I-2), wherein X is a $-A^2-R^4$ group, $X^0$ is a $-A^3-R^6$ group, and $R^4$ and $R^6$ are independently a C1-C6 chain hydrocarbon group which is optionally substituted with a group selected from the group D, a -Q group, a $-T^1$-Q group or a $—C(=A^4)-R^{11}$ group;

an imidate compound represented by the formula (I-2), wherein X is a $-A^2-R^4$ group, $X^0$ is a $-A^3-R^6$ group, and $R^4$ and $R^6$ are independently a C1-C6 chain hydrocarbon group which is optionally substituted with a group selected from the group D, a -Q group or a $-T^1$-Q group;

an imidate compound represented by the formula (I-2), wherein X is a $-A^2-R^4$ group, $X^0$ is a $-A^3-R^6$ group, and $R^4$ and $R^6$ are independently a C1-C6 chain hydrocarbon group which is optionally substituted with a group selected from the group D;

an imidate compound represented by the formula (I-2), wherein X is a $-A^2-R^4$ group, $X^0$ is a $-A^3-R^6$ group, and $R^4$ and $R^6$ are independently a C1-C6 chain hydrocarbon group;

an imidate compound represented by the formula (I-2), wherein X is a $-A^2-R^4$ group, $X^0$ is a $-A^3-R^6$ group, and $R^4$ and $R^6$ are independently a -Q group or a $-T^1$-Q group;

an imidate compound represented by the formula (I-2), wherein X is a $-A^2-R^4$ group, $X^0$ is a $-A^3-R^6$ group, $R^4$ and $R^6$ are independently a -Q group or a $-T^1$-Q group, and Q is a carbocyclic group having 3 to 14 ring-constituting atoms which is optionally substituted with a group selected from the group A;

an imidate compound represented by the formula (I-2), wherein X is a $-A^2-R^4$ group, $X^0$ is a $-A^3-R^6$ group, $R^4$ and $R^6$ are independently a -Q group or a $-T^1$-Q group, and Q is a carbocyclic group having 3 to 14 ring-constituting atoms which is optionally substituted with a group selected from the group A";

an imidate compound represented by the formula (I-2), wherein X is a $-A^2-R^4$ group, $X^0$ is a $-A^3-R^6$ group, $R^4$ and $R^6$ are independently a -Q group or a $-T^1$-Q group, and Q is a phenyl group which is optionally substituted with a group selected from the group A or a naphthyl group which is optionally substituted with a group selected from the group A;

an imidate compound represented by the formula (I-2), wherein X is a $-A^2-R^4$ group, $X^0$ is a $-A^3-R^6$ group, $R^4$ and $R^6$ are independently a -Q group or a $-T^1$-Q group, and Q is a phenyl group which is optionally substituted with a group selected from the group A" or a naphthyl group which is optionally substituted with a group selected from the group A";

an imidate compound represented by the formula (I-2), wherein X is a $-A^2-R^4$ group, $X^0$ is a $-A^3-R^6$ group, $R^4$ and $R^6$ are independently a -Q group or a $-T^1$-Q group, and Q is a monocyclic saturated carbocyclic group having 3 to 8 ring-constituting atoms which is optionally substituted with a group selected from the group A";

an imidate compound represented by the formula (I-2), wherein X is a $-A^2-R^4$ group, $X^0$ is a $-A^3-R^6$ group, $R^4$ and $R^6$ are independently a -Q group or a $-T^1$-Q group, and Q is a monocyclic unsaturated heterocyclic group having 3 to 8 ring-constituting atoms which is optionally substituted with a group selected from the group A";

an imidate compound represented by the formula (I-2), wherein X is a $-A^2-R^4$ group, $X^0$ is a $-A^3-R^6$ group, $A^2$ and $A^3$ are sulfur atoms, and $R^4$ and $R^6$ are independently a C1-C6 chain hydrocarbon group which is optionally substituted with a group selected from the group D, a -Q group or a $-T^1$-Q group;

an imidate compound represented by the formula (I-2), wherein X is a $-A^2-R^4$ group, $X^0$ is a $-A^3-R^6$ group, $A^2$ and $A^3$ are sulfur atoms, and $R^4$ and $R^6$ are a C1-C6 chain hydrocarbon group which is optionally substituted with a group selected from the group D;

an imidate compound represented by the formula (I-2), wherein X is a $-A^2-R^4$ group, $X^0$ is a $-A^3-R^6$ group, $A^2$ and $A^3$ are sulfur atoms, and $R^4$ and $R^6$ are a C1-C6 chain hydrocarbon group;

an imidate compound represented by the formula (I-2), wherein X is a $-A^2-R^4$ group, $X^0$ is a $-A^3-R^6$ group, $A^2$ and $A^3$ are sulfur atoms, and $R^4$ and $R^6$ are independently a -Q group or a $-T^1$-Q group;

an imidate compound represented by the formula (I-2), wherein X is a $-A^2-R^4$ group, $X^0$ is a $-A^3-R^6$ group, $A^2$ and $A^3$ are sulfur atoms, $R^4$ and $R^6$ are independently a -Q group or a $-T^1$-Q group, and Q is a carbocyclic group having 3 to 14 ring-constituting atoms which is optionally substituted with a group selected from the group A;

an imidate compound represented by the formula (I-2), wherein X is a $-A^2-R^4$ group, $X^0$ is a $-A^3-R^6$ group, $A^2$ and $A^3$ are sulfur atoms, $R^4$ and $R^6$ are independently a -Q group or a $-T^1$-Q group, and Q is a carbocyclic group having 3 to 14 ring-constituting atoms which is optionally substituted with a group selected from the group A";

an imidate compound represented by the formula (I-2), wherein X is a $-A^2-R^4$ group, $X^0$ is a $-A^3-R^6$ group, $A^2$ and $A^3$ are sulfur atoms, $R^4$ and $R^6$ are independently a -Q group or a $-T^1$-Q group, and Q is a phenyl group which is optionally substituted with a group selected from the group A, or a naphthyl group which is optionally substituted with a group selected from the group A;

an imidate compound represented by the formula (I-2), wherein X is a $-A^2-R^4$ group, $X^0$ is a $-A^3-R^6$ group, $A^2$ and $A^3$ are sulfur atoms, $R^4$ and $R^6$ are independently a -Q group or a $-T^1$-Q group, and Q is a phenyl group which is optionally substituted with a group selected from the group A", or a naphthyl group which is optionally substituted with a group selected from the group A";

an imidate compound represented by the formula (I-2), wherein X is a $-A^2-R^4$ group, $X^0$ is a $-A^3-R^6$ group, $A^2$ and $A^3$ are sulfur atoms, $R^4$ and $R^6$ are independently a -Q group or a $-T^1$-Q group, and Q is a monocyclic saturated carbocyclic group having 3 to 8 ring-constituting atoms which is optionally substituted with a group selected from the group A";

an imidate compound represented by the formula (I-2), wherein X is a -A²-R⁴ group, X⁰ is a -A³-R⁶ group, A² and A³ are sulfur atoms, R⁴ and R⁶ are independently a -Q group or a -T¹-Q group, and Q is a monocyclic unsaturated heterocyclic group having 3 to 8 ring-constituting atoms which is optionally substituted with a group selected from the group A";

an imidate compound represented by the formula (I-2), wherein X and X⁰ are taken together to form a -A²-T⁰-A³- group;

an imidate compound represented by the formula (I-2), wherein X and X⁰ are taken together to form a -A²-T⁰-A³- group, and A² and A³ are sulfur atoms;

an imidate compound represented by the formula (I-2), wherein X and X⁰ are taken together to form a -A²-T⁰-A³- group, A² and A³ are sulfur atoms, and T⁰ is a C2-C6 alkanediyl group or an o-phenylene group;

an imidate compound represented by the formula (I-2),
wherein X and X⁰ are independently a phenylthio group, a 4-methylphenylthio group, a 4-ethylphenylthio group, a 4-isopropylphenylthio group, a 4-methoxyphenylthio group, a 4-(2-pyridyl)phenylthio group, a 4-phenylphenylthio group, a 4-chlorophenylthio group, a 4-fluorophenylthio group, a 4-nitrophenylthio group, a 3-methylphenylthio group, a 3-ethylphenylthio group, a 3-isopropylphenylthio group, a 3-phenylphenylthio group, a 3-chlorophenylthio group, a 3-fluorophenylthio group, a 3-(trifluoromethyl)phenylthio group, a 3,4-dimethylphenylthio group, a 1-naphthylthio group, a 2-naphthylthio group, a 5-indanylthio group, a cyclopropylthio group, a cyclopentylthio group, a cyclohexylthio group, a 2-perhydronaphthylthio group, a benzylthio group, a phenethylthio group, an α-methylbenzylthio group, a cyclopropylmethylthio group, a cyclopentylmethylthio group or a cyclohexylmethylthio group;

an imidate compound represented by the formula (I-2), wherein G is a -A¹-R¹ group, X is a -A²-R⁴ group, and X⁰ is a -A³-R⁶ group;

an imidate compound represented by the formula (I-2), wherein G is a -A¹-R¹ group, X is a -A²-R⁴ group, X⁰ is a -A³-R⁶ group, and R¹, R⁴ and R⁶ are independently a C1-C20 chain hydrocarbon group which is optionally substituted with a group selected from the group D, a -Q group or a -T¹-Q group;

an imidate compound represented by the formula (I-2), wherein G is a -A¹-R¹ group, X is a -A²-R⁴ group, X⁰ is a -A³-R⁶ group, R¹, R⁴ and R⁶ are independently a C1-C20 chain hydrocarbon group which is optionally substituted with a group selected from the group D, a -Q group or a -T¹-Q group, and Q is a carbocyclic group having 3 to 14 ring-constituting atoms which is optionally substituted with a group selected from the group A;

an imidate compound represented by the formula (I-2), wherein G is a -A¹-R¹ group, X is a -A²-R⁴ group, X⁰ is a -A³-R⁶ group, R¹, R⁴ and R⁶ are independently a C1-C20 chain hydrocarbon group which is optionally substituted with a group selected from the group D, a -Q group or a -T¹-Q group, and Q is a carbocyclic group having 3 to 14 ring-constituting atoms which is optionally substituted with a group selected from the group A";

an imidate compound represented by the formula (I-2), wherein G is a -A¹-R¹ group, X is a -A²-R⁴ group, X⁰ is a -A³-R⁶ group, and A¹, A² and A³ are sulfur atoms;

an imidate compound represented by the formula (I-2), wherein G is a -A¹-R¹ group, X is a -A²-R⁴ group, X⁰ is a -A³-R⁶ group, A¹, A² and A³ are sulfur atoms, and R¹, R⁴ and R⁶ are independently a C1-C20 chain hydrocarbon group which is optionally substituted with a group selected from the group D, a -Q group or a -T¹-Q group;

an imidate compound represented by the formula (I-2), wherein G is a -A¹-R¹ group, X is a -A²-R⁴ group, X⁰ is a -A³-R⁶ group, A¹, A² and A³ are sulfur atoms, R¹, R⁴ and R⁶ are independently a C1-C20 chain hydrocarbon group which is optionally substituted with a group selected from the group D, a -Q group or a -T¹-Q group, and Q is a carbocyclic group having 3 to 14 ring-constituting atoms which is optionally substituted with a group selected from the group A;

an imidate compound represented by the formula (I-2), wherein G is a -A¹-R¹ group, X is a -A²-R⁴ group, X⁰ is a -A³-R⁶ group, A¹, A² and A³ are sulfur atoms, R¹, R⁴ and R⁶ are independently a C1-C20 chain hydrocarbon group which is optionally substituted with a group selected from the group D, a -Q group or a -T¹-Q group, and Q is a carbocyclic group having 3 to 14 ring-constituting atoms which is optionally substituted with a group selected from the group A";

an imidate compound represented by the formula (I-2), wherein G is a -A¹-R¹ group or a —N(R³)—R¹ group, X is a -A²-R⁴ group, X⁰ is a -A³-R⁶ group, or X and X⁰ are taken together to form a -A²-T⁰-A³- group;

an imidate compound represented by the formula (I-2), wherein G is a -A¹-R¹ group or a —N(R³)—R¹ group, X is a -A²-R⁴ group, X⁰ is a -A³-R⁶ group, or X and X⁰ are taken together to form a -A²-T⁰-A³- group, and R⁴ and R⁶ are independently a C1-C6 chain hydrocarbon group which is optionally substituted with a group selected from the group D, a -Q group, a -T¹-Q group or a —C(=A⁴)-R¹¹ group;

an imidate compound represented by the formula (I-2), wherein G is a -A¹-R¹ group or a —N(R³)—R¹ group, X is a -A²-R⁴ group, X⁰ is a -A³-R⁶ group, and R⁴ and R⁶ are independently a C1-C6 chain hydrocarbon group which is optionally substituted with a group selected from the group D, a -Q group, a -T¹-Q group or a —C(=A⁴)-R¹¹ group;

an imidate compound represented by the formula (I-2), wherein G is a -A¹-R¹ group or a —N(R³)—R¹ group, X is a -A²-R⁴ group, X⁰ is a -A³-R⁶ group, and R⁴ and R⁶ are independently a C1-C6 chain hydrocarbon group which is optionally substituted with a group selected from the group D, a -Q group or a -T¹-Q group;

an imidate compound represented by the formula (I-2), wherein Z is a carbocyclic group having 3 to 14 ring-constituting atoms which is optionally substituted with a group selected from the group A' or a heterocyclic group having 3 to 14 ring-constituting atoms which is optionally substituted with a group selected from the group A', G is a -A¹-R¹ group or a —N(R³)—R¹ group, and X is a -A²-R⁴ group and X⁰ is a -A³-R⁶ group, or X and X⁰ are taken together to form a -A²-T⁰-A³- group;

an imidate compound represented by the formula (I-2), wherein Z is a carbocyclic group having 3 to 14 ring-constituting atoms which is optionally substituted with a group selected from the group A' or a heterocyclic group having 3 to 14 ring-constituting atoms which is optionally substituted with a group selected from the group A', G is a -A¹-R¹ group or a —N(R³)—R¹ group, X is a -A²-R⁴ group and X⁰ is a -A³-R⁶ group, or X and X⁰ are taken together to form a -A²-T⁰-A³- group, and R⁴ and R⁶ are independently a C1-C6 chain hydrocarbon group which is optionally substituted with a group selected from the group D, a -Q group, a -T¹-Q group or a —C(=A⁴)-R¹¹ group;

an imidate compound represented by the formula (I-2), wherein Z is a carbocyclic group having 3 to 14 ring-constituting atoms which is optionally substituted with a group selected from the group A' or a heterocyclic group having 3 to 14 ring-constituting atoms which is optionally substituted with a group selected from the group A', G is a -A¹-R¹ group or a —N(R³)—R¹ group, X is a -A²-R⁴ group, X⁰ is a -A³-R⁶ group, and $R^4$ and $R^6$ are independently a C1-C6 chain hydrocarbon group which is optionally substituted with a group selected from the group D, a -Q group, a -$T^1$-Q group or a —C(=$A^4$)-$R^{11}$ group; and an imidate compound represented by the formula (I-2), wherein Z is a carbocyclic group having 3 to 14 ring-constituting atoms which is optionally substituted with a group selected from the group A' or a heterocyclic group having 3 to 14 ring-constituting atoms which is optionally substituted with a group selected from the group A', G is a -$A^1$-$R^1$ group or a —N($R^3$)—$R^1$ group, X is a -$A^2$-$R^4$ group, $X^0$ is a -$A^3$-$R^6$ group, and $R^4$ and $R^6$ are independently represents a C1-C6 chain hydrocarbon group which is optionally substituted with a group selected from the group D, a -Q group or a -$T^1$-Q group.

Then, processes for producing the compound of the present compound are explained. The compound of the present invention can be produced by, for example, the production processes as described below.

Production Process 1

Of the compounds of the present invention, a compound represented by the formula (Ia):

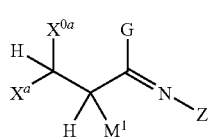

(Ia)

wherein $X^a$ represents a -$A^2$-$R^4$ group, $X^{0a}$ represents a -$A^3$-$R^6$ group, and G, Z, $A^2$, $R^4$, $A^3$ and $R^6$ are as defined above (hereinafter referred to as the compound (Ia)) can be produced by reacting a compound represented by the formula (II):

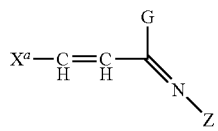

(II)

wherein $X^a$, G and Z are as defined above (hereinafter referred to as the compound (II)) with a compound represented by the formula (III):

(III)

wherein $X^{0a}$ is as defined above (hereinafter referred to as the compound (III)).

Although the compound (II) may be reacted with an excessive amount of the compound (III), 1 equivalent of the compound (II) is reacted with preferably 0.8 to 5 equivalents, more preferably 0.8 to 1.2 equivalents of the compound (III).

The reaction may be carried out in the presence of a base or an acid, as necessary.

Examples of the base include alkali metal alcoholates such as sodium ethylate, sodium methylate and potassium tert-butoxide; nitrogen-containing organic compounds such as triethylamine, diisopropylethylamine, pyridine, 4-dimethylaminopyridine and N,N-dimethylaniline; carbonates such as potassium carbonate, sodium carbonate, sodium hydrogen carbonate and potassium hydrogen carbonate; hydroxides such as sodium hydroxide and potassium hydroxide; metal hydrides such as lithium hydride, sodium hydride and potassium hydride; and organic lithium such as butyl lithium and lithium diisopropylamide.

The amount of the base to be used is not particularly limited as long as the base exerts no adverse effect on the reaction. Preferably 0.01 to 1 equivalent, more preferably from 0.01 to 0.2 equivalent of the base is used in the reaction of 1 equivalent of the compound (II).

Examples of the acid include mineral acids such as hydrochloric acid, sulfuric acid and nitric acid; organic acids such as formic acid, acetic acid, propionic acid, trifluoroacetic acid, methanesulfonic acid, benzenesulfonic acid and p-toluenesulfonic acid; acid addition salts of amines such as triethylamine hydrochloride and pyridine hydrochloride; and Lewis acids such as aluminum chloride, zinc chloride, zinc iodide, titanium tetrachloride, cerium chloride, ytterbium triflate and a boron trifluoride-ether complex.

The amount of the acid to be used is not particularly limited as long as the acid exerts no adverse effect on the reaction. Preferably 0.01 to 1 equivalent, more preferably from 0.01 to 0.2 equivalent of the acid is used in the reaction of 1 equivalent of the compound (II).

The reaction can be carried out in a suitable solvent.

Examples of the solvent include aliphatic hydrocarbons such as pentane, hexane, heptane and petroleum ether; aromatic hydrocarbons such as benzene, toluene and xylene; alcohols such as methanol and ethanol; esters such as methyl acetate, ethyl acetate, ethyl formate and ethyl propionate; ketones such as acetone and methyl ethyl ketone; ethers such as diethyl ether, dipropyl ether, diisopropyl ether, dibutyl ether, tetrahydrofuran and dioxane; nitriles such as acetonitrile and propionitrile; acid amides such as dimethylformamide and dimethylacetamide; sulfoxide such as dimethylsulfoxide; sulfones such as sulfolane; phosphoramides such as hexamethylphosphoramide; halogenated hydrocarbons such as dichloromethane, chloroform, 1,2-dichloroethane and carbon tetrachloride; and aromatic amines such as pyridine, picoline, lutidine and quinoline. These solvents may be used in combination, or may be used as a mixture with water.

The temperature of the reaction is usually from −50 to 150° C., preferably from −20 to 120° C., and more preferably from −10 to 80° C. The reaction time is usually from 0.1 to 96 hours, and preferably from 0.1 to 24 hours.

After the completion of the reaction, the compound (Ia) can be isolated by conventional posttreatment, for example, concentration of a reaction mixture, or pouring of a reaction mixture into water and then extraction with an organic solvent, followed by concentration. The isolated compound (Ia) can be purified by a conventional method such as distillation, reprecipitation, recrystallization or chromatography.

Production Process 2

Of the compounds of the present invention, a compound represented by the formula (Ib):

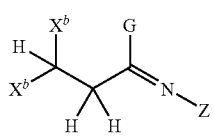

(Ib)

wherein $X^b$ represents a -$A^2$-$R^4$ group, or two $X^b$s are optionally taken together to form a -$A^2$-$T^0$-$A^3$- group, and G, Z, $A^2$, $A^3$, $R^4$ and $T^0$ are as defined above (hereinafter referred to as the compound (Ib)) can be produced by reacting a compound represented by the formula (IV):

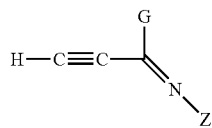

wherein G and Z are as defined above (hereinafter referred to as the compound (IV)) with a compound represented by the formula (IIIb):

wherein $X^b$ is as defined above (hereinafter referred to as the compound (IIIb)).

Although the compound (IV) may be reacted with an excessive amount of the compound (IIIb), 1 equivalent of the compound (IV) is reacted with preferably 1 to 5 equivalents, more preferably 1 to 3 equivalents of the compound (IIIb).

The reaction may be carried out in the presence of a base or an acid, as necessary.

Examples of the base include alkali metal alcoholates such as sodium ethylate, sodium methylate and potassium tert-butoxide; nitrogen-containing organic compounds such as triethylamine, diisopropylethylamine, pyridine, 4-dimethylaminopyridine and N,N-dimethylaniline; carbonates such as potassium carbonate, sodium carbonate, sodium hydrogen carbonate and potassium hydrogen carbonate; hydroxides such as sodium hydroxide and potassium hydroxide; metal hydrides such as lithium hydride, sodium hydride and potassium hydride; and organic lithium such as butyl lithium and lithium diisopropylamide.

The amount of the base to be used is not particularly limited as long as the base exerts no adverse effect on the reaction. Preferably 0.01 to 1 equivalent, more preferably from 0.01 to 0.2 equivalent of the base is used in the reaction of 1 equivalent of the compound (IV).

Examples of the acid include mineral acids such as hydrochloric acid, sulfuric acid and nitric acid; organic acids such as formic acid, acetic acid, propionic acid, trifluoroacetic acid, methanesulfonic acid, benzenesulfonic acid and p-toluenesulfonic acid; acid addition salts of amines such as triethylamine hydrochloride and pyridine hydrochloride; and Lewis acids such as aluminum chloride, zinc chloride, zinc iodide, titanium tetrachloride, cerium chloride, ytterbium triflate and a boron trifluoride-ether complex.

The amount of the acid to be used is not particularly limited as long as the acid exerts no adverse effect on the reaction. Preferably 0.01 to 1 equivalent, more preferably from 0.01 to 0.2 equivalent of the acid is used in the reaction of 1 equivalent of the compound (IV).

The reaction can be carried out in a suitable solvent.

Examples of the solvent include aliphatic hydrocarbons such as pentane, hexane, heptane and petroleum ether; aromatic hydrocarbons such as benzene, toluene and xylene; esters such as methyl acetate, ethyl acetate, ethyl formate and ethyl propionate; ketones such as acetone and methyl ethyl ketone; ethers such as diethyl ether, dipropyl ether, diisopropyl ether, dibutyl ether, tetrahydrofuran and dioxane; nitriles such as acetonitrile and propionitrile; acid amides such as dimethylformamide and dimethylacetamide; sulfoxide such as dimethylsulfoxide; sulfones such as sulfolane; phosphoramides such as hexamethylphosphoramide; halogenated hydrocarbons such as dichloromethane, chloroform, 1,2-dichloroethane and carbon tetrachloride; and aromatic amines such as pyridine, picoline, lutidine and quinoline. These solvents may be used in combination, or may be used as a mixture with water.

The temperature of the reaction is usually from −50 to 150° C., preferably from −20 to 120° C., and more preferably from −10 to 80° C. The reaction time is usually from 0.1 to 96 hours, and preferably from 0.1 to 24 hours.

After the completion of the reaction, the compound (Ib) can be isolated by conventional posttreatment, for example, concentration of a reaction mixture, or pouring of a reaction mixture into water and then extraction with an organic solvent, followed by concentration. The isolated compound (Ib) can be purified by a conventional method such as distillation, reprecipitation, recrystallization or chromatography.

Production Process 3

Of the compounds of the present invention, a compound represented by the formula (Ic):

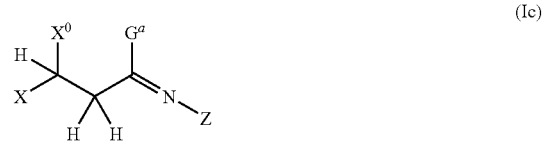

wherein $G^a$ represents a $-A^1-R^1$ group or a $—N(R^3)—R^1$ group, and X, $X^0$, Z, $A^1$, $R^1$ and $R^3$ are as defined above (hereinafter referred to as the compound (Ic)) can be produced by reacting a compound represented by the formula (V):

wherein $J^a$ represents a halogen atom, and X, $X^0$ and Z are as defined above (hereinafter referred to as the compound (V)) with a compound represented by the formula (VI):

wherein $G^a$ is as defined above (hereinafter referred to as the compound (VI)).

Although the compound (V) may be reacted with an excessive amount of the compound (VI), 1 equivalent of the compound (V) is reacted with preferably 0.8 to 5 equivalents, more preferably 0.8 to 1.2 equivalents of the compound (VI).

The reaction may be carried out in the presence of a base, as necessary.

Examples of the base include alkali metal alcoholates such as sodium ethylate, sodium methylate and potassium tert-butoxide; nitrogen-containing compounds such as triethylamine, diisopropylethylamine, pyridine, 4-dimethylaminopyridine and N,N-dimethylaniline; carbonates such as potassium carbonate, sodium carbonate, sodium hydrogen carbonate and potassium hydrogen carbonate; hydroxides such as sodium hydroxide and potassium hydroxide; metal hydrides such as lithium hydride, sodium hydride and potassium hydride; and organic lithium such as butyl lithium and lithium diisopropylamide.

The amount of the base to be used is not particularly limited as long as the base exerts no adverse effect on the reaction.

Preferably 0.8 to 5 equivalents, more preferably from 0.8 to 1.2 equivalents of the base is used in the reaction of 1 equivalent of the compound (V).

The reaction can be carried out in a suitable solvent.

Examples of the solvent include aliphatic hydrocarbons such as pentane, hexane, heptane and petroleum ether; aromatic hydrocarbons such as benzene, toluene and xylene; esters such as methyl acetate, ethyl acetate, ethyl formate and ethyl propionate; ketones such as acetone and methyl ethyl ketone; ethers such as diethyl ether, dipropyl ether, diisopropyl ether, dibutyl ether, tetrahydrofuran and dioxane; nitriles such as acetonitrile and propionitrile; acid amides such as dimethylformamide and dimethylacetamide; sulfoxide such as dimethylsulfoxide; sulfones such as sulfolane; phosphoramides such as hexamethylphosphoramide; halogenated hydrocarbons such as dichloromethane, chloroform, 1,2-dichloroethane and carbon tetrachloride; and aromatic amines such as pyridine, picoline, lutidine and quinoline. These solvents may be used in combination.

The temperature of the reaction is usually from −50 to 150° C., preferably from −20 to 120° C., and more preferably from −10 to 60° C. The reaction time is usually from 0.1 to 96 hours, and preferably from 0.1 to 24 hours.

After the completion of the reaction, the compound (Ic) can be isolated by conventional posttreatment, for example, concentration of a reaction mixture, or pouring of a reaction mixture into water and then extraction with an organic solvent, followed by concentration. The isolated compound (Ic) can be purified by a conventional method such as distillation, reprecipitation, recrystallization or chromatography.

Production Process 4

Of the compounds of the present invention, a compound represented by the formula (Id):

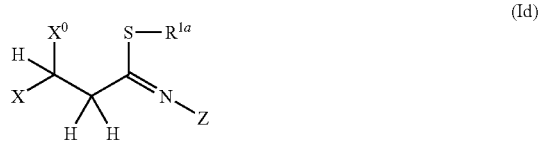

wherein $R^{1a}$ represents a C1-C20 chain hydrocarbon group which is optionally substituted with a group selected from the group D, a -$T^1$-Q group or a -$T^1$-$A^1$-Q group, and X, $X^0$, Z, $T^1$, $A^1$ and Q are as defined above (hereinafter referred to as the compound (Id)) can be produced by reacting a compound represented by the formula (VII):

wherein X, $X^0$ and Z are as defined above (hereinafter referred to as the compound (VII)) with a compound represented by the formula (VIII):

wherein $J^b$ represents a halogen atom, or a leaving group such as an O—S(═O)$_2$-$J^c$ group (wherein $J^c$ represents a C1-C3 alkyl group which is optionally substituted with halogen, such as a methyl group or a trifluoromethyl group, or a phenyl group which is optionally substituted with a C1-C3 alkyl group), and $R^{1a}$ is as defined above (hereinafter referred to as the compound (VIII)).

Although the compound (VII) may be reacted with an excessive amount of the compound (VIII), 1 equivalent of the compound (VII) is reacted with preferably 0.8 to 5 equivalents, more preferably 0.8 to 1.2 equivalents of the compound (VIII).

The reaction may be carried out in the presence of a base, as necessary.

Examples of the base include alkali metal alcoholates such as sodium ethylate, sodium methylate and potassium tert-butoxide; nitrogen-containing compounds such as triethylamine, diisopropylethylamine, pyridine, 4-dimethylaminopyridine and N,N-dimethylaniline; carbonates such as potassium carbonate, sodium carbonate, sodium hydrogen carbonate and potassium hydrogen carbonate; hydroxides such as sodium hydroxide and potassium hydroxide; metal hydrides such as lithium hydride, sodium hydride and potassium hydride; and organic lithium such as butyl lithium and lithium diisopropylamide.

The amount of the base to be used is not particularly limited as long as the base exerts no adverse effect on the reaction. Preferably 0.8 to 5 equivalents, more preferably from 0.8 to 1.2 equivalents of the base is used in the reaction of 1 equivalent of the compound (VII).

The reaction can be carried out in a suitable solvent.

Examples of the solvent include aliphatic hydrocarbons such as pentane, hexane, heptane and petroleum ether; aromatic hydrocarbons such as benzene, toluene and xylene; esters such as methyl acetate, ethyl acetate, ethyl formate and ethyl propionate; ketones such as acetone and methyl ethyl ketone; ethers such as diethyl ether, dipropyl ether, diisopropyl ether, dibutyl ether, tetrahydrofuran and dioxane; nitriles such as acetonitrile and propionitrile; acid amides such as dimethylformamide and dimethylacetamide; sulfoxide such as dimethylsulfoxide; sulfones such as sulfolane; phosphoramides such as hexamethylphosphoramide; halogenated hydrocarbons such as dichloromethane, chloroform, 1,2-dichloroethane and carbon tetrachloride; and aromatic amines such as pyridine, picoline, lutidine and quinoline. These solvents may be used in combination, or may be used as a mixture with water.

The temperature of the reaction is usually from −50 to 150° C., preferably from −20 to 120° C., and more preferably from −10 to 60° C. The reaction time is usually from 0.1 to 96 hours, and preferably from 0.1 to 24 hours.

After the completion of the reaction, the compound (Id) can be isolated by conventional posttreatment, for example, concentration of a reaction mixture, or pouring of a reaction mixture into water and then extraction with an organic solvent, followed by concentration. The isolated compound (Id) can be purified by a conventional method such as distillation, reprecipitation, recrystallization or chromatography.

Production Process 5

Of the compounds of the present invention, a compound represented by the formula (Ie):

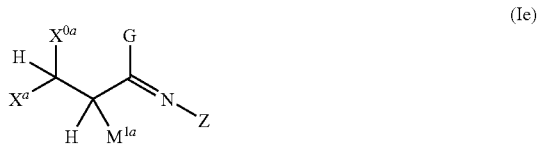

wherein $M^{1a}$ represents a $-R^8$ group, a $-A^8-R^8$ group, or a halogen atom, and $X^a$, $X^{0a}$, G, Z, $A^8$ and $R^8$ are as defined above (hereinafter referred to as the compound (Ie)) can be produced by reacting a compound represented by the formula (II'):

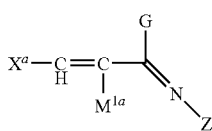

wherein $M^{1a}$, $X^a$, G and Z are as defined above (hereinafter referred to as the compound (II')) with the compound (III)).

Although the compound (II') may be reacted with an excessive amount of the compound (III), 1 equivalent of the compound (II') is reacted with preferably 0.8 to 5 equivalents, more preferably 0.8 to 1.2 equivalents of the compound (III).

The reaction may be carried out in the presence of a base or an acid, as necessary.

Examples of the base include alkali metal alcoholates such as sodium ethylate, sodium methylate and potassium tert-butoxide; nitrogen-containing organic compounds such as triethylamine, diisopropylethylamine, pyridine, 4-dimethylaminopyridine and N,N-dimethylaniline; carbonates such as potassium carbonate, sodium carbonate, sodium hydrogen carbonate and potassium hydrogen carbonate; hydroxides such as sodium hydroxide and potassium hydroxide; metal hydrides such as lithium hydride, sodium hydride and potassium hydride; and organic lithium such as butyl lithium and lithium diisopropylamide.

The amount of the base to be used is not particularly limited as long as the base exerts no adverse effect on the reaction. Preferably 0.01 to 1 equivalent, more preferably from 0.01 to 0.2 equivalent of the base is used in the reaction of 1 equivalent of the compound (II').

Examples of the acid include mineral acids such as hydrochloric acid, sulfuric acid and nitric acid; organic acids such as formic acid, acetic acid, propionic acid, trifluoroacetic acid, methanesulfonic acid, benzenesulfonic acid and p-toluenesulfonic acid; acid addition salts of amines such as triethylamine hydrochloride and pyridine hydrochloride; and Lewis acids such as aluminum chloride, zinc chloride, zinc iodide, titanium tetrachloride, cerium chloride, ytterbium triflate and a boron trifluoride-ether complex.

The amount of the acid to be used is not particularly limited as long as the acid exerts no adverse effect on the reaction. Preferably 0.01 to 1 equivalent, more preferably from 0.01 to 0.2 equivalent of the acid is used in the reaction of 1 equivalent of the compound (II').

The reaction can be carried out in a suitable solvent.

Examples of the solvent include aliphatic hydrocarbons such as pentane, hexane, heptane and petroleum ether; aromatic hydrocarbons such as benzene, toluene and xylene; alcohols such as methanol and ethanol; esters such as methyl acetate, ethyl acetate, ethyl formate and ethyl propionate; ketones such as acetone and methyl ethyl ketone; ethers such as diethyl ether, dipropyl ether, diisopropyl ether, dibutyl ether, tetrahydrofuran and dioxane; nitriles such as acetonitrile and propionitrile; acid amides such as dimethylformamide and dimethylacetamide; sulfoxide such as dimethylsulfoxide; sulfones such as sulfolane; phosphoramides such as hexamethylphosphoramide; halogenated hydrocarbons such as dichloromethane, chloroform, 1,2-dichloroethane and carbon tetrachloride; and aromatic amines such as pyridine, picoline, lutidine and quinoline. These solvents may be used in combination, or may be used as a mixture with water.

The temperature of the reaction is usually from −50 to 150° C., preferably from −20 to 120° C., and more preferably from −10 to 80° C. The reaction time is usually from 0.1 to 96 hours, and preferably from 0.1 to 24 hours.

After the completion of the reaction, the compound (Ie) can be isolated by conventional posttreatment, for example, concentration of a reaction mixture, or pouring of a reaction mixture into water and then extraction with an organic solvent, followed by concentration. The isolated compound (Ie) can be purified by a conventional method such as distillation, reprecipitation, recrystallization or chromatography.

Production Process 6

Of the compounds of the present invention, a compound represented by the formula (If):

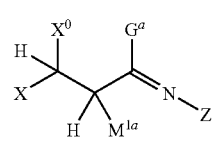

wherein $M^{1a}$, $G^a$, X, $X^0$ and Z are as defined above (hereinafter referred to as the compound (If)) can be produced by reacting a compound represented by the formula (V'):

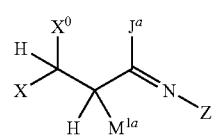

wherein $M^{1a}$, $J^a$, X, $X^0$ and Z are as defined above (hereinafter referred to as the compound (V')) with the compound (VI).

Although the compound (V') may be reacted with an excessive amount of the compound (VI), 1 equivalent of the compound (V') is reacted with preferably 0.8 to 5 equivalents, more preferably 0.8 to 1.2 equivalents of the compound (VI).

The reaction may be carried out in the presence of a base, as necessary.

Examples of the base include alkali metal alcoholates such as sodium ethylate, sodium methylate and potassium tert-butoxide; nitrogen-containing compounds such as triethylamine, diisopropylethylamine, pyridine, 4-dimethylaminopyridine and N,N-dimethylaniline; carbonates such as potassium carbonate, sodium carbonate, sodium hydrogen carbonate and potassium hydrogen carbonate; hydroxides such as sodium hydroxide and potassium hydroxide; metal hydrides such as lithium hydride, sodium hydride and potassium hydride; and organic lithium such as butyl lithium and lithium diisopropylamide.

The amount of the base to be used is not particularly limited as long as the base exerts no adverse effect on the reaction. Preferably 0.8 to 5 equivalents, more preferably from 0.8 to 1.2 equivalents of the base is used in the reaction of 1 equivalent of the compound (V').

The reaction can be carried out in a suitable solvent.

Examples of the solvent include aliphatic hydrocarbons such as pentane, hexane, heptane and petroleum ether; aromatic hydrocarbons such as benzene, toluene and xylene; esters such as methyl acetate, ethyl acetate, ethyl formate and ethyl propionate; ketones such as acetone and methyl ethyl ketone; ethers such as diethyl ether, dipropyl ether, diisopropyl ether, dibutyl ether, tetrahydrofuran and dioxane; nitriles such as acetonitrile and propionitrile; acid amides such as dimethylformamide and dimethylacetamide; sulfoxide such as dimethylsulfoxide; sulfones such as sulfolane; phosphoramides such as hexamethylphosphoramide; halogenated hydrocarbons such as dichloromethane, chloroform, 1,2-dichloroethane and carbon tetrachloride; and aromatic amines such as pyridine, picoline, lutidine and quinoline. These solvents may be used in combination.

The temperature of the reaction is usually from −50 to 150° C., preferably from −20 to 120° C., and more preferably from −10 to 60° C. The reaction time is usually from 0.1 to 96 hours, and preferably from 0.1 to 24 hours.

After the completion of the reaction, the compound (If) can be isolated by conventional posttreatment, for example, concentration of a reaction mixture, or pouring of a reaction mixture into water and then extraction with an organic solvent, followed by concentration. The isolated compound (If) can be purified by a conventional method such as distillation, reprecipitation, recrystallization or chromatography.

Production Process 7

Of the compounds of the present invention, a compound represented by the formula (Ig):

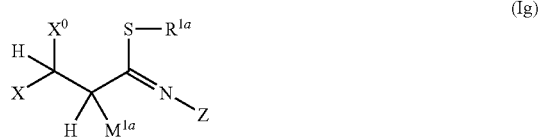

wherein $M^{1a}$, $R^{1a}$, X, $X^0$ and Z are as defined above (hereinafter referred to as the compound (Ig)) can be produced by reacting a compound represented by the formula (VII'):

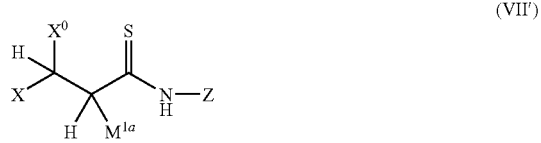

wherein $M^{1a}$, X, $X^0$ and Z are as defined above (hereinafter referred to as the compound (VII')) with the compound (VIII).

Although the compound (VII') may be reacted with an excessive amount of the compound (VIII), 1 equivalent of the compound (VII') is reacted with preferably 0.8 to 5 equivalents, more preferably 0.8 to 1.2 equivalents of the compound (VIII).

The reaction may be carried out in the presence of a base, as necessary.

Examples of the base include alkali metal alcoholates such as sodium ethylate, sodium methylate and potassium tert-butoxide; nitrogen-containing compounds such as triethylamine, diisopropylethylamine, pyridine, 4-dimethylaminopyridine and N,N-dimethylaniline; carbonates such as potassium carbonate, sodium carbonate, sodium hydrogen carbonate and potassium hydrogen carbonate; hydroxides such as sodium hydroxide and potassium hydroxide; metal hydrides such as lithium hydride, sodium hydride and potassium hydride; and organic lithium such as butyl lithium and lithium diisopropylamide.

The amount of the base to be used is not particularly limited as long as the base exerts no adverse effect on the reaction. Preferably 0.8 to 5 equivalents, more preferably from 0.8 to 1.2 equivalents of the base is used in the reaction of 1 equivalent of the compound (VII').

The reaction can be carried out in a suitable solvent.

Examples of the solvent include aliphatic hydrocarbons such as pentane, hexane, heptane and petroleum ether; aromatic hydrocarbons such as benzene, toluene and xylene; esters such as methyl acetate, ethyl acetate, ethyl formate and ethyl propionate; ketones such as acetone and methyl ethyl ketone; ethers such as diethyl ether, dipropyl ether, diisopropyl ether, dibutyl ether, tetrahydrofuran and dioxane; nitriles such as acetonitrile and propionitrile; acid amides such as dimethylformamide and dimethylacetamide; sulfoxide such as dimethylsulfoxide; sulfones such as sulfolane; phosphoramides such as hexamethylphosphoramide; halogenated hydrocarbons such as dichloromethane, chloroform, 1,2-dichloroethane and carbon tetrachloride; and aromatic amines such as pyridine, picoline, lutidine and quinoline. These solvents may be used in combination, or may be used as a mixture with water.

The temperature of the reaction is usually from −50 to 150° C., preferably from −20 to 120° C., and more preferably from −10 to 60° C. The reaction time is usually from 0.1 to 96 hours, and preferably from 0.1 to 24 hours.

After the completion of the reaction, the compound (Ig) can be isolated by conventional posttreatment, for example, concentration of a reaction mixture, or pouring of a reaction mixture into water and then extraction with an organic solvent, followed by concentration. The isolated compound (Ig) can be purified by a conventional method such as distillation, reprecipitation, recrystallization or chromatography.

Next, processes for producing the starting compounds used in production of the compounds of the present invention are shown.

The compound (II) is a known compound, or can be produced by a known method (e.g. a method described in WO2007/063702).

The compound (III) is a known compound, or can be produced by a known method.

The compound (IV) is a known compound, or can be produced from a compound represented by the formula ($IV^a$):

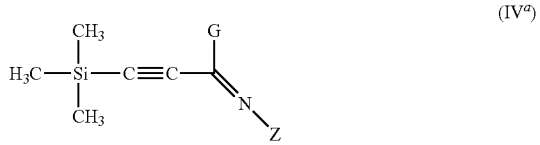

wherein G and Z are as defined above, by a known method (e.g. a method described in Synthesis (1), P100, 1999, Chem. Lett. P1261, 1989, or WO2007/063702).

The compound (V) can be produced by reacting a compound represented by the formula (IX):

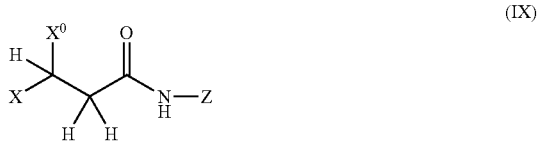

wherein X, $X^0$ and Z are as defined above (hereinafter referred to as the compound (IX)) with a halogenating agent.

Examples of the halogenating agent used in the reaction include thionyl chloride, sulfuryl chloride, phosphorous oxychloride, phosphorous pentachloride, phosphorous tribromide, carbon teterachloride and carbon tetrabromide.

The amount of the halogenating agent to be used is not particularly limited, and an excessive amount of the halogenating agent may be used as a solvent. Preferably, 1 equivalent of the compound (IX) is reacted with 0.8 to 3 equivalents of the halogenating agent.

The reaction may be carried out in the presence of a base, as necessary.

Examples of the base include alkali metal alcoholates such as sodium ethylate, sodium methylate and potassium tert-butoxide; nitrogen-containing compounds such as triethylamine, diisopropylethylamine, pyridine, 4-dimethylaminopyridine and N,N-dimethylaniline; carbonates such as potassium carbonate, sodium carbonate, sodium hydrogen carbonate and potassium hydrogen carbonate; hydroxides such as sodium hydroxide and potassium hydroxide; metal hydrides such as lithium hydride, sodium hydride and potassium hydride; organic lithium such as butyl lithium and lithium diisopropylamide; and phosphorus compounds such as triphenylphosphine.

The amount of the base to be used is not particularly limited as long as the base exerts no adverse effect on the reaction. Preferably 0.8 to 3 equivalents, more preferably from 0.8 to 1.2 equivalents of the base is used in the reaction of 1 equivalent of the compound (IX).

The reaction can be carried out in a suitable solvent.

Examples of the solvent include aliphatic hydrocarbons such as pentane, hexane, heptane and petroleum ether; aromatic hydrocarbons such as benzene, toluene and xylene; esters such as methyl acetate, ethyl acetate, ethyl formate and ethyl propionate; ketones such as acetone and methyl ethyl ketone; ethers such as diethyl ether, dipropyl ether, diisopropyl ether, dibutyl ether, tetrahydrofuran and dioxane; nitriles such as acetonitrile and propionitrile; acid amides such as dimethylformamide and dimethylacetamide; sulfoxide such as dimethylsulfoxide; sulfones such as sulfolane; phosphoramides such as hexamethylphosphoramide; and halogenated hydrocarbons such as dichloromethane, chloroform, 1,2-dichloroethane and carbon tetrachloride. These solvents may be used in combination.

The temperature of the reaction is usually from −50 to 150° C., preferably from −20 to 120° C., and more preferably from −10 to 80° C. The reaction time is usually from 0.1 to 96 hours, and preferably from 0.1 to 24 hours.

After the completion of the reaction, although the compound (V) can be purified from a reaction mixture by a conventional method such as distillation, reprecipitation, recrystallization or chromatography, the reaction mixture may be used as it is in the next step.

The compound (VI) is a known compound, or can be produced by a known method.

The compound (VII) can be produced by reacting the compound (IX) with a sulfurizing agent.

Examples of the sulfurizing agent used in the reaction include diphosphorus pentasulfide, Lawesson's reagent and $(Et_2Al)_2$.

The amount of the sulfurizing agent to be used is not particularly limited, and an excessive amount of the sulfurizing agent may be used. Preferably, 1 equivalent of the compound (IX) is reacted with about 0.8 to 3 equivalents of the sulfurizing agent.

The reaction can be carried out in a suitable solvent.

Examples of the solvent include aliphatic hydrocarbons such as pentane, hexane, heptane and petroleum ether; aromatic hydrocarbons such as benzene, toluene and xylene; esters such as methyl acetate, ethyl acetate, ethyl formate and ethyl propionate; ethers such as diethyl ether, dipropyl ether, diisopropyl ether, dibutyl ether, tetrahydrofuran and dioxane; nitriles such as acetonitrile and propionitrile; sulfoxide such as dimethylsulfoxide; sulfones such as sulfolane; and halogenated hydrocarbons such as dichloromethane, chloroform, 1,2-dichloroethane and carbon tetrachloride. These solvents may be used in combination.

The temperature of the reaction is usually from −50 to 150° C., preferably from −20 to 120° C., and more preferably from 10 to 100° C. The reaction time is usually from 0.1 to 96 hours, and preferably from 0.1 to 24 hours.

After the completion of the reaction, although the compound (VII) can be purified from a reaction mixture by a conventional method such as distillation, reprecipitation, recrystallization or chromatography, the reaction mixture may be used as it is in the next step.

The compound (VIII) is a known compound, or can be produced by a known method.

Of the compounds (IX), a compound represented by the formula (IX$^a$):

(IX$^a$)

wherein $X^a$, $X^{0a}$ and Z are as defined above (hereinafter referred to as the compound (IX$^a$)) can be produced by reacting a compound represented by the formula (X):

(X)

wherein $X^a$ and Z are as defined above (hereinafter referred to as the compound (X)) with the compound (III).

Although the compound (X) may be reacted with an excessive amount of the compound (III), 1 equivalent of the compound (X) is reacted with preferably 0.8 to 5 equivalents, more preferably 0.8 to 1.2 equivalents of the compound (III).

The reaction may be carried out in the presence of a base or an acid, as necessary.

Examples of the base include alkali metal alcoholates such as sodium ethylate, sodium methylate and potassium tert-butoxide; nitrogen-containing compounds such as triethylamine, diisopropylethylamine, pyridine, 4-dimethylaminopyridine and N,N-dimethylaniline; carbonates such as potassium carbonate, sodium carbonate, sodium hydrogen carbonate and potassium hydrogen carbonate; hydroxides such as sodium hydroxide and potassium hydroxide; metal hydrides such as lithium hydride, sodium hydride and potassium hydride; and organic lithium such as butyl lithium and lithium diisopropylamide.

The amount of the base to be used is not particularly limited as long as the base exerts no adverse effect on the reaction. Preferably 0.01 to 1 equivalent, more preferably from 0.01 to 0.2 equivalent of the base is used in the reaction of 1 equivalent of the compound (X).

Examples of the acid include mineral acids such as hydrochloric acid, sulfuric acid and nitric acid; organic acids such as formic acid, acetic acid, propionic acid, trifluoroacetic acid, methanesulfonic acid, benzenesulfonic acid and p-toluenesulfonic acid; acid addition salts of amines such as triethylamine hydrochloride and pyridine hydrochloride; and Lewis acids such as aluminum chloride, zinc chloride, zinc iodide, titanium tetrachloride, cerium chloride, ytterbium triflate and a boron trifluoride-ether complex.

The amount of the acid to be used is not particularly limited as long as the acid exerts no adverse effect on the reaction. Preferably 0.01 to 1 equivalent, more preferably from 0.01 to 0.2 equivalent of the acid is used in the reaction of 1 equivalent of the compound (X).

The reaction can be carried out in a suitable solvent.

Examples of the solvent include aliphatic hydrocarbons such as pentane, hexane, heptane and petroleum ether; aromatic hydrocarbons such as benzene, toluene and xylene; alcohols such as methanol and ethanol; esters such as methyl acetate, ethyl acetate, ethyl formate and ethyl propionate; ketones such as acetone and methyl ethyl ketone; ethers such as diethyl ether, dipropyl ether, diisopropyl ether, dibutyl ether, tetrahydrofuran and dioxane; nitriles such as acetonitrile and propionitrile; acid amides such as dimethylformamide and dimethylacetamide; sulfoxide such as dimethylsulfoxide; sulfones such as sulfolane; phosphoramides such as hexamethylphosphoramide; halogenated hydrocarbons such as dichloromethane, chloroform, 1,2-dichloroethane and carbon tetrachloride; and aromatic amines such as pyridine, picoline, lutidine and quinoline. These solvents may be used in combination, or may be used as a mixture with water.

The temperature of the reaction is usually from −50 to 150° C., preferably from −20 to 120° C., and more preferably from −10 to 80° C. The reaction time is usually from 0.1 to 96 hours, and preferably from 0.1 to 24 hours.

After the completion of the reaction, the compound (IX) can be isolated by conventional posttreatment, for example, concentration of a reaction mixture, or pouring of a reaction mixture into water and then extraction with an organic solvent, followed by concentration. The isolated compound (IX) can be purified by a conventional method such as distillation, reprecipitation, recrystallization or chromatography.

Of the compounds (II'), a compound represented by the formula (IIe):

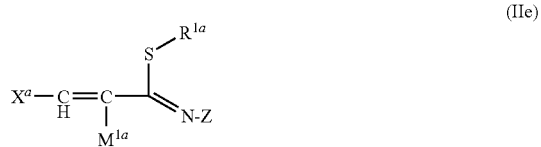

(IIe)

wherein $M^{1a}$, $R^{1a}$, $X^a$ and Z are as defined above can be produced by reacting a compound represented by the formula (XI):

(XI)

wherein $M^{1a}$, $X^a$ and Z are as defined above with the compound (VIII).

The compound of the present invention produced by the above described production processes 1 to 7 can be further subjected to a per se known procedure such as substitution reaction, elimination reaction, oxidation reaction or reduction reaction to replace a substituent on the compound with a desired substituent.

The compound of the present invention may exist as various isomers including geometric isomers and stereoisomers. All isomers of the compound of the present invention and a mixture of the isomers are included in the scope of the present invention.

The compound of the present invention has an excellent controlling effect on pests including hygiene pests, animal parasitic pests and plant parasitic pests, and thus it is effective for pest control. The compound of the present invention exerts an excellent controlling effect on pests when the compound is applied directly to the pests or to places where the pests inhabit.

When the compound of the present invention is used as a composition for pest control, that is, a pesticidal composition, the compound of the present invention may be used as it is. However, the compound of the present invention is usually formulated into forms which usual agrichemicals or animal drugs may take, and then used. In other words, the pesticidal composition of the present invention may be the compound of the present invention itself, and however, it usually comprises the compound of the present invention and additives to take a suitable form for usual agrichemicals or animal drugs. Specifically, the compound of the present invention is dissolved or dispersed in a suitable liquid carrier, mixed with a suitable solid carrier and/or a suitable gaseous carrier, or adsorbed on a suitable solid carrier to prepare the pesticidal composition of the present invention in the form of an emulsifiable concentrate, a liquid formulation, microemulsion, a flowable formulation, an oil solution, a wettable powder, a dust, a granule, a microgranule, a seed-coating agent, a seed-immersion solution, a smoking pesticide, a tablet, a microcapsule, a spray, an aerosol, a carbon dioxide gas formulation, a heating fumigant such as a mosquito coil, an electric mosquito mat or an electric mosquito liquid, EW formulation, an ointment, a poison bait, a capsule, a pellet, a film, an injectable, a liniment, a resin formulation, a shampoo formulation or the like. The pesticidal composition of the present invention may further contain an emulsifier, a suspending agent, a spreading agent, a penetrating agent, a wetting agent, a thickener, a stabilizer, a dispersant or the like. The pesticidal composition of the present invention can be prepared by a known method.

Examples of the liquid carrier include water, alcohols (e.g., methyl alcohol, ethyl alcohol, n-propyl alcohol, isopropyl alcohol, butyl alcohol, hexyl alcohol, benzyl alcohol, ethylene glycol, propylene glycol, phenoxyethanol, etc.), ketones (e.g., acetone, methyl ethyl ketone, methyl isobutyl ketone, cyclohexanone etc.), ethers (e.g., diisopropyl ether, 1,4-dioxane, tetrahydrofuran, ethylene glycol monomethyl ether, ethylene glycol dimethyl ether, diethylene glycol monomethyl ether, diethylene glycol monoethyl ether, propylene glycol monomethyl ether, dipropylene glycol monomethyl ether, 3-methoxy-3-methyl-1-butanol, etc.), aliphatic hydrocarbons (e.g., hexane, cyclohexane, kerosene, fuel oil, machine oil, etc.), aromatic hydrocarbons (e.g., toluene, xylene, ethylbenzene, dodesylbenzene, phenylxylylethane, solvent naphtha, methylnaphthalene, etc.), halogenated hydrocarbons (e.g., dichloromethane, trichloroethane, chloroform, carbon tetrachloride, etc.), acid amides (e.g., N,N-dimethylformamide, N,N-dimethylacetamide, N-methylpyrrolidone, N-octylpyrrolidone, etc.), esters (e.g., butyl lactate, ethyl acetate, butyl acetate, isopropyl myristate, ethyl oleate, diisopropyl adipate, diisobutyl adipate, propylene glycol monomethyl ether acetate, fatty acid glycerin ester, γ-butyrolactone, etc.), nitriles (e.g., acetonitrile, isobutyronitrile, propionitrile, etc.), carbonates (e.g., propylene carbonate, etc.), and vegetable oils (e.g., soybean oil, olive oil, linseed oil, coconut oil, palm oil, peanut oil, malt oil, almond oil, sesame oil, mineral oil, rosmarine oil, geranium oil, rapeseed oil, cottonseed oil, corn oil, safflower oil, orange oil, etc.). These liquid carriers may be used alone, or two or more, preferably one to three of these liquid carriers may be mixed in appropriate proportions and then used.

Examples of the solid carrier (e.g., a diluent or a filler) include vegetable powders (e.g., soybean powder, tobacco powder, flour, wood powder, etc.), mineral powders (e.g., kaolin, Fubasami, bentonite, clay such as acid clay, talc such as talcum powder or agalmatolite powder, diatomaceous earth, silica such as mica powder, etc.), synthetic hydrated silicon oxide, talc, ceramics, other inorganic minerals (e.g., sericite, quartz, hydrated silica, etc.), chemical fertilizers (e.g., ammonium sulfate, ammonium phosphate, ammonium nitrate, ammonium chloride, urea, etc.), alumina, sulfur powder, activated carbon, calcium carbonate, potassium chloride, sodium hydrogen carbonate, and lactose. These solid carriers may be used alone, or two or more, preferably one to three of these solid carriers may be mixed in appropriate proportions and then used.

Examples of the gaseous carrier include fluorocarbon, butane gas, LPG (liquefied petroleum gas), dimethyl ether, and carbon dioxide gas. These gaseous carriers may be used alone, or two or more of these gaseous carriers may be mixed in appropriate proportions and then used. Alternatively, one or more of these gaseous carriers may be used in combination with a suitable liquid carrier.

In the case where the compound of the present invention is formulated into an ointment, examples of a base material for the ointment include polyethylen glycol, pectin, esters of higher fatty acid and polyalcohol such as glyceryl monostearate ester, cellulose derivatives such as methylcellulose, sodium alginate, bentonite, higher alcohol, polyalcohol such as glycerin, petrolatum, white petrolatum, liquid paraffin, lard, vegetable oils, lanolin, anhydrous lanoiln, hydrogenated oils, and resin. These base materials may be used alone, or two or more, preferably one to three of these base materials may be used in combination. Further, a surfactant as listed below may be added to the base material.

A surfactant may be used as an emulsifier, a spreading agent, a penetrating agent, a dispersant or the like in preparing the pesticidal composition of the present invention. Examples of the surfactant include soap; and nonionic and anionic surfactants such as polyoxyethylene alkyl aryl ether [NOIGEN (trade name), E A142 (trade name) manufactured by DAI-ICHI KOGYO SEIYAKU CO., LTD.; NONAL (trade name) manufactured by TOHO CHEMICAL INDUSTRY CO., LTD.], alkyl sulfate [e.g. EMAL 10 (trade name) and EMAL 40 (trade name) manufactured by KAO CORPORATION], alkylbenzene sulfonate [e.g. NEOGEN (trade name) and NEOGEN T (trade name) manufactured by DAI-ICHI KOGYOU SEIYAKU CO., LTD.; NEIPELEX (trade name) manufactured by KAO CORPORATION], polyethylene glycol ether [e.g., NONIPOL 85 (trade name), NONIPOL 100 (trade name), and NONIPOL 160 (trade name) manufactured by SANYO KASEI], polyoxyethylene alkyl ether [e.g. NOIGEN ET-135 (trade name) manufactured by DAI-ICHI KOGYO SEIYAKU CO., LTD.], polyoxyethylene polyoxypropylene block polymer [e.g. NEWPOLE PE-64 (trade name) manufactured by SANYO CHEMICAL INDUSTRIES LTD.], polyalcohol ester [e.g. TWEEN 20 (trade name) and TWEEN 80 (trade name) manufactured by KAO CORPORATION], alkyl sulfosuccinate [e.g. SANMOLIN OT20 (trade name) manufactured by SANYO CHEMICAL INDUSTRIES LTD.; NEWKALGEN EX70 (trade name) manufactured by TAKEMOTO OIL & FAT CO., LTD.], alkyl naphthalenesulfonate [NEWKALGEN WG-1 (trade name) manufactured by TAKEMOTO OIL & FAT CO., LTD.], and alkenyl naphthalenesulfonate [SORPOL 5115 (trade name) manufactured by TOHO CHEMICAL INDUSTRY CO., LTD.]. These surfactants may be used alone, or two or more, preferably one to three of these surfactants may be mixed in appropriate proportions and then used.

Examples of a base material for the resin formulation include vinyl chloride polymers, and polyurethane. To the base material, if necessary, a plasticizer such as phthalate (e.g., dimethyl phthalate, dioctyl phthalate, etc.), adipate, stearic acid or the like may be added. The resin formulation is prepared by kneading the compound of the present invention into the base material using a conventional kneader, followed by molding such as injection molding, extrusion molding, press molding or the like. The resulting resin formulation may be formed into the shape of a plate, a film, a tape, a net, a string or the like via a further step of molding, cutting, or the like, if necessary. These resin formulations may be used, for example, the form of an animal collar, an animal ear tag, a sheet, a lead, or a horticultural post.

Examples of a base material of the poison bait include cereal powder, vegetable oil, sugar, and crystalline cellulose. To the base material, if necessary, an antioxidant such as dibutylhydroxytoluene or nordihydroguaiaretic acid, a preservative such as dehydroacetic acid, an agent for preventing children or pets from erroneously eating such as hot pepper powder, a pest-attractive perfume such as cheese perfume, onion perfume or peanut oil or the like may be added.

In addition, a binder, a dispersant, a colorant, a stabilizer and the like, specifically, casein, gelatin, saccharides (e.g., starch, gum arabic, cellulose derivatives, alginic acid, etc.), lignin derivatives, bentonite, synthetic water-soluble polymers (e.g., polyvinyl alcohol, polyvinyl pyrrolidone, polyacrylic acid, etc.), PAP (acid isopropyl phosphate), BHT (2,6-di-tert-butyl-4-methylphenol), BHA (a mixture of 2-tert-butyl-4-methoxyphenol and 3-tert-butyl-4-methoxyphenol), other substances described in Code of Federal Regulation Title 40 p. 180, USA can be used as pharmaceutical auxiliary agents for preparing the pesticidal composition of the present invention.

The pesticidal composition of the present invention can comprise the compound of the present invention in combination with another pesticidal active ingredient, such as an insecticide (e.g., pyrethroid insecticide, organic phosphorus insecticide, carbamate insecticide, neonicotinoid insecticide, nerve sodium channel blocker, insecticidal macrocyclic lactone, γ-amino butyric acid (GABA) antagonisy, calcium channel activater, urea insecticide, insect hormone mimic, natural insecticide, etc.), an acaricide, a machine oil, a nematocide, a herbicide, a phytohormone agent, a plant growth regulator, a fungicide (e.g., copper fungicide, organic chlorine fungicide, organic sulfur fungicide, phenol fungicide, etc.), a synergist, an attractant, a repellent, a crop injury-reducing agent, a pigment, a fertilizer, an animal feed (e.g., feed for livestock such as cows, pigs and chickens, feed for pet animals such as dogs and cats, feed for cultured fish such as young yellowtail and sea bream, etc.), an animal drug (e.g., a drug for treatment or prevention of disease of livestock, pet animals and cultured fish), a nutritional supplement for animals, or the like.

The pesticidal composition of the present invention contains usually 0.1 to 80% by weight, preferably 1 to 20% by weight of the compound of the present invention. Specifically, when the pesticidal composition of the present invention is in the form of an emulsifiable concentrate, a liquid formulation or a wettable powder (e.g., a wetabble granule), it contains usually 1 to 80% by weight, preferably 1 to 20% by weight of the compound of the present invention. When the pesticidal composition of the present invention is in the form of an emulsifiable concentrate or a dust, it contains usually 0.1 to 50% by weight, preferably 0.1 to 20% by weight of the compound of the present invention. When the pesticidal composition of the present invention is in the form of a granule, it contains usually 1 to 50% by weight, preferably 1 to 20% by weight of the compound of the present invention.

Another pesticidal active ingredient (e.g., insecticide, herbicide, an acaricide, fungicide, etc.) may be present in usually 0.1 to 80% by weight, preferably 1 to 20% by weight in the pesticidal composition of the present invention.

The content of additives other than the pesticidal active ingredient described above in the pesticidal composition of the present invention is usually 0.001 to 99.9% by weight, preferably 1 to 99% by weight, although it is varied depending on the kind and content of the pesticidal active ingredient, the form of the pesticidal composition and the like. Specifically, the content of a surfactant in the pesticidal composition of the present invention is usually 1 to 20% by weight, preferably 1 to 15% by weight. The content of a fluidizing aid in the pesticidal composition of the present invention is usually 1 to 20% by weight. The content of a carrier in the pesticidal composition of the present invention is usually 1 to 90% by weight, preferably 1 to 70% by weight.

When the pesticidal composition of the present invention is in the form of an emulsifiable concentrate or a wettable powder (e.g., a wetabble granule), it is preferably diluted with water or the like as appropriate (e.g., 100 to 5,000 times) and then sprayed.

The compound of the present invention can be used as an insecticide for crop lands such as cultivated lands, paddy fields, lawns and orchards, or non-crop lands. The compound of the present invention can control pests in crop lands and the like where "crop plants" listed below are cultivated without causing adverse effects on the "crop plants", in some cases.

Specific examples of the "crop plant" are listed below.

Agricultural crops: corn, rice, wheat, barley, rye, oat, sorghum, cotton, soybean, peanut, sarrazin, sugar beet, rapeseed, sunflower, sugar cane, tobacco, etc.;

Vegetables: Solanaceae vegetables (eggplant, tomato, green pepper, hot pepper, potato etc.), Cucurbitaceae vegetables (cucumber, pumpkin, zucchini, watermelon, melon etc.), Cruciferae vegetables (Japanese radish, turnip, horseradish, kohlrabi, Chinese cabbage, cabbage, brown mustard, broccoli, cauliflower etc.), Compositae vegetables (burdock, garland chrysanthemum, artichoke, lettuce etc.), Liliaceae vegetables (Welsh onion, onion, garlic, asparagus etc.), Umbelliferae vegetables (carrot, parsley, celery, parsnip etc.), Chenopodiaceae vegetables (spinach, Swiss chard etc.), Labiatae vegetables (Japanese basil, mint, basil etc.), strawberry, sweat potato, yam, aroid, etc.;

Fruit trees: pomaceous fruits (apple, common pear, Japanese pear, Chinese quince, quince etc.), stone fleshy fruits (peach, plum, nectarine, Japanese plum, cherry, apricot, prune etc.), citrus plants (Satsuma mandarin, orange, lemon, lime, grapefruit etc.), nuts (chestnut, walnut, hazel nut, almond, pistachio, cashew nut, *macadamia* nut etc.), berry fruits (blueberry, cranberry, blackberry, raspberry etc.), grape, persimmon, olive, loquat, banana, coffee, date, coconut palm, oil palm, etc.;

Trees other than fruit trees: tea, mulberry, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, elm, horse-chestnut etc.), sweet viburnum, *Podocarpus macrophyllus*, Japanese cedar, Japanese cypress, *croton*, spindle tree, Chainese howthorn, etc.

Lawn: zoysia (Japanese lawn grass, mascarene grass, etc.), Bermuda grass (Cynodon dactylon, etc.), bent grass (creeping bent grass, *Agrostis stolonifera, Agrostis tenuis*, etc.), bluegrass (Kentucky bluegrass, rough bluegrass, etc.), fescue (tall fescue, chewing fescue, creeping fescue, etc.), ryegrass (darnel, perennial ryegrass, etc.), cocksfoot, timothy grass, etc.;

Oil crops: oil palm, Barbados nut, etc.;

Others: flowers (rose, carnation, chrysanthemum, *Eustoma grandiflorum* Shinners (prairie gentian), gypsophila, gerbera, pot marigold, salvia, petunia, verbena, tulip, aster, gentian, lily, pansy, cyclamen, orchid, lily of the valley, lavender, stock, ornamental kale, primula, poinsttia, gladiolus, cattleya, daisy, verbena, cymbidium, begonia, etc.), foliage plant; etc.

The above-described crop plants include those to which resistance to an HPPD inhibitor such as isoxaflutole, an ALS inhibitor such as imazethapyr or thifensulfuron-methyl, an EPSP synthesizing enzyme inhibitor such as glyphosate, a glutamine synthesizing enzyme inhibitor such as glufosinate, an acetyl CoA carboxylase inhibitor such as sethoxydim, a PPO inhibitor such as flumioxazin, or an herbicide such as bromoxynil, dicamba or 2,4-D, has been imparted by a classical breeding method or a genetic engineering technique.

Examples of the crop plant to which the resistance has been imparted by a classical breeding method include rape, wheat, sunflower, rice and corn having resistance to imidazolinone herbicides such as imazethapyr, which are commercially available under the trade name of Clearfield (registered trademark); soybean having resistance to sulfonylurea ALS inhibitor herbicides such as thifensulfuron-methyl, which is commercially available under the trade name of STS soybean; and crop plants having resistance to acetyl CoA carboxylase inhibitors such as trione oxime herbicides and aryloxyphenoxypropionic acid herbicides, an example of which is SR corn. For example, a crop plant to which resistance to an acetyl CoA carboxylase inhibitor has been imparted is found in Proc. Natl. Acad. Sci. USA, 1990, vol. 87, p. 7175-7179. In addition, a mutant acetyl CoA carboxylase which is resistant to an acetyl CoA carboxylase inhibitor is described in Weed Science, vol. 53, p. 728-746, 2005. When a gene encoding the mutant acetyl CoA carboxylase is introduced into a crop plant by a genetic engineering technique or when a mutation related to impartation of the acetyl CoA carboxylase resistance is introduced into a gene encoding acetyl CoA carboxylase of a crop plant, a crop plant resistant to an acetyl CoA carboxylase inhibitor can be produced. Further, nucleic acids for introduction of a base substitution mutation can be introduced into the cells of a crop plant by chimeraplasty (see, Gura T. 1999, Repairing the Genome's Spelling Mistakes, Science 285: 316-318) to induce a site-directed amino acid substitution mutation in the gene which is targeted by an acetyl CoA carboxylase inhibitor or herbicide of the crop plant, and thereby a crop plant resistant to an acetyl CoA carboxylase inhibitor or herbicide can be produced.

Examples of the crop plant to which the resistance has been imparted by a genetic engineering technique include corn, soybean, cotton, rape and sugar beet cultivars which are resistant to glyphosate, which are commercially available under the trade names of RoundupReady™ (registered trademark), AgrisureGT, and the like. Other examples of the crop plant to which the resistance has been imparted by a genetic engineering technique include corn, soybean, cotton and rape cultivars which are resistant to glufosinate, which are commercially available under the trade name of LibertyLink™ and the like. In addition, a genetically engineered cotton cultivar having resistance to bromoxynil is commercially available under the trade name of BXN.

The above-described crop plants include those to which ability to produce an insecticidal toxin, for example a selective toxin which is known to be produced by *Bacillus*, has been imparted by a genetic engineering technique.

Examples of the insecticidal toxin which is produced by such a genetically engineered plant include insecticidal proteins derived from *Bacillus cereus* and *Bacillus popilliae*; δ-endotoxins derived from *Bacillus thuringiensis*, such as Cry1Ab, Cry1Ac, Cry1F, Cry1Fa2, Cry2Ab, Cry3A, Cry3Bb1 and Cry9C; insecticidal proteins derived from *Bacillus thuringiensis*, such as VIP 1, VIP 2, VIP 3 and VIP 3A; insecticidal proteins derived from nematodes; toxins produced by animals such as scorpion toxins, spider toxins, bee toxins and insect-specific nerve toxins; fungal toxins; plant lectin; agglutinin; protease inhibitors such as trypsin inhibitors, serine protease inhibitors, patatin, cystatin, and papain inhibitors; ribosome-inactivating proteins (RIP) such as ricin, corn-RIP, abrin, saporin, and briodin; steroid metabolizing enzymes such as 3-hydroxysteroid oxidase, ecdysteroid-UDP-glucosyltransferase, and cholesterol oxidase; ecdysone inhibitors; HMG-CoA reductase; ion channel inhibitors such as sodium channel inhibitors and calcium channel inhibitors; juvenile hormone esterase; diuretic hormone receptors; stilbene synthase; bibenzyl synthase; chitinase; and glucanase.

The insecticidal toxin which is produced by such a genetically engineered plant also includes hybrid toxins of different insecticidal proteins, for example, insecticidal proteins such as δ-endotoxins such as Cry1Ab, Cry1Ac, Cry1F, Cry1Fa2, Cry2Ab, Cry3A, Cry3Bb1 and Cry9C, VIP 1, VIP 2, VIP 3 and VIP 3A, and toxins in which a part of amino acids constituting an insecticidal protein is deleted or modified. The hybrid toxin is made by combining different domains of the insecticidal proteins by a genetic engineering technique. An example of the toxin in which a part of amino acids constituting an insecticidal protein is deleted includes Cry1Ab in which a part of amino acids is deleted. An example of the toxin in which a part of amino acids constituting an insecticidal protein is modified includes a toxin in which one or more of amino acids of a naturally occurring toxin are substituted.

The insecticidal toxin and the genetically engineered crop plant having the ability to produce the insecticidal toxin are described, for example, in EP-A-0 374 753, WO 93/07278, WO 95/34656, EP-A-0 427 529, EP-A-451878, WO 03/052073, and the like.

The genetically engineered crop plant having the ability to produce the insecticidal toxin particularly has resistance to attack by a coleopteran pest, dipteran pest or a lepidopteran pest.

Genetically engineered plants which have one or more pest-resistance genes and thereby produce one or more insecticidal toxins are also known, and some of them are commercially available. Examples of such genetically engineered plants include YieldGard™ (a corn cultivar expressing Cry1Ab toxin), YieldGard Rootworm™ (a corn cultivar expressing Cry3Bb1 toxin), YieldGard Plus™ (a corn cultivar expressing Cry1Ab and Cry3Bb1 toxins), Herculex I™ (a corn cultivar expressing Cry1Fa2 toxin and phosphinothricin N-acetyltransferase (PAT) for imparting resistance to glupho-sinate), NuCOTN33B™ (a cotton cultivar expressing Cry1Ac toxin), Bollgard I™ (a cotton cultivar expressing Cry1Ac toxin), Bollgard II™ (a cotton cultivar expressing Cry1Ac and Cry2Ab toxins), VIPCOT™ (a cotton cultivar expressing VIP toxin), NewLeaf™ (a potato cultivar expressing Cry3A toxin), NatureGard Agrisure GT Advantage™ (GA[21] glyphosate-resistance character), Agrisure CB Advantage™ (Bt11 corn borer (CB) character), Protecta™, and the like.

The above-described crop plants include those to which ability to produce an anti-pathogen substance has been imparted by a genetic engineering technique.

Examples of the anti-pathogen substance includes PR proteins (PRPs described in EP-A-0 392 225); ion channel inhibitors such as sodium channel inhibitors, and calcium channel inhibitors (e.g. KP1, KP4, KP6 toxins etc. produced by viruses); stilbene synthase; bibenzyl synthase; chitinase; glucanase; substances produced by microorganisms such as peptide antibiotics, heterocycle-containing antibiotics, and protein factors involved in plant disease-resistance (described in WO 03/000906); and the like. Such anti-pathogen substances and genetically engineered plants which produce the anti-pathogen substances are described in EP-A-0 392 225, WO 05/33818, EP-A-0 353 191, and the like.

The above-described crop plants include those to which a beneficial character such as a modified oil component or an enhanced amino acid content has been imparted by a genetic engineering technique. Examples of such crop plants include VISTIVE™ (low linolenic soybean which has a reduced content of linolenic acid), and high-lysine (high-oil) corn (corn which has an increased content of lysine or oil).

Furthermore, the above-described crop plants include stacked plants which have a combination of two or more of beneficial characters such as the above-described classical herbicide-resistant character, or a herbicide-resistance gene, a pest-resistance gene, an anti-pathogen substance-producing gene, a modified oil component, and an enhanced amino acid content.

When the compound of the present invention is used for the herbicide-resistant crop plant as described above, the plant is treated with sequentially or a mixture of the compound of the present invention and the herbicide (e.g., glyphosate or a salt thereof, glufosinate or a salt thereof, dicamba or a salt thereof, imazethapyr or a salt thereof, isoxaflutole, etc.) to which the plant is resistant, and thereby comprehensive weed control can be attained.

Examples of active ingredients of insecticides, acaricides, nematocides, fungicides, herbicides, phytohormone agents, plant growth regulators, synergists and crop injury-reducing agents (hereinafter, referred to as "the active ingredient group X") which can be used in combination with the compound of the present invention are listed below.

Examples of active ingredients of the insecticides include:
(1) Organic Phosphorus Compounds:
acephate, aluminum phosphide, butathiofos, cadusafos, chlorethoxyfos, chlorfenvinphos, chlorpyrifos, chlorpyrifos-methyl, cyanophos (CYAP), diazinon, DCIP (dichlorodiiso-propyl ether), dichlofenthion (ECP), dichlorvos (DDVP), dimethoate, dimethylvinphos, disulfoton, EPN, ethion, etho-prophos, etrimfos, fenthion (MPP), fenitrothion (MEP), fos-thiazate, formothion, hydrogen phosphide, isofenphos, isox-athion, malathion, mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion, phorate, cadusafos, and the like;

(2) Carbamate Compounds:
alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, NAC, oxamyl, pirimicarb, propoxur (PHC), XMC, thiodicarb, xylylcarb, aldicarb, and the like;

(3) Synthetic Pyrethroid Compounds:
acrinathrin, allethrin, beta-cyfluthrin, bifenthrin, cycloprothrin, cyfluthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, 2,3,5,6-tetrafluoro-4-methylbenzyl 2,2-dimethyl-3-(1-propenyl)cyclopropanecarboxylate, 2,3,5,6-tetrafluoro-4-(methoxymethyl)benzyl 2,2-dimethyl-3-(2-methyl-1-propenyl)cyclopropanecarboxylate, 2,3,5,6-tetrafluoro-4-(methoxymethyl)benzyl 2,2-dimethyl-3-(2-cyano-1-propenyl)cyclopropanecarboxylate, 2,3,5,6-tetrafluoro-4-(methoxymethyl)benzyl 2,2,3,3-tetramethylcyclopropanecarboxylate, and the like;

(4) Nereistoxin Compounds:
cartap, bensultap, thiocyclam, monosultap, bisultap, and the like;

(5) Neonicotinoid Compounds:
imidacloprid, nitenpyram, acetamiprid, thiamethoxam, thiacloprid, dinotefuran, clothianidin, and the like;

(6) Benzoylurea Compounds:
chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron, triazuron, and the like;

(7) Phenylpyrazole Compounds:
acetoprole, ethiprole, fipronil, vaniliprole, pyriprole, pyrafluprole, and the like;

(8) Bt Toxin Insecticides:
live spores derived from and crystal toxins produced from *Bacillus thuringiesis* and a mixture thereof;

(9) Hydrazine Compounds:
chromafenozide, halofenozide, methoxyfenozide, tebufenozide, and the like;

(10) Organic Chlorine Compounds:
aldrin, dieldrin, dienochlor, endosulfan, methoxychlor, and the like;

(11) Natural Insecticides:
machine oil, nicotine sulfate, and the like;

(12) Other Insecticides:
avermectin, bromopropylate, buprofezin, chlorphenapyr, cyromazine, D-D (1,3-dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metham-ammonium, metam-sodium, methyl bromide, potassium oleate, protrifenbute, spiromesifen, sulfur, metaflumizone, spirotetramat, pyrifluquinazone, spinetoram, chlorantraniliprole, tralopyril, a compound represented by the following formula (A):

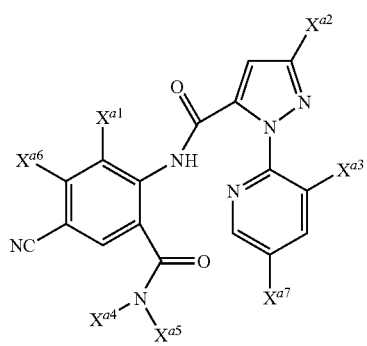

(A)

wherein $X^{a1}$ represents a methyl group, a chlorine atom, a bromine atom or a fluorine atom, $X^{a2}$ represents a fluorine atom, a chlorine atom, a bromine atom, a C1-C4 haloalkyl group or a C1-C4 haloalkoxy group, $X^{a3}$ represents a fluorine atom, a chlorine atom or a bromine atom, $X^{a4}$ represents an optionally substituted C1-C4 alkyl group, an optionally substituted C3-C4 alkenyl group, an optionally substituted C3-C4 alkynyl group, an optionally substituted C3-C5 cycloalkylalkyl group or a hydrogen atom, $X^{a5}$ represents a hydrogen atom or a methyl group, $X^{a6}$ represents a hydrogen atom, a fluorine atom or a chlorine atom, and $X^{a7}$ represents a hydrogen atom, a fluorine atom or a chlorine atom;

a compound represented by the following formula (B):

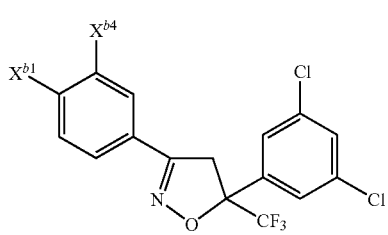

(B)

wherein $X^{b1}$ represents a $X^{b2}$—NH—C(=O) group, a $X^{b2}$—C(=O)—NH—CH$_2$ group, a $X^{b3}$—S(O) group, an optionally substituted pyrrol-1-yl group, an optionally substituted imidazol-1-yl group, an optionally substituted pyrazol-1-yl group, or an optionally substituted 1,2,4-triazol-1-yl group, $X^{b2}$ represents an optionally substituted C1-C4 haloalkyl group, such as a 2,2,2-trifluoroethyl group, or an optionally substituted C3-C6 cycloalkyl group, such as a cyclopropyl group, $X^{b3}$ represents an optionally substituted C1-C4 alkyl group, such as a methyl group, and $X^{b4}$ represents a hydrogen atom, a cyano group or a methyl group;

a compound represented by the following formula (C):

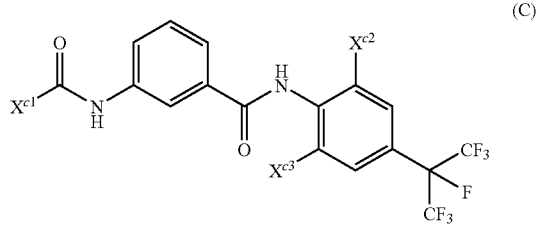

wherein $X^{c1}$ represents an optionally substituted C1-C4 alkyl group, such as a 3,3,3-trifluoropropyl group, an optionally substituted C1-C4 alkoxy group, such as a 2,2,2-trichloroethoxy group, an optionally substituted phenyl group, such as a 4-cyanophenyl group, or an optionally substituted pyridyl group, such as a 2-chloro-3-pyridyl group, $X^{c2}$ represents a methyl group or a trifluoromethylthio group, and $X^{c3}$ represents a methyl group or a halogen atom; and the like.

Examples of active ingredients of the acaricides include acequinocyl, amitraz, benzoximate, bifenazate, bromopropylate, chinomethionate, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite (BPPS), polynactins, pyridaben, pyrimidifen, tebufenpyrad, tetradifon, spirodiclofen, spiromesifen, spirotetramat, amidoflumet, cyenopyrafen, and the like.

Examples of active ingredients of the nematicides include DCIP, fosthiazate, levamisol hydrochloride, methylisothiocyanate, morantel tartarate, imicyafos, and the like.

Examples of active ingredients of the fungicides include azole fungicidal compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol;

cyclic amine fungicidal compounds such as fenpropimorph, tridemorph, and fenpropidin;

benzimidazole fungicidal compounds such as carbendezim, benomyl, thiabendazole, and thiophanate-methyl;

procymidone, cyprodinil, pyrimethanil, diethofencarb, thiuram, fluazinam, mancozeb, iprodione, vinclozolin, chlorothalonil, captan, mepanipyrim, fenpiclonil, fludioxonil, dichlofluanid, folpet, kresoxim-methyl, azoxystrobin, trifloxystrobin, fluoxastrobin, picoxystrobin, pyraclostrobin, dimoxystrobin, spiroxamine, quinoxyfen, fenhexamid, famoxadone, fenamidone, zoxamide, ethaboxam, amisulbrom, iprovalicarb, benthiavalicarb, cyazofamid, mandipropamid, boscalid, metrafenone, fluopiran, bixafen, cyflufenamid, and proquinazid.

Examples of active ingredients of the herbicides and the phytohormone agents include:

(1) phenoxyfatty acid herbicidal compounds such as 2,4-PA, MCP, MCPB, phenothiol, mecoprop, fluoroxypyr, triclopyr, clomeprop, and naproanilide;

(2) benzoic acid herbicidal compounds such as 2,3,6-TBA, dicamba, clopyralid, picloram, aminopyralid, quinclorac, and quinmerac;

(3) urea herbicidal compounds such as diuron, linuron, chlortoluron, isoproturon, fluometuron, isouron, tebuthiuron, methabenzthiazuron, cumyluron, daimuron, and methyldaimuron;

(4) triazine herbicidal compounds such as atrazine, ametoryn, cyanazine, simazine, propazine, simetryn, dimethametryn, prometryn, metribuzin, and triaziflam;

(5) bipyridinium herbicidal compounds such as paraquat, and diquat;

(6) hydroxybenzonitrile herbicidal compounds such as bromoxynil and ioxynil;

(7) dinitroaniline herbicidal compounds such as pendimethalin, prodiamine, and trifluralin;

(8) organic phosphorus herbicidal compounds such as amiprofos-methyl, butamifos, bensulide, piperophos, anilofos, glyphosate, glufosinate, and bialaphos;

(9) carbamate herbicidal compounds such as di-allate, triallate, EPTC, butylate, benthiocarb, esprocarb, molinate, dimepiperate, swep, chlorpropham, phenmedipham, phenisopham, pyributicarb, and asulam;

(10) acid amide herbicidal compounds such as propanil, propyzamide, bromobutide, and etobenzanid;

(11) chloroacetanilide herbicidal compounds such as acetochlor, alachlor, butachlor, dimethenamid, propachlor, metazachlor, metolachlor, pretilachlor, thenylchlor, and pethoxamid;

(12) diphenylether herbicidal compounds such as acifluorfen-sodium, bifenox, oxyfluorfen, lactofen, fomesafen, chlomethoxynil, and aclonifen;

(13) cyclic imide herbicidal compounds such as oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, and benzfendizone;

(14) pyrazole herbicidal compounds such as benzofenap, pyrazolate, pyrazoxyfen, topramezone, and pyrasulfotole;

(15) triketone herbicidal compounds such as isoxaflutole, benzobicyclon, sulcotrione, mesotrione, tembotrione, and tefuryltrione;

(16) aryloxyphenoxypropionic acid herbicidal compounds such as clodinafop-propargyl, cyhalofop-butyl, diclofop-methyl, fenoxaprop-ethyl, fluazifop-butyl, haloxyfop-methyl, and quizalofop-ethyl;

(17) trioneoxime herbicidal compounds such as alloxydim-sodium, sethoxydim, butroxydim, clethodim, cloproxydim, cycloxydim, tepraloxydim, tralkoxydim, and profoxydim;

(18) sulfonylurea herbicidal compounds such as chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and 1-(2-chloro-6-propylimidazo[1,2-a]pyridazin-3-ylsulfonyl)-3-(4,6-dimethoxypyrimidin-2-yl)urea;

(19) imidazolinone herbicidal compounds such as imazamethabenz-methyl, imazamethapyr, imazamox, imazapyr, imazaquin, and imazethapyr;

(20) sulfonamide herbicidal compounds such as flumetsulam, metosulam, diclosulam, florasulam, cloransulam-methyl, penoxsulam, and pyroxsulam;

(21) pyrimidinyloxybenzoic acid herbicidal compounds such as pyrithiobac-sodium, bispyribac-sodium, pyriminobac-methyl, pyribenzoxim, and pyriftalid; and

(22) other herbicidal compounds such as bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, and thiencarbazone-methyl.

Examples of active ingredients of the plant growth regulators include hymexazol, paclobutrazol, uniconazole-P, inabenfide, prohexadione-calcium, aviglycine, 1-naphthylacetamide, abscisic acid, indolebutyric acid, ethychlozate ethyl, ethephon, cloxyfonac, chlormequat, dichlorprop, gibberellin, prohydrojasmon, benzylaminopurine, forchlorfenuron, maleic hydrazide, calcium peroxide, mepiquat chloride) and 4-CPA (4-chlorophenoxyacetic acid).

Examples of active ingredients of the synergists include piperonyl butoxide, sesamex, sulfoxide, N-(2-ethylhexyl)-8, 9,10-trinorborn-5-ene-2,3-dicarboximide (MGK 264), N-declyimidazole, WARF-antiresistant, TBPT, TPP, IBP, PSCP, methyl iodide (CH3I), t-phenylbutenone, diethylmaleate, DMC, FDMC, ETP, and ETN.

Examples of active ingredients of the crop injury-reducing agents include benoxacor, cloquintocet-mexyl, cyometrinil, daimuron, dichlormid, fenchlorazole-ethyl, fenclorim, flurazole, fluxofenim, furilazole, mefenpyr-diethyl, MG191, oxabetrinil, allidochlor, isoxadifen-ethyl, cyprosulfamide, fluxofenim, and 1,8-naphthalic anhydride.

Examples of pests on which the compound of the present invention exhibits a controlling effect include arthropod pests such as harmful insects and harmful mites, and more specifically, the following pets.

Hemiptera:

Planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*), green rice leafhopper (*Nephotettix virescens*), and tea green leafhopper (*Empoasca onukii*); aphids (Aphididae) such as cotton aphid (*Aphis gossypii*), green peach aphid (*Myzus persicae*), cabbage aphid (*Brevicoryne brassicae*), piraea aphid (*Aphis spiraecola*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*), and mealy plum aphid (*Hyalopterus pruni*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), and stink bug (*Halyomorpha mista*); whiteflies (Aleyrodidae) such as greenhouse whitefly (*Trialeurodes vaporariorum*), sweetpotato whitefly (*Bemisia tabaci*), silverleaf whitefly (*Bemisia argentifolii*), citrus whitefly (*Dialeurodes citri*), and citrus spiny white fly (*Aleurocanthus spiniferus*); scales (Coccidae) such as Calfornia red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchasi*), Japanese mealybug (*Planococcus kraunhiae*), Cosmstock mealybug (*Pseudococcus longispinis*), and white peach scale (*Pseudaulacaspis pentagona*); lace bugs (Tingidae); cimices such as *Cimex lectularius*; psyllids (Psyllidae); etc.

Lepidoptera:

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxophyes honmai*), oriental tea tortrix (*Homona magnanima*), apple tortrix (*Archips fuscocupreanus*), and codling moth (*Cydia pomonella*); leafblotch miners (Gracillariidae) such as tea leafroller (*Caloptilia theivora*), and apple leafminer (*Phyllonorycter ringoneella*); Carposinidae such as peach fruit moth (*Carposina niponensis*); lyonetiid moths (Lyonetiidae) such as *Lyonetia* spp.; tussock moths (Lymantriidae) such as *Lymantria* spp., and *Euproctis* spp.; yponomeutid moths (Yponomeutidae) such as diamondback (*Plutella xylostella*); gelechiid moths (Gelechiidae) such as pink bollworm (*Pectinophora gossypiella*), and potato tubeworm (*Phthorimaea operculella*); tiger moths and allies (Arctiidae) such as fall webworm (*Hyphantria cunea*); tineid moths (Tineidae) such as casemaking clothes moth (*Tinea translucens*), and webbing clothes moth (*Tineola bisselliella*); etc.

Thysanoptera:

Thrips (Thripidae) such as yellow citrus *thrips* (*Frankliniella occidentalis*), melon *thrips* (*Thrips palmi*), yellow tea *thrips* (*Scirtothrips dorsalis*), onion *thrips* (*Thrips tabaci*), flower *thrips* (*Frankliniella intonsa*), etc.

Diptera:

Culices such as common mosquito (*Culex pipiens pallens*), *Cluex tritaeniorhynchus*, and *Cluex quinquefasciatus*; *Aedes* spp. such as yellow fever mosquito (*Aedes aegypti*), and Asian tiger mosquito (*Aedes albopictus*); *Anopheles* spp. such as *Anopheles sinensis*; chironomids (Chironomidae); house flies (Muscidae) such as *Musca domestica*, and *Muscina stabulans*; blow flies (Calliphoridae); flesh flies (Sarcophagidae); little house flies (Fanniidae); anthomyiid flies (Anthomyiidae) such as seedcorn fly (*Delia platura*), and onion fly (*Delia antiqua*); leafminer flies (Agromyzidae) such as rice leafminer (*Agromyza oryzae*), little rice leafminer (*Hydrellia griseola*), tomato leafminer (*Liriomyza sativae*), legume leafminer (*Liriomyza trifolii*), and garden pea leafminer (*Chromatomyia horticola*); gout flies (Chloropidae) such as rice stem maggot (*Chlorops oryzae*); fruit flies (Tephritidae) such as melon fly (*Dacus cucurbitae*), and Mediterranean fruit fly (*Ceratitis capitata*); Drosophilidae; humpbacked flies (Phoridae) such as *Megaselia spiracularis*; moth flies (Psychodidae) such as *Clogmia albipunctata*; Simuliidae; Tabanidae such as horsefly (*Tabanus trigonus*); stable flies, etc.

Coleoptera:

Corn root worms (*Diabrotica* spp.) such as Western corn root worm (*Diabrotica virgifera virgifera*), and Southern corn root worm (*Diabrotica undecimpunctata howardi*); scarabs (Scarabaeidae) such as cupreous chafer (*Anomala cuprea*), soybean beetle (*Anomala rufocuprea*), and Japanese beetle (*Popillia japonica*); weevils such as maize weevil (*Sitophilus zeamais*), rice water weevil (*Lissorhoptrus oryzophilus*), azuki bean weevil (*Callosobruchus chinensis*), rice curculio (*Echinocnemus squameus*), boll weevil (*Anthonomus grandis*), and hunting billbug (*Sphenophorus venatus*); darkling beetles (Tenebrionidae) such as yellow mealworm (*Tenebrio molitor*), and red flour beetle (*Tribolium castaneum*); leaf beetles (Chrysomelidae) such as rice leaf beetle (*Oulema oryzae*), cucurbit leaf beetle (*Aulacophora femoralis*), striped flea beetle (*Phyllotreta striolata*), and Colorado potato beetle (*Leptinotarsa decemlineata*); dermestid beetles (Dermestidae) such as varied carper beetle (*Anthrenus verbasci*), and hide beetle (*Dermestes maculates*); deathwatch beetles (Anobiidae) such as cigarette beetle (*Lasioderma serricorne*); *Epilachna* such as Twenty-eight-spotted ladybird (*Epilachna vigintioctopunctata*); bark beetles (Scolytidae) such as powder-post beetle (*Lyctus brunneus*), and pine shoot beetle (*Tomicus piniperda*); false powder-post beetles (Bostrychidae); spider beetles (Ptinidae); longhorn beetles (Cerambycidae) such as white-spotted longicorn beetle (*Anoplophora malasiaca*); click beetles (*Agriotes* spp.); *Paederus fuscipens*, etc.

Orthoptera:

Asiatic locust (*Locusta migratoria*), African mole cricket (*Gryllotalpa africana*), rice grasshopper (*Oxya yezoensis*), rice grasshopper (*Oxya japonica*), Gryllidae, etc.

Shiphonaptera:

Cat flea (*Ctenocephalides felis*), dog flea (*Ctenocephalides canis*), human flea (*Pulex irritans*), oriental rat flea (*Xenopsylla cheopis*), etc.

Anoplura:

Human body louse (*Pediculus humanus corporis*), crab louse (*Phthirus pubis*), short-nosed cattle louse (*Haematopinus eurysternus*), sheep louse (*Dalmalinia ovis*), hog louse (*Haematopinus suis*), etc.

Hymenoptera:

Ants (Formicidae) such as pharaoh ant (*Monomorium pharaosis*), negro ant (*Formica fusca japonica*), black house ant (*Ochetellus glaber*), *Pristomyrmex pungens*, *Pheidole noda*, leaf-cutting ant (*Acromyrmex* spp.), and fire ant (*Solenopsis* spp.); hornets (Vespidae); bethylid wasps (Betylidae); sawflies (Tenthredimidae) such as cabbage sawfly (*Athalia rosae*), and *Athalia japonica*, etc.

Blattodea:

German cockroach (*Blattella germanica*), smokybrown cockroach (*Periplaneta fuliginosa*), American cockroach (*Periplaneta americana*), *Periplaneta brunnea*, oriental cockroach (*Blatta orientalis*);

Isoptera:

Termites such as Japanese subterranean termite (*Reticulitermes speratus*), Formosan subterranean termite (*Coptotermes formosanus*), western drywood termite (*Incisitermes minor*), Daikoku drywood termite (*Cryptotermes domesticus*), *Odontotermes formosanus*, *Neotermes koshunensis*, *Glyptotermes satsumesis*, *Glyptotermes nakajimai*, *Glyptotermes fuscus*, *Glyptotermes kodamai*, *Glyptotermes kushimensis*, Japanese dampwood termite (*Hodotermopsis japonica*), *Coptotermes guangzhoensis*, *Reticulitermes miyatakei*, eastern subterranean termite (*Reticulitermes flavipes amamianus*), *Reticulitermes* sp., *Nasutitermes takasagoesis*, *Pericapritermes nitobei*, *Sinocapritermes mushae*, *Reticuliterumes flavipes*, *Reticulitermes hesperus*, *Reticulitermes virginicus*, *Reticulitermes tibialis*, *Heterotermes aureus*, and *Zootermopsis nevadensis*, etc.

Acarina:

Spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), and *Oligonychus* spp.; eriophyid mites (Eriophyidae) such as pink citrus rust mite (*Aculops pelekassi*), *Phyllocoptruta citri*, tomato rust mite (*Aculops lycopersici*), purple tea mite (*Calacarus carinatus*), pink tea rust mite (*Acaphylla theavagran*), *Eriophyes chibaensis*, and apple rust mite (*Aculus schlechtendali*); tarosonemid mites (Tarsonemidae) such as broad mite (*Polyphagotarsonemus latus*); false spider mites (Tenuipalpidae) such as *Brevipalpus phoenicis*; Tuckerellidae; ticks (Ixodidae) such as *Haemaphysalis longicornis*, *Haemaphysalis flava*, *Dermacentor taiwanicus*, American dog tick (*Dermacentor variabilis*), *Ixodes ovatus*, *Ixodes persulcatus*, black leg tick (*Ixodes scapularis*), lone star tick (*Amblyomma americanum*), *Boophilus microplus*, and *Rhipicephalus sanguineus*; Psoroptidae such as ear mite (*Otodectes cynotis*); itch mites (Sarcoptidae) such as *Sarcoptes scabiei*; folicle mites (Demodicidae) such as dog folicle mite (*Demodex canis*); acarid mites (Acaridae) such as mold mite (*Tyrophagus putrescentiae*), and *Tyrophagus similis*; house dust mites (Pyroglyphidae) such as *Dermatophagoides farinae*, and *Dermatophagoides ptrenyssnus*; cheyletide mites (Cheyletidae) such as *Cheyletus eruditus*, *Cheyletus malaccensis*, and *Cheyletus moorei*; parasitoid mites (Dermanyssidae) such as tropical rat mite (*Ornithonyssus bacoti*), northern fowl mite (*Ornithonyssus sylviarum*), and poultry red mite (*Dermanyssus gallinae*); chiggers (Trombiculidae) such as *Leptotrombidium akamushi*; spiders (Araneae) such as Japanese foliage spider (*Chiracanthium japonicum*), redback spider (*Latrodectus hasseltii*), etc.

Chilopoda: house centipede (*Thereuonema hilgendorfi*), *Scolopendra subspinipes*, etc.;

Diplopoda: garden millipede (*Oxidus gracilis*), *Nedyopus tambanus*, etc.;

Isopoda: common pill bug (*Armadillidium vulgare*), etc.;

Gastropoda: *Limax marginatus*, *Limax flavus*, etc.

Nematoda:

Rice white-tip nematode (*Aphelenchoides besseyi*), strawberry bud nematode (*Nothotylenchus acris*), southern root-knot nematode (*Meloidogyne incognita*), northern root-knot nematode (*Meloidogyne hapla*), Javanese root-knot nematode (*Meloidogyne javanica*), soybean cyst nematode (*Heterodera glycines*), potato cyst nematode (*Globodera rostochiensis*), coffee root-lesion nematode (*Pratylenchus coffeae*), California root-lesion nematode (*Pratylenchus neglectus*), etc.

The pesticidal composition comprising the compound of the present invention or a salt thereof can be used in the field of livestock disease therapy and livestock industry, and also can be used for exterminating organisms and parasites inhabiting the inside and/or outside of the body of vertebrates such as human being, cow, sheep, goat, pig, poultry, dog, cat and fish, to sustain public health. Examples of such organisms and parasites include ticks (*Ixodes* spp.) (e.g. *Ixodes scapularis*), *Boophilus* spp. (e.g. *Boophilus microplus*), *Amblyomma* spp., *Hyalomma* spp., *Rhipicephalus* spp. (e.g. *Rhipicephalus sanguineus*), *Haemaphysalis* spp. (e.g. *Haemaphysalis longicornis*), *dermacentor* spp., *Ornithodoros* spp. (e.g. *Ornithodoros moubata*), parasitoid mites (*Dermahyssus gallinae*), northern fowl mite (*Ornithonyssus sylviarum*), itch mites (*Sarcoptes* spp.) (e.g *Sarcoptes scabiei*), *Psoroptes* spp., *Chorioptes* spp., folicle mites (*Demodex* spp.), chiggers (*Eutrombicula* spp.), *Aedes* spp. (e.g. Asian tiger mosquito (*Aedes albopictus*)), *Anopheles* spp., *Culex* spp., *Culicodes* spp., *Musca* spp., *Hypoderma* spp., *Gasterophilus* spp., *Haematobia* spp., *Tabanus* spp., *Simulium* spp., *Triatoma* spp., lice (Phthiraptera) (e.g. *Damalinia* spp., *Linognathus* spp., *Haematopinus* spp.), fleas (*Ctenocephalides* spp.) (e.g. cat flea (*Ctenocephalides felis*), *Xenosylla* spp.), pharaoh ant (*Monomorium pharaonis*), and Nematoda [for example, trichostrongyle (e.g. *Nippostrongylus brasiliensis*, *Trichostrongylus axei*, and *Trichostrongylus colubriformis*), trichina (e.g. *Trichinella spiralis*), *Haemonchus contortus*, *Nematodirus* (e.g.

*Nematodirus battus*), *Ostertagiai circumcincta*, *Cooperia* spp., *Hymenolepis nana*, and the like.

For the method of controlling a pest of the present invention, the compound of the present invention or a salt thereof may be used as it is, and however, the compound of the present invention is usually formulated into the form of the pesticidal composition of the present invention as described above and then used. The method of controlling a pest of the present invention comprises, for example, applying the compound of the present invention or a salt thereof or the pesticidal composition of the present invention to a pest or a place where the pest inhabits by method same as to an application method for conventional pesticides, to allow the pest to contact with or ingest the compound of the present invention or a salt thereof or the pesticidal composition of the present invention.

Examples of the place where the pest inhabits include a paddy field, a dry field, a cultivated field, a tea field, a fruit orchard, a non-cultivated field, a house, a raising seedling tray, a nursery box, nursery soil, a nursery mat, a water culture medium in a hydroponic farm, and the like.

Examples of such an application method include spray treatment, soil treatment, seed treatment and water culture medium treatment. In the present invention, the spray treatment includes foliage spraying and truck spraying, and specifically comprises treating the plant surface or a pest itself with an active ingredient (the compound of the present invention or a salt thereof), to exert a controlling effect on a pest. The soil treatment comprises, for example, treating rhizosphere soil of a plant to be protected from damage such as eating by a pest with an active ingredient to control the pest directly, or allowing the active ingredient to permeate from the root and the like of the plant to inside of the plant to control the pest. Specific examples of the soil treatment include planting hole treatment (planting hole spraying, soil incorporation after planting hole treatment), plant foot treatment (plant foot spraying, soil incorporation at plant foot, plant foot drenching, plant foot treatment at a later seeding raising stage), planting furrow treatment (planting furrow spraying, soil incorporation after planting furrow treatment), planting row treatment (planting row spraying, soil incorporation after planting row treatment, planting row spraying at a growing stage), planting row treatment at the time of sowing (planting row spraying at the time of sowing, soil incorporation after planting row treatment at the time of sowing), broadcast treatment (overall soil surface spraying, soil incorporation after broadcast treatment), other soil spraying treatment (foliar spraying of a granule at a growth stage, spraying under trunks or around main stems, soil surface spraying, soil surface incorporation, sowing hole spraying, furrow surface spraying, and spraying between plants), other drenching treatment (soil drenching, drenching at a raising seedling stage, chemical injection treatment, plant foot drenching, chemical drip irrigation, chemigation), nursery box treatment (nursery box surface spraying, drenching of nursery box), nursery tray treatment (nursery tray spraying, nursery tray irrigation), nursery bed treatment (nursery bed surface spraying, drenching of nursery bed, lowland nursery bed surface spraying, seedling immersion), bed soil incorporation treatment (bed soil incorporation, presowing bed soil incorporation), and other treatments (ridging incorporation, plowing and fertilizing, surface soil incorporation, soil incorporation under canopy edge, planting position treatment, flower cluster treatment with a granule, paste fertilizer incorporation). The seed treatment comprises, for example, treating the seeds, seed potatoes or bulbs of a crop plant to be protected from damage such as eating by a pest, or the vicinity thereof with an active ingredient to exert a controlling effect on the pest. Specific examples the seed treatment include spraying, smearing, immersion, impregnation, application, film coating and pellet coating. The water culture medium treatment comprises, for example, adding an active ingredient to a water culture medium or the like so as to allow the active ingredient to permeate from the root and the like of a crop plant to be protected from damage such as eating by a pest to inside of the plant, thereby the plant is protected from damage by the pest. Specific examples of the water culture medium treatment include water culture medium incorporation, and water culture medium interfusion.

The application amount of the pesticidal composition of the present invention in the above-described application method may be appropriately changed depending on an application timing, an application place, a formulation form and the like, and it is usually 0.3 to 3,000 g, preferably 50 to 3,000 g of an active ingredient (the compound of the present invention or a salt thereof) per 1 hectare of soil where a plant is grown. When the pesticidal composition of the present invention is in the form of a wettable powder, it is preferred that it is diluted with water to 0.1 to 1,000 ppm, preferably from 10 to 500 ppm of the active ingredient and then applied.

The pesticidal composition of the present invention or a water dilution thereof may be applied directly to a pest or a plant such as a crop plant to be protected from the pest. Alternatively, the soil of a cultivated field may be treated with the pesticidal composition of the present invention or a water dilution thereof so as to control pests inhabiting the soil.

When the pesticidal composition of the present invention is in the form of resin formulation, it can be processed into the form of a sheet or a string, and then applied by winding it around a crop plant, disposing it in the vicinity of a crop plant, laying it on the soil surface at the plant feet, or the like.

When the pesticidal composition of the present invention is used for control of epidemic, the application amount is usually 0.001 to 10 mg/m$^3$ of the compound of the present invention as the active ingredient for application to space, and 0.001 to 100 mg/m$^2$ of the compound of the present invention as the active ingredient for application to a plane. The pesticidal composition in the form of an emulsifiable concentrate, a wettable powder or a flowable formulation is usually applied after dilution with water so as to contain usually 0.001 to 10,000 ppm of the active ingredient. The pesticidal composition in the form of an oil solution, an aerosol formulation, a smoking pesticide or a poison bait is usually applied as it is When the pesticidal composition of the present invention is used for controlling external parasites of livestock such as a cow, a horse, a pig, a sheep, a goat and a chicken, or small animals such as a dog, a cat, a rat and a mouse, it can be applied to said animals by a known method in the veterinary field. Specifically, when systemic control is intended, the pesticidal composition of the present invention is administered, for example, as a tablet, a mixture with feed, a suppository or an injection (e.g., intramuscularly, subcutaneously, intravenously, intraperitoneally, etc.). When non-systemic control is intended, a method of using the pesticidal composition of the present invention includes spraying, pour-on treatment or a spot-on treatment with the pesticidal composition in the form of an oil solution or an aqueous liquid, washing an animal with the pesticidal composition in the form of a shampoo formulation, and attachment of a collar or a ear tag made of the pesticidal composition in the form of a resin formulation to an animal. When administered to an animal, the amount of the compound of the present invention is usually in the range of 0.1 to 1,000 mg per 1 kg body weight of the animal.

Next, examples of the compound of the present invention are shown. Compounds represented by the formula (Iα), the formula (Iβ) and the formula (Iγ) shown below are specific examples of the compound of the present invention.

Compounds represented by the formula (Iα):

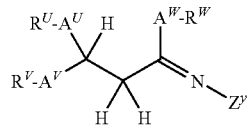

(Iα)

wherein $R^u$, $A^u$, $R^v$, $A^v$, $R^w$, $A^w$ and $Z^y$ are any one of combinations 1 to 487 shown in the following table 1.

TABLE 1

| # | $A^U$ | $R^U$ | $A^V$ | $R^V$ | $A^W$ | $R^W$ | $Z^Y$ |
|---|---|---|---|---|---|---|---|
| 1 | S | Ph | S | Ph | S | Ph | Ph |
| 2 | S | 3-F-Ph | S | 3-F-Ph | S | Ph | 3-Me-Ph |
| 3 | S | 4-F-Ph | S | 4-F-Ph | S | Ph | 4-Me-Ph |
| 4 | S | 3-Cl-Ph | S | 3-Cl-Ph | S | Ph | 3,4-Me₂-Ph |
| 5 | S | 4-Cl-Ph | S | 4-Cl-Ph | S | 3-Me-Ph | [5-indanyl] |
| 6 | O | 3-Me-Ph | O | 3-Me-Ph | O | 2-Me-Ph | 4-iPr-Ph |
| 7 | S | 4-Me-Ph | S | 4-Me-Ph | S | 4-Me-Ph | 3-Cl-Ph |
| 8 | S | 3-MeO-Ph | S | 3-MeO-Ph | S | 3-Hex-Ph | 4-Cl-Ph |
| 9 | S | 4-MeO-Ph | S | 4-MeO-Ph | O | 4-iPr-Ph | 3,4-Cl₂-Ph |
| 10 | S | 3-CF₃-Ph | S | 3-CF₃-Ph | S | 4-tBu-Ph | 4-Ph-Ph |
| 11 | S | 3-Cl-Ph | S | 3-Cl-Ph | O | [5-indanyl] | [2-Me-biphenyl-4′-yl] |
| 12 | S | 3-Cl-Ph | S | [benzo[1,3]dioxol-5-yl] | O | 4-cHx-Ph | 3-Me-4-Cl-Ph |
| 13 | O | Ph | S | Ph | O | 3,4-Me₂-Ph | 3-Cl-4-Me-Ph |
| 14 | S | 3-F-Ph | S | 3-F-Ph | S | 2,5-Me₂-Ph | 4-Ph-3-Me-Ph |
| 15 | O | 4-F-Ph | S | 4-F-Ph | S | 3,4,5-Me₃-Ph | 4-Ph-3-Cl-Ph |
| 16 | S | 4-Cl-Ph | S | 4-Cl-Ph | S | 3-Ay-Ph | Ph |
| 17 | S | 3-Me-Ph | S | 3-Me-Ph | O | 4-Pg-Ph | 3-Me-Ph |
| 18 | O | 4-Me-Ph | O | Ph | S | 4-(PhCH₂)-Ph | 4-Me-Ph |
| 19 | S | 3-MeO-Ph | S | 3-MeO-Ph | O | 4-[CH(Me)Ph]-Ph | 3,4-Me₂-Ph |

TABLE 1-continued

| | $A^U$ | $R^U$ | $A^V$ | $R^V$ | $A^W$ | $R^W$ | $Z^Y$ |
|---|---|---|---|---|---|---|---|
| 20 | | 4-F-Ph | S | 4-F-Ph | S | (2-Me-benzyl-phenyl) | 4-Ph-3-Cl-Ph |
| 21 | | 4-MeO-Ph | S | 4-MeO-Ph | S | (4-Cl-benzyl-phenyl) | (benzo[1,3]dioxol-5-yl) |
| 22 | S | 3-CF$_3$-Ph | S | 3-CF$_3$-Ph | S | 4-MeOCH$_2$-Ph | 4-iPr-Ph |
| 23 | S | 3-CF$_3$-Ph | S | 3-CF$_3$-Ph | S | 4-PhOCH$_2$-Ph | 4-iPr-Ph |
| 24 | S | (benzo[1,3]dithiol-5-yl) | S | (benzo[1,3]dithiol-5-yl) | O | 3-MeSCH$_2$-Ph | 3-Cl-Ph |
| 25 | O | Ph | O | Ph | S | 2-ClCH$_2$-Ph | 4-Cl-Ph |
| 26 | S | 3-F-Ph | S | 3-F-Ph | O | 2-CCl$_3$-Ph | 3,4-Cl$_2$-Ph |
| 27 | S | 4-F-Ph | S | 4-F-Ph | S | 4-CF$_3$-Ph | 4-Ph-Ph |
| 28 | S | 3-Cl-Ph | S | 3-Cl-Ph | S | 3-Vn-Ph | (2-Me-biphenyl-4-yl) |
| 29 | S | 4-Cl-Ph | S | 4-Cl-Ph | O | 4-iPropenyl-Ph | 3-Me-4-Cl-Ph |
| 30 | S | 3 Me-Ph | S | 3-Me-Ph | S | (4-styryl-Ph) | 3-Cl-4-Me-Ph |
| 31 | S | 4-Me-Ph | S | 4-Me-Ph | O | (4-(1-chlorovinyl)-Ph) | 4-Ph-3-Me-Ph |
| 32 | S | 3-MeO-Ph | S | 3-MeO-Ph | S | (4-cyclohexenyl-Ph) | 4-Ph-3-Cl-Ph |

TABLE 1-continued

| # | $A^U$ | $R^U$ | $A^V$ | $R^V$ | $A^W$ | $R^W$ | $Z^Y$ |
|---|---|---|---|---|---|---|---|
| 33 | S | 4-MeO-Ph | S | 4-MeO-Ph | O | 4-methylbiphenyl | Ph |
| 34 | S | 3-CF$_3$-Ph | S | 3-CF$_3$-Ph | S | 2-Ey-Ph | 3-Me-Ph |
| 35 | S | benzo[1,3]dioxole/thiole | S | benzo[1,3]dioxole/thiole | O | 4-MeO—C≡C-Ph | 4-Me-Ph |
| 36 | S | Ph | S | 4-Me-Ph | S | 4-Cl-Ph | 2,3-dihydro-1H-indene |
| 37 | S | 3-F-Ph | S | 3-F-Ph | S | 2,3-Cl$_2$-Ph | |
| 38 | S | 4-F-Ph | S | 4-F-Ph | S | 3-Me-4-Cl-Ph | 4-iPr-Ph |
| 39 | S | 3-Cl-Ph | S | 3-Cl-Ph | O | 3-Me-5-Cl-Ph | 3-Cl-Ph |
| 40 | S | 4-Cl-Ph | S | 4-Cl-Ph | S | 2-HO-Ph | 4-Cl-Ph |
| 41 | S | 3-Me-Ph | S | 3-Me-Ph | S | 4-MeO-Ph | 3,4-Cl$_2$-Ph |
| 42 | S | 4-Me-Ph | S | 4-Me-Ph | O | benzo[1,3]dioxole | 4-Ph-Ph |
| 43 | S | 3-MeO-Ph | S | 3-MeO-Ph | S | 4-CF$_3$O-Ph | 2-Me-biphenyl |
| 44 | S | 4-MeO-Ph | S | 4-MeO-Ph | S | 3-PhO-Ph | 3-Me-4-Cl-Ph |
| 45 | S | 3-CF$_3$-Ph | S | 3-CF$_3$-Ph | O | 4-MeS-Ph | 3-Cl-4-Me-Ph |
| 46 | S | benzo[1,3]dioxole | S | benzo[1,3]dioxole | S | 4-CF$_3$S-Ph | 4-Ph-3-Me-Ph |
| 47 | S | Ph | S | Ph | S | 3-PhS-Ph | 4-Ph-3-Cl-Ph |
| 48 | S | 3-F-Ph | S | 3-F-Ph | S | 4-MeSO-Ph | Ph |
| 49 | S | 4-F-Ph | S | 4-F-Ph | S | 4-PhSO-Ph | 3-Me-Ph |
| 50 | S | 3-Cl-Ph | S | 3-Cl-Ph | S | 3-MeSO$_2$-Ph | 4-Me-Ph |
| 51 | S | 4-Cl-Ph | S | 4-Cl-Ph | S | 4-CF$_3$SO$_2$-Ph | 3,4-Me$_2$-Ph |

TABLE 1-continued

| # | $A^U$ | $R^U$ | $A^V$ | $R^V$ | $A^W$ | $R^W$ | $Z^Y$ |
|---|---|---|---|---|---|---|---|
| 52 | S | 3-Me-Ph | S | 3-Me-Ph | O | 4-PhSO$_2$-Ph | (2,3-dihydro-1H-inden-5-yl) |
| 53 | S | 4-Me-Ph | S | 4-Me-Ph | S | 2-MeSO$_2$O-Ph | 4-iPr-Ph |
| 54 | S | Ph | S | Ph | S | 3-CF$_3$SO$_2$O-Ph | Ph |
| 55 | S | 3-MeO-Ph | S | 3-MeO-Ph | O | 4-PhSO$_2$O-Ph | 3-Cl-Ph |
| 56 | S | 4-MeO-Ph | S | 4-MeO-Ph | S | 3-CHO-Ph | 4-Cl-Ph |
| 57 | S | 3-CF$_3$-Ph | S | 3-CF$_3$-Ph | S | 4-Ac-Ph | 3,4-Cl$_2$-Ph |
| 58 | S | (benzo[d][1,3]dioxol-5-yl) | S | (benzo[d][1,3]dioxol-5-yl) | O | 4-(C(=S)Me)-Ph | 4-Ph-Ph |
| 59 | S | Ph | S | Ph | S | 4-PhCO-Ph | (2-methyl-[1,1'-biphenyl]-4-yl) |
| 60 | S | 4-Me-Ph | S | 4-Me-Ph | S | 4-(3-Me-benzoyl)-Ph | Ph |
| 61 | S | 4-F-Ph | S | 4-F-Ph | S | 4-(2-Cl-benzoyl)-Ph | Ph |
| 62 | S | 3-F-Ph | S | 3-F-Ph | S | 3-PhCS-Ph | 3-Me-4-Cl-Ph |
| 63 | S | 4-F-Ph | S | 4-F-Ph | S | 4-MeOCO-Ph | 3-Cl-4-Me-Ph |
| 64 | S | 3-Cl-Ph | S | 3-Cl-Ph | S | 4-Me$_2$NCO-Ph | 4-Ph-3-Me-Ph |
| 65 | S | 4-Cl-Ph | S | 4-Cl-Ph | S | 4-Me(Ph)NCO-Ph | 4-Ph-3-Cl-Ph |
| 66 | S | 3-Me-Ph | S | 3-Me-Ph | S | 4-H2N-Ph | Ph |
| 67 | S | 4-Me-Ph | S | 4-Me-Ph | O | 2-MeNH-Ph | 3-Me-Ph |
| 68 | S | 3-MeO-Ph | S | 3-MeO-Ph | O | 4-PhNH-Ph | 4-Me-Ph |
| 69 | S | 4-MeO-Ph | S | 4-MeO-Ph | S | 4-Me$_2$N-Ph | 3,4-Me$_2$-Ph |

TABLE 1-continued

| # | $A^U$ | $R^U$ | $A^V$ | $R^V$ | $A^W$ | $R^W$ | $Z^Y$ |
|---|---|---|---|---|---|---|---|
| 70 | S | 3-CF$_3$-Ph | S | 3-CF$_3$-Ph | S | 3-Ph$_2$N-Ph | 5-indanyl (2,3-dihydro-1H-inden-5-yl) |
| 71 | S | | S | | S | 4-(piperidin-1-yl)-Ph | 4-iPr-Ph |
| 72 | S | 2,3-dihydrobenzofuran-5-yl | S | benzo[d][1,3]dioxol-5-yl | S | Ph | 3-Cl-Ph |
| 73 | S | | S | | S | 3-F-Ph | 4-Cl-Ph |
| 74 | S | | S | | S | 4-F-Ph | 3,4-Cl$_2$-Ph |
| 75 | S | | S | | S | 3-Cl-Ph | 4-Ph-Ph |
| 76 | S | | S | | S | 4-Cl-Ph | 4-MeSO$_2$NH-Ph |
| 77 | S | | S | | S | 3-Me-Ph | 4-MeNHNH-Ph |
| 78 | S | | S | | S | 4-Me-Ph | 4-MeNHNMe-Ph |
| 79 | S | | S | | S | 3-MeO-Ph | 3-Me$_2$C=N-Ph |
| 80 | S | | S | | S | 4-MeO-Ph | 3-Ph$_2$C=N-Ph |
| 81 | S | | S | | S | 3-CF$_3$-Ph | |
| 82 | S | benzo[d][1,3]dioxol-5-yl | S | benzo[d][1,3]dioxol-5-yl | S | 4-MeSO$_2$NH-Ph | 2'-Me-biphenyl-4-yl |
| 83 | S | | S | | S | 4-PhSO$_2$NH-Ph | 3-Me-4-Cl-Ph |
| 84 | S | | S | | O | 4-MeSO$_2$N(Me)-Ph | 3-Cl-4-Me-Ph |
| 85 | S | | S | | S | 2-AcNH-Ph | 4-Ph-3-Me-Ph |
| 86 | S | | S | | O | 4-AcN(Me)-Ph | 4-Ph-3-Cl-Ph |
| 87 | S | | S | | S | 4-MeOCONH-Ph | Ph |
| 88 | S | | S | | O | 3-MeNHSO$_2$-Ph | 3-Me-Ph |
| 89 | S | 3-MeO-Ph | S | 3-MeO-Ph | S | 4-PhNHSO$_2$-Ph | 3-Me-Ph |
| | | | | | O | 4-NO$_2$-Ph | 4-Me-Ph |
| | | | | | S | 3-CN-Ph | 3,4-Me$_2$-Ph |
| | | | | | O | 4-(4-pyridyl)-Ph | 3-Cl-Ph |
| | | | | | O | 3-(3-furyl)-Ph | 4-Cl-Ph |
| | | | | | S | 4-(2-thienyl)-Ph | 3,4-Cl$_2$-Ph |
| | | | | | S | 4-(1H-pyrazol-1-yl)-Ph | 4-Ph-Ph |

TABLE 1-continued

| | $A^U$ | $R^U$ | $A^V$ | $R^V$ | $A^W$ | $R^W$ | $Z^Y$ |
|---|---|---|---|---|---|---|---|
| 90 | S | 4-MeO-Ph | S | 4-MeO-Ph | O | (2-benzothiazolyl-phenyl) | (2-Me-biphenyl-4-yl) |
| 91 | S | 3-CF$_3$-Ph | S | 3-CF$_3$-Ph | S | 4-Ph-Ph | 3-Me-4-Cl-Ph |
| 92 | S | (benzo[1,3]dioxol-5-yl) | S | (benzo[1,3]dioxol-5-yl) | O | 4-Ph-2-Me-Ph | 3-Cl-4-Me-Ph |
| 93 | S | Ph | S | Ph | S | 4-Ph-3-Cl-Ph | 4-Ph-3-Me-Ph |
| 94 | S | 3-F-Ph | S | 3-F-Ph | S | (2-Me-biphenyl-4-yl) | 4-Ph-3-Cl-Ph |
| 95 | S | 4-Me-Ph | S | 4-Me-Ph | S | (4'-Cl-4-Me-biphenyl) | 4-Me-Ph |
| 96 | S | 4-F-Ph | S | 4-F-Ph | S | 1-Np | Ph |
| 97 | O | Me | S | 4-F-Ph | O | 2-Np | Ph |
| 98 | S | 3-Cl-Ph | S | 3-Cl-Ph | S | (7-quinolinyl) | 3-Me-Ph |
| 99 | S | 4-Cl-Ph | S | 4-Cl-Ph | S | (dibenzothiophen-yl) | 4-Me-Ph |
| 100 | S | 3-Me-Ph | S | 3-Me-Ph | S | Me | 3,4-Me$_2$-Ph |
| 101 | S | 4-Me-Ph | S | 4-Me-Ph | S | iPr | (2,3-dihydro-1H-inden-5-yl) |

TABLE 1-continued

| | $A^U$ | $R^U$ | $A^V$ | $R^V$ | $A^W$ | $R^W$ | $Z^Y$ |
|---|---|---|---|---|---|---|---|
| 102 | S | 3-MeO-Ph | S | 3-MeO-Ph | S | tBu | 4-iPr-Ph |
| 103 | S | 4-MeO-Ph | S | 4-MeO-Ph | O | n-CH$_3$(CH$_2$)$_{11}$ | 3-Cl-Ph |
| 104 | S | 3-CF$_3$-Ph | S | 3-CF$_3$-Ph | S | [structure] | 4-Cl-Ph |
| 105 | S | [benzodioxole] | S | [benzodioxole] | O | [structure] | 3,4-Cl$_2$-Ph |
| 106 | S | Ph | S | Ph | S | MeO(CH$_2$)4 | 4-Ph-Ph |
| 107 | S | 3-F-Ph | S | 3-F-Ph | S | PhO(CH$_2$)4 | [2-Me-biphenyl structure] |
| 108 | S | 4-F-Ph | S | 4-F-Ph | S | MeS(CH$_2$)4 | 3-Me-4-Cl-Ph |
| 109 | S | 3-Cl-Ph | S | 3-Cl-Ph | S | ClCH$_2$(CH$_2$)3 | 3-Cl-4-Me-Ph |
| 110 | S | 4-Cl-Ph | S | 4-Cl-Ph | S | CF$_3$(CH$_2$)3 | 4-Ph-3-Me-Ph |
| 111 | S | 3-Me-Ph | S | 3-Me-Ph | O | NO$_2$(CH$_2$)4 | 4-Ph-3-Cl-Ph |
| 112 | S | 4-Me-Ph | S | 4-Me-Ph | O | NC(CH$_2$)4 | Ph |
| 113 | S | 3-MeO-Ph | S | 3-MeO-Ph | S | Ac(CH$_2$)4 | 3-Me-Ph |
| 114 | S | 4-MeO-Ph | S | 4-MeO-Ph | S | AcO(CH$_2$)4 | 4-Me-Ph |
| 115 | S | [benzodioxole] | S | [benzodioxole] | S | Ay | [indane structure] |
| 116 | S | 3-F-Ph | S | 3-F-Ph | S | Pg | 3-Cl-Ph |
| 117 | S | 4-F-Ph | S | 4-F-Ph | O | MeOC≡CH— | 4-Cl-Ph |
| 118 | S | Ph | S | Ph | S | [structure] | 4-iPr-Ph |
| 119 | S | 3-F-Ph | S | 3-F-Ph | S | [structure] | 3-Cl-Ph |

TABLE 1-continued

| | $A^U$ | $R^U$ | $A^V$ | $R^V$ | $A^W$ | $R^W$ | $Z^Y$ |
|---|---|---|---|---|---|---|---|
| 120 | S | 4-Me-Ph | S | 4-Me-Ph | O | geranyl (4,8-dimethyl-nona-3,7-dienyl) | Ph |
| 121 | S | 4-F-Ph | S | 4-F-Ph | S | CH₂CH=CH-Cl (3-chloroallyl) | 4-Cl-Ph |
| 122 | S | 3-Cl-Ph | S | 3-Cl-Ph | S | CH₂CH=CH-Ph (cinnamyl) | 3,4-Cl₂-Ph |
| 123 | S | 4-Cl-Ph | S | 4-Cl-Ph | S | CH₂CH=CH-CH₂-OMe | 4-Ph-Ph |
| 124 | S | 3-Me-Ph | S | 3-Me-Ph | O | CH₂CH=CH-CH₂-SMe | 2-Me-biphenyl-4-yl |
| 125 | S | 4-Me-Ph | S | 4-Me-Ph | S | cyclohexyl | 3-Me-4-Cl-Ph |
| 126 | S | 3-MeO-Ph | S | 3-MeO-Ph | O | 4-methylcyclohexyl | 3-Cl-4-Me-Ph |
| 127 | S | 4-MeO-Ph | S | 4-MeO-Ph | S | 4-chlorocyclohexyl | 4-Ph-3-Me-Ph |
| 128 | S | 3-CF₃-Ph | S | 3-CF₃-Ph | S | 4-methoxycyclohexyl | 4-Ph-3-Cl-Ph |
| 129 | S | Ph | S | Ph | S | 3-chlorocyclohexyl | 4-Cl-Ph |
| 130 | S | benzo[1,3]dioxol-5-yl | S | benzo[1,3]dioxol-5-yl | O | cyclohex-2-en-1-yl | Ph |

TABLE 1-continued

| | $A^U$ | $R^U$ | $A^V$ | $R^V$ | $A^W$ | $R^W$ | $Z^Y$ |
|---|---|---|---|---|---|---|---|
| 131 | S | Ph | S | Ph | O | (4-methylcyclohex-3-en-1-yl) | 3-Me-Ph |
| 132 | S | 3-F-Ph | S | 3-F-Ph | S | (cyclohexa-1,3-dien-1-yl) | 4-Me-Ph |
| 133 | S | 4-F-Ph | S | 4-F-Ph | S | (cyclohexa-2,4-dien-1-yl) | 3,4-Me$_2$-Ph |
| 134 | S | 3-Cl-Ph | S | 3-Cl-Ph | S | (cyclohexylmethyl) | (2,3-dihydro-1H-inden-5-yl) |
| 135 | S | Ph | S | Ph | S | (4-methylcyclohexyl)methyl | 3-Me-Ph |
| 136 | S | 4-F-Ph | S | 4-F-Ph | S | (3-chlorocyclohexyl)methyl | Ph |
| 137 | S | 4-Cl-Ph | S | 4-Cl-Ph | S | (cyclopentyl-isopropyl) | 4-iPr-Ph |
| 138 | S | 3-Me-Ph | S | 3-Me-Ph | O | (decahydronaphthalen-2-yl) | 3-Cl-Ph |
| 139 | S | 4-Me-Ph | S | 4-Me-Ph | S | (bicyclo[4.1.0]heptan-3-yl) | 4-Cl-Ph |

TABLE 1-continued

| | $A^U$ | $R^U$ | $A^V$ | $R^V$ | $A^W$ | $R^W$ | $Z^Y$ |
|---|---|---|---|---|---|---|---|
| 140 | S | 3-MeO-Ph | S | 3-MeO-Ph | O | octahydroindanyl | 3,4-Cl$_2$-Ph |
| 141 | S | 4-F-Ph | S | 4-F-Ph | S | indanyl | Ph |
| 142 | S | 4-MeO-Ph | S | 4-MeO-Ph | O | Bn | 4-Ph-Ph |
| 143 | S | 3-CF$_3$-Ph | S | 3-CF$_3$-Ph | S | Me | 2-Me-biphenyl |
| 144 | S | benzodioxolyl | S | benzodioxolyl | O | MeO | 3-Me-4-Cl-Ph |
| 145 | S | Ph | S | Ph | S | Cl | 3-Cl-4-Me-Ph |
| 146 | S | 3-F-Ph | S | 3-F-Ph | S | CHMe(Ph) | 4-Ph-3-Me-Ph |
| 147 | S | 4-F-Ph | S | 4-F-Ph | S | 2-pyridyl-CH$_2$ | 4-Ph-3-Cl-Ph |
| 148 | S | 3-Cl-Ph | S | 3-Cl-Ph | S | 5-Cl-2-pyridyl-CH$_2$ | Ph |

TABLE 1-continued

| | $A^U$ | $R^U$ | $A^V$ | $R^V$ | $A^W$ | $R^W$ | $Z^Y$ |
|---|---|---|---|---|---|---|---|
| 149 | S | 4-Cl-Ph | S | 4-Cl-Ph | S | furfuryl | 3-Me-Ph |
| 150 | S | 3-Me-Ph | S | 3-Me-Ph | O | 5-Me-thienyl-CH2 | 4-Me-Ph |
| 151 | S | 4-Me-Ph | S | 4-Me-Ph | S | 2-pyridyl | 3,4-Me2-Ph |
| 152 | S | 3-MeO-Ph | S | 3-MeO-Ph | S | 5-Cl-2-pyridyl | indanyl |
| 153 | S | 4-MeO-Ph | S | 4-MeO-Ph | O | 6-MeO-2-pyridyl | 4-iPr-Ph |
| 154 | S | 3-CF3-Ph | S | 3-CF3-Ph | S | 2-thienyl | 3-Cl-Ph |
| 155 | S | benzodioxolyl | S | benzodioxolyl | O | 3-furyl | 4-Cl-Ph |
| 156 | S | Ph | S | Ph | O | pyrrolyl | 3,4-Cl2-Ph |
| 157 | S | 3-F-Ph | S | 3-F-Ph | S | 1-Me-tetrazolyl | 4-Ph-Ph |

TABLE 1-continued

| # | $A^U$ | $R^U$ | $A^V$ | $R^V$ | $A^W$ | $R^W$ | $Z^Y$ |
|---|---|---|---|---|---|---|---|
| 158 | S | 4-F-Ph | S | 4-F-Ph | S | oxazol-2-yl | 2-Me-biphenyl-4'-yl |
| 159 | S | 3-Cl-Ph | S | 3-Cl-Ph | S | 2-Me-benzothiazol-2-yl | 3-Me-4-Cl-Ph |
| 160 | S | 4-Cl-Ph | S | 4-Cl-Ph | S | tetrahydrofuran-2-yl | 3-Cl-4-Me-Ph |
| 161 | S | 3-Me-Ph | S | 3-Me-Ph | SO$_2$ | n-butyl | 4-Ph-3-Me-Ph |
| 162 | S | 4-Me-Ph | S | 4-Me-Ph | SO$_2$ | Ph | 4-Ph-3-Cl-Ph |
| 163 | S | 3-MeO-Ph | S | 3-MeO-Ph | | NMe$_2$ | Ph |
| 164 | S | 4-MeO-Ph | S | 4-MeO-Ph | | NMe(CH$_2$Cl) | 3-Me-Ph |
| 165 | S | 3-CF$_3$-Ph | S | 3-CF$_3$-Ph | | NMe(CH$_2$OMe) | 4-Me-Ph |
| 166 | S | benzo[1,3]dioxol-5-yl | S | benzo[1,3]dioxol-5-yl | | N(CH$_2$OMe)2 | 3,4-Me$_2$-Ph |
| 167 | S | Ph | S | Ph | | NMe(CH$_2$OPh) | indan-5-yl |
| 168 | S | 3-F-Ph | S | 3-F-Ph | | NMe(CH$_2$SMe) | 4-iPr-Ph |
| 169 | S | 4-F-Ph | S | 4-F-Ph | | NMe(iPr) | 3-Cl-Ph |
| 170 | S | 4-Me-Ph | S | 4-Me-Ph | | NMe(CH(iBu)(n-Pr)) | Ph |
| 171 | S | 3-F-Ph | S | 3-F-Ph | | N(Me)(CH$_2$CH=CH$_2$) | 3-Me-Ph |

TABLE 1-continued

| | $A^U$ | $R^U$ | $A^V$ | $R^V$ | $A^W$ | $R^W$ | $Z^Y$ |
|---|---|---|---|---|---|---|---|
| 172 | S | 4-F-Ph | S | 4-F-Ph | | Me-N-CH₂C≡CH | 4-Me-Ph |
| 173 | S | 4-Cl-Ph | S | 4-Cl-Ph | | NMePh | 3,4-Cl₂-Ph |
| 174 | S | 3-MeO-Ph | S | 3-MeO-Ph | | NPh2 | 3-Me-4-Cl-Ph |
| 175 | S | 4-MeO-Ph | S | 4-MeO-Ph | | Me-N-(3-Me-Ph) | 3-Cl-4-Me-Ph |
| 176 | S | 3-CF₃-Ph | S | 3-CF₃-Ph | | Me-N-(4-Cl-Ph) | 4-Ph-3-Me-Ph |
| 177 | S | 3,4-methylenedioxyphenyl | S | 3,4-methylenedioxyphenyl | | Me-N-c-Hex | 4-Ph-3-Cl-Ph |
| 178 | S | 4-Me-Ph | S | 4-Me-Ph | | Me-N-(4-Me-c-Hex) | Ph |
| 179 | S | 3-F-Ph | S | 3-F-Ph | | Me-N-(CH₂)₁₁Me | 3-Me-Ph |
| 180 | S | 4-F-Ph | S | 4-F-Ph | | iso-propyl-N-(CH₂)₁₁Me | 4-Me-Ph |
| 181 | S | 3-Cl-Ph | S | 3-Cl-Ph | | c-hex-N-(CH₂)₁₁Me | 3,4-Me₂-Ph |

TABLE 1-continued
| | $A^U$ | $R^U$ | $A^V$ | $R^V$ | $A^W$ | $R^W$ | $Z^Y$ |
|---|---|---|---|---|---|---|---|
| 182 | S | 4-Cl-Ph | S | 4-Cl-Ph | |  Me—N— |  |
| 183 | S | 3-MeO-Ph | S | 3-MeO-Ph | | (CH₂)₁₁CH₃—N— | 4-Cl-Ph |
| 184 | S | 4-MeO-Ph | S | 4-MeO-Ph | | Ph—N— | 3,4-Cl₂-Ph |
| 185 | S | 4-Me-Ph | S | 4-Me-Ph | |  Me—N— (pyrrole) | 3-Cl-Ph |
| 186 | S | 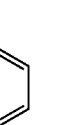 | S |  | | Me—N—Ac |  |
| 187 | S | Ph | S | Ph | | Ph—N—Ac | 3-Me-4-Cl-Ph |
| 188 | S | 3-F-Ph | S | 3-F-Ph | | Me—N—OMe | 3-Cl-4-Me-Ph |
| 189 | S | 4-F-Ph | S | 4-F-Ph | | Ph—N—OMe | 4-Ph-3-Me-Ph |
| 190 | S | 3-Cl-Ph | S | 3-Cl-Ph | | Me—N—NHMe | 4-Ph-3-Cl-Ph |
| 191 | S | 4-Cl-Ph | S | 4-Cl-Ph | | Ph—N—NHMe | 3-Cl-4-Me-Ph |

TABLE 1-continued

| | $A^U$ | $R^U$ | $A^V$ | $R^V$ | $A^W$ | $R^W$ | $Z^Y$ |
|---|---|---|---|---|---|---|---|
| 192 | S | 3-Me-Ph | S | 3-Me-Ph | | | 4-Ph-3-Me-Ph |
| 193 | S | 4-Me-Ph | S | 4-Me-Ph | |  | 4-Ph-3-Cl-Ph |
| 194 | S | Ph | S | Ph | S | Ph | 2-Me-Ph |
| 195 | S | 3-F-Ph | S | 3-F-Ph | S | 2-Cl-Ph | 3-Me-Ph |
| 196 | S | 4-F-Ph | S | 4-F-Ph | S | 3-Cl-Ph | 4-Me-Ph |
| 197 | S | 3-Cl-Ph | S | 3-Cl-Ph | S | 4-Cl-Ph | 4-Hex-Ph |
| 198 | S | 4-Cl-Ph | S | 4-Cl-Ph | S | 2,5-Cl$_2$-Ph | 3-iPr-Ph |
| 199 | S | 3-Me-Ph | S | 3-Me-Ph | S | 3,5-Cl$_2$-Ph | 4-tBu-Ph |
| 200 | S | 4-Me-Ph | S | 4-Me-Ph | O | 3-Me-Ph | 4-cHx-Ph |
| 201 | S | 3-MeO-Ph | S | 3-MeO-Ph | O | 4-Me-Ph | 3,4-Me$_2$-Ph |
| 202 | S | 4-MeO-Ph | S | 4-MeO-Ph | O | 2,3-Me$_2$-Ph | 3,5-Me$_2$-Ph |
| 203 | S | 3-CF$_3$-Ph | S | 3-CF$_3$-Ph | O | 3-MeO-Ph | 3,4,5-Me$_3$-Ph |
| 204 | S | 3-Cl-Ph | S | 3-Cl-Ph | S | 4-MeO-Ph |  |
| 205 | S |  | S |  | S | 1-Np | 3-Ay-Ph |
| 206 | S | Ph | S | Ph | S | 2-Np | 4-Pg-Ph |
| 207 | S | 3-F-Ph | S | 3-F-Ph | S | Ph | 4-Bn-Ph |
| 208 | S | 4-F-Ph | S | 4-F-Ph | S | 2-Cl-Ph |  |
| 209 | S | 3-Me-Ph | S | 3-Me-Ph | O | Ph |  |
| 210 | S | 3-Cl-Ph | S | 3-Cl-Ph | S | 3-Cl-Ph |  |

TABLE 1-continued

| # | $A^U$ | $R^U$ | $A^V$ | $R^V$ | $A^W$ | $R^W$ | $Z^Y$ |
|---|---|---|---|---|---|---|---|
| 211 | S | 4-Cl-Ph | S | 4-Cl-Ph | S | 4-Cl-Ph | 4-MeOCH$_2$-Ph |
| 212 | S | 4-F-Ph | S | 4-F-Ph | S | Ph | 4-PhOCH$_2$-Ph |
| 213 | S | 3-Me-Ph | S | 3-Me-Ph | S | 2,5-Cl$_2$-Ph | 4-MeSCH$_2$-Ph |
| 214 | S | 4-Me-Ph | S | 4-Me-Ph | S | 3,5-Cl$_2$-Ph | 4-ClCH$_2$-Ph |
| 215 | S | 3-MeO-Ph | S | 3-MeO-Ph | O | 3-Me-Ph | 3-CCl$_3$-Ph |
| 216 | S | 4-MeO-Ph | S | 4-MeO-Ph | O | 4-Me-Ph | 4-CF$_3$-Ph |
| 217 | S | 3-CF$_3$-Ph | S | 3-CF$_3$-Ph | O | 2,3-Me$_2$-Ph | 3-Vn-Ph |
| 218 | S | 3-Cl-Ph | S | 3-Cl-Ph | O | 3-MeO-Ph | (4-isopropenylphenyl) |
| 219 | S | (methylenedioxyphenyl) | S | (methylenedioxyphenyl) | S | 4-MeO-Ph | (4-styrylphenyl, Ph-CH=CH-) |
| 220 | S | Ph | S | Ph | S | 1-Np | (4-(1-chlorovinyl)phenyl) |
| 221 | S | 3-F-Ph | S | 3-F-Ph | S | 2-Np | (4-cyclohexenylphenyl) |
| 222 | S | 4-F-Ph | S | 4-F-Ph | S | Ph | (4-cyclohexenylphenyl) |
| 223 | S | 3-Cl-Ph | S | 3-Cl-Ph | S | 2-Cl-Ph | 3-Ey-Ph |
| 224 | S | 4-Cl-Ph | S | 4-Cl-Ph | S | 3-Cl-Ph | 4-MeO—C≡C-Ph |
| 225 | S | 3-Me-Ph | S | 3-Me-Ph | S | 4-Cl-Ph | 4-Cl-Ph |
| 226 | S | 4-Me-Ph | S | 4-Me-Ph | S | 2,5-Cl$_2$-Ph | 3-Me-4-Cl-Ph |
| 227 | S | 3-MeO-Ph | S | 3-MeO-Ph | S | 3,5-Cl$_2$-Ph | 3-Me-5-Cl-Ph |
| 228 | S | 4-MeO-Ph | S | 4-MeO-Ph | O | 3-Me-Ph | 4-HO-Ph |
| 229 | S | 3-CF$_3$-Ph | S | 3-CF$_3$-Ph | O | 4-Me-Ph | 3-MeO-Ph |
| 230 | S | 3-Cl-Ph | S | 3-Cl-Ph | O | 2,3-Me$_2$-Ph | (methylenedioxyphenyl) |

TABLE 1-continued

| # | $A^U$ | $R^U$ | $A^V$ | $R^V$ | $A^W$ | $R^W$ | $Z^Y$ |
|---|---|---|---|---|---|---|---|
| 231 | S | benzo[1,3]dioxol-5-yl | S | benzo[1,3]dioxol-5-yl | O | 3-MeO-Ph | 4-CF$_3$O-Ph |
| 232 | S | Ph | S | Ph | S | 4-MeO-Ph | 4-PhO-Ph |
| 233 | S | 3-F-Ph | S | 3-F-Ph | S | 1-Np | 4-MeS-Ph |
| 234 | S | 4-F-Ph | S | 4-F-Ph | S | 2-Np | 3-CF$_3$S-Ph |
| 235 | S | 3-Cl-Ph | S | 3-Cl-Ph | S | Ph | 4-PhS-Ph |
| 236 | S | 4-Cl-Ph | S | 4-Cl-Ph | S | 2-Cl-Ph | 4-MeSO-Ph |
| 237 | S | 4-Cl-Ph | S | 4-Cl-Ph | S | 2-Cl-Ph | 4-CF$_3$SO-Ph |
| 238 | S | 3-Me-Ph | S | 3-Me-Ph | S | 3-Cl-Ph | 4-PhSO-Ph |
| 239 | S | 4-Me-Ph | S | 4-Me-Ph | S | 4-Cl-Ph | 3-MeO$_2$-Ph |
| 240 | S | 3-MeO-Ph | S | 3-MeO-Ph | S | 2,5-Cl$_2$-Ph | 4-CF$_3$SO$_2$-Ph |
| 241 | S | 4-MeO-Ph | S | 4-MeO-Ph | S | 3,5-Cl$_2$-Ph | 3-PhSO$_2$-Ph |
| 242 | S | 3-CF$_3$-Ph | S | 3-CF$_3$-Ph | O | 3-Me-Ph | 4-MeSO$_2$O-Ph |
| 243 | S | 3-Cl-Ph | S | 3-Cl-Ph | O | 4-Me-Ph | 4-Me-C$_6$H$_4$-O-SO$_2$-O-C$_6$H$_4$- |
| 244 | S | benzo[1,3]dioxol-5-yl | S | benzo[1,3]dioxol-5-yl | O | 2,3-Me$_2$-Ph | 4-CHO-Ph |
| 245 | S | Ph | S | Ph | O | 3-MeO-Ph | 4-Ac-Ph |
| 246 | S | 3-F-Ph | S | 3-F-Ph | S | 4-MeO-Ph | 4-(C(=S)Me)-Ph |
| 247 | S | 4-F-Ph | S | 4-F-Ph | S | 1-Np | 3-PhCO-Ph |
| 248 | S | 3-Me-Ph | S | 3-Me-Ph | S | Ph | 3-(3-Me-C$_6$H$_4$-CO)-Ph |

TABLE 1-continued

| | $A^U$ | $R^U$ | $A^V$ | $R^V$ | $A^W$ | $R^W$ | $Z^Y$ |
|---|---|---|---|---|---|---|---|
| 249 | S | 4-Me-Ph | S | 4-Me-Ph | O | Ph |  |
| 250 | S | 3-Cl-Ph | S | 3-Cl-Ph | S | 2-Np | 4-PhCS-Ph |
| 251 | S | 4-Cl-Ph | S | 4-Cl-Ph | S | Ph | 4-MeOCO-Ph |
| 252 | S | 3-Me-Ph | S | 3-Me-Ph | S | 2-Cl-Ph | 3-Me$_2$NCO-Ph |
| 253 | S | 4-Me-Ph | S | 4-Me-Ph | S | 3-Cl-Ph | 4-Me(Ph)NCO-Ph |
| 254 | S | 3-MeO-Ph | S | 3-MeO-Ph | S | 4-Cl-Ph | 4-H$_2$N-Ph |
| 255 | S | 4-MeO-Ph | S | 4-MeO-Ph | S | 2,5-Cl$_2$-Ph | 3-MeNH-Ph |
| 256 | S | 3-CF$_3$-Ph | S | 3-CF$_3$-Ph | S | 3,5-Cl$_2$-Ph | 4-PhNH-Ph |
| 257 | S | 3-Cl-Ph | S | 3-Cl-Ph | O | 3-Me-Ph | 3-Me$_2$N-Ph |
| 258 | S | 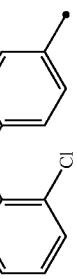 | S | 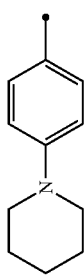 | O | 4-Me-Ph | 4-Ph$_2$N-Ph |
| 259 | S | Ph | S | Ph | O | 2,3-Me$_2$-Ph | 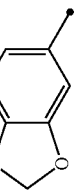 |
| 260 | S | 3-F-Ph | S | 3-F-Ph | O | 3-MeO-Ph | 3-Me-NHNH-Ph |
| 261 | S | 4-F-Ph | S | 4-F-Ph | S | 4-MeO-Ph | 4-MeNHMe-Ph |
| 262 | S | 3-Cl-Ph | S | 3-Cl-Ph | S | 1-Np | 3-Me$_2$C=N-Ph |
| 263 | S | 4-Cl-Ph | S | 4-Cl-Ph | S | 2-Np | 3-Ph$_2$C=N-Ph |
| 264 | S | 3-Me-Ph | S | 3-Me-Ph | S | Ph | 3-MeSO$_2$NH-Ph |
| 265 | S | 4-Me-Ph | S | 4-Me-Ph | S | 2-Cl-Ph | 3-PhSO$_2$NH-Ph |
| 266 | S | 3-MeO-Ph | S | 3-MeO-Ph | S | 3-Cl-Ph | 4-MeSO$_2$N(Me)-Ph |
| 267 | S | 4-MeO-Ph | S | 4-MeO-Ph | S | 4-Cl-Ph | 3-AcNH-Ph |
| 268 | S | 3-CF$_3$-Ph | S | 3-CF$_3$-Ph | S | 2,5-Cl$_2$-Ph | 4-AcN(Me)-Ph |
| 269 | S | 3-Cl-Ph | S | 3-Cl-Ph | S | 3,5-Cl$_2$-Ph | 4-MeOCONH-Ph |
| 270 | S | 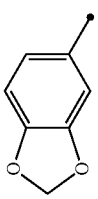 | S | 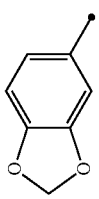 | O | 3-Me-Ph | 4-MeNHSO$_2$-Ph |
| 271 | S | Ph | S | Ph | O | 4-Me-Ph | 3-NO$_2$-Ph |
| 272 | S | 3-F-Ph | S | 3-F-Ph | O | 2,3-Me$_2$-Ph | 4-CN-Ph |
| 273 | S | 4-Cl-Ph | S | 4-Cl-Ph | S | 1-Np | 4-(4-Py)-Ph |
| 274 | S | 3-Me-Ph | S | 3-Me-Ph | S | 2-Np | 3-(3-Fu)-Ph |
| 275 | S | 4-Me-Ph | S | 4-Me-Ph | S | Ph | 4-(2-Th)-Ph |

TABLE 1-continued

| | $A^U$ | $R^U$ | $A^V$ | $R^V$ | $A^W$ | $R^W$ | $Z^Y$ |
|---|---|---|---|---|---|---|---|
| 276 | S | 3-MeO-Ph | S | 3-MeO-Ph | S | 2-Cl-Ph | 1-(4-pyrazolyl)phenyl |
| 277 | S | 4-MeO-Ph | S | 4-MeO-Ph | S | 3-Cl-Ph | 2-(4-phenyl)benzothiazole |
| 278 | S | 3-CF$_3$-Ph | S | 3-CF$_3$-Ph | S | 4-Cl-Ph | 4-Ph-Ph |
| 279 | S | 3-F-Ph | S | 3-F-Ph | S | Ph | 4'-Me-biphenyl |
| 280 | S | 4-F-Ph | S | 4-F-Ph | O | Ph | 4'-Cl-biphenyl |
| 281 | S | 3-Cl-Ph | S | 3-Cl-Ph | S | Ph | 1-Np |
| 282 | S | 3-Cl-Ph | S | 3-Cl-Ph | S | 2,5-Cl$_2$-Ph | 2-Np |
| 283 | S | 3-Cl-Ph | S | 3-Cl-Ph | S | 3,5-Cl$_2$-Ph | quinolinyl |
| 284 | S | Ph | S | Ph | O | 3-Me-Ph | dibenzofuranyl |
| 285 | S | 3-F-Ph | S | 3-F-Ph | O | 4-Me-Ph | cyclohexyl |
| 286 | S | 4-F-Ph | S | 4-F-Ph | O | 2,3-Me$_2$-Ph | 4-methylcyclohexyl |
| 283 | S | benzodioxolyl | S | benzodioxolyl | | | |

TABLE 1-continued

| | $A^U$ | $R^U$ | $A^V$ | $R^V$ | $A^W$ | $R^W$ | $Z^Y$ |
|---|---|---|---|---|---|---|---|
| 287 | S | 3-Cl-Ph | S | 3-Cl-Ph | O | 3-MeO-Ph | 4-Cl-cyclohexyl |
| 288 | S | 4-Cl-Ph | S | 4-Cl-Ph | S | 4-MeO-Ph | 4-MeO-cyclohexyl |
| 289 | S | 3-Me-Ph | S | 3-Me-Ph | S | 1-Np | cyclohexenyl |
| 290 | S | 4-Me-Ph | S | 4-Me-Ph | S | 2-Np | methylcyclohexenyl |
| 291 | S | 3-MeO-Ph | S | 3-MeO-Ph | S | Ph | cyclohexadienyl |
| 292 | S | 4-MeO-Ph | S | 4-MeO-Ph | S | 2-Cl-Ph | cyclohexadienyl |
| 293 | S | Ph | S | Ph | O | Ph | 4-Cl-cyclohexadienyl |
| 294 | S | 3-CF$_3$-Ph | S | 3-CF$_3$-Ph | S | 3-Cl-Ph | decalinyl |
| 295 | S | 3-Cl-Ph | S | 3-Cl-Ph | S | 4-Cl-Ph | bicyclo[4.1.0]heptyl |

TABLE 1-continued

| | $A^U$ | $R^U$ | $A^V$ | $R^V$ | $A^W$ | $R^W$ | $Z^Y$ |
|---|---|---|---|---|---|---|---|
| 296 | S | 3,4-methylenedioxyphenyl | S | 3,4-methylenedioxyphenyl | S | 2,5-Cl$_2$-Ph | hexahydroindanyl |
| 297 | S | Ph | S | Ph | S | Ph | indanyl |
| 298 | S | Ph | S | Ph | S | 3,5-Cl$_2$-Ph | 4-pyridyl |
| 299 | S | 3-F-Ph | S | 3-F-Ph | O | 3-Me-Ph | 2-Cl-5-pyridyl |
| 300 | S | 4-F-Ph | S | 4-F-Ph | O | 4-Me-Ph | 6-MeO-2-pyridyl |
| 301 | S | 3-Cl-Ph | S | 3-Cl-Ph | O | 2,3-Me$_2$-Ph | 2-thienyl |
| 302 | S | 4-Cl-Ph | S | 4-Cl-Ph | O | 3-MeO-Ph | 3-furyl |
| 303 | S | 3-Me-Ph | S | 3-Me-Ph | S | 4-MeO-Ph | N-Me-2-pyrrolyl |
| 304 | S | 4-F-Ph | S | 4-F-Ph | S | Ph | N-pyrrolyl |

TABLE 1-continued

| | $A^U$ | $R^U$ | $A^V$ | $R^V$ | $A^W$ | $R^W$ | $Z^Y$ |
|---|---|---|---|---|---|---|---|
| 305 | S | 4-Me-Ph | S | 4-Me-Ph | S | 1-Np | 1-methylpyrazol-5-yl |
| 306 | S | 3-MeO-Ph | S | 3-MeO-Ph | S | 2-Np | 2,5-dimethylthiazol-4-yl |
| 307 | S | 4-MeO-Ph | S | 4-MeO-Ph | S | Ph | 2-methylbenzothiazol-5-yl |
| 308 | S | 3-CF₃-Ph | S | 3-CF₃-Ph | S | 2-Cl-Ph | tetrahydrofuran-2-yl |
| 309 | S | 4-Hex-Ph | S | 4-Hex-Ph | S | 3-Cl-Ph | Ph |
| 309 | S | 4-Hex-Ph | S | 4-Hex-Ph | S | 3-Cl-Ph | Ph |
| 310 | SO | 4-iPr-Ph | S | 4-iPr-Ph | S | 4-Cl-Ph | 3-Me-Ph |
| 311 | SO₂ | 4-tBu-Ph | S | 4-tBu-Ph | S | 2,5-Cl₂-Ph | 4-Me-Ph |
| 312 | SO | 4-cHx-Ph | SO | 4-cHx-Ph | S | 3,5-Cl₂-Ph | 3,4-Me₂-Ph |
| 313 | SO₂ | 3,4-Me₂-Ph | SO₂ | 3,4-Me₂-Ph | O | 3-Me-Ph | indan-5-yl |
| 314 | S | 3,5-Me₂-Ph | S | 3,5-Me₂-Ph | O | 4-Me-Ph | 4-iPr-Ph |
| 315 | S | 3,4,5-Me₃-Ph | S | 3,4,5-Me₃-Ph | O | 2,3-Me₂-Ph | 3-Cl-Ph |
| 316 | S | indan-5-yl | S | indan-5-yl | O | 3-MeO-Ph | 4-Cl-Ph |
| 317 | S | 4-Ay-Ph | S | 4-Ay-Ph | S | 4-MeO-Ph | 3,4-Cl₂-Ph |
| 318 | S | 3-Pg-Ph | S | 3-Pg-Ph | S | 1-Np | 4-Ph-Ph |

TABLE 1-continued

| | $A^U$ | $R^U$ | $A^V$ | $R^V$ | $A^W$ | $R^W$ | $Z^Y$ |
|---|---|---|---|---|---|---|---|
| 319 | S | 4-Bn-Ph | S | 4-Bn-Ph | S | 2-Np | 2-Me-biphenyl |
| 320 | S | (1-Ph-ethyl)-Ph | S | (1-Ph-ethyl)-Ph | S | 2-Cl-Ph | 3-Me-4-Cl-Ph |
| 321 | S | 4-Me-Bn-Ph | S | 4-Me-Bn-Ph | O | Ph | Ph |
| 322 | S | 4-Cl-Bn-Ph | S | 4-Cl-Bn-Ph | S | 3-Cl-Ph | 3-Cl-4-Me-Ph |
| 323 | S | 4-MeOCH$_2$-Ph | S | 4-MeOCH$_2$-Ph | S | 4-Cl-Ph | 4-Ph-3-Me-Ph |
| 324 | S | 3-MeSCH$_2$-Ph | S | 3-MeSCH$_2$-Ph | S | 2,5-Cl$_2$-Ph | 4-Ph-3-Cl-Ph |
| 325 | S | 4-ClCH$_2$-Ph | S | 4-ClCH$_2$-Ph | S | 3,5-Cl$_2$-Ph | Ph |
| 326 | S | 3-CCl$_3$-Ph | S | 3-CCl$_3$-Ph | O | 3-Me-Ph | 3-Me-Ph |
| 327 | S | 4-AcCH$_2$-Ph | S | 4-AcCH$_2$-Ph | O | 4-Me-Ph | 4-Me-Ph |
| 328 | S | 3-Vn-Ph | S | 3-Vn-Ph | O | 2,3-Me$_2$-Ph | 3,4-Me$_2$-Ph |
| 329 | S | 4-(prop-1-en-2-yl)-Ph | S | 4-(prop-1-en-2-yl)-Ph | O | 3-MeO-Ph | indan-5-yl |
| 330 | S | 4-(1-Ph-prop-1-en-2-yl)-Ph | S | 4-(1-Ph-prop-1-en-2-yl)-Ph | S | 4-MeO-Ph | 4-iPr-Ph |
| 331 | S | 4-(1-Cl-vinyl)-Ph | S | 4-(1-Cl-vinyl)-Ph | S | 1-Np | 3-Cl-Ph |
| 332 | S | 4-cyclohexenyl-Ph | S | 4-cyclohexenyl-Ph | S | 2-Np | 4-Cl-Ph |

TABLE 1-continued

| # | $A^U$ | $R^U$ | $A^V$ | $R^V$ | $A^W$ | $R^W$ | $Z^Y$ |
|---|---|---|---|---|---|---|---|
| 333 | S | 4-methylphenyl-cyclohexenyl | S | 4-methylphenyl-cyclohexenyl | S | 2-Cl-Ph | 3,4-Cl₂-Ph |
| 334 | S | 3-Ey-Ph | S | 3-Ey-Ph | S | 3-Cl-Ph | 4-Ph-Ph |
| 335 | S | 4-MeO—C≡C-Ph | S | 4-MeO—C≡C-Ph | S | 4-Cl-Ph | 2-Me-biphenyl |
| 336 | S | 4-Cl-Ph | S | 4-Cl-Ph | S | 2,5-Cl₂-Ph | 3-Me-4-Cl-Ph |
| 337 | S | 3-Me-4-Cl-Ph | S | 3-Me-4-Cl-Ph | O | 3-Me-Ph | 4-Ph-3-Me-Ph |
| 338 | S | 3-Me-5-Cl-Ph | S | 3-Me-5-Cl-Ph | O | 4-Me-Ph | 4-Ph-3-Cl-Ph |
| 339 | S | 4-HO-Ph | S | 4-HO-Ph | O | 2,3-Me₂-Ph | Ph |
| 340 | S | 4-MeO-Ph | S | 4-MeO-Ph | O | 3-MeO-Ph | 3-Me-Ph |
| 341 | S | benzodioxole-Me | S | benzodioxole-Me | S | 4-MeO-Ph | 4-Me-Ph |
| 342 | S | 3-CF₃O-Ph | S | 3-CF₃O-Ph | S | 1-Np | 3,4-Me₂-Ph |
| 343 | S | 4-PhO-Ph | S | 4-PhO-Ph | S | 2-Np | indanyl |
| 344 | S | 4-MeS-Ph | S | 4-MeS-Ph | S | 2-Cl-Ph | 4-iPr-Ph |
| 345 | S | 3-CF₃S-Ph | S | 3-CF₃S-Ph | S | 3-Cl-Ph | 3-Cl-Ph |
| 346 | S | 4-PhS-Ph | S | 4-PhS-Ph | S | 4-Cl-Ph | 4-Cl-Ph |
| 347 | S | 3-MeSO-Ph | S | 3-MeSO-Ph | S | 2,5-Cl₂-Ph | 3,4-Cl₂-Ph |
| 348 | S | 4-PhSO-Ph | S | 4-PhSO-Ph | S | 3,5-Cl₂-Ph | 4-Ph-Ph |
| 349 | S | 4-MeSO₂-Ph | S | 4-MeSO₂-Ph | O | 3-Me-Ph | 2-Me-biphenyl |
| 350 | S | 4-CF₃SO₂-Ph | S | 4-CF₃SO₂-Ph | O | 4-Me-Ph | 3-Me-4-Cl-Ph |
| 351 | S | 3-PhSO₂-Ph | S | 3-PhSO₂-Ph | O | 2,3-Me₂-Ph | 3-Cl-4-Me-Ph |
| 352 | S | 4-PhSO₂O-Ph | S | 4-PhSO₂O-Ph | S | 4-MeO-Ph | 4-Ph-3-Cl-Ph |
| 353 | S | 3-MeSO₂O-Ph | S | 3-MeSO₂O-Ph | S | 4-MeO-Ph | 4-Ph-3-Cl-Ph |

TABLE 1-continued

| | $A^U$ | $R^U$ | $A^V$ | $R^V$ | $A^W$ | $R^W$ | $Z^Y$ |
|---|---|---|---|---|---|---|---|
| 354 | S | 4-CHO-Ph | S | 4-CHO-Ph | S | 1-Np | Ph |
| 355 | S | 4-Ac-Ph | S | 4-Ac-Ph | S | 2-Np | 3-Me-Ph |
| 356 | S | [4-(1-thioxoethyl)-Ph] | S | [4-(1-thioxoethyl)-Ph] | S | 2-Cl-Ph | 4-Me-Ph |
| 357 | S | 3-PhCO-Ph | S | 3-PhCO-Ph | S | 3-Cl-Ph | 3,4-Me$_2$-Ph |
| 358 | S | [3-methyl-4-(PhC(O))-Ph] | S | [3-methyl-4-(PhC(O))-Ph] | S | Ph | Ph |
| 359 | S | [2-Cl-4-(PhC(O))-Ph] | S | [2-Cl-4-(PhC(O))-Ph] | O | Ph | [indanyl] |
| 360 | S | 4-PhCS-Ph | S | 4-PhCS-Ph | S | 4-Cl-Ph | [6-methyl-indanyl] |
| 361 | S | 4-MeOCO-Ph | S | 4-MeOCO-Ph | S | 2,5-Cl$_2$-Ph | 4-iPr-Ph |
| 362 | S | 4-Me$_2$NCO-Ph | S | 4-Me$_2$NCO-Ph | S | 3,5-Cl$_2$-Ph | 3-Cl-Ph |
| 363 | S | 4-Me(Ph)NCO-Ph | S | 4-Me(Ph)NCO-Ph | O | 3-Me-Ph | 4-Cl-Ph |
| 364 | S | 4-H2N-Ph | S | 4-H2N-Ph | O | 4-Me-Ph | 3,4-Cl$_2$-Ph |
| 365 | S | 3-MeNH-Ph | S | 3-MeNH-Ph | O | 2,3-Me$_2$-Ph | 4-Ph-Ph |
| 366 | S | 4-PhNH-Ph | S | 4-PhNH-Ph | O | 3-MeO-Ph | [2'-methyl-biphenyl-4-yl] |
| 367 | S | 4-Me$_2$N-Ph | S | 4-Me$_2$N-Ph | S | 4-MeO-Ph | 3-Me-4-Cl-Ph |
| 368 | S | 4-Ph2N-Ph | S | 4-Ph2N-Ph | S | 1-Np | 3-Cl-4-Me-Ph |

TABLE 1-continued

| | $A^U$ | $R^U$ | $A^V$ | $R^V$ | $A^W$ | $R^W$ | $Z^Y$ |
|---|---|---|---|---|---|---|---|
| 369 | S | [4-(piperidin-1-yl)phenyl] | S | [4-(piperidin-1-yl)phenyl] | S | 2-Np | 4-Ph-3-Me-Ph |
| 370 | S | 3-MeNHNH-Ph | S | 3-MeNHNH-Ph | S | 2-Cl-Ph | 4-Ph-3-Cl-Ph |
| 371 | S | 4-MeNHNMe-Ph | S | 4-MeNHNMe-Ph | S | 3-Cl-Ph | Ph |
| 372 | S | 3-Me$_2$C=N-Ph | S | 3-Me$_2$C=N-Ph | S | 4-Cl-Ph | 3-Me-Ph |
| 373 | S | 3-Ph$_2$C=N-Ph | S | 3-Ph$_2$C=N-Ph | S | 2,5-Cl$_2$-Ph | 4-Me-Ph |
| 374 | S | 4-MeSO$_2$NH-Ph | S | 4-MeSO$_2$NH-Ph | S | 3,5-Cl$_2$-Ph | 3,4-Me$_2$-Ph |
| 375 | S | 4-PhSO$_2$NH-Ph | S | 4-PhSO$_2$NH-Ph | O | 3-Me-Ph | [indan-5-yl] |
| 376 | S | 4-MeSO$_2$N(Me)-Ph | S | 4-MeSO$_2$N(Me)-Ph | O | 4-Me-Ph | 4-iPr-Ph |
| 377 | S | 3-AcNH-Ph | S | 3-AcNH-Ph | O | 2,3-Me$_2$-Ph | 3-Cl-Ph |
| 378 | S | 4-AcN(Me)-Ph | S | 4-AcN(Me)-Ph | O | 3-MeO-Ph | 4-Cl-Ph |
| 379 | S | 4-MeOCONH-Ph | S | 4-MeOCONH-Ph | S | 4-MeO-Ph | 3,4-Cl$_2$-Ph |
| 380 | S | 4-MeNHSO$_2$-Ph | S | 4-MeNHSO$_2$-Ph | S | 1-Np | 4-Ph-Ph |
| 381 | S | 4-NO$_2$-Ph | S | 4-NO$_2$-Ph | S | 2-Np | [2'-Me-biphenyl-4-yl] |
| 382 | S | 3-CN-Ph | S | 3-CN-Ph | S | 2-Cl-Ph | 3-Me-4-Cl-Ph |
| 383 | S | 4-(4-Py)-Ph | S | 4-(4-Py)-Ph | S | 2,5-Cl$_2$-Ph | 4-Ph-3-Cl-Ph |
| 384 | S | 3-(3-Fu)-Ph | S | 3-(3-Fu)-Ph | S | 3,5-Cl$_2$-Ph | Ph |
| 385 | S | 4-(2-Th)-Ph | S | 4-(2-Th)-Ph | O | 3-Me-Ph | 3-Me-Ph |
| 386 | S | [4-(pyrrol-1-yl)phenyl] | S | [4-(pyrrol-1-yl)phenyl] | O | 4-Me-Ph | 4-Me-Ph |
| 387 | S | [4-(oxazol-2-yl)phenyl] | S | [4-(oxazol-2-yl)phenyl] | O | 2,3-Me$_2$-Ph | 3,4-Me$_2$-Ph |

TABLE 1-continued
| | $A^U$ | $R^U$ | $A^V$ | $R^V$ | $A^W$ | $R^W$ | $Z^Y$ |
|---|---|---|---|---|---|---|---|
| 388 | S | 4-Ph-Ph | S | 4-Ph-Ph | O | 3-MeO-Ph |  |
| 389 | S |  | S |  | S | Ph | 3-Me-Ph |
| 390 | S | 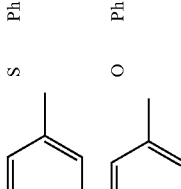 | S |  | O | Ph | 4-Me-Ph |
| 391 | S | 1-Np | S | 1-Np | S | 4-MeO-Ph | 4-iPr-Ph |
| 392 | S | 2-Np | S | 2-Np | S | 4-MeO-Ph | 4-iPr-Ph |
| 393 | S | 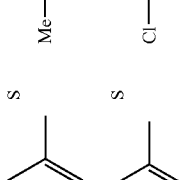 | S |  | S | 1-Np | 3-Cl-Ph |
| 394 | S | 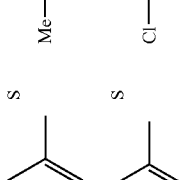 | S |  | S | 2-Np | 4-Cl-Ph |
| 395 | S | Me | S | Me | S | 2-Cl-Ph | 3,4-Cl$_2$-Ph |
| 396 | S | Me | S | Ph | S | 2-Cl-Ph | 3,4-Cl$_2$-Ph |
| 397 | O | Me | S | Ph | S | 2-Cl-Ph | 3,4-Cl$_2$-Ph |
| 398 | SO | iPr | S | iPr | S | 3-Cl-Ph | 4-Ph-Ph |
| 399 | SO$_2$ | tBu | S | tBu | S | 4-Cl-Ph | 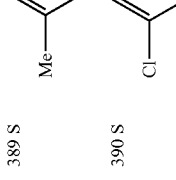 |
| 400 | S | n-CH$_3$(CH$_2$)11 | S | n-CH$_3$(CH$_2$)11 | S | 2,5-Cl$_2$-Ph | 3-Me-4-Cl-Ph |
| 401 | SO | 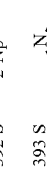 | SO | 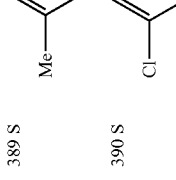 | S | 3,5-Cl$_2$-Ph | 3-Cl-4-Me-Ph |

TABLE 1-continued

| | $A^U$ | $R^U$ | $A^V$ | $R^V$ | $A^W$ | $R^W$ | $Z^Y$ |
|---|---|---|---|---|---|---|---|
| 402 | SO$_2$ |  | SO$_2$ |  | O | 3-Me-Ph | 4-Ph-3-Me-Ph |
| 403 | S | MeO(CH$_2$)$_4$ | S | MeO(CH$_2$)$_4$ | O | 4-Me-Ph | 4-Ph-3-Cl-Ph |
| 404 | S | PhO(CH$_2$)$_4$ | S | PhO(CH$_2$)$_4$ | O | 2,3-Me$_2$-Ph | Ph |
| 405 | S | MeS(CH$_2$)$_4$ | S | MeS(CH$_2$)$_4$ | O | 3-MeO-Ph | 3-Me-Ph |
| 406 | S | ClCH$_2$(CH$_2$)$_3$ | S | ClCH$_2$(CH$_2$)$_3$ | S | 4-MeO-Ph | 4-Me-Ph |
| 407 | S | CF$_3$(CH$_2$)$_3$ | S | CF$_3$(CH$_2$)$_3$ | S | 1-Np | 3,4-Me$_2$-Ph |
| 408 | S | NO$_2$(CH$_2$)$_4$ | S | NO$_2$(CH$_2$)$_4$ | S | 2-Np |  |
| 409 | S | NC(CH$_2$)$_4$ | S | NC(CH$_2$)$_4$ | S | 2-Cl-Ph | 4-iPr-Ph |
| 410 | S | Ac(CH$_2$)$_4$ | S | Ac(CH$_2$)$_4$ | S | 3-Cl-Ph | 3-Cl-Ph |
| 411 | S | AcO(CH$_2$)$_4$ | S | AcO(CH$_2$)$_4$ | S | 4-Cl-Ph | 4-Cl-Ph |
| 412 | SO | Ay- | SO | Ay- | S | 3,5-Cl$_2$-Ph | 4-Ph-Ph |
| 413 | SO$_2$ |  | S | 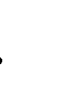 | O | 3-Me-Ph |  |
| 414 | S | 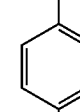 | S | 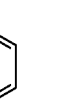 | O | 4-Me-Ph | 3-Me-4-Cl-Ph |
| 415 | SO |  | SO |  | O | 2,3-Me$_2$-Ph | 3-Cl-4-Me-Ph |
| 416 | SO$_2$ |  | SO$_2$ |  | O | 3-MeO-Ph | 4-Ph-3-Me-Ph |
| 417 | S |  | S |  | S | 4-MeO-Ph | 4-Ph-3-Cl-Ph |
| 418 | S | 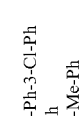 | S |  | S | 1-Np | Ph |
| 419 | S | Pg | S | Pg | S | 2-Cl-Ph | 4-Me-Ph |
| 420 | S |  | S |  | S | 2-Np | 3-Me-Ph |

TABLE 1-continued

| | $A^U$ | $R^U$ | $A^V$ | $R^V$ | $A^W$ | $R^W$ | $Z^Y$ |
|---|---|---|---|---|---|---|---|
| 421 | S | cyclohexyl | S | Ph | S | Ph | 3-Me-Ph |
| 422 | SO | 4-Me-cyclohexyl | S | 4-Me-cyclohexyl | S | 2-Cl-Ph | 4-Me-Ph |
| 423 | SO$_2$ | 4-Cl-cyclohexyl | S | 4-Cl-cyclohexyl | S | 3-Cl-Ph | 3,4-Me$_2$-Ph |
| 424 | S | 4-MeO-cyclohexyl | S | 4-MeO-cyclohexyl | S | 4-Cl-Ph | 5-Me-indanyl |
| 425 | S | cyclohexenyl | S | cyclohexenyl | S | 2,5-Cl$_2$-Ph | 4-iPr-Ph |
| 426 | SO | 3-Me-cyclohexenyl | SO | 3-Me-cyclohexenyl | S | 3,5-Cl$_2$-Ph | 3-Cl-Ph |
| 427 | SO$_2$ | cyclohexadienyl | SO$_2$ | cyclohexadienyl | O | 3-Me-Ph | 4-Cl-Ph |
| 428 | S | cyclohexadienyl | S | cyclohexadienyl | O | 4-Me-Ph | 3,4-Cl$_2$-Ph |
| 429 | S | cyclohexylmethyl | S | cyclohexylmethyl | O | 2,3-Me$_2$-Ph | 4-Ph-Ph |
| 430 | S | 4-Me-cyclohexylmethyl | S | 4-Me-cyclohexylmethyl | S | Ph | Ph |

TABLE 1-continued

| | $A^U$ | $R^U$ | $A^V$ | $R^V$ | $A^W$ | $R^W$ | $Z^Y$ |
|---|---|---|---|---|---|---|---|
| 431 | S | iPr-cyclohexyl | S | iPr-cyclohexyl | O | 3-MeO-Ph | 2-Me-biphenyl-4-yl |
| 432 | S | decalinyl | S | decalinyl | S | 4-MeO-Ph | 3-Me-4-Cl-Ph |
| 433 | SO$_2$ | bicyclo[4.1.0]heptyl | SO$_2$ | bicyclo[4.1.0]heptyl | S | 1-Np | 3-Cl-4-Me-Ph |
| 434 | S | indanyl | S | indanyl | S | 2-Np | 4-Ph-3-Me-Ph |
| 435 | S | indanyl | S | indanyl | O | Ph | Ph |
| 436 | S | Bn | S | Bn | S | 2-Cl-Ph | 4-Ph-3-Cl-Ph |
| 437 | SO | Me-benzyl | S | Me-benzyl | S | 3-Cl-Ph | Ph |
| 438 | SO$_2$ | MeO-benzyl | S | MeO-benzyl | S | 4-Cl-Ph | 3-Me-Ph |
| 439 | S | Cl-benzyl | S | Cl-benzyl | S | 2,5-Cl$_2$-Ph | 4-Me-Ph |

TABLE 1-continued

| # | $A^U$ | $R^U$ | $A^V$ | $R^V$ | $A^W$ | $R^W$ | $Z^Y$ |
|---|---|---|---|---|---|---|---|
| 440 | SO | iPr-Ph | SO | iPr-Ph | S | 3,5-Cl$_2$-Ph | 3,4-Me$_2$-Ph |
| 441 | SO$_2$ | 2-picolyl | SO$_2$ | 2-picolyl | O | 3-Me-Ph | indanyl |
| 442 | S | 5-Cl-pyridin-2-yl-methyl | S | 5-Cl-pyridin-2-yl-methyl | O | 4-Me-Ph | 4-iPr-Ph |
| 443 | S | furfuryl | S | furfuryl | O | 2,3-Me$_2$-Ph | 3-Cl-Ph |
| 444 | S | 5-Me-thien-2-yl-methyl | S | 5-Me-thien-2-yl-methyl | O | 3-MeO-Ph | 4-Cl-Ph |
| 445 | S | pyrazin-2-yl | S | pyrazin-2-yl | S | 4-MeO-Ph | 3,4-Cl$_2$-Ph |
| 446 | SO | 5-Cl-pyridin-2-yl | SO | 5-Cl-pyridin-2-yl | S | 1-Np | 4-Ph-Ph |
| 447 | SO$_2$ | 6-MeO-pyridin-2-yl | SO$_2$ | 6-MeO-pyridin-2-yl | S | 2-Np | 2-Me-4-Ph-Ph |
| 448 | S | thien-2-yl | S | thien-2-yl | S | 2-Cl-Ph | 3-Me-4-Cl-Ph |

TABLE 1-continued

| # | $A^U$ | $R^U$ | $A^V$ | $R^V$ | $A^W$ | $R^W$ | $Z^Y$ |
|---|---|---|---|---|---|---|---|
| 449 | SO | 3-furyl | SO | 3-furyl | S | 3-Cl-Ph | 3-Cl-4-Me-Ph |
| 450 | SO | 3-furyl | SO | Ph | S | 3-Cl-Ph | 3-Cl-4-Me-Ph |
| 451 | SO$_2$ | 1-Me-pyrrol-2-yl | SO$_2$ | 1-Me-pyrrol-2-yl | S | 4-Cl-Ph | 4-Ph-3-Me-Ph |
| 452 | S | 1-Me-tetrazol-5-yl | S | 1-Me-tetrazol-5-yl | S | 2,5-Cl$_2$-Ph | 4-Ph-3-Cl-Ph |
| 453 | S | 2-oxazolyl | S | 2-oxazolyl | S | 3,5-Cl$_2$-Ph | Ph |
| 454 | S | 2-benzothiazolyl | S | 2-benzothiazolyl | O | 3-Me-Ph | 3-Me-Ph |
| 455 | S | 2-tetrahydrothienyl | S | 2-tetrahydrothienyl | O | 4-Me-Ph | 4-Me-Ph |
| 456 | S | Ac | S | Ac | O | 2,3-Me$_2$-Ph | 3,4-Me$_2$-Ph |
| 457 | S | Ph | S | Ph | O | 2,3-Me$_2$-Ph | 3,4-Me$_2$-Ph |
| 458 | O | isobutyryl | O | isobutyryl | O | 3-MeO-Ph | indanyl |
| 459 | S | crotonyl | S | crotonyl | S | 4-MeO-Ph | 4-iPr-Ph |

TABLE 1-continued

| # | $A^U$ | $R^U$ | $A^V$ | $R^V$ | $A^W$ | $R^W$ | $Z^Y$ |
|---|---|---|---|---|---|---|---|
| 460 | S | C(O)C≡CMe | S | C(O)C≡CMe | S | 1-Np | 3-Cl-Ph |
| 461 | S | C(O)-cyclohexyl | S | C(O)-cyclohexyl | S | 2-Np | 4-Cl-Ph |
| 462 | O | CH(F)C(O)- | O | CH(F)C(O)- | S | 2-Cl-Ph | 3,4-Cl$_2$-Ph |
| 463 | S | CH$_2$(OMe)C(O)- | S | Ph | S | 3-Cl-Ph | 4-Ph-Ph |
| 464 | S | CH$_2$(OPh)C(O)- | S | CH$_2$(OPh)C(O)- | S | 4-Cl-Ph | 2-Me-2′-Ph (biphenyl) |
| 465 | S | CH$_2$(SMe)C(O)- | S | CH$_2$(SMe)C(O)- | S | 2,5-Cl$_2$-Ph | 3-Me-4-Cl-Ph |
| 466 | S | CH$_2$(SPh)C(O)- | S | CH$_2$(SPh)C(O)- | S | 3,5-Cl$_2$-Ph | 3-Cl-4-Me-Ph |
| 467 | S | MeOC(O)- | S | MeOC(O)- | O | 3-Me-Ph | 4-Ph-3-Me-Ph |
| 468 | S | C(O)Ph | S | Ph | O | 4-Me-Ph | 4-Ph-3-Cl-Ph |

TABLE 1-continued

| # | $A^U$ | $R^U$ | $A^V$ | $R^V$ | $A^W$ | $R^W$ | $Z^Y$ |
|---|---|---|---|---|---|---|---|
| 469 | S | 4-Me-C6H4-C(O)- | S | 4-Me-C6H4-C(O)- | O | 2,3-Me2-Ph | Ph |
| 470 | O | 3-Cl-C6H4-C(O)- | O | 3-Cl-C6H4-C(O)- | O | 3-MeO-Ph | 3-Me-Ph |
| 471 | S | iPr-C(=S)- | S | iPr-C(=S)- | S | 4-MeO-Ph | 4-Me-Ph |
| 472 | S | (E)-MeCH=CH-C(=S)- | S | PhCH2-C(=S)- | S | 1-Np | 3,4-Me2-Ph |
| 473 | S | MeC≡C-C(=S)- | S | MeC≡C-C(=S)- | S | 2-Np | 5-indanyl |
| 474 | S | Cy-C(=S)- | S | Cy-C(=S)- | S | 2-Cl-Ph | 4-iPr-Ph |
| 475 | S | FCH2-C(=S)- | S | FCH2-C(=S)- | S | 3-Cl-Ph | 3-Cl-Ph |
| 476 | S | MeOCH2-C(=S)- | S | MeOCH2-C(=S)- | S | 4-Cl-Ph | 4-Cl-Ph |
| 477 | S | PhOCH2-C(=S)- | S | Ph-C(=S)- | S | 2,5-Cl2-Ph | 3,4-Cl2-Ph |

TABLE 1-continued

| | $A^U$ | $R^U$ | $A^V$ | $R^V$ | $A^W$ | $R^W$ | $Z^Y$ |
|---|---|---|---|---|---|---|---|
| 478 | S | MeS-CH2-C(=S)- | S | 3,5-Cl2-Ph | S | 3,5-Cl2-Ph | 4-Ph-Ph |
| 479 | S | PhS-CH2-C(=S)- | S | 3-Me-Ph | O | 3-Me-Ph | 2-Me-biphenyl-4-yl |
| 480 | S | MeO-C(=S)- | S | Ph | O | 4-Me-Ph | 3-Me-4-Cl-Ph |
| 481 | S | Ph-C(=S)- | S | Ph | O | 2,3-Me2-Ph | 3-Cl-4-Me-Ph |
| 482 | S | 4-Me-Ph-C(=S)- | S | Ph | O | 3-MeO-Ph | 4-Ph-3-Me-Ph |
| 483 | S | 3-Cl-Ph-C(=S)- | S | Cl-Ph | S | 4-MeO-Ph | 4-Ph-3-Cl-Ph |
| 484 | O | SO2Me | S | Ph | S | 1-Np | Ph |
| 485 | O | SO2Ph | O | Ph | S | 2-Np | 3-Me-Ph |
| 486 | O | 4-Me-Ph-SO2- | S | 4-Cl-Ph | S | 2-Cl-Ph | 4-Me-Ph |
| 487 | | Cl | S | Ph | S | 3-Cl-Ph | 3,4-Me2-Ph |

Compounds represented by the formula (Iβ):

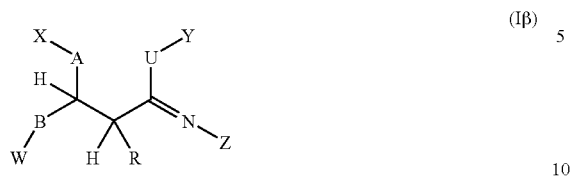
(Iβ)

wherein U, Y, Z, A, X, B, W and R are any one of combinations 1 to 88 shown in the following table 2.

TABLE 2

| NO. | U | Y | Z | A | X | B | W | R |
|---|---|---|---|---|---|---|---|---|
| 1 | S | Ph | Ph | S | Ph | S | Ph | Me |
| 2 | S | 2-Cl-Ph | 3-Me-Ph | S | 3-F-Ph | S | 3-F-Ph | iPr |
| 3 | S | 3-Cl-Ph | 4-Me-Ph | S | 4-F-Ph | O | 4-F-Ph | tBu |
| 4 | S | 4-Cl-Ph | 3,4-Me2-Ph | S | 3-Cl-Ph | S | 3-Cl-Ph | n-C6H13 |
| 5 | O | 3,5-Cl2-Ph | 4-iPr-Ph | O | 3-Me-Ph | O | 3-Me-Ph | MeOCH2 |
| 6 | S | 4-Me-Ph | 4-Cl-Ph | S | 3-MeO-Ph | S | 3-MeO-Ph | MeSCH2 |
| 7 | O | 2,3-Me2-Ph | 3,4-Cl2-Ph | S | 4-MeO-Ph | S | 4-MeO-Ph | ClCH2 |
| 8 | S | 3-MeO-Ph | 4-Ph-Ph | S | 3-CF3-Ph | S | 3-CF3-Ph | CF3 |
| 9 | S | cyclohexylmethyl | 4-Ph-3-Cl-Ph | O | 4-F-Ph | S | 4-F-Ph | Ay- |
| 10 | S | Ph | Ph | S | 4-Cl-Ph | S | 4-Cl-Ph | Pg |
| 11 | S | 3,5-Cl2-Ph | 4-iPr-Ph | S | 4-MeO-Ph | S | 4-MeO-Ph | cyclohexyl |
| 12 | S | 1-naphthyl | 3-Me-4-Cl-Ph | SO | 4-F-Ph | S | 4-F-Ph | 4-Me-cyclohexylmethyl |
| 13 | O | Ph | Ph | S | 4-Me-Ph | S | 4-Me-Ph | Bn |
| 14 | S | 3-Cl-Ph | 4-Me-Ph | S | 3-F-Ph | S | 3-F-Ph | 2-Me-benzyl |
| 15 | O | 3-Cl-Ph | 4-Me-Ph | S | 4-MeO-Ph | S | 4-MeO-Ph | 4-MeO-benzyl |
| 16 | S | 4-Cl-Ph | 3,4-Me2-Ph | S | 3-CF3-Ph | S | 3-CF3-Ph | 4-Cl-benzyl |
| 17 | O | 2,5-Cl2-Ph | indanyl | S | benzodioxolyl | S | benzodioxolyl | 1-(2-SMe-phenyl)ethyl |
| 18 | S | 3,5-Cl2-Ph | 4-iPr-Ph | O | Ph | S | 4-Me-Ph | 2-pyridylmethyl |

TABLE 2-continued

| NO. | U | Y | Z | A | X | B | W | R |
|---|---|---|---|---|---|---|---|---|
| 19 | S | 3-Cl-Ph | 4-Me-Ph | S | 4-F-Ph | S | 4-F-Ph | 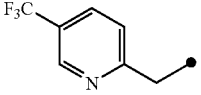 |
| 20 | O | 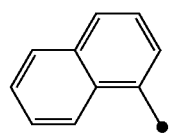 | 3-Me-4-Cl-Ph | S | 4-Me-Ph | O | 4-Me-Ph | 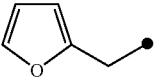 |
| 21 | O | 2-Cl-Ph | 3-Me-Ph | S | Ph | S | Ph | Ph |
| 22 | S | 3-Cl-Ph | 4-Me-Ph | S | 3-F-Ph | S | 3-F-Ph | 3-iPr-Ph |
| 23 | S | 4-MeO-Ph | 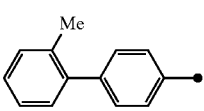 | SO | 4-MeO-Ph | S | 4-MeO-Ph | 2-CF3-Ph |
| 24 | S | 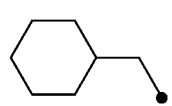 | 4-Ph-3-Cl-Ph | S | 4-Me-Ph | S | 4-Me-Ph | 4-Br-Ph |
| 25 | S | 3-Cl-Ph | 4-Me-Ph | S | 4-F-Ph | S | 4-F-Ph | 4-MeO-Ph |
| 26 | O | 3-Me-Ph | 3-Cl-Ph | S | 4-Me-Ph | S | 4-Me-Ph | 4-MeS-Ph |
| 27 | O | 4-Me-Ph | 4-Cl-Ph | S | 3-MeO-Ph | S | 3-MeO-Ph | 4-CF3S-Ph |
| 28 | S | 3-Me-Ph | 3-Cl-Ph | S | 4-F-Ph | S | 4-F-Ph | 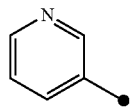 |
| 29 | | | | | | | | 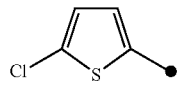 |
| 30 | S | 2-Cl-Ph | 3-Me-Ph | S | 3-F-Ph | S | 3-F-Ph | MeO |
| 31 | S | 3-Cl-Ph | 4-Me-Ph | S | 4-F-Ph | S | 4-F-Ph |  |
| 32 | S | 4-Cl-Ph | 3,4-Me2-Ph | S | 3-Cl-Ph | S | 3-Cl-Ph | MeOCH2O |
| 33 | S | 2,5-Cl2-Ph | 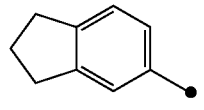 | S | 4-Cl-Ph | S | 4-Cl-Ph | PhOCH2O |
| 34 | O | 3,5-Cl2-Ph | 4-iPr-Ph | S | 3-Me-Ph | S | 3-Me-Ph | MeSCH2O |
| 35 | O | 3-Me-Ph | 3-Cl-Ph | SO2 | 4-Me-Ph | S | 4-Me-Ph | ClCH2O |
| 36 | S | 4-Me-Ph | 4-Cl-Ph | S | 3-MeO-Ph | S | 3-MeO-Ph | CF3CH2O |
| 37 | S | 2,3-Me2-Ph | 3,4-Cl2-Ph | S | 4-MeO-Ph | S | 4-MeO-Ph | 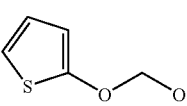 |
| 38 | S | CH3(CH2)5 | 3-Cl-4-Me-Ph | S | Ph | S | Ph | 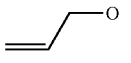 |
| 39 | S | cHx | 4-Ph-3-Me-Ph | S | 3-F-Ph | S | 3-F-Ph | 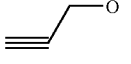 |
| 40 | O | 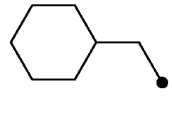 | 4-Ph-3-Cl-Ph | S | 4-Me-Ph | S | 4-Me-Ph |  |

TABLE 2-continued

| NO. | U | Y | Z | A | X | B | W | R |
|---|---|---|---|---|---|---|---|---|
| 41 | S | Ph | Ph | S | 4-F-Ph | S | 4-F-Ph |  |
| 42 | O | 4-Cl-Ph | 3,4-Me2-Ph | SO2 | 3-Me-Ph | SO2 | 3-Me-Ph | 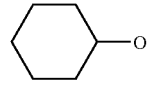 |
| 43 | O | 4-MeO-Ph | | S | Ph | S | Ph | BnO |
| 44 | S | 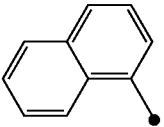 | 3-Me-4-Cl-Ph | S | 3-F-Ph | S | 3-F-Ph | 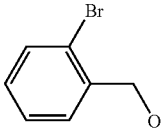 |
| 45 | S | CH3(CH2)5 | 3-Cl-4-Me-Ph | S | 4-F-Ph | S | 4-F-Ph | 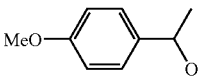 |
| 46 | S | cHx | 4-Ph-3-Me-Ph | S | 3-Cl-Ph | S | 3-Cl-Ph | 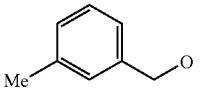 |
| 47 | S | 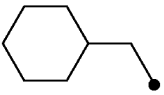 | 4-Ph-3-Cl-Ph | S | Ph | S | Ph | 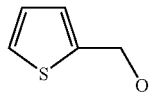 |
| 48 | O | 3-Me-Ph | 3-Cl-Ph | S | 4-MeO-Ph | S | 4-MeO-Ph | PhO |
| 49 | S | 4-Me-Ph | 4-Cl-Ph | S | 3-CF3-Ph | S | 3-CF3-Ph | 3-Me-PhO |
| 50 | S | 4-Me-Ph | 4-Cl-Ph | S | 3-F-Ph | S | 3-F-Ph | 3-Ay-PhO |
| 51 | S | 2,3-Me2-Ph | 3,4-Cl2-Ph | S | 4-F-Ph | S | 4-F-Ph | 4-Pg-PhO |
| 52 | S | CH3(CH2)5 | 3-Cl-4-Me-Ph | S | 3-Me-Ph | S | 3-Me-Ph | 3-Vn-PhO |
| 53 | O | cHx | 4-Ph-3-Me-Ph | S | 4-Me-Ph | S | 4-Me-Ph | 2-Ey-PhO |
| 54 | O | 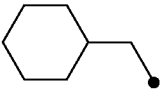 | 4-Ph-3-Cl-Ph | S | 3-Me-Ph | S | 3-Me-Ph | 4-CF3-PhO |
| 55 | O | 3-Cl-Ph | 4-Me-Ph | S | 4-MeO-Ph | S | 4-MeO-Ph | 4-Cl-PhO |
| 56 | O | 2,5-Cl2-Ph | 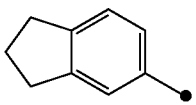 | S | 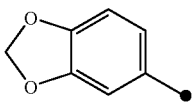 | S | 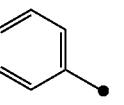 | 4-MeO-PhO |
| 57 | S | 4-Me-Ph | 4-Cl-Ph | S | 4-F-Ph | S | 4-F-Ph | 4-PhS-PhO |
| 58 | S | Ph | Ph | S | 4-Me-Ph | S | 4-Me-Ph | 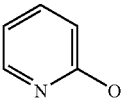 |
| 59 | S | 2-Cl-Ph | 3-Me-Ph | S | 3-MeO-Ph | S | 3-MeO-Ph | 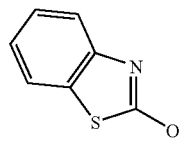 |
| 60 | S | Ph | Ph | S | 4-F-Ph | S | 4-F-Ph | MeS |
| 61 | O | 2-Cl-Ph | 3-Me-Ph | S | 3-Cl-Ph | S | 3-Cl-Ph |  |
| 62 | O | 4-Cl-Ph | 3,4-Me2-Ph | S | 3-Me-Ph | S | 3-Me-Ph | MeOCH2S |

TABLE 2-continued

| NO. | U | Y | Z | A | X | B | W | R |
|---|---|---|---|---|---|---|---|---|
| 63 | O | 2,5-Cl2-Ph | 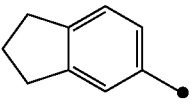 | S | 4-Me-Ph | S | 4-Me-Ph | PhOCH2S |
| 64 | S | 3,5-Cl2-Ph | 4-iPr-Ph | S | 3-MeO-Ph | S | 3-MeO-Ph | MeSCH2S |
| 65 | S | 3-Me-Ph | 3-Cl-Ph | S | 4-MeO-Ph | S | 4-MeO-Ph | ClCH2S |
| 66 | S | 4-Me-Ph | 4-Cl-Ph | S | 3-CF3-Ph | S | 3-CF3-Ph | CF3S |
| 67 | S | CH3(CH2)5 | 3-Cl-4-Me-Ph | S | 4-F-Ph | S | 4-F-Ph | 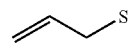 |
| 68 | S | cHx | 4-Ph-3-Me-Ph | S | 3-Me-Ph | S | 3-Me-Ph | 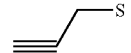 |
| 69 | S | 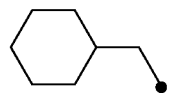 | 4-Ph-3-Cl-Ph | S | 3-Cl-Ph | S | 3-Cl-Ph | 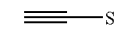 |
| 70 | O | Ph | Ph | S | 4-Cl-Ph | S | 4-Cl-Ph | 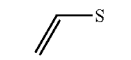 |
| 71 | O | 4-Cl-Ph | 3,4-Me2-Ph | S | 4-Me-Ph | S | 4-Me-Ph | 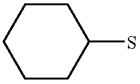 |
| 72 | O | 4-Me-Ph | 4-Cl-Ph | S | 3-Cl-Ph | S | 3-Cl-Ph | BnS |
| 73 | S | 2,3-Me2-Ph | 3,4-Cl2-Ph | S | 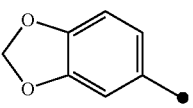 | S | 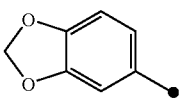 | 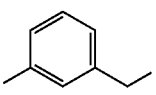 |
| 74 | S | 3-MeO-Ph | 4-Ph-Ph | S | Ph | S | Ph | 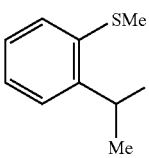 |
| 75 | O | 3-Cl-Ph | 4-Me-Ph | S | 4-Cl-Ph | S | 4-Cl-Ph | PhS |
| 76 | S | 2,5-Cl2-Ph | 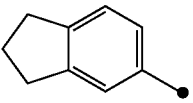 | S | 3-Cl-Ph | S | 3-Cl-Ph | 3-Me-PhS |
| 77 | S | 4-Me-Ph | 4-Cl-Ph | S | 3-F-Ph | S | 3-F-Ph | 3-Ay-PhS |
| 78 | S | 2,3-Me2-Ph | 3,4-Cl2-Ph | S | 4-F-Ph | S | 4-F-Ph | 4-Pg-PhS |
| 79 | S | 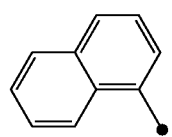 | 3-Me-4-Cl-Ph | S | 4-Cl-Ph | S | 4-Cl-Ph | 4-CF3-PhS |
| 80 | S | CH3(CH2)5 | 3-Cl-4-Me-Ph | S | 3-Me-Ph | S | 3-Me-Ph | 3-Vn-PhS |
| 81 | O | cHx | 4-Ph-3-Me-Ph | S | 4-Me-Ph | S | 4-Me-Ph | 3-Ey-PhS |
| 82 | O | 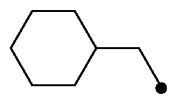 | 4-Ph-3-Cl-Ph | S | 3-MeO-Ph | S | 3-MeO-Ph | 4-Cl-Phs |
| 83 | S | 2-Cl-Ph | 3-Me-Ph | S | 3-CF3-Ph | S | 3-CF3-Ph | 4-MeO-Ph |

TABLE 2-continued
| NO. | U | Y | Z | A | X | B | W | R |
|---|---|---|---|---|---|---|---|---|
| 84 | S | 4-Cl-Ph | 3,4-Me2-Ph | S | 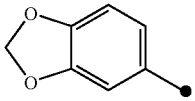 | S | 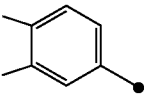 | 4-CF3O-PhS |
| 85 | S | 2,5-Cl2-Ph | 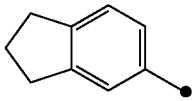 | S | Ph | S | Ph | 4-MeS-PhS |
| 86 | S | 2,3-Me2-Ph | 3,4-Cl2-Ph | S | 4-F-Ph | S | 4-F-Ph |  |
| 87 | S | Ph | Ph | S | 3-F-Ph | S | 3-F-Ph | F |
| 88 | O | 2-Cl-Ph | 3-Me-Ph | S | 4-F-Ph | S | 4-F-Ph | Cl |
Compounds represented by the formula (Iγ):
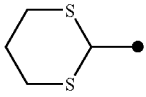
(Iγ)
wherein $X^U$, $R^W$, $A^W$ and $Z^Y$ are any one of combinations 1 to 10 shown in the following table 3.
TABLE 3
| | $X^U$ | $A^W$ | $R^W$ | $Z^Y$ |
|---|---|---|---|---|
| 1 | 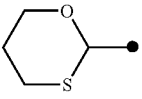 | S | Ph | 3-Cl-Ph |
| 2 | 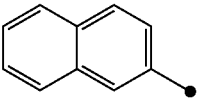 | S | 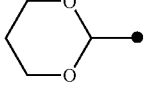 | 4-Cl-Ph |
| 3 | 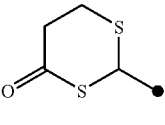 | S | 2-Cl-Ph | 3,4-Cl$_2$-Ph |
| 4 | 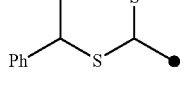 | S | 3-Cl-Ph | 4-Ph-Ph |
| 5 | 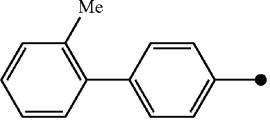 | S | 4-Cl-Ph | 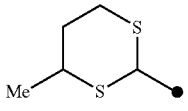 |
| 6 |  | S | 2,5-Cl$_2$-Ph | 3-Me-4-Cl-Ph |

TABLE 3-continued

| | $X^U$ | $A^W$ | $R^W$ | $Z^Y$ |
|---|---|---|---|---|
| 7 | 1,3-dithian-2-yl | S | 3,5-Cl$_2$-Ph | 3-Cl-4-Me-Ph |
| 8 | 1,3-benzodithiol-2-yl | O | 3-Me-Ph | 4-Ph-3-Me-Ph |
| 9 | 3,4-dihydro-1H-2,4-benzodithiin-3-yl | S | Ph | Ph |
| 10 | 2H-naphtho[1,8-de][1,3]dithin-2-yl | O | 4-Me-Ph | 4-Ph-3-Cl-Ph |

EXAMPLES

Hereinafter, the present invention is described in more detail by reference to Production Examples, Reference Production Examples, Formulation Examples and Test Examples which the present invention is not limited to.

In Production Examples and Reference Production Examples, reaction and operation of column chromatography were checked by analysis using TLC (thin layer chromatography) or the like. TLC was conducted by using Kieselgel 60F254 (70 to 230 mesh) manufactured by MERCK & CO., LTD., and a UV detector was employed. Column chromatography was conducted using silica gel 60 (spherical shape, particle size of 63 to 210 nm) manufactured by KANTO CHEMICAL CO., LTD., Florisil (100 to 200 mesh) manufactured by WAKO PURE CHEMICAL INDUSTRIES LTD, or the like. As a medium pressure preparative liquid chromatography, Ultrapack (filler: silica gel) manufactured by YAMAZEN CO. was used. NMR spectra were measured with JEOL AL-400 (400 MHz)-type, Bruker AVANCE 400 (400 MHz)-type spectrometers or the like, using tetramethylsilane as an internal standard (the measurement temperature was 25° C. unless otherwise noted).

In Production Examples and Reference Production Examples, abbreviations and terms have meanings as described below.

s: singlet, br; broad, brs: broad singlet, d: doublet, t: triplet, q: quartet, Me: methyl group, Et: ethyl group, nPr: propyl group, iPr: isopropyl group, cPr: cyclopropyl group, Bu: butyl group, iBu: isobutyl group, sBu: sec-butyl group, tBu: tert-butyl group, Hex: hexyl group, cHx: cyclohexyl group, Ay: allyl group, Pg: propargyl group, Vn: vinyl group, Ey: ethynyl group, Ph: phenyl group, Bn: benzyl group; Py: pyridyl group, Fu: furyl group, Th: thienyl group, THF: tetrahydrofran, DMF: dimethylformamide, room temperature: about 15 to 25° C.; ice-cooling: 0 to 5° C.

Then, Production Examples of the compounds of the present invention are shown.

Production Example 1

Synthesis of phenyl N-(4-methylphenyl)-3,3-bis(phenylthio)thiopropionimidate (hereafter referred to as the present compound 1)

Thiophenol (1.61 g) and tert-butoxypotassium (88.9 mg) were added to a solution of phenyl N-(4-methylphenyl)-3-(phenylthio)thioacrylimidate (2.19 g) in THF (45 mL) at room temperature, and the mixture was stirred at room temperature for 10 hours. A saturated aqueous sodium chloride solution (50 mL) was added to the reaction solution, which was then extracted with ethyl acetate (100 mL). The organic layer was washed with a saturated aqueous sodium chloride solution (50 mL), dried over anhydrous magnesium sulfate, and then concentrated under reduced pressure. The residue was subjected to silica gel column chromatography (hexane:ethyl acetate=30:1 to hexane:ethyl acetate=10:1) to obtain the present compound 1 (2.42 g) as a yellow oil.

$^1$H-NMR (CDCl$_3$) δ (ppm): 2.34 (3H, s), 2.79 (2H, dJ=7.2 Hz), 5.01 (1H, t, J=7.2 Hz), 6.82-6.84 (2H, m), 7.16-7.42 (17H, m).

Production Example 2

Phenyl N-phenyl-3,3-bis(phenylthio)thiopropionimidate (hereafter referred to as the present compound 2) was synthesized in the same manner as in Production Example 1-(1).

$^1$H-NMR (CDCl$_3$) δ (ppm): 2.80 (2H, d, J=7.2 Hz), 5.02 (1H, t, J=7.2 Hz), 7.11-7.40 (20H, m).

Production Example 3

Synthesis of phenyl N-(4-ethylphenyl)-3,3-bis(phenylthio)thiopropionimidate (hereafter referred to as the present compound 3)

Thionyl chloride (0.693 g), triethylamine (0.563 g) and DMF (catalytic amount) were added to a solution of N-(4-ethylphenyl)-3-(phenylthio)acrylamide (1.06 g) in toluene (5 mL) at room temperature, and the mixture was stirred at 60°

C. for 3 hours. After the reaction mixture was left to cool, insoluble substances were filtered off and the filtrate was concentrated under reduced pressure. THF (5 mL) was added to the residue, and thereto a solution of phenylmercaptan sodium salt (1.36 g) in THF (6 mL) was added dropwise under ice-cooling. The mixture was stirred at room temperature for 2 hours. Then, a saturated aqueous sodium chloride solution (50 ml) was added thereto. The mixture solution was extracted twice with 100 mL of ethyl acetate. The organic layers were combined, dried over anhydrous magnesium sulfate, and concentrated under reduced pressure. The residue was subjected to silica gel column chromatography (hexane: ethyl acetate=30:1) to obtain the present compound 3 (0.356 g) as a yellow oil.

$^1$H-NMR (CDCl$_3$) δppm: 0.88 (3H, t, J=6.8 Hz), 2.65 (2H, q, J=6.8 Hz), 2.79 (2H, d, J=7.2 Hz), 5.01 (1H, t, J=7.2 Hz), 6.86 (2H, d, J=8.6 Hz), 7.13-7.56 (17H, m).

Production Examples 4 to 7

The following compounds were synthesized in the same manner as in Production Example 3.

Phenyl N-(4-biphenyl)-3,3-bis(phenylthio)thiopropionimidate (hereafter referred to as the present compound 4)

$^1$H-NMR (CDCl$_3$) δppm: 2.83 (2H, d, J=7.2 Hz), 5.06 (1H, t, J=7.2 Hz), 7.01-7.63 (24H, m).

Phenyl N-(4-chlorophenyl)-3,3-bis(phenylthio)thiopropionimidate (hereafter referred to as the present compound 5)

$^1$H-NMR (CDCl$_3$) δ ppm: 2.78 (2H, d, J=7.5 Hz), 4.97 (1H, t, J=7.5 Hz), 6.84 (2H, d, J=8.9 Hz), 7.21-7.61 (17H, m).

Phenyl N-(3-methylphenyl)-3,3-bis(phenylthio)thiopropionimidate (hereafter referred to as the present compound 6)

$^1$H-NMR (CDCl$_3$) δ ppm: 2.37 (3H, s), 2.79 (2H, d, J=7.1 Hz), 5.02 (1H, t, J=7.1 Hz), 6.69-6.75 (2H, m), 6.92-7.00 (1H, m), 7.21-7.53 (16H, m).

Phenyl N-[4-(1-methylethyl)phenyl]-3,3-bis(phenylthio)thiopropionimidate (hereafter referred to as the present compound 7)

$^1$H-NMR (CDCl$_3$) δppm: 1.25 (6H, d, J=7.0 Hz), 2.79 (2H, d, J=7.2 Hz), 2.88-2.91 (1H, m), 5.03 (1H, t, J=7.2 Hz), 6.86-7.43 (19H, m).

Production Example 8

Synthesis of phenyl N-[2-(methylthio)thiazol-5-yl]-3,3-bis(phenylthio)thiopropionimidate (hereafter referred to as the present compound 8)

Carbon tetrabromide (1.6 g) and triphenylphosphine (1.3 g) were added to a solution of N-[(2-methylthio)thiazol-5-yl)-3-(phenylthio)acrylamide (0.74 g) in acetonitrile (30 mL) at room temperature, and the mixture was stirred for 5 hours while it was heated to reflux. After the reaction mixture was left to cool, insoluble matter were filtered off and the filtrate was concentrated under reduced pressure. DMF (20 mL) was added to the residue, and thereto phenylmercaptan sodium salt (0.38 g) was added thereto under ice-cooling. The mixture was stirred at the same temperature for 0.5 hour, and then at room temperature for 2 hours. To the reaction mixture was added 100 mL of tert-butyl methyl ether, followed by washing with a 1N aqueous sodium hydroxide solution, water and then a saturated aqueous sodium chloride solution. The organic layer was dried over anhydrous magnesium sulfate, and concentrated under reduced pressure. The residue was subjected to silica gel column chromatography (hexane:ethyl acetate=10:1) to obtain the present compound 8 (0.11 g) as a red brown oil.

$^1$H-NMR (CDCl$_3$) δ ppm: 2.69 (3H, s), 2.84 (2H, d, J=7.2 Hz), 4.93 (1H, t, J=7.2 Hz), 7.24-7.27 (6H, m), 7.32-7.43 (9H, m), 7.63 (1H, s).

Production Examples 9 and 10

The following compounds were synthesized in the same manner as in Production Example 1.

Phenyl 3,3-bis(phenylthio)-N-[4-(2-pyridyl)phenyl]thiopropionimidate (hereafter referred to as the present compound 9)

$^1$H-NMR (CDCl$_3$) δ ppm: 2.81 (2H, d, J=7.9 Hz), 5.03 (1H, t, J=7.9 Hz), 7.02 (2H, d, J=8.0 Hz), 7.18-7.41 (16H, m), 7.72-7.74 (2H, m), 2.81 (2H, d, J=8.2 Hz), 8.67-8.69 (1H, m).

Phenyl N-(5-indanyl)-3,3-bis(phenylthio)thiopropionimidate hereafter referred to as the present compound 10).

$^1$H-NMR (CDCl$_3$) δ ppm: 2.05-2.13 (2H, m), 2.87-2.94 (4H, m), 2.78 (2H, d, J=7.2 Hz), 5.02 (1H, t, J=7.2 Hz), 6.69-7.40 (18H, m).

Production Example 11

Synthesis of phenyl 3-benzylthio-N-phenyl-3-(phenylthio)thiopropionimidate (hereafter referred to as the present compound 11)

Thiophenol (0.13 mL) was added dropwise to a solution of phenyl 3-benzylthio-N-(phenyl)thioacrylimidate (0.42 g) in THF (10 mL) under ice-cooling, and the mixture was stirred at the same temperature for 1 hour. To the reaction mixture was added 80 mL of tert-butyl methyl ether, followed by washing with a 1N aqueous sodium hydroxide solution, water and then a saturated aqueous sodium chloride solution. The organic layer was dried over anhydrous magnesium sulfate, and concentrated under reduced pressure. The residue was subjected to silica gel column chromatography (hexane:ethyl acetate=20:1) to obtain the present compound 11 (0.53 g) as a yellow oil.

$^1$H-NMR (CDCl$_3$) δ ppm: 2.66-2.87 (2H, m), 3.80-3.99 (2H, m), 4.46 (1H, t, J=7.4 Hz), 6.87 (2H, d, J=7.5 Hz), 7.10-7.14 (1H, m), 7.23-7.37 (17H, m).

Production Example 12

Phenyl 3-cyclohexylthio-N-phenyl-3-(phenylthio)thiopropionimidate (hereafter referred to as the present compound 12) was synthesized in the same manner as in Production Example 11.

$^1$H-NMR (CDCl$_3$) δ ppm: 1.22-2.10 (10H, m), 2.65-2.84 (2H, m), 2.87-2.94 (1H, m), 4.77 (1H, t, J=7.2 Hz), 6.91 (2H, d, J=7.5 Hz), 7.11-7.15 (1H, m), 7.26-7.44 (12H, m).

Production Example 13

Phenyl 3-methylthio-N-phenyl-3-(phenylthio)thiopropionimidate (hereafter referred to as the present compound 13) was synthesized in the same manner as in Production Example 3.

$^1$H-NMR (CDCl$_3$) δ ppm: 2.14 (3H, s), 2.72-2.88 (2H, m), 4.59 (1H, t, J=7.4 Hz), 6.93 (2H, d, J=7.7 Hz), 7.11-7.15 (1H, m), 7.26-7.45 (12H, m).

Production Example 14

Phenyl 3-ethylthio-N-phenyl-3-(phenylthio)thiopropionimidate (hereafter referred to as the present compound 14) was synthesized in the same manner as in Production Example 3.

$^1$H-NMR (CDCl$_3$) δ ppm: 1.23 (3H, t, J=7.5 Hz), 2.59-2.87 (4H, m), 4.67 (1H, t, J=7.2 Hz), 6.92 (2H, d, J=7.2 Hz), 7.11-7.15 (1H, m), 7.25-7.46 (12H, m).

Production Example 15

Synthesis of Phenyl 2-(benzo[1,3]dithiol-2-yl)-N-(phenyl)thioacetimidate (hereafter referred to as the present compound 15)

Phosphorous pentachloride (0.44 g) was added to a solution of 2-(benzo[1,3]dithiol-2-yl)-N-(phenyl)acetamide (0.60 g) in toluene (3 mL) at room temperature, and the mixture was stirred at room temperature for 2 hours. After the reaction solution was concentrated under reduced pressure, DMF (20 mL) was added to the residue, and then phenylmercaptan sodium salt (0.56 g) was added thereto under ice-cooling. The mixture was stirred for 3 hours at the same temperature. Then, tert-butyl methyl ether (100 mL) was added to the reaction mixture, followed by washing with a 1N aqueous sodium hydroxide solution, water and then a saturated aqueous sodium chloride solution. The organic layer was dried over anhydrous magnesium sulfate, and concentrated under reduced pressure. The residue was subjected to silica gel column chromatography (hexane:ethyl acetate=20:1) to obtain the present compound 15 (0.46 g) as a light yellow crystal.

$^1$H-NMR (CDCl$_3$) δ ppm: 2.88 (2H, d, J=7.2 Hz), 5.35 (1H, t, J=7.2 Hz), 6.94-7.01 (4H, m), 7.14-7.16 (3H, m), 7.27-7.44 (7H, m).

Production Example 16

Phenyl 3,3-bis(4-methylphenylthio)-N-(phenyl)thiopropionimidate (hereafter referred to as the present compound 16) was synthesized in the same manner as in Production Example 11.

$^1$H-NMR (CDCl$_3$) δ ppm: 2.34 (6H, s), 2.75 (2H, d, J=7.2 Hz), 4.88 (1H, t, J=7.2 Hz), 6.92 (2H, dJ=7.5 Hz), 7.07 (4H, d, J=7.7 Hz), 7.13 (1H, t, J=7.5 Hz), 7.30 (6H, d, J=8.0 Hz), 7.36 (5H, t, J=7.4 Hz).

Production Example 17

Synthesis of 3-methylphenyl N-(4-methylphenyl)-3,3-bis(3-methylphenylthio)thiopropionimidate (hereafter referred to as the present compound 17)

To 3-methylphenyl N-(4-methylphenyl)-3-(3-methylphenylthio)thioacrylimidate (0.16 g) was added 3-methylphenylmercaptan (0.51 g), and the mixture was stirred at 80° C. for 6 hours. To the reaction mixture was added ethyl acetate (50 mL), followed by washing with a 1N aqueous sodium hydroxide solution, water and then a saturated aqueous sodium chloride solution. The organic layer was dried over anhydrous magnesium sulfate, and concentrated under reduced pressure. The residue was isolated and purified by a medium pressure preparatuve liquid chromatography system (YAMAZEN SI-40B; hexane:ethyl acetate=9:1) to obtain the present compound 17 (0.21 g) as a yellow oil.

$^1$H-NMR (CDCl$_3$) δ ppm: 2.29 (6H, s), 2.31 (3H, s), 2.35 (3H, s), 2.80 (2H, d, J=7.1 Hz), 5.01 (1H, t, J=7.1 Hz), 6.82-7.21 (16H, m).

Production Examples 18 to 21

The following compounds were synthesized in the same manner as in Production Example 17.

4-Methoxyphenyl 3,3-bis(4-methoxyphenylthio)-N-(4-methylphenyl)thiopropionimidate (hereafter referred to as the present compound 18)

$^1$H-NMR (CDCl$_3$) δ ppm: 2.35 (3H, s), 2.68 (2H, J=7.5 Hz), 3.81 (6H, s), 3.83 (3H, s), 4.68 (1H, t, J=7.5 Hz), 6.78-7.38 (16H, m).

4-Methylphenyl N-(3,4-dimethylphenyl)-3,3-bis(4-methylphenylthio)thiopropionimidate (hereafter referred to as the present compound 19)

$^1$H-NMR (CDCl$_3$) δ ppm: 2.24 (3H, s), 2.26 (3H, s), 2.33 (6H, s), 2.36 (3H, s), 2.74 (2H, d, J=7.2 Hz), 4.90 (1H, t, J=7.2 Hz), 6.46-7.34 (15H, m).

2-Naphthyl 3,3-bis(2-naphthylthio)-N-(phenyl)thiopropionimidate (hereafter referred to as the present compound 20)

$^1$H-NMR (CDCl$_3$) δ ppm: 2.93 (2H, d, J=7.3 Hz), 5.24 (1H, t, J=7.3 Hz), 6.99-7.85 (26H, m).

1-Naphthyl N-(4-methylphenyl)-3,3-bis(1-naphthylthio)thiopropionimidate (hereafter referred to as the present invented compound 21)

$^1$H-NMR (CDCl$_3$) δ ppm: 2.36 (3H, s), 2.72 (2H, d, J=7.2 Hz), 4.90 (1H, t, J=7.2 Hz), 6.98-8.13 (25H, m).

Production Example 22

Synthesis of decahydronaphthalen-2-yl 3,3-bis(4-fluorophenylthio)-N-(3,4-dimethylphenyl)thiopropionimidate (hereafter referred to as the present compound 22)

A 1.57 M solution (3.4 mL) of n-butyllithium in hexane was added to a solution of ethynyltrimethylsilane (0.70 mL) in THF (10 mL) at −70° C. under a nitrogen atmosphere. The mixture was warmed to 0° C. with stirring, and a solution of 3,4-dimethylphenyl isothiocyanate (0.82 g) in THF (3 mL) was added dropwise thereto. The mixture was further warmed to room temperature, and a solution of decahydronaphthalen-2-yl methanesulfonate (1.3 g) in THF (2 mL) was added thereto. The mixture was stirred for 7 hours while it was heated to reflux. A saturated aqueous sodium chloride solution (25 mL) was added to the reaction mixture, which was then extracted twice with t-butyl methyl ether (20 mL). The organic layers were combined, washed with a saturated aqueous sodium chloride solution, dried over anhydrous magnesium sulfate, and concentrated under reduced pressure. The residue was subjected to a Florisil column (ethyl acetate:hexane=1:30), and then concentrated under reduced pressure. Methanol (10 mL) and potassium carbonate (catalytic amount) were added to the resultant residue at room temperature, and the mixture was stirred at room temperature for 2 hours. Then, 4-fluorothiophenol (0.19 mL) was added thereto, and the mixture was further stirred for 2 hours. The reaction solution was concentrated under reduced pressure, and the residue was subjected to silica gel column chromatography (ethyl acetate:hexane=1:99) to obtain the present compound 22 (0.14 g).

$^1$H-NMR (CDCl$_3$) δ (ppm): 1.18-1.92 (16H, m), 2.18-2.25 (6H, m), 2.84 (1.4H, d, J=8.0 Hz), 3.04 (0.6H, d, J=6.5 Hz), 3.66 (0.7H, br), 4.27 (0.4H, t, J=6.5 Hz), 4.40 (0.6H, t, J=8.0 Hz), 4.97 (0.3H, br), 6.39-6.45 (1H, m), 6.58-6.65 (1H, m), 6.92-7.10 (6H, m), 7.24-7.30 (2H, m), 7.53 (1H, br).

Production Example 23

Decahydronaphthalen-2-yl 3,3-bis(4-fluorophenylthio)-N-(phenyl)thiopropionimidate (hereafter referred to as the present compound 23) was synthesized in the same manner as in Production Example 22.

¹H-NMR (CDCl₃) δ (ppm): 1.26-1.90 (16H, m), 2.82-2.84 (1.5H, m), 3.03 (0.5H, br), 3.68 (0.8H, br), 4.41 (1H, br), 4.97 (0.2H, br), 6.66-6.70 (1H, m), 6.81 (1H, br), 6.94-7.04 (5H, m), 7.22-7.34 (5H, m), 7.53 (1H, br).

Production Example 24

Synthesis of cyclohexyl 3,3-bis(4-fluorophenylthio)-N-(phenyl)thiopropionimidate (hereafter referred to as the present compound 24)

Thiophenol (0.74 mL) and triethylamine (catalytic amount) were added to a solution of cyclohexyl N-phenylthiopropionimidate (0.56 g) in chloroform (50 mL) at room temperature, and the mixture was stirred at the same temperature for 6 hours. To the reaction mixture was added 100 mL of chloroform, followed by washing with a 1N aqueous sodium hydroxide solution, water and then a saturated aqueous sodium chloride solution. The organic layer was dried over anhydrous magnesium sulfate, and concentrated under reduced pressure. The residue was subjected to silica gel column chromatography (hexane:ethyl acetate=30:1) to obtain the present compound 24 (0.69 g) as a yellow oil.

¹H-NMR (CDCl₃) δ ppm: 0.92-1.78 (10H, m), 2.60 (2H, d, J=7.7 Hz), 3.47-3.52 (1H, m), 4.17 (1H, t, J=7.7 Hz), 6.42-7.28 (13H, m).

Production Examples 25 to 28

The following compounds were synthesized in the same manner as in Production Example 24.

Cyclohexyl 3,3-bis(4-chlorophenylthio)-N-(phenyl)thiopropionimidate (hereafter referred to as the present compound 25)

¹H-NMR (CDCl₃) δ ppm: 1.10-1.80 (10H, m), 2.04-2.10 (1H, m), 2.77-2.89 (1.5H, m), 3.06 (0.5H, brs), 3.76 (0.5H, brs), 4.51 (0.5H, t, J=7.6 Hz), 6.67-6.79 (2H, m), 7.06-7.45 (11H, m).

Cyclohexyl N-phenyl-3,3-bis(3-trifluoromethylphenylthio)thiopropionimidate (hereafter referred to as the present compound 26)

¹H-NMR (CDCl₃) δ ppm: 1.10-1.81 (10H, m), 2.04-2.11 (1H, m), 2.90-2.97 (1.5H, m), 3.15 (0.5H, brs), 3.78 (0.5H, brs), 4.60 (0.5H, t, J=7.7 Hz), 6.67-6.80 (2H, m), 7.04-7.71 (11H, m).

Cyclohexyl 3,3-bis(4-methylphenylthio)-N-(phenyl)thiopropionimidate (hereafter referred to as the present compound 27)

¹H-NMR (CDCl₃) δppm: 1.10-1.74 (10H, m), 2.04-2.10 (1H, m), 2.33 (6H, s), 2.73-2.85 (1.5H, m), 3.05 (0.5H, brs), 3.75 (0.5H, brs), 4.52 (0.5H, t, J=7.2 Hz), 6.66-6.82 (2H, m), 7.01-7.49 (11H, m).

Cyclohexyl N-phenyl-3,3-bis(phenylthio)thiopropionimidate (hereafter referred to as the present compound 28)

¹H-NMR (CDCl₃) δ ppm: 1.05-1.80 (8H, m), 2.00-2.12 (2H, m), 2.80-2.93 (2H, m), 3.68-3.82 (1H, brs), 4.55-4.67 (1H, brs), 6.63-7.60 (15H, m).

Production Example 29

Synthesis of cyclohexyl 3,3-bis(acetylthio)-N-(phenyl)thiopropionimidate (hereafter referred to as the present compound 29)

Thioacetic acid (0.29 mL) was added to a solution of cyclohexyl N-(phenyl)thiopropionimidate (1.0 g) in acetic anhydride (15 mL) at room temperature, and the mixture was stirred at the same temperature for 1.5 hours. The reaction solution was neutralized with a saturated sodium hydrogen carbonate aqueous solution, followed by extraction twice with 80 mL of tert-butyl methyl ether. The organic layers were combined, washed with water and then a saturated aqueous sodium chloride solution, dried over anhydrous magnesium sulfate, and then concentrated under reduced pressure. The residue was subjected to silica gel column chromatography (hexane:ethyl acetate=20:1) to obtain the present compound 29 (0.17 g) as a yellow oil.

¹H-NMR (CDCl₃) δ ppm: 1.15-2.04 (10H, m), 2.27 (3H, brs), 2.34 (3H, brs), 3.02 (1H, brs), 3.21 (0.5H, brs), 3.39 (1H, brs), 3.75 (0.5H, brs), 5.20 (0.5H, brs), 5.76 (0.5H, brs), 6.71-6.82 (2H, m), 7.08 (1H, brs), 7.29-7.33 (2H, m).

Production Examples 30 to 41

The following compounds were synthesized in the same manner as in Production Example 24.

Cyclohexylmethyl N-phenyl-3,3-bis(phenylthio)thiopropionimidate (hereafter referred to as the present compound 30)

¹H-NMR (CDCl₃) δ ppm: 0.81-1.84 (11H, m), 2.52 (0.6H, brs), 2.92-2.97 (3.4H, m), 4.96 (0.7H, brs), 5.15 (0.3H, brs), 6.67-7.54 (15H, m).

Cyclohexylmethyl 3,3-bis(3-fluorophenylthio)-N-(phenyl)thiopropionimidate (hereafter referred to as the present compound 31)

¹H-NMR (CDCl₃) δ ppm: 0.84-1.84 (11H, m), 2.56 (0.4H, brs), 2.94 (1.6H, d, J=7.8 Hz), 2.99 (1.6H, d, J=5.8 Hz), 3.09 (0.4H, brs), 4.63 (0.8H, t, J=7.8 Hz), 5.23 (0.2H, m), 6.66-7.36 (13H, m).

Cyclohexylmethyl 3,3-bis(4-fluorophenylthio)-N-(hereafter referred to as the present compound 32)

¹H-NMR (CDCl₃) δ ppm: 1.00-1.84 (11H, m), 2.51 (0.47H, brs), 2.87 (1.53H, d, J=7.5 Hz), 2.97 (2H, brs), 4.41 (0.77H, t, J=7.5 Hz), 4.95 (0.23H, brs), 6.67-7.52 (13H, m).

Cyclohexylmethyl 3,3-bis(3-chlorophenylthio)-N-(phenyl)thiopropionimidate (hereafter referred to as the present compound 33)

¹H-NMR (CDCl₃) δ ppm: 0.85-1.88 (11H, m), 2.57 (0.4H, brs), 2.94 (1.6H, d, J=7.8 Hz), 2.99 (1.6H, d, J=5.8 Hz), 3.09 (0.4H, brs), 4.58 (0.8H, t, J=7.8 Hz), 5.21 (0.2H, m), 6.66-7.49 (13H, m).

Cyclohexylmethyl 3,3-bis(4-chlorophenylthio)-N-(phenyl)thiopropionimidate (hereafter referred to as the present compound 34)

¹H-NMR (CDCl₃) δ ppm: 1.01-1.87 (11H, m), 2.52 (0.47H, brs), 2.76 (1.53H, d, J=7.5 Hz), 2.83-3.05 (2H, m), 4.51 (0.77H, t, J=7.5 Hz), 5.09 (0.23H, brs), 6.65-7.45 (13H, m).

Cyclohexylmethyl 3,3-bis(3-bromophenylthio)-N-(phenyl)thiopropionimidate (hereafter referred to as the present compound 35)

¹H-NMR (CDCl₃) δ ppm: 0.85-1.85 (11H, m), 2.57 (0.4H, brs), 2.95 (1.6H, d, J=7.3 Hz), 2.99 (1.6H, d, J=6.3 Hz), 3.09 (0.4H, brs), 4.55 (0.8H, t, J=7.3 Hz), 5.20 (0.2H, m), 6.68-7.63 (13H, m).

Cyclohexylmethyl 3,3-bis(4-bromophenylthio)-N-(phenyl)thiopropionimidate (hereafter referred to as the present compound 36)

¹H-NMR (CDCl₃) δ ppm: 0.83-1.84 (11H, m), 2.52 (0.25H, brs), 2.90 (1.75H, d, J=6.8 Hz), 2.98 (1.75H, d, J=5.3 Hz), 3.03 (0.25H, brs), 4.53 (0.87H, t, J=6.8 Hz), 5.10 (0.13H, m), 6.65-7.44 (13H, m).

Cyclohexylmethyl 3,3-bis(3-methylphenylthio)-N-(phenyl)thiopropionimidate (hereafter referred to as the present compound 37)

$^1$H-NMR (CDCl$_3$) δ ppm: 0.81-1.88 (11H, m), 2.30 (6H, s), 2.53 (0.44H, brs), 2.93 (1.56H, d, J=6.8 Hz), 2.98 (1.56H, d, J=5.8 Hz), 3.07 (0.44H, brs), 4.62 (0.78H, t, J=6.8 Hz), 5.14 (0.22H, m), 6.66-7.51 (13H, m).

Cyclohexylmethyl 3,3-bis(4-methylphenylthio)-N-(phenyl)thiopropionimidate (hereafter referred to as the present compound 38)

$^1$H-NMR (CDCl$_3$) δ ppm: 0.98-1.87 (11H, m), 2.30 (6H, s), 2.49 (0.6H, brs), 2.87 (1.4H, d, J=8.0 Hz), 2.85-3.04 (2H, m), 4.52 (0.7H, t, J=7.5 Hz), 4.98 (0.3H, brs), 6.68-7.44 (13H, m).

Cyclohexylmethyl 3,3-bis(3-methoxyphenylthio)-N-(phenyl)thiopropionimidate (hereafter referred to as the present compound 39)

$^1$H-NMR (CDCl$_3$) δ ppm: 0.82-1.87 (11H, m), 2.54 (0.4H, brs), 2.95 (1.6H, d, J=7.1 Hz), 2.98 (1.6H, d, J=6.6 Hz), 3.10 (0.4H, brs), 3.77 (4.8H, s), 3.78 (1.2H, s), 4.68 (0.8H, t, J=7.1 Hz), 5.20 (0.2H, m), 6.67-7.52 (13H, m).

Cyclohexylmethyl 3,3-bis(4-methoxyphenylthio)-N-(phenyl)thiopropionimidate (hereafter referred to as the present compound 40)

$^1$H-NMR (CDCl$_3$) δ ppm: 0.78-1.88 (11H, m), 2.47 (0.5H, brs), 2.84 (1.5H, d, J=5.8 Hz), 2.98 (2H, brs), 3.80 (6H, s), 4.34 (0.75H, t, J=5.8 Hz), 4.80 (0.25H, m), 6.66-7.51 (13H, m).

Cyclohexylmethyl 3,3-bis(4-nitrophenylthio)-N-(phenyl)thiopropionimidate (hereafter referred to as the present compound 41)

$^1$H-NMR (CDCl$_3$) δ ppm: 0.86-1.86 (11H, m), 2.62 (0.5H, brs), 3.02 (1.5H, d, J=5.3 Hz), 3.05 (1.5H, d, J=6.6 Hz), 3.20 (0.5H, brs), 4.92 (0.75H, t, J=6.6 Hz), 5.61 (0.25H, m), 6.70-8.21 (13H, m).

Production Example 42

Synthesis of cyclohexylmethyl N-(4-phenylfluoro)-3,3-bis(4-fluorophenylthio)thiopropionimidate (hereafter referred to as the present compound 42)

Potassium carbonate (0.10 g) was added to a solution of cyclohexylmethyl N-(4-fluorophenyl)-3-(trimethylsilyl)thiopropiolimidate (0.70 g) in methanol (5 mL) at room temperature, and the mixture was stirred for 10 minutes at the same temperature. Then, a solution of thiophenol (0.38 g) in ethyl acetate (4 mL) and triethylamine (catalytic amount) were added thereto at room temperature. The mixture was stirred at room temperature for 1 hour, and then concentrated under reduced pressure. The residue was subjected to silica gel column chromatography (hexane:ethyl acetate=30:1) to obtain the present compound 42 (0.23 g) as a yellow oil.

$^1$H-NMR (CDCl$_3$) δ ppm: 0.78-1.30 (6H, m), 1.59-1.90 (5H, m), 2.54 (0.6H, brs), 2.85 (1.4H, d, J=7.8 Hz), 2.97 (1.4H, d, J=6.6 Hz), 2.96-3.03 (0.6H, m), 4.39 (0.7H, t, J=7.8 Hz), 4.93 (0.3H, brs), 6.57-6.78 (2H, m), 6.90-7.01 (6H, m), 7.30-7.34 (3H, m), 7.51 (1H, brs).

Production Examples 43 to 46

The following compounds were synthesized in the same manner as in Production Example 42.

Cyclohexylmethyl N-(chlorophenyl)-3,3-bis(4-fluorophenylthio)thiopropionimidate (hereafter referred to as the present compound 43)

$^1$H-NMR (CDCl$_3$) δ ppm: 0.77-1.32 (6H, m), 1.52-1.86 (5H, m), 2.47-2.68 (0.66H, m), 2.85 (1.34H, brs), 2.95 (2H, brs), 4.35 (0.66H, brs), 4.73-4.95 (0.34H, m), 6.52-7.54 (12H, m).

Cyclohexylmethyl 3,3-bis(4-fluorophenylthio)-N-(4-methylphenyl)thiopropionimidate (hereafter referred to as the present compound 44)

$^1$H-NMR (CDCl$_3$) δ ppm: 0.76-1.28 (6H, m), 1.60-1.87 (5H, m), 2.33 (3H, s), 2.52 (0.7H, brs), 2.87 (1.3H, d, J=7.6 Hz), 2.96-3.03 (2H, m), 4.40 (0.7H, t, J=7.6 Hz), 4.95 (0.3H, brs), 6.54-6.72 (2H, m), 6.93-7.12 (6H, m), 7.27-7.36 (3H, m), 7.52 (1H, brs).

Cyclohexylmethyl 3,3-bis(4-fluorophenylthio)-N-(3-methylphenyl)thiopropionimidate (hereafter referred to as the present compound 45)

$^1$H-NMR (CDCl$_3$) δ ppm: 0.75-1.28 (6H, m), 1.58-1.87 (5H, m), 2.27 (2.4H, s), 2.30 (0.6H, s), 2.52 (0.4H, brs), 2.87 (1.6H, d, J=7.1 Hz), 2.95-3.00 (2H, m), 4.41 (0.8H, t, J=7.1 Hz), 4.96 (0.2H, brs), 6.43-6.64 (2H, m), 6.84-7.28 (9H, m), 7.52 (1H, brs).

Cyclohexylmethyl 3,3-bis(4-fluorophenylthio)-N-(4-nitrophenyl)thiopropionimidate (hereafter referred to as the present compound 46)

$^1$H-NMR (CDCl$_3$) δ ppm: 0.96-1.28 (6H, m), 1.54-1.81 (5H, m), 2.82-2.89 (4H, m), 4.52 (1H, brs), 6.79 (2H, d, J=8.8 Hz), 6.98-7.02 (4H, m), 7.31-7.41 (4H, m), 8.15 (2H, d, J=8.8 Hz).

Production Example 47

Cyclopropylmethyl 3,3-bis(4-fluorophenylthio)-N-(phenyl)thiopropionimidate (hereafter referred to as the present compound 47) was synthesized in the same manner as in Production Example 1.

$^1$H-NMR (CDCl$_3$) δ ppm: 0.33 (2H, br), 0.58 (2H, br), 1.13 (1H, br), 2.87 (2H, d, J=7.6 Hz), 3.02 (2H, d, J=6.8 Hz), 4.41 (1H, br), 6.66-6.67 (2H, m), 6.96-7.05 (5H, m), 7.24-7.30 (6H, m).

Production Example 48

Cyclopentylmethyl 3,3-bis(4-fluorophenylthio)-N-(phenyl)thiopropionimidate (hereafter referred to as the present compound 48) was synthesized in the same manner as in Production Example 24.

$^1$H-NMR (CDCl$_3$) δ ppm: 1.20-1.88 (9H, m), 2.82-2.90 (2H, m), 3.05-3.12 (2H, m), 4.41 (1H, brs), 6.62-6.71 (2H, m), 6.79-7.35 (11H, m).

Production Example 49

3-Methyl-1-propylbutyl 3,3-bis(4-fluorophenylthio)-N-(phenyl)thiopropionimidate (hereafter referred to as the present compound 49) was synthesized in the same manner as in Production Example 11.

$^1$H-NMR (CDCl$_3$) δ ppm: 0.91 (9H, s), 1.24-1.63 (6H, m), 1.85 (1H, br.s), 2.85 (2H, d, J=7.1 Hz), 3.96 (1H, brs), 4.42 (1H, brs), 6.65 (2H, d, J=6.8 Hz), 6.92-7.36 (11H, m).

Production Example 50 to 55

The following compounds were synthesized in the same manner as in Production Example 24.

1-Methylpropyl N-(4-methylphenyl)-3,3-bis(phenylthio)thiopropionimidate (hereafter referred to as the present compound 50)

$^1$H-NMR (CDCl$_3$) δ ppm: 1.01 (3H, t, J=7.3 Hz), 1.37 (3H, d, J=6.8 Hz), 1.57-1.67 (2H, m), 2.32 (3H, s), 2.91 (2H, d, J=7.5 Hz), 3.76 (1H, brs), 4.03 (1H, t, J=7.5 Hz), 6.57-7.54 (14H, m).

Allyl N-phenyl-3,3-bis(phenylthio)thiopropionimidate (hereafter referred to as the present compound 51)

$^1$H-NMR (CDCl$_3$) δ ppm: 2.93 (2H, br), 3.72 (2H, br), 4.60 (1H, br), 5.12 (1H, br), 5.28 (1H, br), 5.95 (1H, brs), 6.67 (2H, br), 6.97-7.60 (13H, m).

Propargyl N-phenyl-3,3-bis(phenylthio)thiopropionimidate (hereafter referred to as the present compound 52)

$^1$H-NMR (CDCl$_3$) δ ppm: 2.19 (1H, brs), 2.95 (2H, brs), 3.83 (2H, brs), 4.55 (1H, brs), 6.60-7.60 (15H, m).

Benzyl 3,3-bis(4-fluorophenylthio)-N-(phenyl)thiopropionimidate (hereafter referred to as the present compound 53)

$^1$H-NMR (CDCl$_3$) δ ppm: 2.80-2.95 (2H, m), 4.27-4.39 (3H, m), 6.63-6.74 (2H, m), 6.98-7.09 (4H, m), 7.17-7.45 (12H, m).

4-Chlorobenzyl N-(4-methylphenyl)-3,3-bis(phenylthio)thiopropionimidate (hereafter referred to as the present compound 54)

$^1$H-NMR (CDCl$_3$) δ ppm: 2.33 (3H, s), 2.92 (2H, d, J=7.8 Hz), 4.23 (2H, s), 4.55 (1H, t, J=7.8 Hz), 6.55 (2H, d, J=7.8 Hz), 7.05 (2H, d, J=7.8 Hz), 7.24-7.32 (14H, m).

1-Phenetyl N-phenyl-3,3-bis(phenylthio)thiopropionimidate (hereafter referred to as the present compound 55)

$^1$H-NMR (CDCl$_3$) δ ppm: 1.65-1.80 (3H, brs), 2.80-2.96 (2H, brs), 4.50-4.61 (1H, brs), 4.92-5.07 (1H, brs), 6.60-6.72 (2H, brs), 7.00-7.50 (18H, m).

Production Example 56

Synthesis of phenyl N-phenyl-3,3-bis(phenylthio)thiopropionimidate (hereafter referred to as the present compound 56)

Thiophenol (0.068 mL) was added dropwise to a solution of phenyl N-phenyl-3-(phenylthio)acrylimidate (0.20 g) in THF (4 mL) under ice-cooling, and the mixture was stirred at the same temperature for 3 hours. To the reaction mixture was added 50 mL of a 1N aqueous sodium hydroxide solution, followed by extraction with 50 mL of ethyl acetate. The organic layer was washed with water and then a saturated aqueous sodium chloride solution, dried over anhydrous magnesium sulfate, and concentrated under reduced pressure. The residue was subjected to silica gel column chromatography (hexane:ethyl acetate=100:1 to 50:1) to obtain the present compound 56 (0.096 g) as a yellow oil.

$^1$H-NMR (CDCl$_3$) δ ppm: 2.97 (2H, d, J=8.0 Hz), 4.94 (1H, t, J=8.0 Hz), 6.72-7.40 (20H, m).

Production Examples 57 to 63

The following compounds were synthesized in the same manner as in Production Example 56.

3-Methylphenyl 3,3-bis(4-fluorophenylthio)-N-(4-methylphenyl)propionimidate (hereafter referred to as the present compound 57)

$^1$H-NMR (CDCl$_3$) δ (ppm): 2.30 (3H, s), 2.35 (3H, s), 2.89 (2H, d, J=8.0 Hz), 4.70 (1H, t, J=8.0 Hz), 6.60-6.62 (1H, m), 6.81-6.83 (1H, m), 6.94-7.03 (8H, m), 7.17-7.19 (1H, m), 7.24-7.28 (1H, m), 7.33-7.41 (4H, m).

3-Methylphenyl N-(3,4-dimethylphenyl)-3,3-bis(phenylthio)propionimidate (hereafter referred to as the present compound 58)

$^1$H-NMR (CDCl$_3$) δ ppm: 2.17 (2.7H, s), 2.18 (0.3H, s), 2.20 (2.7H, s), 2.24 (0.3H, s), 2.26 (0.3H, s), 2.34 (2.7H, s), 2.78 (0.2H, d, J=7.2 Hz), 2.97 (1.8H, d, J=8.0 Hz), 4.92 (0.9H, t, J=8.0 Hz), 5.02 (0.1H, t, J=7.2 Hz), 6.46-7.43 (17H, m).

3-Methylphenyl 3,3-bis(4-fluorophenylthio)-N-(3,4-dimethylphenyl)propionimidate (hereafter referred to as the present compound 59)

$^1$H-NMR (CDCl$_3$) δ ppm: 2.16 (3H, s), 2.20 (3H, s), 2.35 (3H, s), 2.91 (2H, d, J=8.0 Hz), 4.70 (1H, t, J=8.0 Hz), 6.44-7.44 (15H, m).

3-Methylphenyl N-(3,4-dimethylphenyl)-3,3-bis(4-methylphenylthio)propionimidate (hereafter referred to as the present compound 60)

$^1$H-NMR (CDCl$_3$) δ ppm: 2.17 (3H, s), 2.20 (3H, s), 2.33 (6H, s), 2.34 (3H, s), 2.92 (2H, d, J=8.0 Hz), 4.80 (1H, t, J=8.0 Hz), 6.46-7.32 (15H, m).

3-Methylphenyl N-(3,4-dimethylphenyl)-3,3-bis(4-nitrophenylthio)propionimidate (hereafter referred to as the present compound 61)

$^1$H-NMR (CDCl$_3$) δ ppm: 2.18 (3H, s), 2.23 (3H, s), 2.35 (3H, s), 3.11 (2H, d, J=7.9 Hz), 5.22 (1H, t, J=7.9 Hz), 6.45-8.20 (15H, m).

3-Methylphenyl 3,3-bis(benzylthio)-N-(3,4-dimethylphenyl)propionimidate (hereafter referred to as the present compound 62)

$^1$H-NMR (CDCl$_3$) δ ppm: 2.16 (6H, s), 2.32 (3H, s), 2.83 (2H, d, J=7.9 Hz), 3.63 (2H, d, J=13.3 Hz), 3.77 (2H, d, J=13.3 Hz), 4.10 (1H, t, J=7.9 Hz), 6.39-7.29 (17H, m).

3-Methylphenyl N-(3,4-dimethylphenyl)-3,3-bis(2-thienylthio)propionimidate (hereafter referred to as the present compound 63)

$^1$H-NMR (CDCl$_3$) δ ppm: 2.16 (3H, s), 2.18 (3H, s), 2.35 (3H, s), 2.93 (2H, d, J=7.9 Hz), 4.51 (1H, t, J=7.9 Hz), 6.45-7.44 (13H, m).

Production Example 64

Synthesis of 3-methylphenyl 3,3-bis(cyclohexylthio)-N-(3,4-dimethylphenyl)propionimidate (hereafter referred to as the present compound 64)

Cyclohexylmercaptan (0.46 g) and a catalytic amount of a 28% solution of sodium methoxide in methanol were added to 3-methylphenyl 3-cyclohexylthio-N-(3,4-dimethylphenyl)acrylimidate (0.15 g), and the mixture was stirred at 60° C. for 6 hours, and then at 80° C. for 4 hours. To the reaction mixture was added ethyl acetate (100 mL), which was then washed with a 1N aqueous sodium hydroxide solution, water and then a saturated aqueous sodium chloride solution, dried over anhydrous sodium sulfate, and then concentrated under reduced pressure. The resultant residue was subjected to medium pressure preparative liquid chromatography (Yamazen SI-40B, hexane:ethyl acetate=19:1) to obtain the present compound 64 (0.14 g) as a yellow oil.

$^1$H-NMR (CDCl$_3$) δ ppm: 1.22-1.98 (20H, m), 2.17 (3H, s), 2.18 (3H, s), 2.35 (3H, s), 2.78-2.80 (2H, m), 2.92 (2H, d, J=8.0 Hz), 4.33 (1H, t, J=8.0 Hz), 6.50-7.26 (7H, m).

Production Example 65

Synthesis of N-methyl-3,3-bis(4-methylphenylthio)-N,N'-(diphenyl)propionamidine (hereafter referred to as the present compound 65)

A solution of 4-methylthiophenol (0.12 g) in chloroform (5 mL) was added dropwise to a solution of N-methyl-N,N'-(diphenyl)propynamidine (0.23 g) in chloroform (5 mL) under ice-cooling. The mixture was allowed to stand overnight at room temperature. After the reaction solution was concentrated under reduced pressure, the residue was subjected to silica gel column chromatography (hexane:ethyl acetate=5:1) to obtain the present compound 65 (0.30 g) as an oil.

$^1$H-NMR (CDCl$_3$) δ ppm: 2.32 (6H, s), 2.89 (2H, d, J=8.2 Hz), 3.33 (3H, s), 4.05 (1H, t, J=8.2 Hz), 6.55-7.40 (18H, m).

Production Example 66

Synthesis of phenyl 2-methyl-N-phenyl-3,3-bis(phenylthio)thiopropionimidate (hereinafter referred to as the present compound 66)

Thiophenol (0.85 mL) and a catalytic amount of 28% sodium methoxide (in methanol) were added dropwise to a solution of phenyl 2-methyl-N-phenyl-3-(phenylthio)thioacrylimidate (0.30 g) in methanol (5 mL) at room temperature, and the mixture was heated to reflux for 9 hours. To the mixture was added tert-butyl methyl ether, which was washed with a 1N aqueous sodium hydroxide solution, purified water and then a saturated aqueous sodium chloride solution, dried over anhydrous sodium sulfate, and then concentrated under reduced pressure. The residue was isolated and purified by medium pressure preparative liquid chromatography (Yamazen SI-40B, hexane:ethyl acetate=20:1) to obtain the present compound 66 (0.30 g) as a yellow oil.

$^1$H-NMR (CDCl$_3$) δ ppm: 1.42 (3H, d, J=6.8 Hz), 2.88~2.98 (1H, m), 4.81 (1H, d, J=9.4 Hz), 6.89 (2H, d, J=7.7 Hz), 7.08~7.42 (18H, m).

Production Example 67

Phenyl 2-ethyl-N-phenyl-3,3-bis(phenylthio)thiopropionimidate (hereinafter referred to as the present compound 67) was synthesized in the same manner as in Production Example 66.

$^1$H-NMR (CDCl$_3$) δ ppm: 0.950 (3H, t, J=7.1 Hz), 1.82~1.96 (1H, m), 2.08~2.20 (1H, m), 2.80~2.88 (1H, m), 4.74 (1H, d, J=8.9 Hz), 6.85 (2H, d, J=7.9 Hz), 7.08~7.42 (18H, m)

Production Example 68

Synthesis of phenyl 2-(bis(phenylthio)methyl)-N-phenyl-thiopentanimidate (hereinafter referred to as the present compound 68)

Thiophenol (4.7 mL) and triethylamine (0.32 mL) were added to a solution (5 mL) of phenyl 2-propyl-N-phenyl-3-(phenylthio)thioacrylimidate (0.89 g) in methanol (5 mL) at room temperature, and the mixture was heated to reflux for 7 hours. To the mixture was added tert-butyl methyl ether, which was washed with a 1N aqueous sodium hydroxide solution, purified water and then a saturated aqueous sodium chloride solution, dried over anhydrous sodium sulfate, and then concentrated under reduced pressure. The residue was isolated and purified by medium pressure preparative liquid chromatography (Yamazen SI-40B, hexane:ethyl acetate=30:1) to obtain the present compound 68 (0.64 g) as a yellow oil.

$^1$H-NMR (CDCl$_3$) δ ppm: 0.840~0.909 (3H, m), 1.21~1.50 (2H, m), 1.82~1.95 (1H, m), 2.02~2.13 (1H, m), 2.89~3.00 (1H, m), 4.70~4.80 (1H, m), 6.84~7.47 (20H, m).

Production Examples 69 to 72

The following compounds were synthesized in the same manner as in Production Example 68.

Phenyl N-phenyl-2-bis(phenylthio)methyl)thiohexanimidate (hereinafter referred to as the present compound 69)

$^1$H-NMR (CDCl$_3$) δ ppm: 0.890 (3H, t, J=7.0 Hz), 1.19~1.42 (4H, m), 1.83~1.95 (1H, m), 2.02~2.13 (1H, m), 2.87~2.94 (1H, m), 4.74 (1H, d, J=8.5 Hz), 6.88 (2H, d, J=7.2 Hz), 7.08~7.42 (18H, m).

Phenyl 2-methylthio-N-phenyl-3,3-bis(phenylthio)thiopropionimidate (hereinafter referred to as the present compound 70)

$^1$H-NMR (CDCl$_3$) δ ppm: 2.11 (3H, s), 3.49 (1H, d, J=10.6 Hz), 5.04 (1H, d, J=10.6 Hz), 6.87 (2H, d, J=7.7 Hz), 7.11~7.51 (18H, m).

Phenyl N-phenyl-3,3-bis(phenylthio)-2-(3-thienyl)thiopropionimidate (hereinafter referred to as the present compound 71)

$^1$H-NMR (CDCl$_3$) δ ppm: 4.07~4.14 (1H, m), 5.10~5.17 (1H, m), 6.78~7.49 (23H, m).

Phenyl 2-fluoro-N-phenyl-3,3-bis(phenylthio)thiopropionimidate (hereinafter referred to as the present compound 72)

$^1$H-NMR (CDCl$_3$) δ ppm: 4.82~5.00 (2H, m), 6.84 (2H, d, J=7.5 Hz), 7.10~7.43 (18H, m).

Production Examples 73 and 74

The following compounds were synthesized in the same manner as in Production Example 17.

3-Trifluoromethylphenyl N-(4-methylphenyl)-3,3-bis(3-trifluoromethylphenylthio)thiopropionimidate (hereinafter referred to as the present compound 73)

$^1$H-NMR (CDCl$_3$) δ ppm: 2.34 (3H, s), 2.79 (2H, d, J=7.0 Hz), 5.11 (1H, t, J=7.0 Hz), 6.30-7.66 (16H, m).

2-Thienyl N-(4-methylphenyl)-3,3-bis(2-thienylthio)thiopropionimidate (hereinafter referred to as the present compound 74)

$^1$H-NMR (CDCl$_3$) δ ppm: 2.34 (3H, s), 2.82 (2H, J=7.1 Hz), 4.61 (1H, t, J=7.1 Hz), 6.85-7.46 (13H, m).

Production Example 75

Cyclohexyl 3,3-bis(benzoylthio)-N-(phenyl)thiopropionimidate (hereinafter referred to as the present compound 75) was synthesized in the same manner as in Production Example 29.

$^1$H-NMR (CDCl$_3$) δ ppm: 1.32~2.34 (10H, m), 3.26~3.77 (3H, m), 5.47~6.37 (1H, m), 6.77~8.17 (15H, m).

Production Example 76

Synthesis of cyclohexylmethyl 2-(benzo[1,3]oxothiol-2-yl)-N-(phenyl)thioacetimidate (hereinafter referred to as the present compound 76)

A catalytic amount of potassium carbonate was added to a solution of cyclohexylmethyl N-phenyl-3-(trimethylsilyl)thiopropiolimidate (1.0 g) in methanol (20 mL) at room temperature, and the mixture was stirred at the same temperature for 30 minutes. The mixture was concentrated under reduced pressure. The residue was filtered on silica gel (hexane:ethyl acetate=10:1). The filtrate was concentrated under reduced pressure. To the residue was added THF (20 mL) at room temperature, and then, 2-hydroxythiophenol (0.38 g) and triethylamine (0.51 mL) were added thereto. The mixture was stirred at room temperature for 3 hours. After tert-butyl methyl ether (150 mL) was added to the mixture, which was washed with a 1N aqueous sodium hydroxide solution, purified water and then a saturated aqueous sodium chloride solution, dried over anhydrous sodium sulfate, and then concentrated under reduced pressure. The residue was isolated and purified by medium pressure preparative liquid chromatography (Yamazen SI-40B, hexane:ethyl acetate=20:1) to obtain the present compound 76 (0.18 g) as a yellow oil.

$^1$H-NMR (CDCl$_3$) δ ppm: 0.90~1.85 (11H, m), 2.73~3.47 (4H, m), 6.26~7.33 (10H, m).

Production Examples 77 and 78

The following compounds were synthesized in the same manner as in Production Example 76.

Cyclohexylmethyl 2-([1,3]dithiolan-2-yl)-N-(phenyl)thioacetimidate (hereinafter referred to as the present compound 77)

$^1$H-NMR (CDCl$_3$) δ ppm: 0.87~1.84 (11H, m), 2.74~3.24 (8H, m), 4.79 (0.66H, brs), 5.08 (0.34H, brs), 6.76~7.29 (5H, m).

Cyclohexylmethyl 2-(1,5-dihydro-benzo[1,3]dithiepin-3-yl)-N-(phenyl)thioacetimidate (hereinafter referred to as the present compound 78)

$^1$H-NMR (CDCl$_3$) δ ppm: 0.86~1.86 (11H, m), 2.66~3.00 (4H, m), 3.61~4.14 (4.3H, m), 4.49 (0.7H, brs), 6.70~7.29 (9H, m).

Production Example 79

Synthesis of cyclohexylmethyl 2-(2-oxo-1,2,3,5-tetrahydro-2λ$^4$-benzo[e][1,3]dithiepin-3-yl)-N-(phenyl)thioacetimidate (hereinafter referred to as the present compound 79)

A solution of m-chlorobenzoic acid (0.32 g) in chloroform (10 mL) was added dropwise to a solution of cyclohexylmethyl 2-(1,5-dihydro-benzo[1,3]dithiepin-3-yl)-N-(phenyl)thioacetimidate (0.62 g) in chloroform (15 mL) under ice-cooling, and the mixture was stirred at the same temperature for 1 hour. To the reaction mixture was added chloroform (50 mL), which was washed with a saturated aqueous sodium hydrogen carbonate solution, purified water and then a saturated aqueous sodium chloride solution, dried over anhydrous sodium sulfate, and then concentrated under reduced pressure. The residue was isolated and purified by medium pressure preparative liquid chromatography (Yamazen SI-40B, hexane:ethyl acetate=5:1) to obtain the present compound 79 (0.42 g) as a light yellow oil.

$^1$H-NMR (CDCl$_3$) δ ppm: 1.01~1.88 (11H, m), 2.66~3.00 (4H, m), 3.82~4.30 (5H, m), 6.68~7.34 (9H, m).

Production Example 80

Synthesis of cyclohexylmethyl 3-(4-fluorophenylthio)-3-methoxy-N-(phenyl)thioacetimidate (hereinafter referred to as the present compound 80)

A catalytic amount of potassium carbonate was added to a solution of cyclohexylmethyl N-phenyl-3-(trimethylsilyl)propionimidate (1.0 g) in methanol (20 mL) at room temperature, and the mixture was stirred at the same temperature for 30 minutes. The mixture was concentrated under reduced pressure. The residue was filtered on silica gel (hexane:ethyl acetate=10:1). The filtrate was concentrated under reduced pressure. To the residue was added THF (15 mL) at room temperature, and then, methanol (0.13 mL) and trinormalbutylphosphine (0.37 mL) were added thereto. The mixture was stirred at room temperature for 3 hours. The residue was isolated and purified by medium pressure preparative liquid chromatography (Yamazen SI-40B, hexane:ethyl acetate=20:1) to obtain the main product (0.14 g). To the product was added THF (5 mL) at room temperature, and then 4-fluorothiophenol was added thereto. The mixture was stirred at room temperature for 3 hours, and then concentrated under reduced pressure. The residue was isolated and purified by medium pressure preparative liquid chromatography (Yamazen SI-40B, hexane:ethyl acetate=20:1) to obtain the present compound 80 (0.12 g) as a light yellow oil.

$^1$H-NMR (CDCl$_3$) δ ppm: 0.87~1.81 (11H, m), 2.49~2.93 (4H, m), 3.42 (3H, s), 4.76 (1H, s), 6.61~7.51 (9H, m).

Production Example 81

Synthesis of cyclohexylmethyl 3-(4-fluorophenylthio)-3-furfuryloxy-N-(phenyl)thioacetimidate (hereinafter referred to as the present compound 81)

A catalytic amount of potassium carbonate was added to a solution of cyclohexylmethyl N-phenyl-3-(trimethylsilyl)thiopropiolimidate (1.0 g) in methanol (20 mL) at room temperature, and the mixture was stirred at the same temperature for 30 minutes. The mixture was concentrated under reduced pressure. The residue was filtered on silica gel (hexane:ethyl acetate=10:1). The filtrate was concentrated under reduced pressure. To the residue was added THF (15 mL) at room temperature, and then, furfurylalcohol (0.26 mL) and trinormalbutylphosphine (0.37 mL) were added thereto. The mixture was stirred at room temperature for 3 hours. The residue was isolated and purified by medium pressure preparative liquid chromatography (Yamazen SI-40B, hexane:ethyl acetate=20:1) to obtain the main product (0.30 g). To the product was added THF (10 mL) and then, 4-fluorothiophenol (0.092 mL) was added thereto under ice-cooling. The mixture was stirred at the same temperature for 2 hours, and the at room temperature for 8 hours, and then concentrated under reduced pressure to obtain the present compound 81 (0.44 g) as a red oil.

$^1$H-NMR (CDCl$_3$) δ ppm: 0.74~1.85 (11H, m), 2.47~2.93 (4H, m), 4.34~5.32 (3H, m), 6.25~7.58 (12H, m).

Production Example 82

Cyclohexylmethyl 3-bis(4-fluorophenylthio)-N-(4-methoxyphenyl)thiopropionimidate (hereinafter referred to as the present compound 82) was synthesized in the same manner as in Production Example 42.

$^1$H-NMR (CDCl$_3$) δ ppm: 0.87~1.87 (11H, m), 2.52 (0.6H, d, J=6.8 Hz), 2.88 (1.4H, d, J=8.0 Hz), 2.97~3.02 (2H, m), 3.80 (3H, s), 4.41 (0.7H, t, J=8.0 Hz), 4.95 (0.3H, t, J=6.8 Hz), 6.57~7.51 (12H, m).

Production Example 83

Synthesis of butyl N-phenyl-3,3-bis(phenylthio)thiopropionimidate (hereinafter referred to as the present compound 83)

Butyl iodide (44 mg) was added to a solution of N-phenyl-3,3-bis(phenylthio)thiopropionamide (76 mg) in anhydrous DMF (2 mL). The mixture was stirred at room temperature for 5 minutes. After potassium carbonate (30 mg) was added, the mixture was stirred at room temperature for 2.5 hours. To the mixture was added t-butyl methyl ether (50 mL), which was washed with a saturated aqueous sodium chloride solution, dried over anhydrous magnesium sulfate, and concentrated under reduced pressure. The residue was isolated and purified by medium pressure preparative liquid chromatography (Yamazen SI-40B, hexane:ethyl acetate=30:1) to obtain the present compound 83 (51 mg) as a colorless oil.

$^1$H-NMR (CDCl$_3$) δ ppm: 0.84-1.69 (7H, m), 2.63 (0.4H, brs), 2.92 (1.6H, d, J=7.5 Hz), 3.05 (2H, m), 4.62 (0.8H, t, J=7.5 Hz), 5.16 (0.2H, brs), 6.76-7.54 (15H, m).

Production Examples 84 to 95

The following compounds were synthesized in the same manner as in Production Example 83.

1-Methylpropyl N-phenyl-3,3-bis(phenylthio)thiopropionimidate (hereinafter referred to as the present compound 84)

$^1$H-NMR (CDCl$_3$) δ ppm: 1.02 (3H, t, J=6.8 Hz), 1.37 (3H, d, J=5.8 Hz), 1.66~1.73 (2H, m), 2.91 (1.6H, d, J=7.3 Hz), 3.12 (0.4H, brs), 3.73~3.82 (1H, m), 4.63 (0.8H, t, J=7.3 Hz), 5.13 (0.2H, brs), 6.68~7.54 (15H, m).

2-Methylpropyl N-phenyl-3,3-bis(phenylthio)thiopropionimidate (hereinafter referred to as the present compound 85)

$^1$H-NMR (CDCl$_3$) δ ppm: 0.86 (1.2H, brs), 1.01 (2.4H, s), 1.02 (2.4H, s), 1.61 (0.2H, brs), 1.88~2.03 (0.8H, brs), 2.50 (0.4H, brs), 2.94 (1.6H, d, J=7.5 Hz), 2.98 (1.6H, d, J=6.5 Hz), 3.07 (0.4H, brs), 4.64 (0.8H, t, J=7.5 Hz), 5.16 (0.2H, brs), 6.66~7.54 (15H, m).

1-Methylpentyl N-phenyl-3,3-bis(phenylthio)thiopropionimidate (hereinafter referred to as the present compound 86)

$^1$H-NMR (CDCl$_3$) δ ppm: 0.87-1.83 (12H, m), 2.90 (1.44H, d, J=7.5 Hz), 3.12 (0.56H, brs), 3.80-3.86 (1H, m), 4.63 (0.72H, t, J=7.5 Hz), 5.14 (0.28H, brs), 6.68-7.54 (15H, m).

1-Methylpentyl 3,3-bis(4-fluorophenylthio)-N-(phenyl)thiopropionimidate (hereinafter referred to as the present compound 87)

$^1$H-NMR (CDCl$_3$) δ ppm: 0.88~1.69 (12H, m), 2.84 (1.62H, d, J=7.5 Hz), 3.05 (0.38H, brs), 3.81~3.84 (1H, m), 4.41 (0.81H, t, J=7.5 Hz), 4.95 (0.19H, brs), 6.66~7.52 (13H, m).

Hexyl N-phenyl-3,3-bis(phenylthio)thiopropionimidate (hereinafter referred to as the present compound 88)

$^1$H-NMR (CDCl$_3$) δ ppm: 0.83~1.68 (11H, m), 2.62 (0.46H, brs), 2.92 (1.54H, d, J=7.3 Hz), 3.04 (2H, t, J=6.5 Hz), 4.62 (0.77H, t, J=7.3 Hz), 5.15 (0.23H, brs), 6.67~7.54 (15H, m).

Hexyl 3,3-bis(4-fluorophenylthio)-N-(phenyl)thiopropionimidate (hereinafter referred to as the present compound 89)

$^1$H-NMR (CDCl$_3$) δ ppm: 0.85-1.68 (11H, m), 2.62 (0.44H, brs), 2.87 (1.56H, d, J=7.2 Hz), 3.03-3.07 (2H, m), 4.40 (0.78H, t, J=7.2 Hz), 4.97 (0.22H, brs), 6.65-7.52 (13H, m).

Cyclopentyl N-phenyl-3,3-bis(phenylthio)thiopropionimidate (hereinafter referred to as the present compound 90)

$^1$H-NMR (CDCl$_3$) δ ppm: 1.45~2.15 (8H, m), 2.90 (1.28H, d, J=6.8 Hz), 3.14 (0.72H, brs), 3.25 (0.36H, brs), 3.93 (0.64H, brs), 4.62 (0.64H, t, J=6.8 Hz), 5.18 (0.36H, brs), 6.68~7.54 (15H, m).

Cyclopentyl 3,3-bis(4-fluorophenylthio)-N-(phenyl)thiopropionimidate (hereinafter referred to as the present compound 91)

$^1$H-NMR (CDCl$_3$) δ ppm: 1.48~2.20 (8H, m), 2.84 (1.34H, d, J=7.5 Hz), 3.08 (0.66H, brs), 3.27 (0.33H, brs), 3.92~3.96 (0.67H, m), 4.39 (0.67H, t, J=7.5 Hz), 4.99 (0.33H, brs), 6.68~7.54 (13H, m).

Cyclopentylmethyl N-phenyl-3,3-bis(phenylthio)thiopropionimidate (hereinafter referred to as the present compound 92)

$^1$H-NMR (CDCl$_3$) δ ppm: 1.06~1.82 (8H, m), 2.15~2.22 (1H, m), 2.61 (0.40H, brs), 2.93 (1.6H, d, J=7.5 Hz), 3.07~3.10 (2H, m), 4.63 (0.80H, t, J=7.5 Hz), 5.15 (0.20H, brs), 6.66~7.54 (15H, m).

(Tetrahydrofuran-3-yl)methyl 3,3-bis(4-fluorophenylthio)-N-(phenyl)thiopropionimidate (hereinafter referred to as the present compound 93)

$^1$H-NMR (CDCl$_3$) δ ppm: 1.71~1.74 (1H, m), 2.06~2.13 (1H, m), 2.59~2.67 (1H, m), 2.87 (1.78H, d, J=7.5 Hz), 3.02 (0.22H, brs), 3.07~3.21 (2H, m), 3.35~3.58 (1H, m), 3.71~3.80 (1H, m), 3.86~3.93 (2H, m), 4.38 (0.89H, t, J=7.5 Hz), 4.95 (0.11H, brs), 6.65~7.52 (13H, m).

3,3,3-Trifluoropropyl 3,3-bis(4-fluorophenylthio)-N-(phenyl)thiopropionimidate (hereinafter referred to as the present compound 94)

$^1$H-NMR (CDCl$_3$) δ ppm: 2.26 (2H, m), 2.88 (2H, d, J=8.0 Hz), 3.20 (2H, t, J=7.6 Hz), 4.34 (1H, t, J=8.0 Hz), 6.65~7.48 (13H, m).

(Trimethylsilyl)methyl 3,3-bis(4-fluorophenylthio)-N-(phenyl)thiopropionimidate (hereinafter referred to as the present compound 95)

$^1$H-NMR (CDCl$_3$) δ ppm: 0.01 (1.62H, brs), 0.14 (7.38H, s), 2.26 (2H, s), 2.90 (1.62H, d, J=7.6 Hz), 3.07 (0.38H, brs), 4.38 (0.81H, t, J=7.6 Hz), 4.95 (0.19H, brs), 6.65~7.50 (13H, m).

Production Example 96

Synthesis of trifluoromethyl N-phenyl-3,3-bis(phenylthio)thiopropionimidate (hereinafter referred to as the present compound 96)

S-trifluoromethyl-3,7-dinitrobenzothiophenium trifluoromethanesulfonate (MEC-12) (0.13 g) was added to a solution of N-phenyl-3,3-bis(phenylthio)thiopropionamide (0.10 g) in anhydrous DMF (2 mL) under a nitrogen atmosphere under ice-cooling. The mixture was stirred under a nitrogen atmosphere under ice-cooling for 10 minutes. To the mixture was added potassium carbonate (36 mg). The mixture was stirred under a nitrogen atmosphere for 6.5 hours while it was slowly warmed to room temperature. To the reaction mixture was added t-butyl methyl ether (50 mL), which was washed with a saturated aqueous sodium chloride solution, dried over anhydrous magnesium sulfate, and then concentrated under reduced pressure. The residue was isolated and purified by medium pressure preparative liquid chromatography (Yamazen SI-40B, hexane:ethyl acetate=30:1) to obtain the present compound 96 (10 mg) as a yellow oil.

$^1$H-NMR (CDCl$_3$) δ ppm: 3.33 (2H, d, J=5.4 Hz), 5.12 (1H, t, J=5.4 Hz), 6.76~7.52 (15H, m).

Production Example 97

Synthesis of (2-chlorothiazol-5-yl)methyl 3,3-bis(4-fluorophenylthio)-N-(phenyl)thiopropionimidate (hereinafter referred to as the present compound 97)

2-Chloro-5-(chloromethyl)thiazole (0.24 g) was added to a solution of 3,3-bis(4-fluorophenylthio)-N-(phenyl)thiopropionamide (0.30 g) in anhydrous DMF (1 mL). The mixture was stirred at room temperature for 5 minutes. To the mixture was added potassium carbonate (99 mg). The mixture was stirred at room temperature for 2.5 hours. To the reaction mixture was added t-butyl methyl ether (50 mL), which was washed with a saturated aqueous sodium chloride solution, dried over anhydrous magnesium sulfate, and then concentrated under reduced pressure. The residue was isolated and purified by medium pressure preparative liquid chromatography (Yamazen SI-40B, hexane:ethyl acetate=88:12) to obtain the present compound 97 (0.25 g) as a yellow oil.

$^1$H-NMR (CDCl$_3$) δ ppm: 2.88 (1.86H, d, J=8.0 Hz), 3.15 (0.14H, d, J=7.2 Hz), 4.34 (1.86H, s), 4.55 (0.14H, s), 4.29 (0.93H, t, J=8.0 Hz), 5.09 (0.07H, t, J=7.2 Hz), 6.71~8.38 (14H, m).

Production Example 98

(2-Thienyl)methyl 3,3-bis(4-fluorophenylthio)-N-(phenyl)thiopropionimidate (hereinafter referred to as the present compound 98) was synthesized in the same manner as in Production Example 97.

$^1$H-NMR (CDCl$_3$) δ ppm: 2.87 (1.78H, d, J=7.7 Hz), 3.02 (0.22H, brs), 4.34 (0.89H, t, J=7.7 Hz), 4.51 (1.78H, s), 4.70 (0.22H, s), 4.93 (0.11H, brs), 6.72-7.50 (16H, m).

Production Example 99

Synthesis of (3-thienyl)methyl 3,3-bis(4-fluorophenylthio)-N-(phenyl)thiopropionimidate (hereinafter referred to as the present compound 99)

Thionyl chloride (0.29 mL) was added to a solution of (3-thienyl)methanol (0.23 g) in anhydrous THF (2 mL). The mixture was stirred at 50° C. for 2 hours. The reaction mixture was concentrated under reduced pressure. To the residue was added anhydrous DMF (3 mL). Then, a solution of 3,3-bis(4-fluorophenylthio)-N-(phenyl)thiopropionamide (0.84 g) in anhydrous DMF (1 mL), sodium iodide (0.30 g) and potassium carbonate (0.28 g) were added thereto at room temperature, and the mixture was stirred at room temperature for 3 hours. To the reaction mixture was added t-butyl methyl ether (50 mL), which was washed with a saturated aqueous sodium chloride solution, dried over anhydrous magnesium sulfate, and then concentrated under reduced pressure. The residue was isolated and purified by medium pressure preparative liquid chromatography (Yamazen SI-40B, hexane:ethyl acetate=92:8) to obtain the present compound 99 (0.46 g) as a yellow oil.

$^1$H-NMR (CDCl$_3$) δ ppm: 2.86 (1.62H, d, J=7.8 Hz), 2.99 (0.38H, brs), 4.35 (0.81H, t, J=7.8 Hz), 4.29 (1.62H, s), 4.51 (0.38H, s), 4.94 (0.19H, brs), 6.66~7.46 (16H, m).

Production Example 100

(2-Chloropyridin-5-yl)methyl 3,3-bis(4-fluorophenylthio)-N-(phenyl)thiopropionimidate (hereinafter referred to as the present compound 100) was synthesized in the same manner as in Production Example 99.

$^1$H-NMR (CDCl$_3$) δ ppm: 2.86 (2H, d, J=8.0 Hz), 4.22 (2H, s), 4.28 (1H, t, J=8.0 Hz), 6.61~8.43 (16H, m).

Production Examples 101 to 112

The following compounds were synthesized in the same manner as in Production Example 56.

Phenyl N-(5-indanyl)-3,3-bis(phenylthio)propionimidate (hereinafter referred to as the present compound 101)

$^1$H-NMR (CDCl$_3$) δ ppm: 2.01~2.08 (2H, m), 2.79~2.86 (4H, m), 3.00 (2H, d, J=8.0 Hz), 4.94 (1H, t, J=8.0 Hz), 6.50~7.40 (18H, m).

Phenyl 3,3-bis(4-fluorophenylthio)-N-(5-indanyl)propionimidate (hereinafter referred to as the present compound 102)

$^1$H-NMR (CDCl$_3$) δ ppm: 2.02~2.09 (2H, m), 2.79~2.87 (4H, m), 2.93 (2H, d, J=8.0 Hz), 4.72 (1H, t, J=8.0 Hz), 6.46~7.41 (16H, m).

Phenyl N-(5-indanyl)-3,3-bis(3-methylphenylthio)propionimidate (hereinafter referred to as the present compound 103)

$^1$H-NMR (CDCl$_3$) δ ppm: 2.00~2.07 (2H, m), 2.27 (6H, m), 2.79~2.85 (4H, m), 3.01 (2H, d, J=8.0 Hz), 4.95 (1H, t, J=8.0 Hz), 6.49~7.36 (16H, m).

Phenyl N-(5-indanyl)-3,3-bis(4-methoxyphenylthio)propionimidate (hereinafter referred to as the present compound 104)

$^1$H-NMR (CDCl$_3$) δ ppm: 2.01~2.08 (2H, m), 2.79~2.86 (4H, m), 2.91 (2H, d, J=8.0 Hz), 3.78 (6H, m), 4.64 (1H, t, J=8.0 Hz), 6.48~7.38 (16H, m).

Phenyl N-(5-indanyl)-3,3-bis(3-trifluoromethylphenylthio)propionimidate (hereinafter referred to as the present compound 105)

$^1$H-NMR (CDCl$_3$) δ ppm: 2.01~2.09 (2H, m), 2.79~2.86 (4H, m 3.05 (2H, d, J=7.9 Hz), 5.02 (1H, t, J=7.9 Hz), 6.48~7.64 (16H, m).

Phenyl N-(5-indanyl)-3,3-bis(2-thienylthio)propionimidate (hereinafter referred to as the present compound 106)

$^1$H-NMR (CDCl$_3$) δ ppm: 1.99~2.06 (2H, m), 2.78~2.83 (4H, m), 2.95 (2H, d, J=7.7 Hz), 4.53 (1H, t, J=7.7 Hz), 6.47~7.38 (14H, m).

Phenyl N-(5-indanyl)-3,3-bis(2-naphthylthio)propionimidate (hereinafter referred to as the present compound 107)

$^1$H-NMR (CDCl$_3$) δ ppm: 1.97~2.04 (2H, m), 2.72~2.82 (4H, m), 3.10 (2H, d, J=7.9 Hz), 5.15 (1H, t, J=7.9 Hz), 6.50~7.88 (22H, m).

Phenyl N-(4-biphenyl)-3,3-bis(phenylthio)propionimidate (hereinafter referred to as the present compound 108)

$^1$H-NMR (CDCl$_3$) δ ppm: 3.02 (2H, d, J=7.8 Hz), 4.96 (1H, t, J=7.8 Hz), 6.79~7.61 (24H, m).

Phenyl 3,3-bis(3-methylphenylthio)-N-(4-biphenyl)propionimidate (hereinafter referred to as the present compound 109)

$^1$H-NMR (CDCl$_3$) δ ppm: 2.27 (6H, s), 3.03 (2H, d, J=8.0 Hz), 4.97 (1H, t, J=8.0 Hz), 6.80~7.61 (22H, m).

Phenyl 3,3-bis(4-fluorophenylthio)-N-(4-biphenyl)propionimidate (hereinafter referred to as the present compound 110)

$^1$H-NMR (CDCl$_3$) δ ppm: 2.96 (2H, d, J=8.0 Hz), 4.74 (1H, t, J=8.0 Hz), 6.78~7.61 (22H, m).

Phenyl N-(4-biphenyl)-3,3-bis(3-trifluoromethylphenylthio)propionimidate (hereinafter referred to as the present compound 111)

$^1$H-NMR (CDCl$_3$) δ ppm: 3.07 (2H, d, J=7.8 Hz), 5.04 (1H, t, J=7.8 Hz), 6.73~8.07 (22H, m).

Phenyl N-(4-biphenyl)-3,3-bis(2-thienylthio)propionimidate (hereinafter referred to as the present compound 112)

$^1$H-NMR (CDCl$_3$) δ ppm: 2.98 (2H, d, J=8.0 Hz), 4.55 (1H, t, J=8.0 Hz), 6.78~7.61 (20H, m).

Production Example 113

Synthesis of 3-methylphenyl N-(3,4-dimethylphenyl)-3-phenylsulfonyl-3-phenylthio-propionimidate (hereinafter referred to as the present compound 113)

Thiophenol (0.062 mL) was added to a solution of 3-methylphenyl N-(3,4-dimethylphenyl)-3-phenylsulfonylacrylimidate (0.30 g) in THF (10 mL) under ice-cooling, and the mixture was stirred for 1 hour. The mixture was concentrated under reduced pressure. The residue was isolated and purified by silica gel column chromatography (hexane:ethyl acetate=10:1) to obtain the present compound 113 (0.10 g) as a yellow oil.

$^1$H-NMR (CDCl$_3$) δ ppm: 2.18 (3H, s), 2.20 (3H, s), 2.32 (3H, s), 2.99~3.06 (1H, m), 3.30~3.34 (1H, m), 4.84~4.88 (1H, m), 6.45~6.50 (2H, m), 6.89~7.58 (13H, m), 7.80~7.82 (2H, m).

Production Example 114

Synthesis of 3-methylphenyl 3,3-bis(benzyloxy)-N-(3,4-dimethylphenyl)propionimidate (hereinafter referred to as the present compound 114)

3-Methylphenyl 3-benzyloxy-N-(3,4-dimethylphenyl) acrylimidate (0.72 g) was added to a solution of 10% palladium on carbon (0.20 g) in ethyl acetate (50 mL) under ice-cooling under a nitrogen atmosphere. The mixture was stirred for 1.5 hours under a hydrogen atmosphere. Insoluble substances were filtered off, and the filtrate was concentrated under reduced pressure. The residue was isolated and purified by silica gel column chromatography (hexane:ethyl acetate=20:1) to obtain the present compound 114 (0.12 g) as a light yellow oil.

$^1$H-NMR (CDCl$_3$) δ ppm: 2.13 (3H, s), 2.17 (3H, s), 2.32 (3H, s), 2.89 (2H, d, J=6.0 Hz), 4.53~4.66 (4H, m), 5.30 (1H, t, J=6.0 Hz), 6.47~6.51 (2H, m), 6.89~6.96 (4H, m), 7.19~7.34 (11H, m).

Production Example 115

Synthesis of ethyl N-(4-biphenyl)-3,3-bis(3-trifluoromethylphenylthio)propionimidate (hereinafter referred to as the present compound 115)

A solution of 3-trifluoromethylphenylmercaptan (0.10 mg) in THF (0.5 mL) was added to a solution of a mixture (PhO form:EtO form=79:21) (0.27 mL) of phenyl N-(4-biphenyl)-3-(3-trifluoromethylphenylthio)acrylimidate and ethyl N-(4-biphenyl)-3-(3-trifluoromethylphenylthio)acrylimidate in THF (3 mL) under ice-cooling. The mixture was stirred for 10.5 hours, while it was slowly warmed to room temperature. The mixture was allowed to stand overnight. To the reaction mixture was added ethyl acetate (50 mL), which was washed with a 1N aqueous sodium hydroxide solution, water and then a saturated aqueous sodium chloride solution, dried over anhydrous magnesium sulfate, and then concentrated under reduced pressure. The residue was isolated and purified by medium pressure preparative liquid chromatography (Yamazen SI-40B, hexane:ethyl acetate=40:1 to 30:1) to obtain phenyl N-(4-biphenyl)-3,3-di(3-trifluoromethylphenylthio) propionimidate (0.12 g) and the present compound 115 (36 mg) as a yellow oil.

$^1$H-NMR (CDCl$_3$) δ ppm: 1.34 (3H, d, J=7.0 Hz), 2.86 (2H, d, J=7.8 Hz), 4.27 (2H, t, J=7.0 Hz), 4.84 (1H, t, J=7.8 Hz), 6.59~7.71 (17H, m).

The structural formulae of the present compounds 1 to 115 are shown below:

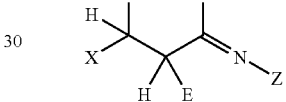

wherein $Y^O$, Z, X, $X^O$, and E are any one of combinations shown in the following table 4.

TABLE 4

| Compound No. | $Y^O$ | Z | X | $X^O$ | E |
|---|---|---|---|---|---|
| 1 | PhS | 4-Me-Ph | PhS | PhS | H |
| 2 | PhS | Ph | PhS | PhS | H |
| 3 | PhS | 4-Et-Ph | PhS | PhS | H |
| 4 | PhS | 4-Ph-Ph | PhS | PhS | H |
| 5 | PhS | 4-Cl-Ph | PhS | PhS | H |
| 6 | PhS | 3-Me-Ph | PhS | PhS | H |
| 7 | PhS | 4-isoPr-Ph | PhS | PhS | H |
| 8 | PhS | MeS-thiazolyl | PhS | PhS | H |
| 9 | PhS | pyridyl-phenyl | PhS | PhS | H |
| 10 | PhS | indanyl | PhS | PhS | H |

TABLE 4-continued

| Compound No. | $Y^O$ | Z | X | $X^O$ | E |
|---|---|---|---|---|---|
| 11 | PhS | Ph | PhS | benzyl-S | H |
| 12 | PhS | Ph | PhS | cyclohexyl-S | H |
| 13 | PhS | Ph | PhS | MeS | H |
| 14 | PhS | Ph | PhS | EtS | H |
| 15 | PhS | Ph | | 1,2-benzenedithiol | H |
| 16 | PhS | Ph | 4-Me-PhS | 4-Me-PhS | H |
| 17 | 3-Me-PhS | 4-Me-Ph | 3-Me-PhS | 3-Me-PhS | H |
| 18 | 4-MeO-PhS | 4-Me-Ph | 4-MeO-PhS | 4-MeO-PhS | H |
| 19 | 4-Me-PhS | 3,4-Me$_2$-Ph | 4-Me-PhS | 4-Me-PhS | H |
| 20 | 2-naphthyl-S | Ph | 2-naphthyl-S | 2-naphthyl-S | H |
| 21 | 1-naphthyl-S | 4-Me-Ph | 1-naphthyl-S | 1-naphthyl-S | H |
| 22 | decahydronaphthyl-S | 3,4-Me$_2$-Ph | 4-F-PhS | 4-F-PhS | H |
| 23 | decahydronaphthyl-S | Ph | 4-F-PhS | 4-F-PhS | H |
| 24 | cyclohexyl-S | Ph | 4-F-PhS | 4-F-PhS | H |
| 25 | cyclohexyl-S | Ph | 4-Cl-PhS | 4-Cl-PhS | H |
| 26 | cyclohexyl-S | Ph | 3-CF3-PhS | 3-CF3-PhS | H |
| 27 | cyclohexyl-S | Ph | 4-Me-PhS | 4-Me-PhS | H |
| 28 | cyclohexyl-S | Ph | PhS | PhS | H |
| 29 | cyclohexyl-S | Ph | MeC(O)S | MeC(O)S | H |

TABLE 4-continued
| Compound No. | Y$^O$ | Z | X | X$^O$ | E |
|---|---|---|---|---|---|
| 30 | 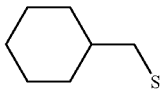 | Ph | PhS | PhS | H |
| 31 | 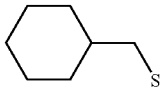 | Ph | 3-F-PhS | 3-F-PhS | H |
| 32 | 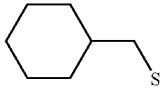 | Ph | 4-F-PhS | 4-F-PhS | H |
| 33 | 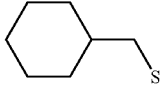 | Ph | 3-Cl-PhS | 3-Cl-PhS | H |
| 34 | 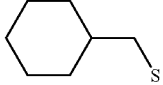 | Ph | 4-Cl-PhS | 4-Cl-PhS | H |
| 35 | 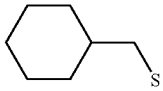 | Ph | 3-Br-PhS | 3-Br-PhS | H |
| 36 | 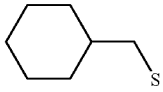 | Ph | 4-Br-PhS | 4-Br-PhS | H |
| 37 | 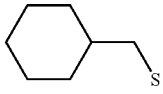 | Ph | 3-Me-PhS | 3-Me-PhS | H |
| 38 | 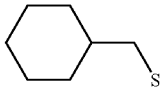 | Ph | 4-Me-PhS | 4-Me-PhS | H |
| 39 | 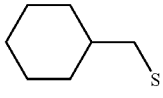 | Ph | 3-MeO-PhS | 3-MeO-PhS | H |
| 40 | 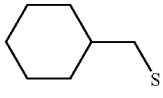 | Ph | 4-MeO-PhS | 4-MeO-PhS | H |
| 41 | 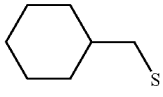 | Ph | 4-NO2-PhS | 4-NO2-PhS | H |
| 42 | 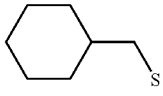 | 4-F-Ph | 4-F-PhS | 4-F-PhS | H |
| 43 | 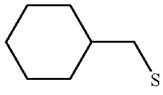 | 4-Cl-Ph | 4-F-PhS | 4-F-PhS | H |

TABLE 4-continued

| Compound No. | Y$^O$ | Z | X | X$^O$ | E |
|---|---|---|---|---|---|
| 44 | cyclohexyl-CH$_2$-S | 4-Me-Ph | 4-F-PhS | 4-F-PhS | H |
| 45 | cyclohexyl-CH$_2$-S | 3-Me-Ph | 4-F-PhS | 4-F-PhS | H |
| 46 | cyclohexyl-CH$_2$-S | 4-NO2-Ph | 4-F-PhS | 4-F-PhS | H |
| 47 | cyclopropyl-CH$_2$-S | Ph | 4-F-PhS | 4-F-PhS | H |
| 48 | cyclopentyl-CH$_2$-S | Ph | 4-F-PhS | 4-F-PhS | H |
| 49 | (Me)$_2$CHCH$_2$CH(Me)CH$_2$-S | Ph | 4-F-PhS | 4-F-PhS | H |
| 50 | Me(Me)CH(Et)-S | 4-Me-Ph | PhS | PhS | H |
| 51 | CH$_2$=CHCH$_2$-S | Ph | PhS | PhS | H |
| 52 | HC≡CCH$_2$-S | Ph | PhS | PhS | H |
| 53 | PhCH$_2$-S | Ph | 4-F-PhS | 4-F-PhS | H |
| 54 | 4-Cl-PhCH$_2$-S | 4-Me-Ph | PhS | PhS | H |
| 55 | PhCH(Me)-S | Ph | PhS | PhS | H |
| 56 | PhO | Ph | PhS | PhS | H |
| 57 | 3-Me-PhO | 4-Me-Ph | 4-F-PhS | 4-F-PhS | H |
| 58 | 3-Me-PhO | 3,4-Me$_2$-Ph | PhS | PhS | H |
| 59 | 3-Me-PhO | 3,4-Me$_2$-Ph | 4-F-PhS | 4-F-PhS | H |
| 60 | 3-Me-PhO | 3,4-Me$_2$-Ph | 4-Me-PhS | 4-Me-PhS | H |
| 61 | 3-Me-PhO | 3,4-Me$_2$-Ph | 4-NO2-PhS | 4-NO2-PhS | H |
| 62 | 3-Me-PhO | 3,4-Me$_2$-Ph | PhCH$_2$-S | PhCH$_2$-S | H |
| 63 | 3-Me-PhO | 3,4-Me$_2$-Ph | 2-thienyl-S | 2-thienyl-S | H |

TABLE 4-continued
| Compound No. | $Y^O$ | Z | X | $X^O$ | E |
|---|---|---|---|---|---|
| 64 | 3-Me-PhO | 3,4-Me$_2$-Ph | 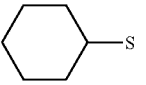 | 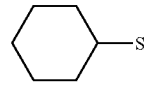 | H |
| 65 | 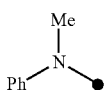 | Ph | 4-Me-PhS | 4-Me-PhS | H |
| 66 | PhS | Ph | PhS | PhS | Me |
| 67 | PhS | Ph | PhS | PhS | Et |
| 68 | PhS | Ph | PhS | PhS | nPr |
| 69 | PhS | Ph | PhS | PhS | nBu |
| 70 | PhS | Ph | PhS | PhS | SMe |
| 71 | PhS | Ph | PhS | PhS | 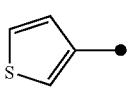 |
| 72 | PhS | Ph | PhS | PhS | F |
| 73 | 3-CF3-PhS | 4-Me-Ph | 3-CF3-PhS | 3-CF3-PhS | H |
| 74 | 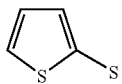 | 4-Me-Ph | 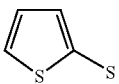 | 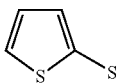 | H |
| 75 | 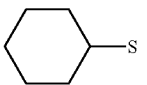 | Ph | 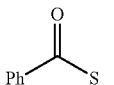 | 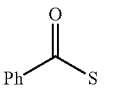 | H |
| 76 | 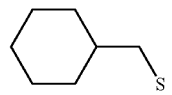 | Ph | 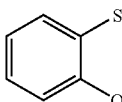 | | H |
| 77 | 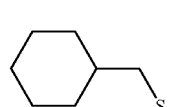 | Ph |  | | H |
| 78 | 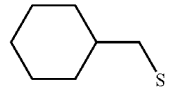 | Ph | 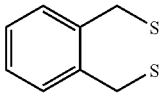 | | H |
| 79 | 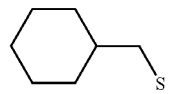 | Ph | 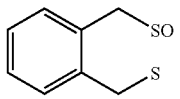 | | H |
| 80 | 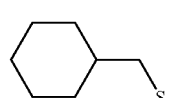 | Ph | 4-F-PhS | MeO | H |
| 81 | 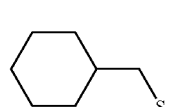 | Ph | 4-F-PhS | 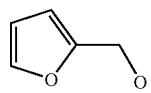 | H |
| 82 | 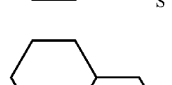 | 4-MeO-Ph | 4-F-PhS | 4-F-PhS | H |
| 83 | 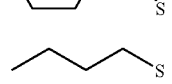 | Ph | PhS | PhS | H |

TABLE 4-continued

| Compound No. | Y$^O$ | Z | X | X$^O$ | E |
|---|---|---|---|---|---|
| 84 | (Me)(Me)CH-CH2-S (isobutyl-like, with Me groups) | Ph | PhS | PhS | H |
| 85 | Me-CH(Me)-CH2-S | Ph | PhS | PhS | H |
| 86 | CH3CH2CH2CH2-CH(S)-CH3 | Ph | PhS | PhS | H |
| 87 | CH3CH2CH2CH2-CH(S)-CH3 | Ph | 4-F-PhS | 4-F-PhS | H |
| 88 | n-hexyl-S | Ph | PhS | PhS | H |
| 89 | n-hexyl-S | Ph | 4-F-PhS | 4-F-PhS | H |
| 90 | cyclopentyl-S | Ph | PhS | PhS | H |
| 91 | cyclopentyl-S | Ph | 4-F-PhS | 4-F-PhS | H |
| 92 | cyclopentyl-CH2-S | Ph | PhS | PhS | H |
| 93 | (tetrahydrofuran-3-yl)-CH2-S | Ph | 4-F-PhS | 4-F-PhS | H |
| 94 | F3C-CH2-CH2-S | Ph | 4-F-PhS | 4-F-PhS | H |
| 95 | TMS-CH2-S | Ph | 4-F-PhS | 4-F-PhS | H |
| 96 | CF3S | Ph | PhS | PhS | H |
| 97 | 2-chloro-thiazol-5-yl-CH2-S | Ph | 4-F-PhS | 4-F-PhS | H |
| 98 | thiophen-2-yl-CH2-S | Ph | 4-F-PhS | 4-F-PhS | H |
| 99 | thiophen-3-yl-CH2-S | Ph | 4-F-PhS | 4-F-PhS | H |
| 100 | 6-chloro-pyridin-3-yl-CH2-S | Ph | 4-F-PhS | 4-F-PhS | H |

TABLE 4-continued

| Compound No. | $Y^O$ | Z | X | $X^O$ | E |
|---|---|---|---|---|---|
| 101 | PhO | 5-indanyl | PhS | PhS | H |
| 102 | PhO | 5-indanyl | 4-F-PhS | 4-F-PhS | H |
| 103 | PhO | 5-indanyl | 3-Me-PhS | 3-Me-PhS | H |
| 104 | PhO | 5-indanyl | 4-MeO-PhS | 4-MeO-PhS | H |
| 105 | PhO | 5-indanyl | 3-CF3-PhS | 3-CF3-PhS | H |
| 106 | PhO | 5-indanyl | 2-thienyl-S | 2-thienyl-S | H |
| 107 | PhO | 5-indanyl | 2-naphthyl-S | 2-naphthyl-S | H |
| 108 | PhO | 4-Ph-Ph | PhS | PhS | H |
| 109 | PhO | 4-Ph-Ph | 3-Me-PhS | 3-Me-PhS | H |
| 110 | PhO | 4-Ph-Ph | 4-F-PhS | 4-F-PhS | H |
| 111 | PhO | 4-Ph-Ph | 3-CF3-PhS | 3-CF3-PhS | H |
| 112 | PhO | 4-Ph-Ph | 2-thienyl-S | 2-thienyl-S | H |
| 113 | 3-Me-PhO | 3,4-Me$_2$-Ph | PhSO2 | PhS | H |
| 114 | 3-Me-PhO | 3,4-Me$_2$-Ph | PhCH$_2$O | PhCH$_2$O | H |
| 115 | EtO | 4-Ph-Ph | 3-CF3-PhS | 3-CF3-PhS | H |

The following Reference Production Examples show production of starting compounds for producing the compounds of the present invention.

Reference Production Example 1

Production of phenyl N-(5-indanyl)-3-(phenylthio)thioacrylimidate

Thionyl chloride (0.75 mL) and DMF (catalytic amount) were added to a solution of N-(5-indanyl)-3(phenylthio)acrylamide (1.21 g) in toluene (50 mL) at room temperature, and the mixture was stirred at 70° C. for 2 hours. The reaction mixture was concentrated under reduced pressure. To the residue was added THF (40 mL), and then a solution (0.62 mol/L, 10 mL) of phenylmercaptan sodium salt in THF was added thereto under ice-cooling. The mixture was stirred at room temperature for 2 hours, and then alkalilized by addition of a 1N aqueous sodium hydroxide solution, followed by extraction with ethyl acetate (250 mL). The organic layer was washed with water and then a saturated aqueous sodium chloride solution, dried over anhydrous magnesium sulfate, and concentrated under reduced pressure. The residue was subjected to silica gel column chromatography (hexane:ethyl acetate=100:1 to 50:1) to obtain phenyl N-(5-indanyl)-3-(phenylthio)thioacrylimidate (Z-isomer: 0.27 g, E-isomer: 0.94 g).

Z-Isomer:
$^1$H-NMR (CDCl$_3$) δ ppm: 2.03-2.06 (2H, m), 2.85-2.92 (4H, m), 5.79 (1H, d, J=10.1 Hz), 6.72-7.53 (14H, m)

E-Isomer:
$^1$H-NMR (CDCl$_3$) δ ppm: 1.93-2.03 (2H, m), 2.72-2.90 (4H, m), 5.70 (1H, d, J=14.7 Hz), 6.70-7.40 (13H, m), 7.53 (1H, d, J=14.7 Hz).

Reference Production Example 2-(1)

Production of 3-methylphenyl N-(4-methylphenyl)-3-(3-methylphenylthio)thioacrylimidate Thionyl chloride (0.54 mL) and DMF (catalytic amount) were added to a solution of 3-(3-methylphenyl)-N-(4-methylphenyl)acrylamide (E/Z=4/1) (0.84 g) in toluene (15 mL), and the mixture was stirred at 70° C. for 1 hour. The mixture was concentrated under reduced pressure. To the residue was added anhydrous THF (15 mL). Sodium hydride (60%) (0.21 g) was added to a solution (5 mL) of 3-methylmercaptan (0.44 g) in anhydrous THF (5 mL) under a nitrogen atmosphere under ice-cooling, and the mixture was stirred at room temperature under a nitrogen atmosphere for 30 minutes. The reaction mixture was added to the above-described reaction mixture under ice-cooling, and the mixture was stirred at room temperature for 2 hours. To the reaction mixture was added ethyl acetate (150 mL), which was washed with a 1N aqueous sodium hydroxide solution, water and then a saturated aqueous sodium chloride solution, dried over anhydrous magnesium sulfate, and then concentrated under reduced pressure. The residue was isolated and purified by medium pressure preparative liquid chromatography (Yamazen SI-40B, hexane:ethyl acetate=30:1) to obtain 3-methylphenyl N-(4-methylphenyl)-3-(3-methylphenylthio)thioacrylimidate (0.75 g) as a yellow oil.

$^1$H-NMR (CDCl$_3$) δ ppm: 2.29 (4.2H, s), 2.31 (0.9H, s), 2.32 (2.1H, s), 2.34 (0.9H, s), 2.36 (0.9H, s), 5.67 (0.7H, d, J=14.7 Hz), 5.81 (0.3H, d, J=10.1 Hz), 6.58-7.47 (12.3H, m), 7.53 (0.7H, d, J=14.7 Hz).

Reference Production Examples 2-(2) to (5)

The following compounds were synthesized in the same manner as in Reference Production Example 2-(1).

4-Methoxylphenyl N-(4-methylphenyl)-3-(4-methoxylphenylthio)thioacrylimidate $^1$H-NMR (CDCl$_3$) δ ppm: 2.33 (2.5H, s), 2.36 (0.5H, s), 3.79 (0.5H, s), 3.82 (0.5H, s), 3.82 (2.5H, s), 3.84 (2.5H, s), 5.39 (0.83H, d, J=14.5 Hz), 5.74 (0.17H, d, J=10.1 Hz), 6.52-7.43 (12.17H, m), 7.48 (0.83H, d, J=14.5 Hz).

1-Naphthyl N-(4-methylphenyl)-3-(1-naphthylthio)thioacrylimidate $^1$H-NMR (CDCl$_3$) δ ppm: 2.34 (2.4H, s), 2.41 (0.6H, s), 5.01 (0.79H, d, J=14.5 Hz), 5.56 (0.21H, d, J=10.1 Hz), 6.22-8.38 (19H, m).

3-Trifluoromethylphenyl N-(4-methylphenyl)-3-(3-trifluoromethylphenylthio)thioacrylimidate $^1$H-NMR (CDCl$_3$) δ ppm: 2.28 (0.42H, s), 2.32 (1.20H, s), 2.36 (1.38H, s), 5.59 (0.46H, d, J=14.7 Hz), 5.83 (0.54H, d, J=10.1 Hz), 6.56~7.83 (13H, m).

2-Thienyl N-(4-methylphenyl)-3-(2-thienylthio)thioacrylimidate $^1$H-NMR (CDCl$_3$) δ ppm: 2.32 (1.71H, s), 2.34 (1.29H, s), 5.59 (0.43H, d, J=14.5 Hz), 5.83 (0.57H, d, J=9.9 Hz), 6.74-7.47 (11H, m).

Reference Production Example 3-(1)

Production of phenyl 2-methyl-N-phenyl-3-(phenylthio)thioacrylimidate

Toluene (4 mL) was added to a mixture of 2-methyl-N-phenyl-3-(phenylthio)acrylamide (0.80 g) and phosphorus pentachloride (0.62 g), and the mixture was stirred at room temperature for 4 hours. The mixture was concentrated under reduced pressure. To the concentrate was added DMF (35 mL), and then, phenylmercaptan sodium salt (793 mg) was added portionwise thereto. The mixture was stirred at room temperature for 2 hours. To the reaction mixture was added tert-butyl methyl ether, and then a 1 N aqueous sodium hydroxide solution was added, thereby the solution was separated. The organic layer was washed with water three times, dried and then concentrated. The residue was subjected to silica gel column chromatography (hexane/ethyl acetate=20/1) to obtain phenyl 2-methyl-N-phenyl-3-(phenylthio)thioacrylimidate (0.4 g).

$^1$H-NMR (CDCl$_3$) δ ppm: 1.56 (3H, s), 6.79 (1H, s), 6.81 (1H, s), 7.00~7.39 (15H, m).

Reference Production Examples 3-(2) to (4)

The following compounds were synthesized in the same manner as in Reference Production Example 3-(1).

Phenyl 2-methylthio-N-phenyl-3-(phenylthio)thioacrylimidate $^1$H-NMR (CDCl$_3$) δ ppm: 2.25 (0.7H, s), 2.45 (2.3H, s), 6.76~7.71 (16H, m).

Phenyl N-phenyl-3-(phenylthio)-2-(3-thienyl)thioacrylimidate $^1$H-NMR (CDCl$_3$) δ ppm: 6.87~7.62 (19H, m).

Phenyl 2-fluoro-N-phenyl-3-(phenylthio)thioacrylimidate $^1$H-NMR (CDCl$_3$) δ ppm: 6.84 (2H, d, J=7.5 Hz), 6.91 (1H, d, J=32.4 Hz), 7.08 (1H, t, J=7.5 Hz), 7.16~7.32 (12H, m).

Reference Production Example 4-(1)

Production of phenyl 2-ethyl-N-phenyl-3-(phenylthio)thioacrylimidate

Toluene (20 mL) was added to 2-ethyl-N-phenyl-3-(phenylthio)acrylamide (3.68 g), and then thionyl chloride (1.9 mL) and DMF (10 mg) were added thereto. The mixture was stirred with heating under reflux for 1 hour. The mixture was concentrated under reduced pressure. To the concentrate was added DMF (35 mL), and then, phenylmercaptan sodium salt (2.0 g) was added portionwise thereto under ice-cooling. The mixture was stirred at room temperature for 1 hour. To the reaction mixture was added tert-butyl methyl ether, and then a 1 N aqueous sodium hydroxide solution was added, thereby the solution was separated. The organic layer was washed with water three times, dried and then concentrated. The residue was subjected to silica gel column chromatography (hexane/ethyl acetate=20/1) to obtain phenyl 2-ethyl-N-phenyl-3-(phenylthio)thioacrylimidate (2.03 g).

$^1$H-NMR (CDCl$_3$) δ ppm: 1.17 (3H, t, J=7.1 Hz), 2.51-2.67 (2H, br), 6.80 (2H, d, J=7.3 Hz), 7.00-7.33 (14H, m).

Reference Production Examples 4-(2) and (3)

The following compounds were synthesized in the same manner as in Reference Production Example 4-(1).

Phenyl 2-propyl-N-phenyl-3-(phenylthio)thioacrylimidate $^1$H-NMR (CDCl$_3$) δ ppm: 0.99 (3H, t, J=7.2 Hz), 1.57~1.70 (2H, br), 2.49~2.61 (2H, br), 6.76~6.84 (2H, br), 7.00~7.38 (14H, br).

Phenyl 2-butyl-N-phenyl-3-(phenylthio)thioacrylimidate $^1$H-NMR (CDCl$_3$) δ ppm: 0.96 (3H, t, J=7.2 Hz), 1.32~1.45 (2H, m), 1.51~1.63 (2H, m), 2.49~2.63 (2H, m), 6.76~6.83 (2H, m), 7.01~7.35 (14H, m).

Reference Production Example 5

Production of phenyl N-(5-indanyl)-3-(phenylthio)acrylimidate

Thionyl chloride (1.53 mL) and DMF (catalytic amount) were added to a solution of N-(5-indanyl)-3-(phenylthio) acrylamide (2.47 g) in toluene (80 mL), and the mixture was stirred at 70° C. for 1 hour. The reaction mixture was concentrated under reduced pressure. To the residue was added anhydrous THF (40 mL). To a solution of phenol (1.18 g) in anhydrous THF (20 mL) was added sodium hydride (60%) (0.769 g) under a nitrogen atmosphere under ice-cooling, and then stirred at room temperature under a nitrogen atmosphere for 30 minutes. The reaction mixture was added to the above-described reaction mixture under ice-cooling, and the mixture was stirred at room temperature for 2.5 hours. To the reaction mixture was added ethyl acetate (200 mL), which was washed with a 1N aqueous sodium hydroxide solution, water and then a saturated aqueous sodium chloride solution, dried over anhydrous magnesium sulfate, and then concentrated under reduced pressure. The residue was isolated and purified by silica gel column chromatography (hexane:ethyl acetate=5:1) to obtain phenyl N-(5-indanyl)-3-(phenylthio) acrylimidate (2.56 g) as a orange oil.

$^1$H-NMR (CDCl$_3$) δ ppm: 2.00~2.08 (2H, m), 2.80~2.85 (4H, m), 5.90 (0.43H, d, J=10.9 Hz), 5.99 (0.57H, d, J=15.2 Hz), 6.49~7.50 (13.43H, m), 7.67 (0.57H, d, J=15.2 Hz).

Reference Production Example 6

Production of phenyl N-(4-biphenyl)-3-(phenylthio)acrylimidate

Thionyl chloride (5.85 mL) and DMF (catalytic amount) were added to a solution of N-(4-biphenyl)-3-(phenylthio) acrylamide (10.64 g) in toluene (400 mL), and the mixture was stirred at 70° C. for 3 hours. The reaction mixture was concentrated under reduced pressure. To the residue was added anhydrous THF (320 mL). To a solution of phenol (4.53 g) in anhydrous THF (80 mL) was added sodium hydride (60%) (2.95 g) under a nitrogen atmosphere under ice-cooling, and then stirred at room temperature under a nitrogen atmosphere for 30 minutes. The reaction mixture was added to the above-described reaction mixture under ice-cooling, and the mixture was stirred at room temperature for 2 hours. To the reaction mixture were added a 1N aqueous sodium hydroxide solution and a saturated aqueous sodium chloride solution, followed by extraction with ethyl acetate (500 mL) three times. The extract was concentrated under reduced pressure. To the residue was added ethyl acetate (200 mL), which was washed with a 1N aqueous sodium hydroxide solution, water and then a saturated aqueous sodium chloride solution, dried over anhydrous magnesium sulfate, and then concentrated under reduced pressure. The residue was isolated and purified by silica gel column chromatography (hexane:ethyl acetate=5:1) to obtain phenyl N-(4-biphenyl)-3-(phenylthio)acrylimidate (5.91 g) as a yellow oil.

$^1$H-NMR (CDCl$_3$) δ ppm: 5.93 (1H, d, J=15.1 Hz), 6.78~7.57 (19H, m), 7.72 (1H, d, J=15.1 Hz).

Reference Production Example 7

Production of 3-methylphenyl N-(3,4-dimethylphenyl)-3-(4-nitrophenylthio)acrylimidate To a solution of N-nitrothiophenol (0.31 g) in DMF (10 mL) was added 60% sodium hydride (0.12 g), and the mixture was stirred at room temperature for 30 minutes. The reaction mixture was added dropwise to a solution of 3-methylphenyl N-(3,4-dimethylphenyl)-3-(phenylsulfonyl)acrylimidate (0.81 g) in anhydrous DMF (10 mL) under ice-cooling. The mixture was stirred at room temperature for 1.5 hours. To the reaction mixture was added tert-butyl methyl ether (150 mL), which was washed with a 1N aqueous sodium hydroxide solution, water and then a saturated aqueous sodium chloride solution. The organic layer was dried over anhydrous magnesium sulfate, and then concentrated under reduced pressure. The residue was subjected to silica gel column chromatography (hexane:ethyl acetate=87:13) to obtain 3-methylphenyl N-(3,4-dimethylphenyl)-3-(4-nitrophenylthio)acrylimidate (0.52 g) as a yellow oil.

$^1$H-NMR (CDCl$_3$) δ ppm: 2.20 (3H, s), 2.36 (6H, s), 6.21 (1H, d, J=15.2 Hz), 6.50-7.50 (9H, m), 7.65 (1H, d, J=15.2 Hz), 8.17 (2H, m).

Reference Production Example 8-(1)

Production of phenyl 3-(4-fluorophenylthio)-N-(5-indanyl)acrylimidate

To a solution of 4-fluorothiophenol (0.22 g) in DMF (6 mL) was added 60% sodium hydride (84 mg), and the mixture was stirred at room temperature for 30 minutes under a nitrogen atmosphere. The reaction mixture was added to a solution of phenyl N-(5-indanyl)-3-(phenylsulfonyl)acrylimidate (0.65 g) in anhydrous DMF (3 mL) under ice-cooling. The mixture was stirred at room temperature for 2 hours. To the reaction mixture was added tert-butyl methyl ether (50 mL), which was washed with a 1N aqueous sodium hydroxide solution, water and then a saturated aqueous sodium chloride solution, dried over anhydrous magnesium sulfate, and then concentrated under reduced pressure. The residue was isolated and purified by medium pressure preparative liquid chromatography (Yamazen SI-40B, hexane:ethyl acetate=19:1) to obtain phenyl 3-(4-fluorophenylthio)-N-(5-indanyl)acrylimidate (0.16 g).

$^1$H-NMR (CDCl$_3$) δ ppm: 1.95~2.21 (2H, m), 2.79~2.89 (4H, m), 5.81 (1H, m), 6.46~8.18 (13H, m).

Reference Production Examples 8-(2) to (6)

The following compounds were synthesized in the same manner as Reference Production Examples 8-(1).

Phenyl N-(5-indanyl)-3-(3-methylphenylthio)acrylimidate $^1$H-NMR (CDCl$_3$) δ ppm: 2.01~2.09 (2H, m), 2.32 (3H, s), 2.81~2.85 (4H, m), 5.97 (1H, d, J=15.2 Hz), 6.49~7.44 (12H, m), 7.67 (1H, d, J=15.2 Hz).

Phenyl N-(5-indanyl)-3-(4-methoxyphenylthio)acrylimidate $^1$H-NMR (CDCl$_3$) δ ppm: 2.00-2.08 (2H, m), 2.79-2.84 (4H, m), 3.78 (3H, m), 5.80 (1H, d, J=15.1 Hz), 6.46-7.40 (12H, m), 7.59 (1H, d, J=15.1 Hz).

Phenyl N-(5-indanyl)-3-(3-trifluoromethylphenylthio)acrylimidate $^1$H-NMR (CDCl$_3$) δ ppm: 2.01~2.08 (2H, m), 2.80~2.85 (4H, m), 5.80 (0.20H, d, J=15.0 Hz), 6.02 (0.75H, d, J=15.2 Hz), 6.13 (0.05H, d, J=9.9 Hz), 6.48~7.80 (12.80H, m), 8.00 (0.20H, d, J=15.0 Hz).

Phenyl N-(5-indanyl)-3-(2-thienylthio)acrylimidate $^1$H-NMR (CDCl$_3$) δ ppm: 1.96~2.10 (2H, m), 2.77~2.91 (4H, m), 5.84 (0.74H, d, J=15.0 Hz), 5.99 (0.13H, d, J=15.2 Hz), 6.09 (0.13H, d, J=9.9 Hz), 6.47~8.04 (11.13H, m), 7.67 (0.74H, d, J=15.2 Hz), 8.00 (0.13H, d, J=15.0 Hz).

Phenyl N-(5-indanyl)-3-(2-naphthylthio)acrylimidate $^1$H-NMR (CDCl$_3$) δ ppm: 1.96~2.19 (2H, m), 2.57~3.05 (4H, m), 5.65~5.82 (0.50H, m), 5.99 (0.50H, d, J=15.1 Hz), 6.47~8.26 (16H, m).

Reference Production Example 9-(1)

Production of phenyl N-(4-biphenyl)-3-(3-methylphenylthio)acrylimidate

To a solution of 3-methylphenylmercaptan (0.11 g) in anhydrous DMF (10 mL) was added 60% sodium hydride (44 mg) under a nitrogen atmosphere under ice-cooling, and the mixture was stirred at room temperature for 30 minutes. The reaction mixture was added to a solution of phenyl N-(4-biphenyl)-3-(phenylsulfonyl)acrylimidate (0.40 g) in anhydrous DMF (10 mL) under ice-cooling. The mixture was stirred at room temperature for 2 hours. To the reaction mixture was added tert-butyl methyl ether (150 mL), which was washed with a 1N aqueous sodium hydroxide solution, water and then a saturated aqueous sodium chloride solution, dried over anhydrous magnesium sulfate, and then concentrated under reduced pressure. The residue was isolated and purified by medium pressure preparative liquid chromatography (Yamazen SI-40B, hexane:ethyl acetate=19:1) to obtain phenyl N-(4-biphenyl)-3-(3-methylphenylthio)acrylimidate (0.18 g).

$^1$H-NMR (CDCl$_3$) δ ppm: 2.28 (3H, s), 5.92 (1H, d, J=15.0 Hz), 6.79~7.74 (18H, m), 7.72 (1H, d, J=15.0 Hz).

Reference Production Examples 9-(2) to (5)

The following compounds were synthesized in the same manner as Reference Production Examples 9-(1).

Phenyl 3-(4-fluorophenylthio)-N-(4-biphenyl)acrylimidate $^1$H-NMR (CDCl$_3$) δ ppm: 5.84 (1H, d, J=15.1 Hz), 6.76~7.58 (18H, m), 7.63 (1H, d, J=15.1 Hz).

Phenyl N-(4-biphenyl)-3-(3-trifluoromethylphenylthio)acrylimidate $^1$H-NMR (CDCl$_3$) δ ppm: 5.87 (0.29H, d, J=15.1 Hz), 5.96 (0.66H, d, J=15.1 Hz), 6.19 (0.05H, d, J=9.8 Hz), 6.73~7.97 (19H, m).

Phenyl N-(4-biphenyl)-3-(2-thienyl)acrylimidate $^1$H-NMR (CDCl$_3$) δ ppm: 5.78 (1H, d, J=15.0 Hz), 6.76~7.64 (17H, m), 7.85 (1H, d, J=15.0 Hz).

Ethyl N-(4-biphenyl)-3-(3-methylphenylthio)acrylimidate $^1$H-NMR (CDCl$_3$) δ ppm: 1.37 (3H, t, J=7.1 Hz), 4.30 (2H, q, J=7.1 Hz), 5.87 (1H, t, J=15.1 Hz), 6.57~8.19 (14H, m).

Reference Production Example 10

Production of 3-methylphenyl 3-benzyloxy-N-(3,4-dimethylphenyl)acrylimidate

To a solution of benzyl alcohol (0.78 g) in THF (15 mL) was added 60% sodium hydride (90 mg) under a nitrogen atmosphere under ice-cooling, and the mixture was stirred at the same temperature for 30 minutes. The reaction mixture was added dropwise to a solution of 3-methylphenyl N-(3,4-dimethylphenyl)-3-(phenylsulfonyl)acrylimidate (0.78 g) in anhydrous THF (15 mL) under ice-cooling. The mixture was stirred at the same temperature for 3 hours. To the reaction mixture was added tert-butyl methyl ether (80 mL), which was washed with a 1N aqueous sodium hydroxide solution, water and then a saturated aqueous sodium chloride solution. The organic layer was dried over anhydrous magnesium sulfate, and then concentrated under reduced pressure to obtain 3-methylphenyl 3-benzyloxy-N-(3,4-dimethylphenyl)acrylimidate (0.82 g).

$^1$H-NMR (CDCl$_3$) δ ppm: 2.19 (6H, s), 2.35 (3H, s), 4.81 (2H, s), 5.41 (1H, d, J=12.6 Hz), 6.49~6.54 (2H, m), 6.95~7.00 (4H, m), 7.22~7.38 (6H, m), 7.62 (1H, d, J=12.6 Hz).

Reference Production Example 11-(1)

Production of 2-methyl-N-phenyl-3-(phenylthio)acrylamide

To 2-methyl-3-(phenylthio)acrylic acid (2.5 g) were added toluene (25 mL), and then thionyl chloride (3.5 g) and DMF (10 mg), and the mixture was stirred for 1 hour while it was heated to reflux. The reaction mixture was concentrated. To the residue was added ethyl acetate (25 mL), and then was added dropwise aniline (2.9 g) under ice-cooling. The mixture was stirred at room temperature for 30 minutes. The reaction mixture was washed sequentially with 1N hydrochloric acid, a saturated aqueous sodium hydrogen carbonate solution and then a saturated aqueous sodium chloride solution. The organic layer was dried, and then concentrated to obtain 2-methyl-N-phenyl-3-(phenylthio)acrylamide (3.0 g).

$^1$H-NMR (CDCl$_3$) δ ppm: 2.11 (3H, s), 7.08~7.59 (11H, m).

Reference Production Examples 11-(2) to (7)

The following compounds were synthesized in the same manner as Reference Production Examples 11-(1).

2-Ethyl-N-phenyl-3-(phenylthio)acrylamide $^1$H-NMR (CDCl$_3$) δ ppm: 1.20 (3H, t, J=7.6 Hz), 2.56 (2H, q, Hz), 7.11 (1H, t, J=7.4 Hz), 7.28~7.41 (7H, m), 7.44~7.49 (2H, m), 7.54 (2H, d, J=7.7 Hz).

N-Phenyl-3-phenylthio-2-(propyl)acrylamide $^1$H-NMR (CDCl$_3$) δ ppm: 1.03 (3H, t, J=7.4 Hz), 1.55~1.68 (2H, m), 2.53 (2H, t, J=7.7 Hz), 7.10 (1H, t, J=7.4 Hz), 7.28~7.41 (7H, m), 7.43~7.48 (2H, m), 7.53 (2H, d, J=7.6 Hz).

2-Butyl-N-phenyl-3-(phenylthio)acrylamide $^1$H-NMR (CDCl$_3$) δ ppm: 0.98 (3H, t, J=7.2 Hz), 1.36~1.62 (4H, m), 2.55 (2H, t, J=7.6 Hz), 7.11 (1H, t, J=7.5 Hz), 7.28~7.41 (7H, m), 7.43~7.48 (2H, m), 7.51~7.57 (2H, m).

2-(Methylthio)-N-phenyl-3-(phenylthio)acrylamide $^1$H-NMR (CDCl$_3$) δ ppm: 2.38 (3H, s), 7.13 (1H, t, J=7.5 Hz), 7.32~7.42 (5H, m), 7.50~7.55 (2H, m), 7.63 (2H, d, J=7.5 Hz), 8.43 (1H, s), 9.12 (1H, brs).

N-Phenyl-3-phenylthio-2-(2-thienyl)acrylamide $^1$H-NMR (CDCl$_3$) δ ppm: 7.10 (1H, t, J=7.4 Hz), 7.19~7.24 (2H, m), 7.27~7.40 (5H, m), 7.44~7.52 (5H, m), 7.56 (1H, dd, J=4.3, 1.9 Hz), 8.14 (1H, s).

2-Fluoro-N-phenyl-3-(phenylthio)acrylamide $^1$H-NMR (CDCl$_3$) δ ppm: 7.16 (1H, t, J=7.5 Hz), 7.17 (1H, d, J=35.2 Hz), 7.31~7.41 (5H, m), 7.48 (2H, d, J=7.5 Hz), 7.58 (2H, d, J=8.5 Hz), 7.80 (1H, brs).

Reference Production Example 12

Production of N-(4-biphenyl)-3-(phenylthio)acrylamide

To a solution of N-(4-bromophenyl)-3-(phenylthio)acryl chloride (2.1 g) in a mixture of N-methylpyrrolidone (36 mL)/ion-exchanged water (18 mL) were added phenylboric acid (1.1 g), tetrakistriphenylphosphine palladium (0.14 g) and sodium hydrogen carbonate (1.0 g) at room temperature, and the mixture was stirred at 80° C. for 8 hours. The reaction mixture was extracted with ethyl acetate (400 mL). The organic layer was washed with water and then a saturated aqueous sodium chloride solution, dried over anhydrous magnesium sulfate, and then concentrated under reduced pressure. The residue was subjected to silica gel column chromatography (hexane:ethyl acetate=4:1 to 2:1) to obtain N-(4-biphenyl)-3-(phenylthio)acrylamide (1.5 g) as a light yellow crystal.

$^1$H-NMR (DMSO) δ ppm: 6.06 (0.8H, d, J=14.7 Hz), 6.28 (0.2H, d, J=9.9 Hz), 7.19~7.80 (15H, m), 10.05 (1H, brs).

Reference Production Example 13-(1)

Production of N-[2-(methylthio)thiazol-5-yl]-3-(phenylthio)acrylamide

To a solution of 3-(phenylthio)acrylic acid (3.69 g) in acetonitrile (50 mL) were added a solution of 5-amino-2-(methylthio)thiazole (3.00 g) in acetonitrile (10 mL) and triethylamine (2.80 mL) under ice-cooling. The mixture was stirred at the same temperature for 2 hours and then at room temperature for 3 hours, and then concentrated under reduced pressure. To the residue was added 1N hydrochloric acid (50 mL), which was extracted with ethyl acetate (100 mL) twice. The organic layers were combined, washed with water and then a saturated aqueous sodium chloride solution, dried over anhydrous magnesium sulfate, and then concentrated under reduced pressure. The residue was subjected to silica gel column chromatography (hexane:ethyl acetate=1:1) to obtain N-[2-(methylthio)thiazol-5-yl]-3-(phenylthio)acrylamide (1.90 g) as a dark yellow crystal.

$^1$H-NMR (CDCl$_3$) δ ppm: 2.61 (3H, s), 5.81 (1H, d, J=14.6 Hz), 7.25~7.46 (6H, m), 7.89 (1H, d, J=14.6 Hz), 9.12 (1H, brs).

Reference Production Example 13-(2)

The following compound was synthesized in the same manner as Reference Production Examples 13-(1).

N-(5-indanyl)-3-(phenylthio)acrylamide $^1$H-NMR (CDCl$_3$) δ ppm: 1.99~2.07 (2H, m), 2.81~2.85 (4H, m), 5.84 (0.8H, d, J=14.5 Hz), 5.99 (0.2H, d, J=9.9 Hz), 7.09~7.71 (9.2H, m), 7.78 (0.8H, d, J=14.5 Hz).

Reference Production Example 14

Production of N-(4-methylphenyl)-3-(3-methylphenylthio)acrylamide

To a solution of 3-methylthiophenol (0.85 g) in DMF (10 mL) was added 60% sodium hydride (81 mg) under a nitrogen atmosphere under ice-cooling. The mixture was stirred at room temperature for 30 minutes under a nitrogen atmosphere, and then was added dropwise to a solution of N-(4-methylphenyl)-3-(phenylsulfonyl)acrylamide (0.85 g) in DMF (10 mL) under ice-cooling. The mixture was stirred at room temperature for 2 hours, alkalinized by addition of a 1N aqueous sodium hydroxide solution, and then extracted with tert-butyl methyl ether (100 mL). The organic layer was washed with water and then a saturated aqueous sodium chloride solution, dried over anhydrous magnesium sulfate, and then concentrated under reduced pressure. The residue was subjected to silica gel column chromatography (hexane:ethyl acetate=3:1) to obtain N-(4-methylphenyl)-3-(3-methylphenylthio)acrylamide (0.45 g) as a white crystal.

¹H-NMR (CDCl₃) δ ppm: 2.25 (4.5H, s), 2.31 (0.75H, s), 2.36 (0.75H, s), 5.97 (0.25H, d, J=9.9 Hz), 6.01 (0.75H, d, J=14.7 Hz), 7.00~7.51 (8.5H, m), 7.71 (0.75H, d, J=14.7 Hz), 8.68 (0.75H, brs).

Reference Production Examples 14-(2) to (5)

The following compounds were synthesized in the same manner as Reference Production Examples 14-(1).

N-(4-methylphenyl)-3-(4-methoxyphenylthio)acrylamide

E-Isomer:
¹H-NMR (CDCl₃) δ ppm: 2.30 (3H, s), 3.85 (3H, s), 5.56 (1H, d, J=14.5 Hz), 6.80~7.45 (9H, m), 7.77 (1H, d, J=14.5 Hz).
Z-Isomer:
¹H-NMR (CDCl₃) δ ppm: 2.32 (3H, s), 3.82 (3H, s), 5.93 (1H, d, J=9.7 Hz), 6.88~7.52 (10H, m).

N-(4-methylphenyl)-3-(1-naphthylthio)acrylamide

E-Isomer:
¹H-NMR (CDCl₃) δ ppm: 2.27 (3H, s), 5.39 (1H, d, J=14.4 Hz), 6.83 (1H, brs), 7.01~8.30 (11H, m), 7.80 (1H, d, J=14.4 Hz).
Z-Isomer:
¹H-NMR (CDCl₃) δ ppm: 2.33 (3H, s), 5.97 (1H, d, J=9.7 Hz), 6.70 (1H, brs), 7.07 (1H, d, J=9.7 Hz), 7.14~8.44 (11H, m).

N-(4-methylphenyl)-3-(2-thienyl)acrylamide

¹H-NMR (CDCl₃) δ ppm: 2.30 (3H, s), 5.66 (1H, d, J=14.4 Hz), 6.99~7.56 (8H, m), 7.65 (1H, d, J=14.4 Hz).

N-(4-methylphenyl)-3-(3-trifluoromethylphenylthio)acrylamide

¹H-NMR (CDCl₃) δ ppm: 2.31 (3H, s), 5.88 (1H, J=14.6 Hz), 6.97~7.75 (9H, m), 7.80 (1H, d, J=14.6 Hz).

Reference Production Example 15

Production of N-(4-methylphenyl)-3-(phenylsulfonyl)acrylamide

To a solution of N-(4-methylphenyl)-3-(phenylthio)acrylamide (0.20 g) in chloroform (15 mL) was added m-chloroperbenzoic acid (65%) (0.27 g) under ice-cooling, and the mixture was stirred at the same temperature for 3.5 hours. To the reaction mixture was added chloroform (50 mL), which was washed with a saturated aqueous sodium bicarbonate solution, water and then a saturated aqueous sodium chloride solution, dried over anhydrous magnesium sulfate, and then concentrated under reduced pressure. The residue was subjected to silica gel column chromatography (hexane:ethyl acetate=2:1) to obtain N-(4-methylphenyl)-3-(phenylsulfonyl)acrylamide (0.16 g) as a white crystal.
¹H-NMR (CDCl₃) δ ppm: 2.31 (3H, s), 7.12 (0.64H, d, J=8.5 Hz), 7.19 (0.36H, d, J=14.7 Hz), 7.42~7.96 (11H, m).

Reference Production Example 16

Production of phenyl N-(5-indanyl)-3-(phenylsulfonyl)acrylimidate

To a solution of phenyl N-(5-indanyl)-3-(phenylthio)acrylimidate (1.96 g) in chloroform (50 mL) was added m-chloroperbenzoic acid (65%) (3.50 g) under ice-cooling, and the mixture was stirred for 4.5 hours while it was slowly warmed to room temperature. The reaction mixture was washed with a saturated aqueous sodium hydrogen carbonate solution, water and then a saturated aqueous sodium chloride solution, dried over anhydrous magnesium sulfate, and then concentrated under reduced pressure. The residue was isolated and purified by medium pressure preparative liquid chromatography (YAMAZEN SI-40C, hexane:ethyl acetate=3:1) to obtain phenyl N-(5-indanyl)-3-(phenylsulfonyl)acrylimidate (0.650 g) as a blackish brown oil.
¹H-NMR (CDCl₃) δ ppm: 2.00~2.15 (2H, m), 2.80~2.94 (4H, m 6.48~8.35 (15H, m).

Reference Production Example 17

Production of ethyl N-(4-biphenyl)-3-(phenylsulfonyl)acrylimidate and phenyl N-(4-biphenyl)-3-(phenylsulfonyl)acrylimidate To phenyl N-(4-biphenyl)-3-(phenylthio)acrylimidate (5.70 g) was added chloroform (300 mL) containing 1% of ethanol, and then was added m-chloroperbenzoic acid (65%) (8.08 g) under ice-cooling. The mixture was stirred for 6 hours while it was slowly warmed to room temperature. The reaction mixture was washed with a saturated aqueous sodium hydrogen carbonate solution, water and then a saturated aqueous sodium chloride solution, dried over anhydrous magnesium sulfate, and then concentrated under reduced pressure. The residue was isolated and purified by silica gel column chromatography (hexane:ethyl acetate=3:1) to obtain ethyl N-(4-biphenyl)-3-(phenylsulfonyl)acrylimidate (0.410 g) as a brown oil and phenyl N-(4-biphenyl)-3-(phenylsulfonyl)acrylimidate (4.23 g) as a brown oil.

Ethyl N-(4-biphenyl)-3-(phenylsulfonyl)acrylimidate

¹H-NMR (CDCl₃) δ ppm: 1.35 (3H, t, J=7.1 Hz), 4.30 (2H, q, J=7.1 Hz), 6.81~8.07 (16H, m).

Phenyl N-(4-biphenyl)-3-(phenylsulfonyl)acrylimidate

¹H-NMR (CDCl₃) δ ppm: 6.81~8.07 (21H, m).

Reference Production Example 18

Production of 3-(ethylthio)-N-(phenyl)acrylamide

To a solution of 3-(ethylthio)acrylic acid (5.67 g) in toluene (50 mL) were added thionyl chloride (3.48 mL) and DMF (catalytic amount) at room temperature, and the mixture was stirred at 80° C. for 2 hours. The reaction mixture was concentrated under reduced pressure. To the residue was added acetonitrile (50 mL), and then was added dropwise a solution of aniline (8.78 g) in acetonitrile (10 mL) under ice-cooling. The mixture was stirred at the same temperature for 1 hour and then at room temperature for 3 hours, and then concentrated under reduced pressure. To the residue was added 1N hydrochloric acid (50 mL), and the mixture was stirred at room temperature for 0.5 hour. The formed crystals were collected by filtration, washed with water, filtered, and then dried to obtain 3-(ethylthio)-N-(phenyl)acrylamide (8.03 g) as a white crystal.

¹H-NMR (CDCl₃) δ ppm: 1.32~1.36 (3H, m), 2.75~2.81 (2H, m), 5.91 (0.8H, d, J=14.6 Hz), 5.95 (0.2H, d, J=10.0 Hz), 7.00 (0.2H, d, J=10.0 Hz), 7.07~7.56 (6H, m), 7.72 (0.8H, d, J=14.6 Hz).

Reference Production Example 19

Production of
2-(benzo[1,3]dithiol-2-yl)-N-(phenyl)acetamide

To a solution of 2-(benzo[1,3]dithiol-2-yl)acetic acid (1.35 g) in toluene (30 mL) were added thionyl chloride (0.600 mL) and DMF (catalytic amount) at room temperature, and the mixture was stirred at 80° C. for 2 hours. The reaction mixture was concentrated under reduced pressure. To the residue was added acetonitrile (30 mL), and then was added dropwise a solution of aniline (1.54 g) in acetonitrile (10 mL) under ice-cooling. The mixture was stirred at the same temperature for 1 hour and then at room temperature for 3 hours, and then concentrated under reduced pressure. To the residue was added 1N hydrochloric acid (50 mL), and the mixture was stirred at room temperature for 0.5 hour. The formed crystals were collected by filtration, washed with water, filtered, and then dried to obtain 2-(benzo[1,3]dithiol-2-yl)-N-(phenyl)acetamide (1.83 g) as a white crystal.
¹H-NMR (CDCl₃) δ ppm: 2.98 (2H, d, J=7.4 Hz), 5.26 (1H, t, J=7.4 Hz), 7.06~7.15 (4H, m), 7.25~7.35 (4H, m), 7.48~7.50 (2H, m).

Reference Production Example 20-(1)

Production of
N-phenyl-3,3-bis(phenylthio)thiopropionamide

To N-phenyl-3,3-bis(phenylthio)propionamide (0.90 g) were added Lawesson's reagent (2.0 g) and 1,4-dioxane (20 mL), and the mixture was heated to reflux for 1.5 hours. The reaction mixture was left to cool to room temperature, and then concentrated under reduced pressure. The residue was isolated and purified by medium pressure preparative liquid chromatography (YAMAZEN SI-40B, hexane:ethyl acetate=3:1) to obtain N-phenyl-3,3-bis(phenylthio)thiopropionamide (0.69 g) as an orange oil.
¹H-NMR (CDCl₃) δ ppm: 3.04 (0.34H, d, J=7.4 Hz), 3.20 (1.66H, d, J=7.1 Hz), 5.21 (0.83H, t, J=7.1 Hz), 5.44 (0.17H, t, J=7.4 Hz), 7.13~7.67 (15H, m), 8.97 (0.83H, brs), 9.50 (0.17H, brs).

Reference Production Example 20-(2)

The following compound was synthesized in the same manner as Reference Production Examples 20-(1).

3,3-Bis(4-fluorophenylthio)-N-phenylpropionamide

¹H-NMR (CDCl₃) δ ppm: 2.97 (0.4H, d, J=7.5 Hz), 3.14 (1.6H, d, J=7.2 Hz), 5.06 (0.8H, t, J=7.2 Hz), 5.23 (0.2H, t, J=7.5 Hz), 6.93~7.67 (13H, m), 8.94 (0.8H, brs), 9.53 (0.2H, brs).

Reference Production Example 21-(1)

Production of
N-phenyl-3,3-bis(phenylthio)propionamide

To N-phenyl-3,3-bis(phenylthio)acrylamide (2.04 g) were added thiophenol (8.21 mL) and triethylamine (1.12 mL), and the mixture was stirred at room temperature for 11 hours. To the reaction mixture was added ethyl acetate (50 mL), which was washed with a 1N aqueous sodium hydroxide solution, water and then a saturated aqueous sodium chloride solution, dried over anhydrous magnesium sulfate, and then concentrated under reduced pressure. The residue was isolated and purified by medium pressure preparative liquid chromatography (YAMAZEN SI-40C, hexane:ethyl acetate=85:15) to obtain N-phenyl-3,3-bis(phenylthio)propionamide (3.00 g) as an orange oil.
¹H-NMR (CDCl₃) δ ppm: 2.82 (2H, d, J=7.1 Hz), 4.96 (1H, t, J=7.1 Hz), 7.11~7.53 (16H, m).

Reference Production Example 21-(2)

The following compound was synthesized in the same manner as Reference Production Examples 21-(1).

3,3-Bis(4-fluorophenylthio)-N-phenylpropionamide

¹H-NMR (CDCl₃) δ ppm: 2.78 (2H, d, J=7.1 Hz), 4.79 (1H, t, J=7.1 Hz), 6.97~7.50 (14H, m).

Reference Production Example 22-(1)

Production of 2-ethyl-3-(phenylthio)acrylic acid

To methyl 2-ethyl-3-(phenylthio)acrylate (4.39 g) were added ethanol (40 mL) and then a 2N aqueous sodium hydroxide solution (20 mL), and the mixture was refluxed at room temperature for 2 hours. After the reaction mixture was cooled to room temperature, water (100 mL) was added thereto, and further tert-butyl methyl ether was added, thereby layers were separated. The aqueous layer was adjusted to pH 2 by addition of conc. hydrochloric acid, and then extracted with tert-butyl methyl ether. The organic layer was washed with a saturated aqueous sodium chloride solution, dried, and then concentrated to obtain 2-ethyl-3-(phenylthio)acrylic acid (4.07 g).
¹H-NMR (CDCl₃) δ ppm: 1.12 (3H, t, J=7.5 Hz), 2.43 (2H, q, J=7.5 Hz), 7.30~7.41 (3H, m), 7.44~7.49 (2H, m), 7.79 (1H, s).

Reference Production Examples 22-(2) to (6)

The following compounds were synthesized in the same manner as Reference Production Examples 22-(1).

2-Methyl-3-(phenylthio)acrylic acid

¹H-NMR (CDCl₃) δ ppm: 1.96 (3H, d, J=1.1 Hz), 7.31~7.40 (3H, m), 7.43~7.50 (2H, m), 7.82 (1H, d, J=1.1 Hz).

3-(Phenylthio)-2-propylacrylic acid

¹H-NMR (CDCl₃) δ ppm: 0.98 (3H, t, J=7.4 Hz), 1.50~1.65 (2H, m), 2.39 (2H, t, J=7.6 Hz), 7.29~7.40 (3H, m), 7.42~7.50 (2H, m), 7.83 (1H, s).

2-Butyl-3-(phenylthio)acrylic acid

¹H-NMR (CDCl₃) δ ppm: 0.95 (3H, t, J=7.2 Hz), 1.34~1.57 (4H, m), 2.41 (2H, t, J=7.6 Hz), 7.29~7.40 (3H, m), 7.43~7.48 (2H, m), 7.81 (1H, s).

2-(Methylthio)-3-(phenylthio)acrylic acid $^1$H-NMR (CDCl$_3$) δ ppm: 2.40 (3H, s), 7.35~7.44 (3H, m), 7.46-7.54 (2H, m), 8.31 (1H, s).

3-(Phenylthio)-2-(3-thienyl)acrylic acid $^1$H-NMR (CDCl$_3$) δ ppm: 7.31 (1H, dd, J=5.1, 1.2 Hz), 7.34~7.42 (4H, m), 7.46~7.50 (2H, m), 7.53 (1H, dd, J=2.9, 1.2 Hz), 8.13 (1H, s).

2-Fluoro-3-(phenylthio)acrylic acid $^1$H-NMR (CDCl$_3$) δ ppm: 7.25 (1H, d, J=31.2 Hz), 7.35~7.43 (3H, m), 7.46~7.53 (2H, m), 10.39 (1H, brs).

Reference Production Example 23-(1)

Production of methyl 2-methyl-3-(phenylthio)acrylate

To chloroform (100 mL) were added methyl 2-methyl-3-(p-toluenesulfonyloxy)acrylate (11.0 g) and thiophenol (6.3 g), and then added dropwise triethylamine (33 mL), and the mixture was stirred at 50° C. for 9 hours. To the reaction mixture were added tert-butyl methyl ether, and then a 1N aqueous sodium hydroxide solution, thereby layers were separated. The organic layer was washed with a saturated aqueous sodium chloride solution, dried, and then concentrated. The residue was subjected to silica gel column chromatography (hexane/ethyl acetate=10/1) to obtain methyl 2-methyl-3-(phenylthio)acrylate (6.5 g).

$^1$H-NMR (CDCl$_3$) δ ppm: 1.97 (3H, s), 3.74 (3H, s), 7.27~7.50 (5H, m), 7.65 (1H, s).

Reference Production Examples 23-(2) to (4)

The following compounds were synthesized in the same manner as Reference Production Examples 23-(1).

Methyl 2-ethyl-3-(phenylthio)acrylate $^1$H-NMR (CDCl$_3$) δ ppm: 1.11 (3H, t, J=7.5 Hz), 2.44 (2H, q, J=7.5 Hz), 3.74 (3H, s), 7.30~7.40 (3H, m), 7.44~7.49 (2H, m), 7.62 (1H, s).

Methyl 2-propyl-3-(phenylthio)acrylate $^1$H-NMR (CDCl$_3$) δ ppm: 0.98 (3H, t, J=7.3 Hz), 1.49~1.61 (2H, m), 2.40 (2H, t, J=7.7 Hz), 3.73 (3H, s), 7.29~7.40 (3H, m), 7.43~7.48 (2H, m), 7.65 (1H, s).

Methyl 2-butyl-3-(phenylthio)acrylate $^1$H-NMR (CDCl$_3$) δ ppm: 0.95 (3H, t, J=7.2 Hz), 1.34~1.54 (4H, m), 2.42 (2H, t, J=7.6 Hz), 3.73 (3H, s), 7.29~7.40 (3H, m), 7.43~7.48 (2H, m), 7.63 (1H, s).

Reference Production Example 24-(1)

Production of methyl 2-methylthio-3-(phenylthio)acrylate

To a mixture of methyl 2-methylthio-3-(p-toluenesulfonyloxy)acrylate (3.05 g), triethylamine (2 mL) and chloroform (20 mL) was added slowly thiophenol (1.28 g) under ice-cooling, and the mixture was stirred at room temperature for 1 hour. To the reaction mixture were added tert-butyl methyl ether, and then a 1N aqueous sodium hydroxide solution, thereby layers were separated. The organic layer was washed with a saturated aqueous sodium chloride solution, dried, and then concentrated. The residue was subjected to silica gel column chromatography (hexane/ethyl acetate=10/1) to obtain methyl 2-methylthio-3-(phenylthio)acrylate (1.64 g).

$^1$H-NMR (CDCl$_3$) δ ppm: 2.39 (3H, s), 3.79 (3H, s), 7.35~7.42 (3H, m), 7.46~7.54 (2H, m), 8.12 (1H, s).

Reference Production Examples 24-(2) and (3)

The following compounds were synthesized in the same manner as Reference Production Examples 24-(1).

Methyl 2-(3-thienyl)-3-(phenylthio)acrylate $^1$H-NMR (CDCl$_3$) δ ppm: 3.78 (3H, s), 7.28 (1H, dd, J=5.1, 1.2 Hz), 7.34~7.41 (4H, m), 7.46~7.51 (3H, m), 7.96 (1H, s).

Methyl 2-fluoro-3-(phenylthio)acrylate $^1$H-NMR (CDCl$_3$) δ ppm: 1.33 (3H, t, J=7.2 Hz), 4.29 (2H, q, J=7.2 Hz), 7.05 (1H, d, J=31.5 Hz), 7.32~7.42 (3H, m), 7.45~7.51 (2H, m).

Reference Production Example 25-(1)

Production of methyl 2-methyl-3-(p-toluenesulfonyloxy)acrylate

To a mixture of methyl propionate (17.6 g), methyl formate (24.0 g) and DMF (200 mL) was added portionwise 60% sodium hydride (17.6 g) under ice-cooling, and the mixture was stirred at room temperature overnight. The reaction mixture was poured into iced water, and tert-butyl methyl ether was added thereto, thereby layers were separated. The aqueous layer was adjusted to pH 2 by addition of conc. hydrochloric acid, and then extracted with tert-butyl methyl ether. The organic layer was washed with a saturated aqueous sodium chloride solution, dried, and then concentrated to obtain a residue (7.6 g). To the residue were added ethyl acetate (40 mL), triethylamine (8.0 g) and then p-toluenesulfonyl chloride (13.7 g), and the mixture was stirred at room temperature overnight. The reaction mixture was washed with water, dried and then concentrated. The residue was subjected to silica gel column chromatography (hexane/ethyl acetate=5/1) to obtain methyl 2-methyl-3-(p-toluenesulfonyloxy)acrylate (11.0 g).

$^1$H-NMR (CDCl$_3$) δ ppm: 1.73 (3H, s), 2.47 (3H, s), 3.73 (3H, s), 7.38 (2H, d, J=8.2 Hz), 7.60 (1H, s), 7.82 (2H, d, J=8.2 Hz).

Reference Production Examples 25-(2) to (5)

The following compounds were synthesized in the same manner as Reference Production Examples 25-(1).

Methyl 2-ethyl-3-(p-toluenesulfonyloxy)acrylate $^1$H-NMR (CDCl$_3$) δ ppm: 0.87 (3H, t, J=7.5 Hz), 2.22 (2H, q, J=7.5 Hz), 2.47 (3H, s), 3.73 (3H, s), 7.26 (1H, s), 7.38 (2H, d, J=8.2 Hz), 7.82 (2H, d, J=8.2 Hz).

Methyl 2-propyl-3-(p-toluenesulfonyloxy)acrylate $^1$H-NMR (CDCl$_3$) δ ppm: 0.77 (3H, t, J=7.4 Hz), 1.23~1.34 (2H, m), 2.18 (2H, dd, J=8.7, 6.3 Hz), 2.47 (3H, s), 3.72 (3H, s), 7.38 (2H, d, J=8.4 Hz), 7.62 (1H, s), 7.82 (2H, d, J=8.4 Hz).

Methyl 2-butyl-3-(p-toluenesulfonyloxy)acrylate $^1$H-NMR (CDCl$_3$) δ ppm: 0.80 (3H, t, J=7.0 Hz), 1.09-1.24 (4H, m), 2.19 (2H, t, J=7.0 Hz), 2.47 (3H, s), 3.72 (3H, s), 7.38 (2H, d, J=8.4 Hz), 7.60 (1H, s), 7.82 (2H, d, J=8.4 Hz).

Methyl 2-(3-thienyl)-3-(p-toluenesulfonyloxy)acrylate $^1$H-NMR (CDCl$_3$) δ ppm: 2.45 (3H, s), 3.80 (3H, s), 7.18 (1H, dd, J=5.1, 1.2 Hz), 7.25 (1H, dd, J=5.1, 2.9 Hz), 7.36 (2H, d, J=8.3 Hz), 7.47 (1H, dd, J=2.9, 1.2 Hz), 7.79 (2H, d, J=8.3 Hz), 7.81 (1H, s).

Reference Production Example 26

Production of methyl 2-(methylthio)-3-(p-toluenesulfonyloxy)acrylate

To a mixture of methyl 2-(methylthio)-2-propenoate (25.8 g), methyl formate (24.0 g) and DMF (200 mL) was added portionwise 60% sodium hydride (21.4 g) under ice-cooling, and the mixture was stirred at room temperature overnight. The reaction mixture was poured into iced water, and tert-butyl methyl ether was added thereto, thereby layers were separated. The aqueous layer was adjusted to pH 2 by addition of conc. sulfuric acid, and then extracted with tert-butyl methyl ether. The organic layer was washed with a saturated aqueous sodium chloride solution, dried, and then concentrated to obtain a residue (21.7 g). To the residue were added ethyl acetate (200 mL), triethylamine (30 mL) and then p-toluenesulfonyl chloride (27.0 g), and the mixture was stirred at room temperature overnight. The reaction mixture was washed with water, dried and then concentrated. The residue was subjected to silica gel column chromatography (hexane/ethyl acetate=5/1) to obtain methyl 2-(methylthio)-3-(p-toluenesulfonyloxy)acrylate (9.72 g).

$^1$H-NMR (CDCl$_3$) δ ppm: 2.23 (3H, s), 2.47 (3H, s), 3.79 (3H, s) 7.39 (2H, d, J=8.3 Hz), 7.85 (2H, d, J=8.3 Hz), 7.93 (1H, s).

Reference Production Example 27

Production of 2-(benzo[1,3]dithiol-2-yl)acetic acid

To a solution of methyl propiolate (0.75 mL) in THF (10 mL) were added a solution of benzene-1,2-dithiol (1.2 g) in THF (10 mL) and tert-butoxy potassium (catalytic amount) under ice-cooling, and the mixture was stirred at the same temperature for 3 hours and then at room temperature for 3 hours. The reaction mixture was concentrated under reduced pressure. To the residue was added methanol (5 mL) at room temperature, and then an aqueous solution (10 mL) of sodium hydroxide (0.45 g). The mixture was stirred at 80° C. for 2 hours. To the reaction mixture was added ion-exchanged water (20 mL), which was washed with ethyl acetate. The aqueous layer was adjusted to pH 2 by addition of 1N hydrochloric acid, and then extracted with ethyl acetate (70 mL) twice. The organic layers were combined, washed with water and then a saturated aqueous sodium chloride solution, dried over anhydrous magnesium sulfate, and then concentrated under reduced pressure to obtain 2-(benzo[1,3]dithiol-2-yl) acetic acid (1.35 g) as a yellow crystal.

$^1$H-NMR (CDCl$_3$) δ ppm: 3.05 (2H, d, J=7.5 Hz), 5.06 (1H, t, J=7.5 Hz), 7.05~7.07 (2H, m), 7.23~7.26 (2H, m).

Reference Production Example 28-(1)

Production of cyclohexylmethyl N-(4-fluorophenyl)-3-(trimethylsilyl) thiopropiolimidate To a solution of ethynyltrimethylsilane (0.89 g) in THF (15 mL) was added a 1.57M solution (5.0 mL) of n-butyllithium in hexane at −78° C. under a nitrogen atmosphere, and the mixture was stirred at the same temperature for 0.5 hours. After the reaction mixture was warmed to 0° C., a 4-fluorophenyl isothiocyanate (1.30 g) in THF (5 mL) was added dropwise thereto at −78° C. Then, the reaction mixture was slowly warmed to 0° C. At the same temperature, a solution of cyclohexylmethyl bromide (1.52 g) in THF (5 mL) was added dropwise thereto, and the mixture was stirred at 50° C. for 7 hours. The solvent was distilled off under reduced pressure. The residue was subjected to silica gel column chromatography (hexane:ethyl acetate=20:1) to obtain cyclohexylmethyl N-(4-fluorophenyl)-3-(trimethylsilyl)thiopropionimidate (0.38 g) as a brown oil.

$^1$H-NMR (CDCl$_3$) δ ppm: 0.12 (6H, s), 0.29 (3H, s), 0.89~1.28 (5H, m), 1.59~1.88 (6H, m), 3.00~3.03 (2H, m), 6.86~7.05 (4H, m).

Reference Production Examples 28-(2) to (5)

The following compounds were synthesized in the same manner as Reference Production Examples 28-(1).

Cyclohexylmethyl N-(4-chlorophenyl)-3-(trimethylsilyl)thiopropiolimidate $^1$H-NMR (CDCl$_3$) δ ppm: 0.12 (6H, s), 0.29 (3H, s), 0.91~1.07 (5H, m), 1.60~1.88 (6H, m), 3.00~3.03 (2H, m), 6.85 (0.6H, d, J=8.5 Hz), 6.98 (1.4H, d, J=8.7 Hz), 7.26 (1.2H, d, J=8.7 Hz), 7.30 (0.8H, d, J=8.5 Hz).

Cyclohexylmethyl N-(3-methylphenyl)-3-(trimethylsilyl)thiopropiolimidate $^1$H-NMR (CDCl$_3$) δ ppm: 0.11 (6H, s), 0.29 (3H, s), 0.86~1.32 (5H, m), 1.57~1.91 (6H, m), 2.33 (2H, s), 2.34 (1H, s), 2.99 (0.7H, d, J=7.0 Hz), 3.03 (1.3H, d, J=7.0 Hz), 6.71 (0.7H, d, J=6.8 Hz), 6.82~6.89 (1.3H, m), 6.90~6.96 (1H, m), 7.15~7.25 (1H, m).

Cyclohexylmethyl N-(4-methoxyphenyl)-3-(trimethylsilyl)thiopropionlmidate $^1$H-NMR (CDCl$_3$) δ ppm: 0.15 (6H, s), 0.29 (3H, s), 0.91~1.28 (5H, m), 1.64~1.88 (6H, m), 3.28 (2H, d, J=6.5 Hz), 3.80 (3H, s), 6.83~7.13 (4H, m).

Cyclohexylmethyl N-(4-nitrophenyl)-3-(trimethylsilyl)thiopropionlmidate $^1$H-NMR (CDCl$_3$) δ ppm: 0.10 (6H, s), 0.31 (3H, s), 0.93~1.28 (5H, m), 1.62~1.88 (6H, m), 3.04 (2H, d, J=6.6 Hz), 6.95~7.08 (2H, m), 8.16~8.21 (2H, m).

Reference Production Example 29

Production of
N-methyl-N,N'-(diphenyl)propiolamidine

To a suspension of N-methyl-N,N'-(diphenyl)urea (2.0 g) in toluene (15 mL) was added phosphorus pentachloride (1.84 g) at room temperature, and the mixture was stirred for 3 hours while it was heated to reflux. The reaction mixture was concentrated under reduced pressure. To the residue was added THF (15 mL), and then added dropwise a 0.5M solution (35 mL) of ethynylmagnesium bromide in THF under ice-cooling. The mixture was stirred at room temperature for 1 hour. Then, water (200 mL) was added to the reaction mixture, followed by extraction with ethyl acetate (200 mL). The organic layer was washed with water, dried over anhydrous magnesium sulfate, and then concentrated under reduced pressure. The residue was subjected to silica gel column chromatography (hexane:ethyl acetate=5:1) to obtain N-methyl-N,N'-(diphenyl)propiolamidine (1.50 g) as a crystal.

$^1$H-NMR (CDCl$_3$) δ ppm: 2.28 (1H, s), 3.47 (3H, s), 6.93~7.07 (3H, m), 7.22 (7H, m).

Next, Formulation Examples are described. Herein, the term "part(s)" means "part(s) by weight".

Formulation Example 1

Ten parts of any one of the present compounds 1 to 115 is dissolved in a mixture of 35 parts of xylene and 35 parts of N,N-dimethylformamide. Thereto 14 parts of polyoxyethylene styryl phenyl ether and 6 parts of calcium dodecylbenzenesulfonate are added, and mixed by stirring thoroughly to obtain a 10% emulsifiable concentrate.

Formulation Example 2

Twenty parts of any one of the present compounds 1 to 115 is added to a mixture of 4 parts of sodium lauryl sulfate, 2 parts of calcium lignin sulfonate, 20 parts of synthetic hydrous silicon oxide fine powder and 54 parts of diatomaceous earth, and mixed by stirring thoroughly to obtain a 20% wettable powder.

Formulation Example 3

One part of synthetic hydrous silicon oxide fine powder, 2 parts of calcium lignin sulfonate, 30 parts of bentonite and 65 parts of kaoline clay are added to 2 part of any one of the present compounds 1 to 115, and mixed by stirring thoroughly. To this mixture an appropriate amount of water is added. The mixture is further stirred, granulated with a granulator, and then air-dried to obtain a 2% granule.

Formulation Example 4

One part of any one of the present compounds 1 to 115 is dissolved in an appropriate amount of acetone. Thereto 5 parts of synthetic hydrous silicon oxide fine powder, 0.3 part of PAP (isopropyl acid phosphate) and 93.7 parts of agalmatolite clay are added, and mixed by stirring thoroughly. The acetone is evaporated to obtain a 1% dust.

Formulation Example 5

Ten parts of any one of the present compounds 1 to 115, 30 parts of a mixture of cyclohexanone with dimethylsulfoxide (weight ratio 90/10), 35 parts of a mixture of white carbon with polyoxyethylene alkylether sulfate ammonium salt (weight ratio 50/50), and 25 parts of water are mixed and then finely-divided by a wet grinding method to obtain a 10% flowable formulation.

Formulation Example 6

Zero point one part of any one of the present compounds 1 to 115 is dissolved in a mixture of 5 parts of xylene and 5 parts of trichloroethane. This solution is mixed with 89.9 parts of deodorized kerosene to obtain a 0.1% oil solution.

Formulation Example 7

Ten milligrams of any one of the present compounds 1 to 115 is dissolved in 0.5 mL of acetone. This solution is mixed homogeneously with 5 g of a powdered solid animal feed (powdered solid feed for breeding, CE-2 manufactured by Clea Japan Inc.). The acetone was evaporated to obtain a poison bait.

Formulation Example 8

Ten parts of any one of the present compounds 1 to 115, 35 parts of a mixture of white carbon with polyoxyethylene alkylether sulfate ammonium salt (weight ratio 50/50), and 55 parts of water are mixed and then finely-divided by a wet grinding method to obtain a 10% flowable formulation.

Formulation Example 9

Ten parts of the present compound (37) and 10 parts of any one of insecticides, acaricides, nematocides, fungicides, herbicides, phytohormone agents, plant growth regulators, synergists and crop injury-reducing agents listed in the group I described below are added into a mixture of 4 parts of sodium lauryl sulfate, 2 parts of calcium lignin sulfonate, 20 parts of synthetic hydrous silicon oxide fine powder and 54 parts of diatomaceous earth, and mixed by stirring thoroughly to obtain a mixed wettable powder.

Formulation Example 10

Ten parts of the present compound (41) and 10 parts of any one of insecticides, acaricides, nematocides, fungicides, herbicides, phytohormone agents, plant growth regulators, synergists and crop injury-reducing agents listed in the group I described below are added into a mixture of 4 parts of sodium lauryl sulfate, 2 parts of calcium lignin sulfonate, 20 parts of synthetic hydrous silicon oxide fine powder and 54 parts of diatomaceous earth, and mixed by stirring thoroughly to obtain a mixed wettable powder.

Formulation Example 11

Ten parts of the present compound (64) and 10 parts of any one of insecticides, acaricides, nematocides, fungicides, herbicides, phytohormone agents, plant growth regulators, synergists and crop injury-reducing agents listed in the group I described below are added into a mixture of 4 parts of sodium lauryl sulfate, 2 parts of calcium lignin sulfonate, 20 parts of synthetic hydrous silicon oxide fine powder and 54 parts of diatomaceous earth, and mixed by stirring thoroughly to obtain a mixed wettable powder.

Formulation Example 12

Ten parts of the present compound (67) and 10 parts of any one of insecticides, acaricides, nematocides, fungicides, herbicides, phytohormone agents, plant growth regulators, synergists and crop injury-reducing agents listed in the group I described below are added into a mixture of 4 parts of sodium lauryl sulfate, 2 parts of calcium lignin sulfonate, 20 parts of synthetic hydrous silicon oxide fine powder and 54 parts of diatomaceous earth, and mixed by stirring thoroughly to obtain a mixed wettable powder.

Formulation Example 13

Ten parts of the present compound (76) and 10 parts of any one of insecticides, acaricides, nematocides, fungicides, herbicides, phytohormone agents, plant growth regulators, synergists and crop injury-reducing agents listed in the group I described below are added into a mixture of 4 parts of sodium lauryl sulfate, 2 parts of calcium lignin sulfonate, 20 parts of synthetic hydrous silicon oxide fine powder and 54 parts of diatomaceous earth, and mixed by stirring thoroughly to obtain a mixed wettable powder.

Formulation Example 14

Ten parts of the present compound (80) and 10 parts of any one of insecticides, acaricides, nematocides, fungicides, herbicides, phytohormone agents, plant growth regulators, synergists and crop injury-reducing agents listed in the group I described below are added into a mixture of 4 parts of sodium lauryl sulfate, 2 parts of calcium lignin sulfonate, 20 parts of synthetic hydrous silicon oxide fine powder and 54 parts of diatomaceous earth, and mixed by stirring thoroughly to obtain a mixed wettable powder.

Formulation Example 15

Ten parts of the present compound (95) and 10 parts of any one of insecticides, acaricides, nematocides, fungicides, herbicides, phytohormone agents, plant growth regulators, synergists and crop injury-reducing agents listed in the group I described below are added into a mixture of 4 parts of sodium lauryl sulfate, 2 parts of calcium lignin sulfonate, 20 parts of synthetic hydrous silicon oxide fine powder and 54 parts of diatomaceous earth, and mixed by stirring thoroughly to obtain a mixed wettable powder.

The group I consists of:
any insecticides of:
(1) Organic Phosphorus Compounds:
acephate, aluminum phosphide, butathiofos, cadusafos, chlorethoxyfos, chlorfenvinphos, chlorpyrifos, chlorpyrifos-methyl, cyanophos (CYAP), diazinon, DCIP (dichlorodiisopropyl ether), dichlofenthion (ECP), dichlorvos (DDVP), dimethoate, dimethylvinphos, disulfoton, EPN, ethion, ethoprophos, etrimfos, fenthion (MPP), fenitrothion (MEP), fosthiazate, formothion, hydrogen phosphide, isofenphos, isoxathion, malathion, mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion, phorate and cadusafos;

(2) Carbamate Compounds:
alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, NAC, oxamyl, pirimicarb, propoxur (PHC), XMC, thiodicarb, xylylcarb and aldicarb;
(3) Synthetic Pyrethroid Compounds:
acrinathrin, allethrin, benfluthrin, beta-cyfluthrin, bifenthrin, cycloprothrin, cyfluthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, 2,3,5,6-tetrafluoro-4-methylbenzyl 2,2-dimethyl-3-(1-propenyl)cyclopropanecarboxylate, 2,3,5,6-tetrafluoro-4-(methoxymethyl)benzyl 2,2-dimethyl-3-(2-methyl-1-propenyl)cyclopropanecarboxylate, 2,3,5,6-tetrafluoro-4-(methoxymethyl)benzyl 2,2-dimethyl-3-(2-cyano-1-propenyl)cyclopropanecarboxylate, and 2,3,5,6-tetrafluoro-4-(methoxymethyl)benzyl 2,2,3,3-tetramethylcyclopropanecarboxylate;
(4) Nereistoxin Compounds:
cartap, bensultap, thiocyclam, monosultap and bisultap;
(5) Neonicotinoid Compounds:
imidacloprid, nitenpyram, acetamiprid, thiamethoxam, thiacloprid and clothianidin;
(6) Benzoylurea Compounds:
chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron and triazuron;
(7) Phenylpyrazole Compounds:
acetoprole, ethiprole, fipronil, vaniliprole, pyriprole and pyrafluprole;
(8) Bt Toxin Insecticides:
live spores derived from and crystal toxins produced from *Bacillus thuringiesis* and a mixture thereof;
(9) Hydrazine Compounds:
chromafenozide, halofenozide, methoxyfenozide and tebufenozide;
(10) Organic Chlorine Compounds:
aldrin, dieldrin, dienochlor, endosulfan and methoxychlor;
(11) Natural Insecticides:
machine oil and nicotine sulfate;
(12) Other Insecticides:
avermectin-B, bromopropylate, buprofezin, chlorphenapyr, cyromazine, D-D (1,3-dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, potassium oleate, protrifenbute, spiromesifen, sulfur, metaflumizone, spirotetramat, pyrifluquinazone, spinetoram, chlorantraniliprole, tralopyril, a compound represented by the following formula (A):

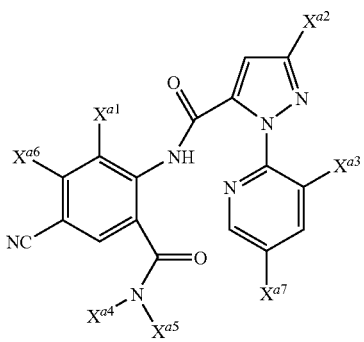

(A)

wherein $X^{a1}$ represents a methyl group, a chlorine atom, a bromine atom or a fluorine atom, $X^{a2}$ represents a fluorine atom, a chlorine atom, a bromine atom, a C1-C4 haloalkyl group or a C1-C4 haloalkoxy group, $X^{a3}$ represents a fluorine atom, a chlorine atom or a bromine atom, $X^{a4}$ represents an optionally substituted C1-C4 alkyl group, an optionally substituted C3-C4 alkenyl group, an optionally substituted C3-C4 alkynyl group, an optionally substituted C3-C5 cycloalkylalkyl group or a hydrogen atom, $X^{a5}$ represents a hydrogen atom or a methyl group, $X^{a6}$ represents a hydrogen atom, a fluorine atom or a chlorine atom, and $X^{a7}$ represents a hydrogen atom, a fluorine atom or a chlorine atom;

a compound represented by the following formula (B):

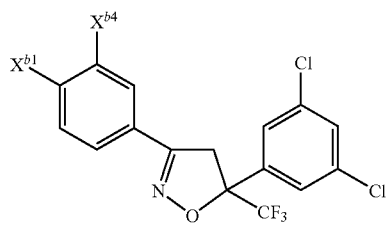

(B)

wherein $X^{b1}$ represents a $X^{b2}$—NH—C(=O) group, a $X^{b2}$—C(=O)—NH—CH$_2$ group, a $X^{b3}$—S(O) group, an optionally substituted pyrrol-1-yl group, an optionally substituted imidazol-1-yl group, an optionally substituted pyrazol-1-yl group, or an optionally substituted 1,2,4-triazol-1-yl group, $X^{b2}$ represents an optionally substituted C1-C4 haloalkyl group, such as a 2,2,2-trifluoroethyl group, or an optionally substituted C3-C6 cycloalkyl group, such as a cyclopropyl group, $X^{b3}$ represents an optionally substituted C1-C4 alkyl group, such as a methyl group, and $X^{b4}$ represents a hydrogen atom, a cyano group or a methyl group;

a compound represented by the following formula (C):

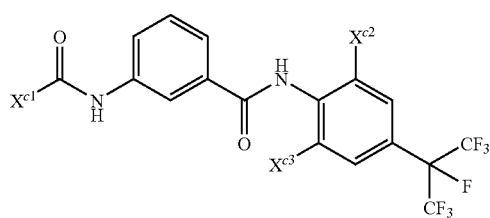

(C)

wherein $X^{c1}$ represents an optionally substituted C1-C4 alkyl group, such as a 3,3,3-trifluoropropyl group, an optionally substituted C1-C4 alkoxy group, such as a 2,2,2-trichloroethoxy group, an optionally substituted phenyl group, such as a 4-cyanophenyl group, or an optionally substituted pyridyl group, such as a 2-chloro-3-pyridyl group, $X^{c2}$ represents a methyl group or a trifluoromethylthio group, and $X^{c3}$ represents a methyl group and a halogen atom;

any acaricides of acequinocyl, amitraz, benzoximate, bifenazate, bromopropylate, chinomethionate, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite (BPPS), polynactins, pyridaben, pyrimidifen, tebufenpyrad, tetradifon, spirodiclofen, spiromesifen, spirotetramat, amidoflumet and cyenopyrafen;

any nematicides of DCIP, fosthiazate, levamisol hydrochloride, methylisothiocyanate, morantel tartarate and imicyafos;

any fungicides of azole fungicidal compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol;

cyclic amine fungicidal compounds such as fenpropimorph, tridemorph, and fenpropidin;

benzimidazole fungicidal compounds such as carbendezim, benomyl, thiabendazole, and thiophanate-methyl; procymidone, cyprodinil, pyrimethanil, diethofencarb, thiuram, fluazinam, mancozeb, iprodione, vinclozolin, chlorothalonil, captan, mepanipyrim, fenpiclonil, fludioxonil, dichlofluanid, folpet, kresoxim-methyl, azoxystrobin, trifloxystrobin, fluoxastrobin, picoxystrobin, pyraclostrobin, dimoxystrobin, spiroxamine, quinoxyfen, fenhexamid, famoxadone, fenamidone, zoxamide, ethaboxam, amisulbrom, iprovalicarb, benthiavalicarb, cyazofamid, mandipropamid, boscalid, metrafenone, fluopiran, bixafen, cyflufenamid, and proquinazid;

any herbicides and any phytohormone agents of:

(1) phenoxyfatty acid herbicidal compounds such as 2,4-PA, MCP, MCPB, phenothiol, mecoprop, fluoroxypyr, triclopyr, clomeprop, and naproanilide;

(2) benzoic acid herbicidal compounds such as 2,3,6-TBA, dicamba, clopyralid, picloram, aminopyralid, quinclorac, and quinmerac;

(3) urea herbicidal compounds such as diuron, linuron, chlortoluron, isoproturon, fluometuron, isouron, tebuthiuron, methabenzthiazuron, cumyluron, daimuron, and methyldaimuron;

(4) triazine herbicidal compounds such as atrazine, ametoryn, cyanazine, simazine, propazine, simetryn, dimethametryn, prometryn, metribuzin, and triaziflam;

(5) bipyridinium herbicidal compounds such as paraquat, and diquat;

(6) hydroxybenzonitrile herbicidal compounds such as bromoxynil and ioxynil;

(7) dinitroaniline herbicidal compounds such as pendimethalin, prodiamine, and trifluralin;

(8) organic phosphorus herbicidal compounds such as amiprofos-methyl, butamifos, bensulide, piperophos, anilofos, glyphosate, glufosinate, and bialaphos;

(9) carbamate herbicidal compounds such as di-allate, tri-allate, EPTC, butylate, benthiocarb, esprocarb, molinate, dimepiperate, swep, chlorpropham, phenmedipham, phenisopham, pyributicarb, and asulam;

(10) acid amide herbicidal compounds such as propanil, propyzamide, bromobutide, and etobenzanid;

(11) chloroacetanilide herbicidal compounds such as acetochlor, alachlor, butachlor, dimethenamid, propachlor, metazachlor, metolachlor, pretilachlor, thenylchlor, and pethoxamid;

(12) diphenylether herbicidal compounds such as acifluorfen-sodium, bifenox, oxyfluorfen, lactofen, fomesafen, chlomethoxynil, and aclonifen;

(13) cyclic imide herbicidal compounds such as oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, and benzfendizone;

(14) pyrazole herbicidal compounds such as benzofenap, pyrazolate, pyrazoxyfen, topramezone, and pyrasulfotole;

(15) triketone herbicidal compounds such as isoxaflutole, benzobicyclon, sulcotrione, mesotrione, tembotrione, and tefuryltrione;

(16) aryloxyphenoxypropionic acid herbicidal compounds such as clodinafop-propargyl, cyhalofop-butyl, diclofop-methyl, fenoxaprop-ethyl, fluazifop-butyl, haloxyfop-methyl, and quizalofop-ethyl;

(17) trioneoxime herbicidal compounds such as alloxydim-sodium, sethoxydim, butroxydim, clethodim, cloproxydim, cycloxydim, tepraloxydim, tralkoxydim, and profoxydim;

(18) sulfonylurea herbicidal compounds such as chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and 1-(2-chloro-6-propylimidazo[1,2-a]pyridazin-3-ylsulfonyl)-3-(4,6-dimethoxypyrimidin-2-yl)urea;

(19) imidazolinone herbicidal compounds such as imazamethabenz-methyl, imazamethapyr, imazamox, imazapyr, imazaquin, and imazethapyr;

(20) sulfonamide herbicidal compounds such as flumetsulam, metosulam, diclosulam, florasulam, cloransulam-methyl, penoxsulam, and pyroxsulam;

(21) pyrimidinyloxybenzoic acid herbicidal compounds such as pyrithiobac-sodium, bispyribac-sodium, pyriminobac-methyl, pyribenzoxim, and pyriftalid; and

(22) other herbicidal compounds such as bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, and thiencarbazone-methyl;

any plant growth regulators of hymexazol, paclobutrazol, uniconazole-P, inabenfide, prohexadione-calcium, aviglycine, 1-naphthylacetamide, abscisic acid, indolebutyric acid, ethychlozate ethyl, ethephon, cloxyfonac, chlormequat, dichlorprop, gibberellin, prohydrojasmon, benzylaminopurine, forchlorfenuron, maleic hydrazide, calcium peroxide, mepiquat-chloride) and 4-CPA (4-chlorophenoxyacetic acid);

any synergists of piperonyl butoxide, sesamex, sulfoxide, N-(2-ethylhexyl)-8,9,10-trinorborn-5-ene-2,3-dicarboximide (MGK 264), N-declyimidazole, WARF-antiresistant, TBPT, TPP, IBP, PSCP, methyl iodide (CH3I), t-phenylbutenone, diethylmaleate, DMC, FDMC, ETP, and ETN; and any crop injury-reducing agents of benoxacor, cloquintocet-mexyl, cyometrinil, daimuron, dichlormid, fenchlorazole-ethyl, fenclorim, flurazole, fluxofenim, furilazole, mefenpyr-diethyl, MG191, oxabetrinil, allidochlor, isoxadifen-ethyl, cyprosulfamide, fluxofenim, and 1,8-naphthalic anhydride.

The following Test Examples show that the compound of the present invention is effective for pest control.

In Test Examples 1 to 9, the formulation obtained in Formulation Example 5 was diluted with ion-exchanged water so that the concentration of the active ingredient could be 500 ppm to prepare a test solution.

Test Example 1

*Spodoptera litura*

A filter paper having a diameter of 5.5 cm was spread on the bottom of a polyethylene cup having a diameter of 5.5 cm, and an artificial diet, Insecta LF (Nosan Kogyo Corp.) which was sliced into 6 mm pieces in thickness and further cut into half, was placed on the filter paper. Then, 2 mL of the test solution was poured onto the filter paper. After the filter paper was air dried, 5 forth-instar larvae of *Spodoptera litura* were released into the polyethylene cup, and the cup was sealed with a lid. After 6 days, the number of dead insects was counted.

The death rate was calculated by the following equation.

Death rate(%)=(Number of dead insects/Number of tested insects)×100

The effect of the tested compound was evaluated with indexes of 4: 100%, 3: 80-99%, 2: 60-79%, 1: 30-59% and 0: 0-29% in terms of death rate.

As a result, the present compounds 1, 2, 4, 5, 6, 7, 11, 12, 13, 14, 16, 17, 18, 21, 22, 23, 24, 25, 26, 27, 29, 30, 31, 32, 33, 34, 38, 47, 48, 49, 50, 51, 52, 53, 54, 55, 57, 58, 59, 60, 61, 63, 65, 66, 67, 72, 73, 76, 80, 83, 84, 85, 88, 89, 90, 91, 92, 95, 96, 98, 99, 101, 102, 103, 106, 108, 109, 110, 111 and 115 were evaluated as index 3 or greater.

Test Example 2

*Adoxophyes orana*

A filter paper having a diameter of 5.5 cm was spread on the bottom of a polyethylene cup having a diameter of 5.5 cm, and an artificial diet, Silkmate 2S (Nosan Kogyo Corp.) which was sliced into 2 mm pieces in thickness, was placed on the filter paper. Then, 1 mL of the test solution was poured onto the filter paper. Immediately after the filter paper was air dried, a filter paper having a diameter of 5.5 cm was placed thereon. Then, 30 first-instar larvae of *Adoxophyes orana* were released into the polyethylene cup, and the cup was sealed with a lid. After 7 days, the number of surviving insects was counted.

The death rate was calculated by the following equation.

Death rate(%)=(Number of dead insects/Number of tested insects)×100

The effect of the tested compound was evaluated with indexes of 4: 100%, 3: 80-99%, 2: 60-79%, 1: 30-59% and 0: 0-29% in terms of death rate.

As a result, the present compounds 1, 2, 4, 5, 6, 7, 9, 11, 12, 13, 14, 16, 17, 18, 20, 21, 22, 23, 24, 25, 26, 27, 28, 30, 31, 32, 33, 34, 38, 47, 48, 49, 50, 51, 52, 53, 54, 55, 57, 58, 59, 60, 61, 62, 73, 76, 80, 83, 84, 85, 88, 89, 90, 91, 92, 94, 95, 96, 98, 99, 101, 102, 103, 106, 108, 110, 111 and 115 were evaluated as index 3 or greater.

Test Example 3

*Aphis gossypii*

On the leaves of cucumber at a one-leaf stage grown in a one-ounce cup, 30 individuals of *Aphis gossypii* (including imagoes and larvae) were released. The next day, 20 mL of the test solution was sprayed on the leaves. After 6 days, the number of surviving insects was counted.

The survival rate of tested insects on the basis of the number of insects provided in an untreated cup was calculated by the following equation.

Survival rate(%)=(Number of surviving insects in test cup/Number of insects provided in untreated cup)×100

The effect of the tested compound was evaluated with indexes of 4: 0%, 3: 1-10%, 2: 11-40%, 1: 41-70%, and 0: >70% in terms of survival rate.

As result, the present compounds 1, 6, 14, 16, 17, 18, 22, 23, 24, 25, 27, 28, 30, 32, 34, 38, 48, 49, 50, 57, 72, 73, 83, 88, 89, 90, 91 and 92 were evaluated as index 3 or greater.

Test Example 4

*Nilaparvata lugens*

A rice plant was grown in a 90 mL plastic cup, and at a two- or three-leaf stage, the stem was cut at 5 cm from the base. Then, 20 mL/pot of the test solution was sprayed on the plant. After air dried, 30 first-instar larvae of *Nilaparvata lugens* were released into the cup, and the cup was sealed with a lid. After 6 days, the number of surviving insects was counted.

The survival rate of tested insects on the basis of the number of insects provided in an untreated cup was calculated by the following equation.

Survival rate(%)=(Number of surviving insects in test cup/Number of insects provided in untreated cup)×100

The effect of the tested compound was evaluated with indexes of 4: 0%, 3: 1-10%, 2: 11-40%, 1: 41-70%, and 0: >70% in terms of survival rate.

As result, the present compounds 1, 2, 13, 17, 22, 23, 24, 25, 27, 28, 30, 31, 32, 33, 34, 47, 48, 49, 50, 51, 52, 57, 84, 85, 88, 89, 90, 91, 92 and 95 were evaluated as index 3 or greater.

Test Example 5

*Musca domestica*

A filter paper having a diameter of 5.5 cm was spread on the bottom of a polyethylene cup having a diameter of 5.5 cm, and 0.7 ml of the test solution was added dropwise onto the filter paper. As a bait 30 mg of sucrose was uniformly placed on the filter paper. Into the polyethylene cup, 10 female imagoes of *Musca domestica* were released and the cup was sealed with a lid. After 24 hours, the number of dead insects was counted.

The death rate was calculated by the following equation.

Death rate(%)=(Number of dead insects/Number of tested insects)×100

The effect of the tested compound was evaluated with indexes of 4: 100%, 3: 70-99%, 2: 40-69%, 1: 10-39% and 0: 0-9% in terms of death rate.

As a result, the present compounds 1, 2, 5, 6, 16, 24, 25, 26, 28, 32, 47, 48, 50, 51, 57, 83, 85, 88, 89, 90, 91, 92 and 95 were evaluated as index 3 or greater.

Test Example 6

*Blattalla germanica*

A filter paper having a diameter of 5.5 cm was spread on the bottom of a polyethylene cup having a diameter of 5.5 cm, and 0.7 ml of the test solution was added dropwise onto the filter paper. As a bait 30 mg of sucrose was uniformly placed on the filter paper. Into the polyethylene cup, 2 male imagoes of *Blattalla germanica* were released and the cup was sealed with a lid. After 6 days, the number of dead insects was counted.

The death rate was calculated by the following equation.

Death rate(%)=(Number of dead insects/Number of tested insects)×100

The effect of the tested compound was evaluated with indexes of 4: 100%, 2: 50%, and 0: 0% in terms of death rate.

As a result, the present compounds 1, 4, 6, 13, 16, 23, 24, 25, 27, 28, 32, 34, 47, 48, 49, 50, 51, 53, 57, 59, 60, 83, 84, 85, 88, 89, 90, 91, 92 and 95 were evaluated as index 4.

Test Example 7

*Culex pipiens pallens*

To 100 mL of ion-exchanged water was added 0.7 mL of the test solution (the active ingredient concentration: 3.5 ppm). Into the solution, 20 last-instar larvae of *Culex pipiens pallens* were released. After 1 day, the number of dead insects was counted.

The death rate was calculated by the following equation.

Death rate(%)=(Number of dead insects/Number of tested insects)×100

The effect of the tested compound was evaluated with indexes of 4: 91-100%, 2: 11-90%, and 0: 0-10% in terms of death rate.

As a result, the present compounds 1, 2, 5, 13, 14, 16, 23, 24, 25, 26, 28, 50, 51, 53, 57, 83, 85, 90, 96, 99, 110 and 112 were evaluated as index 4.

Test Example 8

*Tetranychus urticae*

A leaf of a bean plant with many individuals of *Tetranychus urticae* being parasitizing thereon was cut out, and then placed on a leaf of a bean plant which was grown for a week after seeding in a 3 ounce cup. It was left for a day so that the insects could move from the cut leaf to the leaf of the bean plant planted in the cup. The next day, the leaf used for inoculation was removed using a pair of tweezers, and 20 mL of the test solution was sprayed on the plant. After 8 days, the number of female imagoes surviving on a primary leaf of the bean plant in the cup was counted.

The effect of the tested compound was evaluated with 5 stages of index 4: 0 to 3; index 3: 4 to 10; index 2: 11 to 20; index 1: 21 to 30, and index 0: 31 or more in terms of the surviving number.

As a result, the present compounds 1, 3, 6 and 10 were evaluated as index 3 or greater.

Test Example 9

*Plutella xylostella*

On cabbage (*Brassicae oleacea*) at a 4-leaf stage, 20 mL of the test solution was sprayed. After the test solution was dried, the aboveground part of the cabbage was cut off, and then placed in a polyethylene cup (volume: 100 mL) together with 5 second-instar larvae of *Plutella xylostella*. The cup was kept at 25° C. After 5 days, the number of dead insects was counted.

The death rate was calculated by the following equation.

Death rate(%)=(Number of dead insects/Number of tested insects)×100

The effect of the tested compound was evaluated with indexes of 4: 100%, 3: 80-99%, 2: 60-79%, 1: 30-59% and 0: 0-29% in terms of death rate.

As a result, the present compounds 1, 2, 4, 5, 7, 13, 14, 16, 17, 18, 20, 22, 23, 24, 25, 26, 27, 28, 30, 31, 32, 33, 34, 38, 47, 48, 49, 50, 51, 53, 54, 55, 57, 58, 62, 63, 68, 72, 73, 76, 80, 83, 84, 85, 86, 88, 89, 90, 91, 92, 95, 96, 99, 101, 102, 103, 108 and 110 were evaluated as index 3 or greater.

Test Example 10

*Bemisia tabaci*

In a mixture of 0.1 mL of an organic solvent (xylene:DMF=1:1) and 0.04 mL of a mixture solution of xylene and Sorpol 3005X (trademark; manufactured by Toho Chemical Industry Co., Ltd.) (mixture ratio in volume; xylene:Sorpol 3005X=1:9), 40 mg of any one of the present compounds was dissolved, and then diluted with 80 mL of ion-exchanged water to prepare a 500 ppm solution. Then, 30 mL of the 500 ppm solution was diluted with 45 mL of ion-exchanged water to prepare a 200 ppm solution. Then, 20 mL of the 200 ppm solution was diluted with 60 mL of ion-exchanged water to prepare a 50 ppm solution. Further, 20 mL of the 50 ppm solution was diluted with 60 mL of ion-exchanged water to prepare a 12.5 ppm solution. To each solution was added Dyne (trademark; manufactured by Takeda pharmaceutical Co., Ltd.) in such an amount that dyne could be diluted 3,000 times to prepare a test solution.

Cabbage was grown in a three-ounce cup for about 3 weeks, and then, except for a second true leaf, all leaves were removed. On the cabbage, imagoes of *Bemisia tabaci* were released and allowed to lay eggs for 3 days. Then, the imagoes were removed. The cup was stored in a greenhouse for 8 days to incubate the eggs. Then, 20 mL of the test solution was sprayed on the plant. After 7 days, the number of dead insects was counted.

The effect of the tested compound was evaluated with 5 stages of index 4: death rate of 100%, index 3: death rate of 90-99% (attachment area of larvae is 1 to 10% of that in a non-treatment case), index 2: death rate of 60-89% (attachment area of larvae is 11 to 40% of that in a non-treatment case), index 1: death rate of 30-59% (attachment area of larvae is 41 to 70% of that in a non-treatment case), and index 0: death rate of 0-29% (attachment area of larvae is 71% or more of that in a non-treatment case).

As a result, the present compounds 1, 2 and 55 at 500 ppm were evaluated as index 3 or greater. The present compounds 14, 16, 17, 18, 22, 30, 34, 37, 42, 44, 49, 50, 51, 60, 70, 73, 74, 86, 87, 88, 89, 90, 91, 92, 105, 111, 112 and 115 at 200 ppm were evaluated as index 3 or greater. The present compounds 5, 19, 24 and 28 at 50 ppm were evaluated as index 3 or greater. The present compounds 23, 25, 57 and 59 at 12.5 ppm were evaluated as index 3 or greater.

Test Example 11

*Haemaphysalis longicornis*

In 1 mL of acetone, 0.5 mg of any one of the present compounds was dissolved, and the solution was spread uniformly on one side of a filter paper (TOYO No. 2; 5×10 cm). After dried, the filter paper was folded into two, and the sides were clipped to make a pouch. Into the pouch, tested ticks (Haemaphysalis longicornis, non-blood sucking nymphal ticks, 10 ticks in a group) were placed. The pouch was clipped and sealed. After 2 days, the number of dead ticks was counted.

As a result, the present compounds 1, 24, 26, 28, 42, 47, 48, 49, 50, 51, 83, 90 and 91 gave a death rate of 90% or more.

Test Example 12

*Spodoptera litura*

In a mixture of 0.1 mL of an organic solvent (xylene:DMF=1:1) and 0.04 mL of a mixture solution of xylene and Sorpol 3005X (trademark; manufactured by Toho Chemical Industry Co., Ltd.) (mixture ratio; xylene:Sorpol 3005X=1:9), 16 mg of any one of the present compounds was dissolved, and then diluted with 80 mL of ion-exchanged water to prepare a 200 ppm solution. Then, 20 mL of the 200 ppm solution was diluted with 60 mL of ion-exchanged water to prepare a 50 ppm solution. To each solution was added Dyne (trademark; manufactured by Takeda pharmaceutical Co., Ltd.) in such an amount that dyne could be diluted 3,000 times to prepare a test solution.

On Cabbage at a five-leaf stage growing in a three-ounce cup, 20 mL of the test solution was sprayed. After air-dried, 10 forth-instar larvae of *Spodoptera litura* were released on the plant. After 4 days, the number of dead insects was counted.

The death rate was calculated by the following equation.

Death rate(%)=(Number of dead insects/Number of tested insects)×100

The effect of the tested compound was evaluated with indexes of 4: 100%, 3: 80-99%, 2: 60-79%, 1: 30-59% and 0: 0-29% in terms of death rate.

As a result, the present compounds 3, 10, 19, 74, 86 and 87 at 50 ppm were evaluated as index 3 or greater. The present compounds 104, 105, 112 and 113 at 200 ppm were evaluated as index 3 or greater.

Test Example 13

*Adoxophyes orana*

In a mixture of 0.1 mL of an organic solvent (xylene:DMF=1:1) and 0.04 mL of a mixture solution of xylene and Sorpol 3005X (trademark; manufactured by Toho Chemical Industry Co., Ltd.) (mixture ratio in volume; xylene:Sorpol 3005X=1:9), 16 mg of any one of the present compounds was dissolved, and then diluted with 80 mL of ion-exchanged water to prepare a 200 ppm solution. Then, 20 mL of the 200 ppm solution was diluted with 60 mL of ion-exchanged water to prepare a 50 ppm solution. Then, 20 mL of the 50 ppm solution was diluted with 60 mL of ion-exchanged water to prepare a 12.5 ppm solution. To each solution was added Dyne (trademark; manufactured by Takeda pharmaceutical Co., Ltd.) in such an amount that dyne could be diluted 3,000 times to prepare a test solution.

On an apple seedling with about 12 to 15 cm high planted in a 3-ounce cup, 20 mL of the test solution was sprayed. After air-dried, about 60 first-instar larvae of *Adoxophyes orana* were released on the plant.

After 7 days, the number of surviving insects was counted. The death rate was calculated by the following equation.

Death rate(%)={[(Number of tested insects)−(Number of surviving insects)]/(Number of tested insects)}×100

The effect of the tested compound was evaluated with indexes of 4: 100%, 3: 80-99%, 2: 60-79%, 1: 30-59% and 0: 0-29% in terms of death rate.

As a result, the present compounds 10, 19, 74, 86, 87, 93, 104, 105, 112 and 113 at 50 ppm were evaluated as index 3 or greater. The present compound 3 at 12.5 ppm was evaluated as index 3 or greater.

Industrial Applicability

The compound of the present invention has an excellent controlling effect on pest, and thus it is useful as an active ingredient for a pesticidal composition.

The invention claimed is:
1. An imidate compound represented by the formula (I-1):

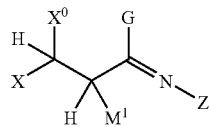

wherein,
Z represents a carbocyclic group having 3 to 14 ring-constituting atoms which is optionally substituted with a group selected from the group A described below, or a heterocyclic group having 3 to 14 ring-constituting atoms which is optionally substituted with a group selected from the group A described below;
G represents a -$A^1$-$R^1$ group, a —S(=O)$_2$—$R^2$ group or a —N($R^3$)—$R^1$ group;
X represents a -$A^2$-$R^4$ group, a —S(=O)—$R^5$ group or a —S(=O)$_2$—$R^5$ group;
$X^0$ represents a -$A^3$-$R^6$ group, a —S(=O)—$R^7$ group, a —S(=O)$_2$—$R^7$ group or a halogen atom; or
X and $X^0$ are optionally taken together to form a -$A^2$-$T^0$-$A^3$- group;
$M^1$ represents a —$R^8$ group, a -$A^8$-$R^8$ group, a halogen atom or a hydrogen atom;
$A^1$, $A^2$ and $A^3$ independently represent an oxygen atom or a sulfur atom;
$R^1$ represents a C1-C20 chain hydrocarbon group which is optionally substituted with a group selected from the group D described below, a -Q group, a -$T^1$-Q group, a -$T^1$-S-Q group or a -$T^1$-O-Q group;
$R^2$ represents a C1-C20 chain hydrocarbon group which is optionally substituted with a group selected from the group E described below or a phenyl group which is optionally substituted with a group selected from the group B described below;
$R^3$ represents a C1-C20 chain hydrocarbon group which is optionally substituted with a group selected from the group D described below, a -Q group, a -$T^1$-Q group, a C1-C6 alkoxy group, a C2-C7 alkanoyl group, a mono(C1-C7 alkyl)amino group, a di(C1-C7 alkyl)amino group or a (C1-C7 alkyl)phenylamino group;
$R^4$ and $R^6$ independently represent a C1-C6 chain hydrocarbon group which is optionally substituted with a group selected from the group D described below, a -Q group, a -$T^1$-Q group, a —C(=$A^4$)-$R^{11}$ group, a —C(=$A^4$)-$A^5$-$R^{11}$ group or a —S(=O)$_2$—$R^{11}$ group;
$R^5$ and $R^7$ independently represent a C1-C6 chain hydrocarbon group which is optionally substituted with a group selected from the group E described below, a -$Q^1$ group or a -$T^2$-$Q^1$ group;
$R^8$ represents a C1-C20 chain hydrocarbon group which is optionally substituted with a group selected from the group E described below, a -Q group or a -$T^1$-Q group;
$A^8$ represents an oxygen atom or a sulfur atom;
$T^0$ represents a C2-C6 alkanediyl group which is optionally substituted with a halogen atom or a phenyl group and wherein a carbon-carbon single bond of the alkanediyl group may be interrupted by an oxygen atom, a sulfur atom and/or a carbonyl group, a -$Q^9$- group, a -$T^1$-$Q^9$- group or a $T^1$-$Q^9$-$T^2$- group;
Q represents a carbocyclic group having 3 to 14 ring-constituting atoms which is optionally substituted with a group selected from the group A described below, or a heterocyclic group having 3 to 14 ring-constituting atoms which is optionally substituted with a group selected from the group A described below;
$Q^1$ represents a carbocyclic group having 3 to 14 ring-constituting atoms which is optionally substituted with a group selected from the group B described below, or a heterocyclic group having 3 to 14 ring-constituting atoms which is optionally substituted with a group selected from the group B described below;
$T^1$ and $T^2$ independently represent a C1-C6 alkanediyl group which is optionally substituted with a halogen atom, or a C2-C6 alkenediyl group;
$A^4$ and $A^5$ independently represent an oxygen atom or a sulfur atom;
$Q^9$ represents an o-phenylene group or a naphthalene-1,8-diyl group;
$R^{11}$ represents a C1-C6 chain hydrocarbon group which is optionally substituted with a group selected from the group E described below, or a carbocyclic group having 3 to 14 ring-constituting atoms which is optionally substituted with a group selected from the group B described below, The group A consists of: a halogen atom, a cyano group, a nitro group, a formyl group, a C1-C6 chain hydrocarbon group which is optionally substituted with a halogen atom, a -$A^6$-$L^1$ group, a —N($L^3$)-$L^2$ group, a —N($L^3$)-N($L^2$)-$L^1$ group, a —N=C($L^3$)-$L^2$ group, a —S(=O)-$L^1$ group, a —S(=O)$_2$-$L^1$ group, a —S(=O)$_2$—N($L^3$)-$L^2$ group, a —O—S(=O)$_2$-$L^1$ group, a —N$L^2$-S(=O)$_2$-$L^1$ group, a —C(=$A^7$)-$L^1$ group, a —C(=$A^7$)-O-$L^1$ group, a —O—C(=$A^7$)-$L^1$ group, a —N$L^2$-C(=$A^7$)-$L^1$ group, a —O—C(=O)—O-$L^1$ group, a —C(=$A^7$)-$T^4$-$A^6$-$L^1$ group, a —C(=$A^7$)-N($L^3$)-$L^2$ group, a -$Q^2$ group, a -$T^3$-$Q^2$ group, a -$A^6$-$Q^2$ group, a -$A^6$-$T^4$-$Q^2$ group, a —N($L^3$)-$Q^2$ group, a —N($L^3$)-N($L^2$)-$Q^2$ group, a —N=C($R^{12}$)-$Q^2$ group, a —S(=O)-$Q^2$ group, a —S(=O)$_2$-$Q^2$ group, a —S(=O)$_2$—N($L^3$)-$Q^2$ group, a —O—S(=O)$_2$-$Q^2$ group, a —N$L^2$-S(=O)$_2$-$Q^2$ group, a —C(=$A^7$)-$Q^2$ group, a —C(=$A^7$)-$A^6$-$Q^2$ group, a -$A^6$-

C(=A⁷)-Q² group, a —NL²-C(=A⁷)-Q² group, a —C(=A⁷)-T⁴-A⁶-Q² group, and a —C(=A⁷)-N(L³)-Q² group;

The group B consists of: a halogen atom, a cyano group, a nitro group, a C1-C6 alkyl group which is optionally substituted with a halogen atom, a C2-C6 alkenyl group which is optionally substituted with a halogen atom, a C2-C6 alkynyl group which is optionally substituted with a halogen atom, a C1-C6 alkylthio group, and a C1-C6 alkoxy group;

The group D consists of: a halogen atom, a cyano group, a nitro group, a C1-C6 alkoxy group which is optionally substituted with a halogen atom, a C1-C6 alkylthio group which is optionally substituted with a halogen atom, a C1-C6 alkylsulfonyl group which is optionally substituted with a halogen atom, a (C1-C6 alkyl)carbonyl group which is optionally substituted with a halogen atom, a (C1-C6 alkoxy)carbonyl group which is optionally substituted with a halogen atom, and a (C1-C6 alkoxy)carbonyloxy group which is optionally substituted with a halogen atom; and The group E consists of: a halogen atom, a cyano group, a nitro group, a C1-C6 alkylthio group, and a C1-C6 alkoxy group;

wherein, $A^6$ and $A^7$ independently represent an oxygen atom or a sulfur atom;

$L^1$ represents a C1-C6 chain hydrocarbon group which is optionally substituted with a halogen atom;

$L^2$ and $L^3$ independently represent a hydrogen atom, a C1-C6 alkyl group which is optionally substituted with a halogen atom;

$Q^2$ represents a carbocyclic group having 3 to 14 ring-constituting atoms which is optionally substituted with a group selected from the group B described above, or a heterocyclic group having 3 to 14 ring-constituting atoms which is optionally substituted with a group selected from the group B described above;

$T^3$ and $T^4$ independently represent a C1-C6 alkanediyl group which is optionally substituted with a halogen atom; and $R^{12}$ represents a C1-C6 chain hydrocarbon group which is optionally substituted with a halogen atom or a phenyl group which is optionally substituted with a halogen atom.

2. The imidate compound according to claim 1, wherein $M^1$ is a C1-C6 alkyl group, a C1-C6 alkoxy group, a C1-C6 alkylthio group, a phenyl group which is optionally substituted with a group selected from the E group, a phenoxy group which is optionally substituted with a group selected from the E group, a phenylthio group which is optionally substituted with a group selected from the E group, a monocyclic unsaturated heterocyclic group having 3 to 8 ring-constituting atoms which is optionally substituted with a group selected from the E group, a halogen atom or a hydrogen atom.

3. The imidate compound according to claim 1, wherein $M^1$ is a methyl group, an ethyl group, a propyl group, a butyl group, a phenyl group, a 2-methylphenyl group, a 3-methylphenyl group, a 4-methylphenyl group, a 2-fluorophenyl group, a 3-fluorophenyl group, a 4-fluorophenyl group, a 2-chlorophenyl group, a 3-chlorophenyl group, a 4-chlorophenyl group, a methoxy group, an ethoxy group, a propoxy group, a phenoxy group, a 2-methylphenoxy group, a 3-methylphenoxy group, a 4-methylphenoxy group, a 2-fluoropheoxy group, a 3-fluorophenoxy group, a 4-fluorophenoxy group, a 2-chlorophenoxy group, a 3-chlorophenoxy group, a 4-chlorophenoxy group, a methylthio group, an ethylthio group, a propylthio group, a butylthio group, a phenylthio group, a 2-methylphenylthio group, a 3-methylphenylthio group, a 4-methylphenylthio group, a 2-fluorophenylthio group, a 3-fluorophenylthio group, a 4-fluorophenylthio group, a 2-chlorophenylthio group, a 3-chlorophenylthio group, a 4-chlorophenylthio group, a 2-thienyl group, a 3-thienyl group, a 2-furyl group, a 3-furyl group, a fluorine atom, a chlorine atom or a hydrogen atom.

4. The imidate compound according to claim 1, wherein $M^1$ is a methyl group, an ethyl group, a propyl group, a butyl group, a methoxy group, an ethoxy group, a propoxy group, a methylthio group, an ethylthio group, a propylthio group, a fluorine atom, or a hydrogen atom.

5. The imidate compound according to claim 1, wherein $M^1$ is a hydrogen atom.

6. The imidate compound according to claim 1, wherein Z is a carbocyclic group having 3 to 14 ring-constituting atoms which is optionally substituted with a group selected from the group A' described below, or a heterocyclic group having 3 to 14 ring-constituting atoms which is optionally substituted with a group selected from the group A' described below, and the group A' consists of: a halogen atom, a cyano group, a nitro group, a formyl group, a C1-C6 chain hydrocarbon group which is optionally substituted with a halogen atom, a -A⁶-L¹ group, a —C(=A⁷)-L¹ group, a —C(=A⁷)-O-L¹ group, a —O—C(=A⁷)-L¹ group, a —NL²-C(=A⁷)-L¹ group, a —C(=A⁷)-N(L³)-L² group, a -Q² group, a -T³-Q² group, a -A⁶-Q² group, a -A⁶-T⁴-Q² group, a —C(=A⁷)-Q² group, a —C(=A⁷)-O-Q² group, a —O—C(=A⁷)-Q² group, a —NL³-C(=A⁷)-Q² group and a —C(=A⁷)-N(L³)-Q² group.

7. The imidate compound according to claim 1, wherein Z is a carbocyclic group having 3 to 14 ring-constituting atoms which is optionally substituted with a group selected from the group $A^{2'}$ described below, or a heterocyclic group having 3 to 14 ring-constituting atoms which is optionally substituted with a group selected from the group $A^{2'}$ described below, and the group $A^{2'}$ consists of: a halogen atom, a C1-C6 alkyl group which is optionally substituted with a halogen atom, a C2-C6 alkenyl group which is optionally substituted with a halogen atom, a C2-C6 alkynyl group which is optionally substituted with a halogen atom, a C1-C6 alkylthio group which is optionally substituted with a halogen atom, a C1-C6 alkoxy group which is optionally substituted with a halogen atom, and a phenyl group which is optionally substituted with a group selected from the B group as defined in claim 1.

8. The imidate compound according to claim 7, wherein Z is a carbocyclic group having 3 to 14 ring-constituting atoms which is optionally substituted with a group selected from the group $A^{2'}$.

9. The imidate compound according to claim 8, wherein Z is a phenyl group which is optionally substituted with a group selected from the group $A^{2'}$, a 5-indanyl group, or a naphthyl group.

10. The imidate compound according to claim 1, wherein Z is a phenyl group which is optionally substituted with a group selected from the group $A^{3'}$ described below, a 5-indanyl group, or a naphthyl group, and the group $A^{3'}$ consists of: a halogen atom, a methyl group, an ethyl group, a propyl group, an isopropyl group, a butyl group, a trifluoromethyl group, a methoxy group, an ethoxy group, a propoxy group, an isopropoxy group, a butoxy group, a trifluoromethoxy group, a 3,4-methylenedioxy group, a methylthio group, an ethylthio group, a propylthio group, an isopropylthio group, a butylthio group, a trifluoromethylthio group, a phenyl group, a 2-methylphenyl group, a 3-methylphenyl group, a 4-methylphenyl group, a 2-ethylphenyl group, a 3-ethylphenyl group, a 4-ethylphenyl group, a 2-propylphenyl group, a 3-propylphenyl group, a 4-propylphenyl group, a 2-isopropylphenyl group, a 3-isopropylphenyl group, a 4-isopropylphenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, and a 4-bromophenyl group.

11. The imidate compound according to claim 1, wherein G is a $-A^1-R^1$ group or a $-N(R^3)-R^1$ group.

12. The imidate compound according to claim 1, wherein G is a $-A^1-R^1$ group.

13. The imidate compound according to claim 1, wherein G is a $-A^1-R^1$ group, and $R^1$ is a -Q group or a $-T^1$-Q group in which Q is $Q^1$ as defined in claim 1, or a C1-C20 chain hydrocarbon group which is optionally substituted with a group selected from the group consisting of a halogen atom, a cyano group, a nitro group, a C1-C6 alkylthio group and a C1-C6 alkoxy group.

14. The imidate compound according to claim 1, wherein G is a $-A^1-R^1$ group; $A^1$ is S; and $R^1$ is a -Q group or a $-T^1$-Q group in which Q is a carbocyclic group having 3 to 14 ring-constituting atoms which is optionally substituted with a group selected from the group B as defined in claim 1, or a C1-C20 chain hydrocarbon group which is optionally substituted with a group selected from the group consisting of a halogen atom, a cyano group, a nitro group, a C1-C6 alkylthio group and a C1-C6 alkoxy group.

15. The imidate compound according to claim 1, wherein G is a $-A^1-R^1$ group; $A^1$ is S; and $R^1$ is a C1-C20 chain hydrocarbon group which is optionally substituted with a group selected from the group consisting of a halogen atom, a cyano group, a nitro group, a C1-C6 alkylthio group and a C1-C6 alkoxy group, or a -Q group or a $-T^1$-Q group in which Q is a phenyl group which is optionally substituted with a group selected from the group B as defined in claim 1 or a naphthyl group which is optionally substituted with a group selected from the group B as defined in claim 1.

16. The imidate compound according to claim 1, wherein G is a $-A^1-R^1$ group; $A^1$ is O; and $R^1$ is a -Q group in which Q is a phenyl group which is optionally substituted with a group selected from the group B as defined in claim 1 or a naphthyl group which is optionally substituted with a group selected from the group B as defined in claim 1.

17. The imidate compound according to claim 1, wherein X is a $-A^2-R^4$ group and $X^0$ is a $-A^3-R^6$ group, or X and $X^0$ are taken together to form a $-A^2-T^0-A^3-$ group.

18. The imidate compound according to claim 1, wherein X is a $-A^2-R^4$ group and $X^0$ is a $-A^3-R^6$ group.

19. The imidate compound according to claim 1, wherein X is a $-A^2-R^4$ group; $X^0$ is a $-A^3-R^6$ group; and $R^4$ and $R^6$ are independently a -Q group or a $-T^1$-Q group in which Q is $Q^1$ as defined in claim 1, or a C1-C6 chain hydrocarbon group which is optionally substituted with a group selected from the group consisting of a halogen atom, a cyano group, a nitro group, a C1-C6 alkylthio group and a C1-C6 alkoxy group.

20. The imidate compound according to claim 1, wherein X is a $-A^2-R^4$ group; $X^0$ is a $-A^3-R^6$ group; and $R^4$ and $R^6$ are independently a -Q group or a $-T^1$-Q group in which Q is $Q^1$ as defined in claim 1.

21. The imidate compound according to claim 1, wherein X is a $-A^2-R^4$ group; $X^0$ is a $-A^3-R^6$ group; and $R^4$ and $R^6$ are independently a -Q group in which Q is a phenyl group which is optionally substituted with a group selected from the group B as defined in claim 1.

22. The imidate compound according to claim 1, wherein X is a $-A^2-R^4$ group; $X^0$ is a $-A^3-R^6$ group; $A^2$ and $A^3$ are each S; and $R^4$ and $R^6$ are independently a -Q group in which Q is a phenyl group which is optionally substituted with a group selected from the group B as defined in claim 1.

23. A pesticidal composition comprising the compound according to claim 1 as an active ingredient.

24. A method of controlling a pest, which comprises applying the compound according to claim 1 to the pest or a place where the pest inhabits.

* * * * *